(12) United States Patent
Angell et al.

(10) Patent No.: US 11,584,761 B2
(45) Date of Patent: Feb. 21, 2023

(54) PROCESS OF MAKING CFTR MODULATORS

(71) Applicant: Vertex Pharmaceuticals Incorporated, Boston, MA (US)

(72) Inventors: Paul Angell, Carlsbad, CA (US); John E. Cochran, Marshfield, MA (US); Benjamin J. Littler, Carlsbad, CA (US); David Siesel, San Diego, CA (US); Armando Urbina, San Diego, CA (US); Corey Don Anderson, Brighton, MA (US); Jeremy J. Clemens, San Diego, CA (US); Thomas Cleveland, San Marcos, CA (US); Timothy Richard Coon, Carlsbad, CA (US); Bryan Frieman, La Jolla, CA (US); Peter Grootenhuis, Del Mar, CA (US); Sara Sabina Hadida Ruah, La Jolla, CA (US); Jason McCartney, Cardiff by the Sea, CA (US); Mark Thomas Miller, San Diego, CA (US); Prasuna Paraselli, San Diego, CA (US); Fabrice Pierre, La Jolla, CA (US); Sara E. Swift, San Diego, CA (US); Jinglan Zhou, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/992,419

(22) Filed: Aug. 13, 2020

(65) Prior Publication Data

US 2021/0047345 A1 Feb. 18, 2021

Related U.S. Application Data

(60) Provisional application No. 62/886,660, filed on Aug. 14, 2019.

(51) Int. Cl.
| | | |
|---|---|---|
| C07D 513/22 | (2006.01) | |
| C07D 207/08 | (2006.01) | |
| C07D 213/71 | (2006.01) | |
| C07D 213/82 | (2006.01) | |
| C07D 231/20 | (2006.01) | |
| C07D 401/04 | (2006.01) | |
| C07D 401/14 | (2006.01) | |

(52) U.S. Cl.
CPC ......... *C07D 513/22* (2013.01); *C07D 207/08* (2013.01); *C07D 213/71* (2013.01); *C07D 213/82* (2013.01); *C07D 231/20* (2013.01); *C07D 401/04* (2013.01); *C07D 401/14* (2013.01)

(58) Field of Classification Search
None
See application file for complete search history.

(56) References Cited

U.S. PATENT DOCUMENTS

| | | |
|---|---|---|
| 2,677,682 A | 5/1954 | Fahrenbach et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 11,066,417 B2 | 7/2021 | Clemens et al. |
| 2011/0098311 A1 | 4/2011 | Van Goor et al. |
| 2013/0317000 A1 | 11/2013 | Chowdhury et al. |
| 2013/0317001 A1 | 11/2013 | Andrez et al. |
| 2018/0099932 A1 | 4/2018 | Altenbach et al. |
| 2018/0141954 A1 | 5/2018 | Strohbach et al. |
| 2018/0162839 A1 | 6/2018 | Abela et al. |
| 2018/0170938 A1 | 6/2018 | Strohbach et al. |

(Continued)

FOREIGN PATENT DOCUMENTS

| | | |
|---|---|---|
| EP | 0 846 687 A1 | 6/1998 |
| WO | WO 2001/090092 A1 | 11/2001 |

(Continued)

OTHER PUBLICATIONS

Database Registry Chemical Abstracts Service, Columbus, Ohio, Accession No. RN 128583-07-3, Entered STN: Aug. 3, 1990.*

(Continued)

*Primary Examiner* — Samantha L Shterengarts

(74) *Attorney, Agent, or Firm* — Finnegan, Henderson, Farabow, Garrett & Dunner, LLP

(57) ABSTRACT

The disclosure provides processes for synthesizing Compound I, and pharmaceutically acceptable salts thereof.

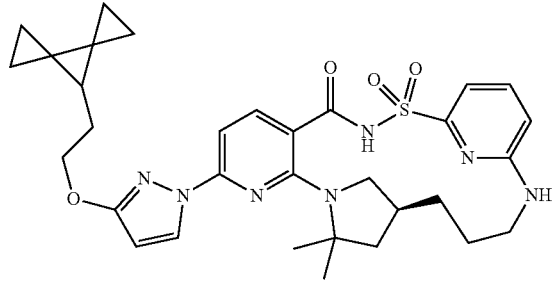

Compound I

37 Claims, No Drawings

(56) References Cited

U.S. PATENT DOCUMENTS

| | | |
|---|---|---|
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0119253 A1 | 4/2019 | Dhamankar et al. |
| 2019/0153000 A1 | 5/2019 | Munoz et al. |
| 2019/0240197 A1 | 8/2019 | Chu et al. |
| 2019/0248809 A1 | 8/2019 | Clemens et al. |
| 2019/0269683 A1 | 9/2019 | Miller et al. |
| 2022/0041621 A1 | 2/2022 | Clemens et al. |
| 2022/0047564 A1 | 2/2022 | Altshuler et al. |
| 2022/0106331 A1 | 4/2022 | Clemens et al. |

FOREIGN PATENT DOCUMENTS

| | | |
|---|---|---|
| WO | WO 2005/049018 A1 | 6/2005 |
| WO | WO 2005/075435 A1 | 8/2005 |
| WO | WO 2006/002421 A2 | 1/2006 |
| WO | WO 2007/021982 A2 | 2/2007 |
| WO | WO 2007/053641 A2 | 5/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/127399 A2 | 10/2008 |
| WO | WO 2008/154241 A1 | 12/2008 |
| WO | WO 2009/006315 A1 | 1/2009 |
| WO | WO 2009/038683 A2 | 3/2009 |
| WO | WO 2009/073757 A1 | 6/2009 |
| WO | WO 2009/076142 A2 | 6/2009 |
| WO | WO 2010/019239 A2 | 2/2010 |
| WO | WO 2010/053471 A1 | 5/2010 |
| WO | WO 2010/054138 A2 | 5/2010 |
| WO | WO 2010/108162 A1 | 9/2010 |
| WO | WO 2011/019413 A1 | 2/2011 |
| WO | WO 2011/072241 A1 | 6/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/133751 A2 | 10/2011 |
| WO | WO 2011/133951 A1 | 10/2011 |
| WO | WO 2012/027247 A2 | 3/2012 |
| WO | WO 2012/027731 A2 | 3/2012 |
| WO | WO 2012/170061 A1 | 12/2012 |
| WO | WO 2013/064984 A1 | 5/2013 |
| WO | WO 2013/070961 A1 | 5/2013 |
| WO | WO 2013/112804 A1 | 8/2013 |
| WO | WO 2013/130669 A1 | 9/2013 |
| WO | WO 2013/158121 A1 | 10/2013 |
| WO | WO 2013/160419 A1 | 10/2013 |
| WO | WO 2013/185112 A1 | 12/2013 |
| WO | WO 2014/014841 A1 | 1/2014 |
| WO | WO 2014/071122 A1 | 5/2014 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/160945 A1 | 10/2016 |
| WO | WO 2017/053455 A1 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/113089 A1 | 6/2019 |
| WO | WO 2019/113476 A2 | 6/2019 |
| WO | WO 2019/152940 A1 | 8/2019 |
| WO | WO 2019/161078 A1 | 8/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/102346 A1 | 5/2020 |
| WO | WO 2020/128925 A1 | 6/2020 |
| WO | WO 2020/191227 A1 | 9/2020 |
| WO | WO 2020/206080 A1 | 10/2020 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |
| WO | WO 2021/030555 A1 | 2/2021 |
| WO | WO 2021/030556 A1 | 2/2021 |
| WO | WO 2021/097057 A1 | 5/2021 |
| WO | WO 2022/032068 A1 | 2/2022 |
| WO | WO 2022/036060 A1 | 2/2022 |

OTHER PUBLICATIONS

Donaldson, S.H. et al. (2017) "Tezacaftor/Ivacaftor in Subjects with Cystic Fibrosis and F508del/F508del-CFTR orF508del/G551D-CFTR", *Am. J. Respir. Crit. Care Med.*, 197(2): 214-224.

International Patent Application No. PCT/U2020/026331: International Search Report and Written Opinion, dated May 29, 2020 (14 pages).

International Patent Application No. PCT/US2019/018042: International Search Report and Written Opinion, dated Apr. 17, 2019 (10 pages).

International Patent Application No. PCT/US2019/061171: International Search Report and Written Opinion, dated Feb. 12, 2020 (14 pages).

International Patent Application No. PCT/US2021/053853: International Search Report and Written Opinion, dated Dec. 21, 2021 (12 pages).

International Patent Application No. PCT/US2021/053855: International Search Report and Written Opinion, dated Jan. 3, 2022 (12 pages).

International Patent Application No. PCT/US2021/053856: International Search Report and Written Opinion, dated Dec. 22, 2021 (12 pages).

International Patent Application No. PCT/US2021/053858: International Search Report and Written Opinion, dated Mar. 17, 2022 (14 pages).

International Patent Application No. PCT/US2021/053860: International Search Report and Written Opinion, dated Dec. 23, 2021 (12 pages).

International Patent Application No. PCT/US2021/053861: International Search Report and Written Opinion, dated Dec. 22, 2021 (12 pages).

International Patent Application No. PCT/US2021/053862: International Search Report and Written Opinion, dated Dec. 22, 2021 (12 pages).

International Patent Application No. PCT/US2021/053863: International Search Report and Written Opinion, dated Feb. 4, 2022 (16 pages).

International Patent Application No. PCT/US2021/053864: International Search Report and Written Opinion, dated Mar. 15, 2022 (17 pages).

International Patent Application No. PCT/US2021/053865: International Search Report and Written Opinion, dated Jan. 26, 2022 (16 pages).

Newkome, G.R. et al. (1979) "Nicotinic Acid Crown Ethers. Synthesis, Reactions, and Complexation of Nicotinonitrile Macrocycles", *J Org Chem*, 44(15): 2639-2697.

(56) References Cited

OTHER PUBLICATIONS

Nishida, H. et al. (2017) "Exploration of pyrrole derivatives to find an effective potassium competitive acid blocker with moderately long-lasting suppression of gastric acid secretion", *Bioorg Med Chem*, 25(13): 3447-3460.
Prashantha, G. et al. (2017) "Selective IKur Inhibitors for the Potential Treatment of Atrial Fibrillation: Optimization of the Phenyl Quinazoline Series Leading to Clinical Candidate 5-[5-Phenyl-4-(pyridin-2-ylmethylamino)quinazolin-2-yl]pyridine-3-sulfonamide", *J Med Chem*, 60(9): 3795-3803.
Rewcastle, G.W. et al. (1996) "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor", *J Med Chem*, 39(9): 1823-1835.
"Symdeko in Cystic Fibrosis Patients", ClinicalTrials.gov, Jul. 23, 2018 (Apr. 23, 2018), XP055661778, Retrieved from the Internet: URL:https://clinicaltrials.gov/ct2/show/record/NCT03506061 [retrieved on Jan. 24, 2020].
U.S. Appl. No. 16/992,419, filed Aug. 13, 2021, by Angell et al.
U.S. Appl. No. 16/992,441, filed Aug. 13, 2021, by Shi et al.
U.S. Appl. No. 16/992,448, filed Aug. 13, 2021, by Anderson et al.
U.S. Appl. No. 16/992,675, filed Aug. 13, 2021, by Abela et al.
U.S. Appl. No. 17/546,649, filed Dec. 9, 2021, by Borek et al.
U.S. Appl. No. 17/600,829, filed Oct. 1, 2021, by Abela et al.

\* cited by examiner

PROCESS OF MAKING CFTR MODULATORS

This application claims priority from U.S. Provisional Application No. 62/886,660, filed Aug. 14, 2019, which is hereby incorporated by reference in its entirety.

Disclosed herein are processes for making a modulator of cystic fibrosis transmembrane conductance regulator ("CFTR").

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion, causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with CF are infertile, and fertility is reduced among females with CF.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on 412 of these identified mutations, with sufficient evidence to define 346 mutations as disease-causing. The most prevalent disease-causing mutation is a deletion of phenylalanine at position 508 of the CFTR amino acid sequence and is commonly referred to as the ΔF508 mutation. This mutation occurs in most of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the ΔF508 mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to ΔF508, other disease-causing mutations in CFTR that result in defective trafficking, synthesis, and/or channel gating could be up-regulated or down-regulated to alter anion secretion and modify disease progression and/or severity.

CFTR is a cAMP/ATP-mediated anion channel that is expressed in a variety of cell types, including absorptive and secretory epithelial cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$—$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$—$K^+$-ATPase pump, and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

(14S)-8-[3-(2-{dispiro[2.0.2$^4$.1$^3$]heptan-7-yl}ethoxy)-1H-pyrazol-1-yl]-12,12-dimethyl-2$\lambda^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound I):

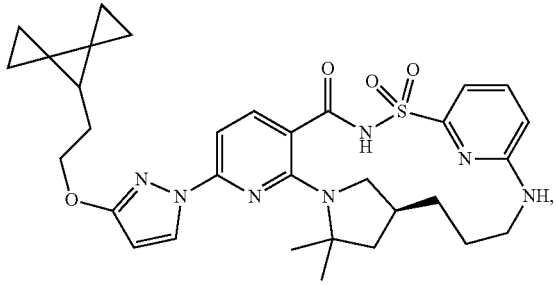

Compound I also known as (14S)-8-[3-(2-{dispiro[2.0.2.1]heptan-7-yl}ethoxy)-1H-pyrazol-1-yl]-12,12-dimethyl-2λ6-thia-3,9,11,18,23-pentaazatetracyclo[17.3.1.111,14.05,10]tetracosa-1(22),5,7,9,19(23),20-hexaene-2,2,4-trione, is disclosed in PCT Application No. PCT/US2019/018042, which is incorporated herein by reference in its entirety, as a modulator of CFTR activity and thus useful in treating CFTR-mediated diseases such as CF. There remains, however, a need for efficient processes for the synthesis of Compound I that delivers this compound or pharmaceutically acceptable salts thereof, for example, in higher yield, with higher selectivity, or with higher purity relative to known processes.

Disclosed herein are processes for making (14S)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I):

Compound I

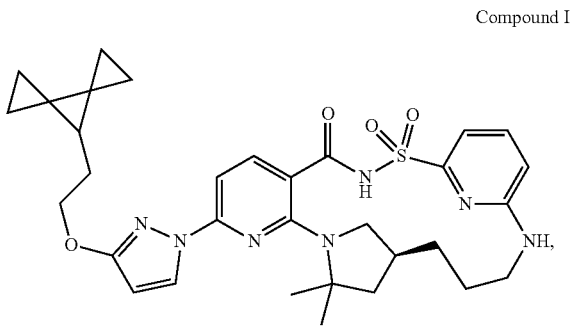 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

and pharmaceutically acceptable salts thereof.

Definitions

As used herein, "CFTR" means cystic fibrosis transmembrane conductance regulator.

As used herein, the terms "treatment," "treating," and the like generally mean the improvement of CF or its symptoms, or lessening the severity of CF or its symptoms, or a delay in the onset of CF or its symptoms, in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

The terms "patient" and "subject" are used interchangeably and refer to an animal, including humans.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. In general, a genetic defect or mutation, or a change in the nucleotides in a gene results in a mutation in the CFTR protein translated from that gene, or a frame shift(s).

The term "ΔF508" refers to a mutant CFTR protein which is lacking the amino acid phenylalanine at position 508.

As used herein, the term "modulator" refers to a compound that increases the activity of a biological compound or molecule such as a protein. For example, a CFTR modulator is a compound that increases the activity of CFTR. The increase in activity resulting from a CFTR modulator includes, but is not limited to, compounds that correct, potentiate, stabilize, and/or amplify CFTR.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e., exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See US 2004/0006237 for a comparison of XRPDs of an amorphous material and a crystalline material.

As used herein, the term "substantially amorphous" refers to a solid material having little or no long-range order in the position of its molecules. For example, substantially amorphous materials have less than 15% crystallinity (e.g., less than 10% crystallinity or less than 5% crystallinity). It is also noted that the term "substantially amorphous" includes the descriptor "amorphous," which refers to materials having no (0%) crystallinity.

The term "stable," as used herein, refers to compounds that are not substantially altered when subjected to conditions to allow for their production, detection, and preferably their recovery, purification, and use for one or more of the purposes disclosed herein.

The term "chemically stable," as used herein, means that the solid form of Compound I does not decompose into one or more different chemical compounds when subjected to specified conditions, e.g., 40° C./75% relative humidity, for a specific period of time, e.g., 1 day, 2 days, 3 days, 1 week, 2 weeks, or longer. In some embodiments, less than 25% of the solid form of Compound I decomposes. In some embodiments, less than about 20%, less than about 15%, less than about 10%, less than about 5%, less than about 3%, less than about 1%, less than about 0.5% of the form of Compound I decomposes under the conditions specified. In some embodiments, no detectable amount of the solid form of Compound I decomposes.

The term "physically stable," as used herein, means that the solid form of Compound I does not change into one or more different physical forms of Compound I (e.g., different solid forms as measured by XRPD, DSC, etc.) when subjected to specific conditions, e.g., 40° C./75% relative humidity, for a specific period of time, e.g, 1 day, 2 days, 3 days, 1 week, 2 weeks, or longer. In some embodiments, less than 25% of the solid form of Compound I changes into one or more different physical forms when subjected to specified conditions. In some embodiments, less than about 20%, less than about 15%, less than about 10%, less than about 5%, less than about 3%, less than about 1%, less than about 0.5% of the solid form of Compound I changes into one or more different physical forms of Compound I when subjected to specified conditions. In some embodiments, no detectable amount of the solid form of Compound I changes into one or more physically different solid forms of Compound I.

As used herein, the terms "about" and "approximately," when used in connection with amounts, volumes, reaction times, reaction temperatures, etc. mean an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%,25%,20%, 15%,10%,9%, 8%,7%, 6%,5%, 4%, 3%, 2%,1%,0.5%, 0.1%, or 0.05% of a given value or range.

The term "compound," when referring to a compound of this disclosure, refers to a collection of molecules having an identical chemical structure, except that there may be isotopic variation among the constituent atoms of the molecules.

Compounds described herein may optionally be substituted with one or more substituents, such as are illustrated generally above, or as exemplified by particular classes, subclasses, and species of the disclosure. It will be appreciated that the phrase "optionally substituted" is used interchangeably with the phrase "substituted or unsubstituted." In general, the term "substituted," whether preceded by the term "optionally" or not, indicates that at least one hydrogen of the "substituted" group is replaced with a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Combinations of substituents envisioned by this disclosure are preferably those that result in the formation of stable or chemically feasible compounds.

The term "stable compounds," as used herein, refers to compounds which possess sufficient stability to allow for their manufacture and which maintain the integrity of the compounds for a sufficient period of time to be useful for the purposes detailed herein (e.g., formulation into therapeutic products, intermediates for use in production of therapeutic compounds, isolatable or storable intermediates, and/or treating a disease or condition responsive to therapeutic agents).

The term "aliphatic" or "aliphatic group," as used herein, means a straight-chain (i.e., unbranched) or branched, substituted, or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic," or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_{3-8}$ hydrocarbon or bicyclic or tricyclic $C_{8-14}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof, such as (cycloalkyl)alkyl, (cycloalkenyl)alkyl, and (cycloalkyl)alkenyl. Suitable cycloaliphatic groups include cycloalkyl, bicyclic cycloalkyl (e.g., decalin), bridged bicycloalkyl such as norbornyl or [2.2.2]bicyclo-octyl, and bridged tricyclic such as adamantyl.

The term "unsaturated," as used herein, means that a moiety has one or more units of unsaturation.

As used herein, the term "alkyl group" refers to a saturated, branched, or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

As used herein, the term "haloalkyl group" refers to an alkyl group substituted with one or more halogen atoms.

The term "halogen" or "halo" means F, Cl, Br, or I.

As used herein, "cycloalkyl group" refers to a cyclic, non-aromatic hydrocarbon group containing 3-12 carbons in a ring (such as, for example, 3-10 carbons). Cycloalkyl groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, spiro[2.2]pentane, and dispiro[2.0.2.1]heptane. Cycloalkyl groups may be substituted or unsubstituted.

The term "heteroaliphatic," as used herein, means aliphatic groups wherein one or two carbon atoms are independently replaced with one or more heteroatoms, for example, oxygen, sulfur, nitrogen, phosphorus, or silicon. Heteroaliphatic groups may be substituted or unsubstituted, branched or unbranched, cyclic or acyclic, and include "heterocycle," "heterocyclyl," "heterocycloaliphatic," and "heterocyclic" groups.

The term "heteroatom" means one or more of oxygen, sulfur, nitrogen, phosphorus, or silicon (including any oxidized form of nitrogen, sulfur, phosphorus, or silicon; the quaternized form of any basic nitrogen; and a substitutable nitrogen of a heterocyclic ring, for example, N (as in 3,4-dihydro-2H-pyrrolyl), NH (as in pyrrolidinyl) or NR (as in N-substituted pyrrolidinyl)).

The term "heterocycle," "heterocyclyl," "heterocycloaliphatic," or "heterocyclic" as used herein means non-aromatic monocyclic, bicyclic, or tricyclic ring systems in which one or more ring members is an independently chosen heteroatom. In some embodiments, the "heterocycle," "heterocyclyl," "heterocycloaliphatic," or "heterocyclic" group has three to fourteen ring members in which one or more ring members is a heteroatom independently chosen from oxygen, sulfur, nitrogen, and phosphorus, and each ring in the system contains three to seven ring members.

The terms "haloaliphatic" and "haloalkoxy" means aliphatic or alkoxy, as the case may be, substituted with one or more halo atoms. Examples of haloaliphatic include $-CHF_2$, $-CH_2F$, $-CF_3$, $-CF_2-$, and perhaloalkyl, such as $-CF_2CF_3$.

The term "alkoxy group" as used herein refers to an alkyl or cycloalkyl group covalently bonded to an oxygen atom. Alkoxy groups may be substituted or unsubstituted and branched or unbranched.

The term "aryl" used alone or as part of a larger moiety as in "aralkyl," "aralkoxy," or "aryloxyalkyl," refers to monocyclic, bicyclic, and tricyclic ring systems having a total of five to fourteen ring members, wherein at least one ring in the system is aromatic and wherein each ring in the system contains three to seven ring members. The term "aryl" also refers to heteroaryl ring systems as defined herein below.

The term "heteroaryl," used alone or as part of a larger moiety as in "heteroaralkyl" or "heteroarylalkoxy," refers to monocyclic, bicyclic, and tricyclic ring systems having a total of five to fourteen ring members, wherein at least one ring in the system is aromatic, at least one ring in the system contains one or more heteroatoms, and wherein each ring in the system contains three to seven ring members.

An aryl (including aralkyl, aralkoxy, aryloxyalkyl and the like) or heteroaryl (including heteroaralkyl and heteroarylalkoxy and the like) group may be optionally substituted with one or more substituents.

The term "protecting group," as used herein, refers to any chemical group introduced into a molecule by chemical modification of a functional group in order to obtain chemoselectivity in a subsequent chemical reaction.

Methods of adding (a process generally referred to as "protecting") and removing (process generally referred to as "deprotecting") protecting groups are well-known in the art and available, for example, in P. J. Kocienski, *Protecting Groups,* 3$^{rd}$ edition (Thieme, 2005), and in Greene and Wuts, *Protective Groups in Organic Synthesis,* 4th edition (John Wiley & Sons, New York, 2007), both of which are hereby incorporated by reference in their entirety.

Non-limiting examples of useful protecting groups for amines that may be used in this disclosure include monovalent protecting groups, for example, t-butyloxycarbonyl (Boc), benzyl (Bn), β-methoxyethoxytrityl (MEM), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts); and divalent protecting groups, for example, benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

Non-limiting examples of useful protecting groups for alcohols that may be used in this disclosure include, for example, acetyl (Ac), benzoyl (Bz), benzyl (Bn), β-methoxyethoxymethyl (MEM), dimethoxytrityl (DMT), methoxymethyl (MOM), methoxytrityl (MMT), p-methoxybenzyl (PMB), pivaloyl (Piv), tetrahydropyranyl (THP), trityl (Tr), trimethylsilyl (TMS), triethylsilyl (TES), triisopropylsilyl (TIPS), t-butyldimethylsilyl (TBS), and t-butyldiphenylsilyl (TBDPS).

Non-limiting examples of useful protecting groups for carboxylic acids that may be used in this disclosure include, for example, methyl or ethyl esters, substituted alkyl esters such as 9-fluorenylmethyl, methoxymethyl (MOM), methylthiomethyl (MTM), tetrahydropyranyl (THP), tetrahydrofuranyl, β-methoxyethoxymethyl (MEM), 2-(trimethylsilyl)ethoxymethyl (SEM), benzyloxymethyl (BOM), pivaloyloxymethyl (POM), phenylacetoxymethyl, and cyanomethyl, acetyl (Ac), phenacyl, substituted phenacyl esters, 2,2,2-trichloroethyl, 2-haloethyl, ω-chloroalkyl, 2-(trimethylsilyl)ethyl, 2-methylthioethyl, t-butyl, 3-methyl-3-pentyl, dicyclopropylmethyl, cyclopentyl, cyclohexyl, allyl, methallyl, cinnamyl, phenyl (Ph), silyl esters, benzyl and substituted benzyl esters, 2,6-dialkylphenyl, and pentafluorophenyl (PFP).

Non-limiting examples of suitable solvents that may be used in this disclosure include, for example, water ($H_2O$), methanol (MeOH), methylene chloride or dichloromethane (DCM; $CH_2Cl_2$), acetonitrile (MeCN; $CH_3CN$), N,N-dimethylformamide (DMF), dimethylsulfoxide (DMSO), methyl acetate (MeOAc), ethyl acetate (EtOAc), isopropyl acetate (IPAc), tert-butyl acetate (t-BuOAc), isopropyl alcohol (IPA), tetrahydrofuran (THF), 2-methyl tetrahydrofuran (2-MeTHF), methyl ethyl ketone (MEK), tert-butanol, diethyl ether ($Et_2O$), methyl tert-butyl ether (MTBE), 1,4-dioxane, and N-methylpyrrolidone (NMP).

Non-limiting examples of amine bases that may be used in this disclosure include, for example, 1,8-diazabicyclo[5.4.0]undec-7-ene (DBU), N-methylmorpholine (NMM), triethylamine ($Et_3N$; TEA), diisopropylethyl amine (i-$Pr_2EtN$; DIPEA), pyridine, 2,2,6,6-tetramethylpiperidine, 7-methyl-1,5,7-triazabicyclo[4.4.0]dec-5-ene (MTBD), t-Bu-tetramethylguanidine, pyridine, 1,5-diazabicyclo[4.3.0]non-5-ene (DBN), and potassium bis(trimethylsilyl)amide (KHMDS). In some embodiments, the amine base is in IPA.

Non-limiting examples of carbonate bases that may be used in this disclosure include, for example, sodium carbonate ($Na_2CO_3$), potassium carbonate ($K_2CO_3$), cesium carbonate ($Cs_2CO_3$), lithium carbonate ($Li_2CO_3$), sodium bicarbonate ($NaHCO_3$), and potassium bicarbonate ($KHCO_3$).

Non-limiting examples of alkoxide bases that may be used in this disclosure include, for example, t-AmOLi (lithium t-amylate), t-AmONa (sodium t-amylate), t-AmOK (potassium t-amylate), sodium tert-butoxide (NaOtBu), potassium tert-butoxide (KOtBu), and sodium methoxide (NaOMe; $NaOCH_3$). In some embodiments, the alkoxide base is in THF. In some embodiments, the alkoxide base is in 2-MeTHF. In some embodiments, the alkoxide base is in IPA.

Non-limiting examples of hydroxide bases that may be used in this disclosure include, for example, sodium hydroxide (NaOH), potassium hydroxide (KOH), and lithium hydroxide (LiOH). In some embodiments, the hydroxide base is in THF. In some embodiments, the hydroxide base is in 2-MeTHF. In some embodiments, the hydroxide base is in IPA.

Non-limiting examples of phosphate bases that may be used in this disclosure include, for example, sodium phosphate tribasic ($Na_3PO_4$), potassium phosphate tribasic ($K_3PO_4$), potassium phosphate dibasic ($K_2HPO_4$), and potassium phosphate monobasic ($KH_2PO_4$).

Non-limiting examples of suitable sulfonate esters —$OSO_2R$ that may be used in this disclosure include, for example, methanesulfonyl (R=Me), p-toluenesulfonyl (R=4-$MeC_6H_4$—), and 4-nitrobenzylsulfonyl (R=4-$NO_2C_6H_4$—).

Unless otherwise stated, structures depicted herein are also meant to include all isomeric forms of the structure, e.g., geometric (or conformational), such as (Z) and (E) double bond isomers, and (Z) and (E) conformational isomers. Therefore, geometric and conformational mixtures of the compounds of the disclosure are within the scope of the disclosure.

Unless otherwise stated, all tautomeric forms of the compounds of the disclosure are within the scope of the disclosure.

"Stereoisomer" refers to both enantiomers and diastereomers.

"Tert" and "t-" are used interchangeably and mean tertiary.

The disclosure also provides processes for preparing salts of the compounds of the disclosure.

A salt of a compound of this disclosure is formed between an acid and a basic group of the compound, such as an amino functional group, or a base and an acidic group of the compound, such as a carboxyl functional group. In some embodiments, the salt is a pharmaceutically acceptable salt.

The term "pharmaceutically acceptable," as used herein, refers to a component that is, within the scope of sound medical judgment, suitable for use in contact with the tissues of humans and other mammals without undue toxicity, irritation, allergic response, and the like, and is commensurate with a reasonable benefit/risk ratio.

A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient. One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "10 mg of at least one compound chosen from Compound I and pharmaceutically acceptable salts thereof" includes 10 mg of Compound I and a concentration of a pharmaceutically acceptable salt of Compound I equivalent to 10 mg of Compound I.

Suitable pharmaceutically acceptable salts are, for example, those disclosed in S. M. Berge, et al. *J. Pharm. Sci.*, 1977, 66, 1-19. For example, Table 1 of that article provides the following pharmaceutically acceptable salts:

TABLE 1

| Pharmaceutically Acceptable Salts |
| --- |
| Acetate |
| Benzenesulfonate |
| Benzoate |
| Bicarbonate |
| Bitartrate |
| Bromide |
| Calcium edetate |
| Camsylate |
| Carbonate |
| Chloride |
| Citrate |
| Dihydrochloride |
| Edetate |
| Edisylate |
| Estolate |
| Esylate |
| Fumarate |
| Gluceptate |
| Gluconate |
| Glutamate |
| Glycollylarsanilate |
| Hexylresorcinate |
| Hydrabamine |
| Hydrobromide |
| Hydrochloride |
| Hydroxynaphthoate |
| Iodide |
| Isethionate |
| Lactate |
| Lactobionate |
| Malate |
| Maleate |
| Mandelate |
| Mesylate |
| Methylbromide |
| Methylnitrate |
| Methylsulfate |
| Mucate |
| Napsylate |
| Nitrate |
| Pamoate (Embonate) |
| Pantothenate |
| Phosphate/diphosphate |
| Polygalacturonate |
| Salicylate |
| Stearate |
| Subacetate |
| Succinate |
| Sulfate |
| Tannate |
| Tartrate |
| Teociate |

TABLE 1-continued

| Pharmaceutically Acceptable Salts |
| --- |
| Triethiodide |
| Benzathine |
| Chloroprocaine |
| Choline |
| Diethanolamine |
| Ethylenediamine |
| Meglumine |
| Procaine |
| Aluminum |
| Calcium |
| Lithium |
| Magnesium |
| Potassium |
| Sodium |
| Zinc |

Non-limiting examples of pharmaceutically acceptable salts derived from appropriate acids include: salts formed with inorganic acids, such as hydrochloric acid, hydrobromic acid, phosphoric acid, sulfuric acid, and perchloric acid; salts formed with organic acids, such as acetic acid, oxalic acid, maleic acid, tartaric acid, citric acid, succinic acid, or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions, such as halide, hydroxide, carboxylate, sulfate, phosphate, nitrate, lower alkyl sulfonate, and aryl sulfonate. Other suitable, non-limiting examples of pharmaceutically acceptable salts include besylate and glucosamine salts.

In the compounds of this disclosure, any atom not specifically designated as a particular isotope is meant to represent any stable isotope of that atom. Unless otherwise stated, when a position is designated specifically as "H" or "hydrogen," the position is understood to have hydrogen at its natural abundance isotopic composition.

The term "derivative" as used herein refers to a collection of molecules having a chemical structure identical to a compound of this disclosure, except that one or more atoms of the molecule may have been substituted with another atom. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C or $^{14}$C are within the scope of this disclosure. Such compounds are useful as, for example, analytical tools, probes in biological assays, or compounds with improved therapeutic profiles.

In some embodiments, the derivative is a silicon derivative, in which at least one carbon atom in a disclosed compound has been replaced with silicon. In some embodiments, the at least one carbon atom replaced with silicon may be a non-aromatic carbon. In some embodiments, the at least one carbon atom replaced with silicon may be an aromatic carbon. In certain embodiments, the silicon derivatives of the invention may also have one or more hydrogen atoms replaced with deuterium and/or germanium.

In other embodiments, the derivative is a germanium derivative, in which at least one carbon atom in a disclosed compound has been replaced with germanium. In certain embodiments, the germanium derivatives of the invention may also have one or more hydrogen atoms replaced with deuterium and/or silicon.

Because the general properties of silicon and germanium are similar to those of carbon, replacement of carbon by silicon or germanium can result in compounds with similar biological activity to a carbon-containing original compound.

The disclosure provides a method of preparing Compound I:

Compound I

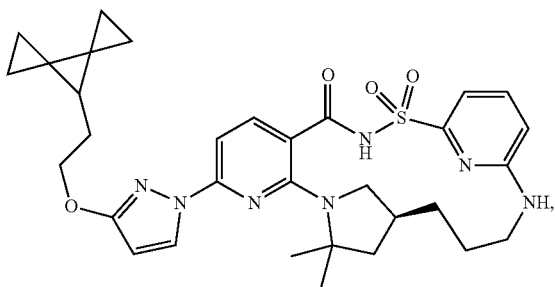

or a pharmaceutically acceptable salt thereof, comprising converting a compound of Formula (I):

(I)

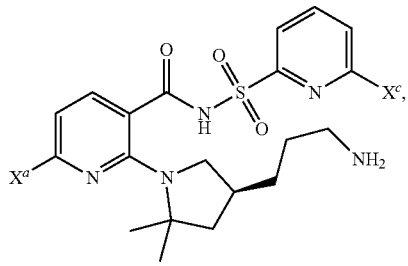

or a salt thereof, into Compound I, or a pharmaceutically acceptable salt thereof, wherein:
$X^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and
$X^c$ is selected from F, Cl, Br, and I.

In some embodiments, $X^a$ is Br and $X^c$ is F.

In some embodiments, the conversion of the compound of Formula (I), or a salt thereof, into Compound I, or a pharmaceutically acceptable salt thereof, comprises the steps of:
1) combining the compound of Formula (I), or a salt thereof, with at least one first base to produce a compound of Formula (II):

(II)

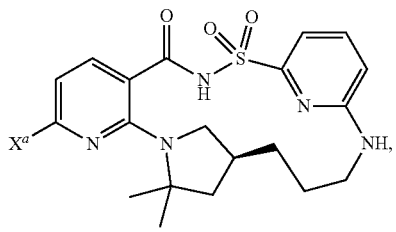

or a salt thereof; and
2) combining the compound of Formula (II), or a salt thereof, with compound 1:

1

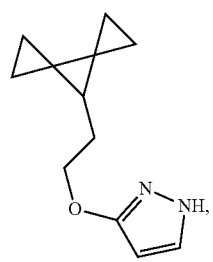

or a salt thereof, and at least one second base to produce Compound I, or a pharmaceutically acceptable salt thereof, wherein in the compound of Formula (II), or a salt thereof:
$X^a$ is selected from F, Cl, Br, I, and —OSO$_2$R; and
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro.

In some embodiments, in the compound of Formula (II), or a salt thereof, $X^a$ is Br.

In some embodiments, the at least one first base is selected from carbonate bases, hydroxide bases, alkoxide bases, acetate bases, amine bases, phosphate bases, and sulfate bases. In some embodiments, the at least one first base is selected from sodium carbonate (Na$_2$CO$_3$), potassium carbonate (K$_2$CO$_3$), 2,2,6,6-tetramethylpiperidine, 1,8-diazabicyclo[5.4.0]undec-7-ene (DBU), 7-methyl-1,5,7-triazabicyclo[4.4.0]dec-5-ene (MTBD), t-Bu-tetramethylguanidine, potassium bicarbonate (KHCO$_3$), and potassium phosphate tribasic (K$_3$PO$_4$).

In some embodiments, the combination of the compound of Formula (II), or a salt thereof, with compound 1, or a salt thereof, comprises at least one metal catalyst. In some embodiments, the at least one metal catalyst is selected from palladium catalysts and copper catalysts.

In some embodiments, the palladium catalyst is selected from [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), [1,1'-bis(di-tert-butylphosphino)ferrocene]dichloropalladium(II), tris(dibenzylideneacetone)dipalladium(0) (Pd$_2$dba$_3$)/2-di-tertbutylphosphino-2',4',6'-triisopropylbiphenyl)Pd₂dba₃/N-phenyl-2-(di-tert-butylphosphino)pyrrole, Pd₂dba₃/2-di-tert-butylphosphino-2'-methylbiphenyl, Pd₂dba₃/5-(di-tert-butylphosphino)-1', 5'-triphenyl-1'H-[1,4']bipyrazole, Pd₂dba₃/2-(di-tert-butylphosphino)-1-(2-methoxyphenyl)-1H-pyrrole, Pd₂dba₃/2-dicyclohexylphosphino-2',6'-dimethoxybiphenyl, Pd₂dba₃/2-(dicyclohexylphosphino)3,6-dimethoxy-2',4',6'-triisopropyl-1,1'-biphenyl (Pd₂dba₃/BrettPhos), Pd₂dba₃/di-tert-butyl(2,2-diphenyl-1-methyl-1-cyclopropyl)phosphine, Pd₂dba₃/1-(dicyclohexylphosphino)-2,2-diphenyl-1-methylcyclopropane, dichloro[1,3-bis(2,6-di-3-pentylphenyl)imidazol-2-ylidene](3-chloropyridyl) palladium(II), Pd₂dba₃/1,1'-bis(diphenylphosphino) ferrocene, dichloro[1,1'-bis(dicyclohexylphosphino) ferrocene] palladium(II), (2-dicyclohexylphosphino-2',4',6'-triisopropyl-1,1'-biphenyl)[2-(2'-amino-1,1'-biphenyl)] palladium(II) methanesulfonate (XPhos Pd G3), dichloro[2,2'-bis(diphenylphosphino)-1,1'-binaphthyl]palladium(II) (Pd(BINAP)Cl₂), Pd₂dba₃/bis[(2-diphenylphosphino)phenyl] ether (Pd₂dba₃/DPEPhos), Pd₂dba₃/1,2,3,4,5-pentaphenyl-1'-(di-tert-butylphosphino)ferrocene, Pd₂dba₃/2-(di-tert-butylphosphino)-2',4',6'-triisopropyl-3,6-dimethoxy-1,1'-biphenyl, Pd₂dba₃/2-dicyclohexylphosphino-2'-(N,N-dimethylamino)biphenyl, Pd₂dba₃/1,1'-bis(di-tert-butylphosphino)ferrocene, 2-di-tert-butylphosphino-2',4',6'-triisopropylbiphenyl/Pd₂dba₃ (tert-butyl XPhos/Pd₂dba₃), [2-(di-tert-butylphosphino)-2',4',6'-triisopropyl-1,1'-biphenyl][2-(2-aminoethyl)phenyl]]palladium(II) chloride (tBuXPhos-Pd-G1), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/Pd₂dba₃ (t-BuBrettPhos/Pd₂dba₃), trifluoromethanesulfonate allyl[(2-di-tert-butylphosphino-3,6-dimethoxy-2',4',6'-triisopropyl-1,1'-biphenyl)-2-(2'-amino-1,1'-biphenyl)] palladium(II), (2-dicyclohexylphosphino-2',6'-dimethoxybiphenyl) [2-(2'-amino-1,1'-biphenyl)]palladium(II) methanesulfonate/Pd₂dba₃ (SPhos/Pd₂dba₃), [1,1'-bis(diphenylphosphino)ferrocene]dichloropalladium(II) (Pd(dppf)Cl₂), [1,1'-bis(di-tert-butylphosphino)ferrocene]dichloropalladium(II) (Pd(dtbpf)Cl₂), dichloro[1,3-bis(2,6-di-3-pentylphenyl)imidazol-2-ylidene](3-chloropyridyl)palladium(II) (PEPSII-pent), di-tert-butyl(2,2-diphenyl-1-methyl-1-cyclopropyl) phosphine/Pd₂dba₃ (cBRIDP/Pd₂dba₃), and 1-(dicyclohexylphosphino)-2,2-diphenyl-1-methylcyclopropane/Pd₂dba₃ (Cy-cBRIDP/Pd₂dba₃). The active catalyst, palladium (0) 2-di-tert-butylphosphino-2',4',6'-triisopropylbiphenyl (tBuXPhos, tert-Butyl XPhos) can be generated using palladium (II) tBuXPhos precatalyst (G1-G3) or a combination of a palladium (0) source, for example Pd₂(dba)₃ or Pd(PPh₃)₄, and di-tert-butylphosphino-2',4',6'-triisopropylbiphenyl (tBuXPhos, tert-Butyl XPhos) and finally by using palladium (II) source, such as Pd(OAc)₂ or Pd(Cl)₂ in the presence of a reducing agent and di-tert-butylphosphino-2',4',6'-triisopropylbiphenyl (tBuXPhos, tert-Butyl XPhos).

In some embodiments, the copper catalyst is selected from copper(II) fluoride, copper(I) bromide (CuBr), copper (I) iodide (CuI), copper (I) thiophene-2-carboxylate, and copper(I) trifluoromethanesulfonate toluene complex, optionally substituted with a ligand such as N,N-dimethylethylenediamine, N,N-dimethylcyclohexane-1,2-diamine), 1,10-phenanthroline, 8-hydroxyquinoline, trans-cyclohexane-1,2-diamine, cis-cyclohexane-1,2-diamine, N,N-di-methylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, and N-cyclohexyl-2,6-bis(1-methylethyl)benzenamine. In some embodiments, the copper catalyst is optionally substituted with a ligand selected from N,N-diisopropyl-1,3-propanediamine

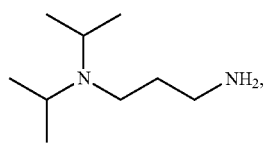

trans-1,2-diaminocyclohexane

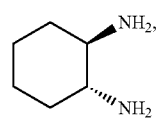

N,N'-dimethyl-1,3-propanediamine

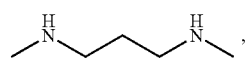

N,N'-diethylethane-1,2-diamine

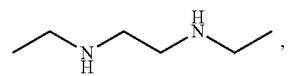

3-(dimethylamino)-propylamine

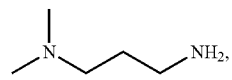

1,4-diaminocyclohexane

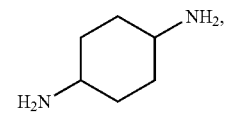

N,N'-dimethylethane-1,2-diamine

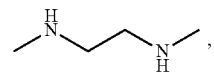

diethylenetriamine

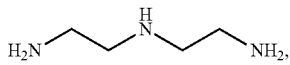

and trans-N,N-dimethylcyclohexane-1,2-diamine

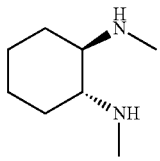

In some embodiments, the at least one metal catalyst is [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), bis(dibenzylideneacetone)palladium(0) (Pd₂dba₃), copper iodide (CuI), or a combination thereof.

In some embodiments, step 2) further comprises excess 2-di-tert-butylphosphino-2',4',6'-triisopropylbiphenyl (tBuXPhos) relative to [(2-di-tert-butylphosphino-2',4',6'-triisopropyl-1,1'-biphenyl)-2-(2'-amino-1,1'-biphenyl)]palladium(II) methanesulfonate (tBuXPhos Pd G3). In some embodiments, the at least one second base is a carbonate base, such as potassium carbonate ($K_2CO_3$) or cesium carbonate ($Cs_2CO_3$).

In some embodiments, the conversion of the compound of Formula (I), or a salt thereof, into Compound I, or a pharmaceutically acceptable salt thereof, comprises the steps of combining the compound of Formula (I), or a salt thereof, with compound 1:

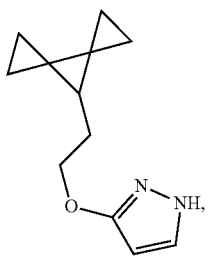

1 or a salt thereof, and at least one third base to produce Compound I, or a pharmaceutically acceptable salt thereof, wherein in the compound of Formula (I), or a salt thereof:
 $X^a$ is selected from F, Cl, Br, I, and —OSO₂R;
 R is selected from —$C_{1-10}$ alkyl, —$C_{1-10}$ haloalkyl, and aryl optionally substituted with —$C_{1-10}$ alkyl, —$C_{1-10}$ haloalkyl, halo, or nitro; and
 $X^c$ is selected from F, Cl, Br, and I.

In some embodiments, in the compound of Formula (I), or a salt thereof, $X^a$ is Br and $X^c$ is F.

In some embodiments, the at least one third base is selected from carbonate bases, hydroxide bases, alkoxide bases, acetate bases, amine bases, phosphate bases, and sulfate bases. In some embodiments, the at least one third base is selected from sodium carbonate ($Na_2CO_3$), potassium carbonate ($K_2CO_3$), 2,2,6,6-tetramethylpiperidine, 1,8-diazabicyclo[5.4.0]undec-7-ene (DBU), 7-methyl-1,5,7-triazabicyclo[4.4.0]dec-5-ene (MTBD), t-Bu-tetramethylguanidine, potassium bicarbonate ($KHCO_3$), and potassium phospahate ($K_3PO_4$).

In some embodiments, the combination of the compound of Formula (II), or a salt thereof, with compound 1, or a salt thereof, further comprises at least one metal catalyst. In some embodiments, the at least one metal catalyst is selected from palladium catalysts and copper catalysts.

In some embodiments, the palladium catalyst is selected from [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), [1,1'-bis(di-tert-butylphosphino)ferrocene]dichloropalladium(II), tris(dibenzylideneacetone)dipalladium(0) (Pd₂dba₃)/2-di-tert-butylphosphino-2',4',6'-triisopropylbiphenyl)Pd₂dba₃/N-phenyl-2-(di-tert-butylphosphino)pyrrole, Pd₂dba₃/2-di-tert-butylphosphino-2'-methylbiphenyl, Pd₂dba₃/5-(di-tert-butylphosphino)-1', 3', 5'-triphenyl-1'H-[1,4']bipyrazole, Pd₂dba₃/2-(di-tert-butylphosphino)-1-(2-methoxyphenyl)-1H-pyrrole, Pd₂dba₃/2-dicyclohexylphosphino-2',6'-dimethoxybiphenyl, Pd₂dba₃/2-(dicyclohexylphosphino)3,6-dimethoxy-2',4',6'-triisopropyl-1,1'-biphenyl (Pd₂dba₃/BrettPhos), Pd₂dba₃/di-tert-butyl(2,2-diphenyl-1-methyl-1-cyclopropyl)phosphine, Pd₂dba₃/1-(dicyclohexylphosphino)-2,2-diphenyl-1-methylcyclopropane, dichloro[1,3-bis(2,6-di-3-pentylphenyl)imidazol-2-ylidene](3-chloropyridyl)palladium(II), Pd₂dba₃/1,1'-bis(diphenylphosphino)ferrocene, dichloro[1,1'-bis(dicyclohexylphosphino)ferrocene] palladium(II), (2-dicyclohexylphosphino-2',4',6'-triisopropyl-1,1'-biphenyl)[2-(2'-amino-1,1'-biphenyl)]palladium(II) methanesulfonate (XPhos Pd G3), dichloro[2,2'-bis(diphenylphosphino)-1,1'-binaphthyl]palladium(II) (Pd(BINAP)Cl₂), Pd₂dba₃/bis[(2-diphenylphosphino)phenyl] ether (Pd₂dba₃/DPEPhos), Pd₂dba₃/1,2,3,4,5-pentaphenyl-1'-(di-tert-butylphosphino)ferrocene, Pd₂dba₃/2-(di-tert-butylphosphino)-2',4',6'-triisopropyl-3,6-dimethoxy-1,1'-biphenyl, Pd₂dba₃/2-dicyclohexylphosphino-2'-(N,N-dimethylamino)biphenyl, Pd₂dba₃/1,1'-bis(di-tert-butylphosphino)ferrocene, 2-di-tert-butylphosphino-2',4',6'-triisopropylbiphenyl/Pd₂dba₃ (tert-Butyl XPhos/Pd₂dba₃), [2-(di-tert-butylphosphino)-2',4',6'-triisopropyl-1,1'-biphenyl][2-(2-aminoethyl)phenyl)]palladium(II) chloride (tBuXPhos-Pd-G1), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/Pd₂dba₃ (t-BuBrettPhos/Pd₂dba₃), trifluoromethanesulfonate allyl[(2-di-tert-butylphosphino-3,6-dimethoxy-2',4',6'-triisopropyl-1,1'-biphenyl)-2-(2'-amino-1,1'-biphenyl)]palladium(II), (2-dicyclohexylphosphino-2',6'-dimethoxybiphenyl) [2-(2'-amino-1,1'-biphenyl)]palladium(II) methanesulfonate/Pd₂dba₃ (SPhos/Pd₂dba₃), [1,1'-bis(diphenylphosphino)ferrocene]dichloropalladium(II) (Pd(dppf)Cl₂, [1,1'-bis(di-tert-butylphosphino)ferrocene]dichloropalladium(II) (Pd(dtbpf)Cl₂), dichloro[1,3-bis(2,6-di-3-pentylphenyl)imidazol-2-ylidene](3-chloropyridyl)palladium(II) (PEPSII-pent), di-tert-butyl(2,2-diphenyl-1-methyl-1-cyclopropyl) phosphine/Pd₂dba₃ (cBRIDP/Pd₂dba₃), and 1-(dicyclohexylphosphino)-2,2-diphenyl-1-methylcyclopropane/Pd₂dba₃ (Cy-cBRIDP/Pd₂dba₃). The active catalyst, palladium (0) 2-di-tert-butylphosphino-2',4',6'-triisopropylbiphenyl (tBuXPhos, tert-Butyl XPhos) can be generated using palladium (II) tBuXPhos precatalyst (G1-G3) or a combination of a palladium (0) source, for example Pd₂(dba)₃ or Pd(PPh₃)₄, and di-tert-butylphosphino-2',4',6'- triisopropylbiphenyl (tBuXPhos, tert-Butyl XPhos) and finally by using palladium (II) source, such as Pd(OAc)$_2$ or Pd(Cl)$_2$ in the presence of a reducing agent and di-tert-butylphosphino-2',4',6'-triisopropylbiphenyl (tBuXPhos, tert-Butyl XPhos).

In some embodiments, the copper catalyst is selected from copper(II) fluoride, copper(I) bromide (CuBr), copper (I) iodide (CuI), copper(I) thiophene-2-carboxylate, and copper(I) trifluoromethanesulfonate toluene complex, optionally substituted with a ligand such as N,N'-dimethylethylenediamine, N,N'-dimethylcyclohexane-1,2-diamine), 1,10-phenanthroline, 8-hydroxyquinoline, trans-cyclohexane-1,2-diamine, cis-cyclohexane-1,2-diamine, N,N-dimethylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, and N-cyclohexyl-2,6-bis(1-methylethyl)benzeneamine. In some embodiments, the copper catalyst is optionally substituted with a ligand selected from N,N-diisopropyl-1,3-propanediamine, trans-1,2-diaminocyclohexane, N,N'-dimethyl-1,3-propanediamine, N,N'-diethylethane-1,2-diamine, 3-(dimethylamino)-propylamine, 1,4-diaminocyclohexane, N,N'-dimethylethane-1,2-diamine, diethylenetriamine, and trans-N,N-dimethylcyclohexane-1,2-diamine.

In some embodiments, the at least one metal catalyst is [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), bis(dibenzylideneacetone)palladium(0) (Pd$_2$dba$_3$), copper iodide (CuI), or a combination thereof.

In some embodiments, the compound of Formula (I):

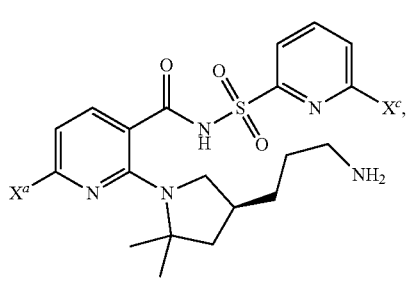

(I)

or a salt thereof, is prepared by converting a compound of Formula (III):

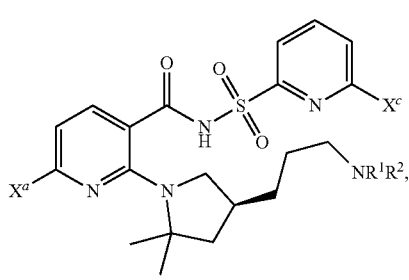

(III)

or a salt thereof, into the compound of Formula (I), or a salt thereof, wherein in the compound of Formula (III), or a salt thereof:
X$^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro;
X$^c$ is selected from F, Cl, Br, and I; and
wherein:
R$^1$ is hydrogen and R$^2$ is a monovalent nitrogen protecting group;
R$^1$ and R$^2$ are independently selected from monovalent nitrogen protecting groups; or
R$^1$ and R$^2$, together with the atoms to which they are attached, form a nitrogen protecting group.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, R$^1$ and R$^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (III), or a salt thereof, X$^a$ is Br, X$^c$ is F, and R$^1$ and R$^2$, together with the atoms to which they are attached, form N-phthalimide.

In some embodiments, the conversion of the compound of Formula (III), or a salt thereof, into the compound of Formula (I), or a salt thereof, comprises the steps of:
1) combining the compound of Formula (III), or a salt thereof, in the presence of water and a base selected from lithium hydroxide (LiOH), hydrazine, ethanolamine, and N-methylamine; and
2) optionally combining the product of step 1) with an acid selected from oxalic acid, hydrochloric acid (HCl), phosphoric acid (H$_3$PO$_4$), and citric acid; then treating the reaction mixture with water and a base selected from potassium carbonate (K$_2$CO$_3$) and cesium carbonate (Cs$_2$CO$_3$) to produce the compound of Formula (I), or a salt thereof.

In some embodiments, the compound of Formula (III):

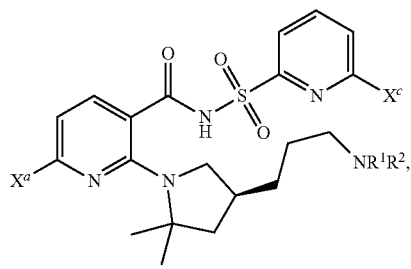

(III)

or a salt thereof, is prepared by combining a compound of Formula (IV):

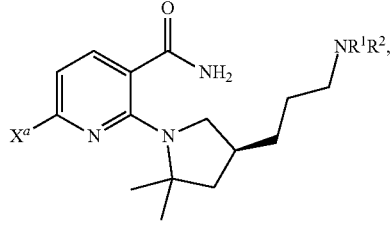

or a salt thereof, with a compound of Formula (V):

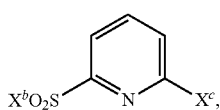

or a salt thereof, to produce the compound of Formula (III), or a salt thereof,
wherein:
$X^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro;
$X^b$ is selected from Cl, F, —OC$_6$F$_5$,

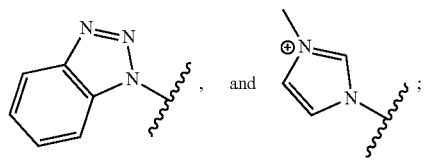

$X^c$ is selected from F, Cl, Br, and I; and
wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (IV), or a salt thereof, $X^a$ is Br, and $R^1$ and $R^2$, together with the atoms to which they are attached, form N-phthalimide. In some embodiments, in the compound of Formula (IV), or a salt thereof, $X^a$ is Br, $R^1$ is hydrogen, and $R^2$ is benzyloxycarbonyl (Cbz).

In some embodiments, in the compound of Formula (V), or a salt thereof, $X^b$ is —OC$_6$F$_5$ and $X^c$ is F. In some embodiments, the amide of the compound of Formula (IV), or the amide of a salt thereof, is protected with a nitrogen protecting group.

In some embodiments, the combination of the compound of Formula (IV), or a salt thereof, with the compound of Formula (V), or a salt thereof, is performed in the presence of at least one fourth base. In some embodiments, the at least one fourth base is an alkoxy base. In some embodiments, the alkoxy base is selected from lithium t-amylate (t-AmOLi), sodium t-amylate (t-AmONa), potassium t-amylate (t-AmOK), and lithium t-butoxide (LiOt-Bu).

In some embodiments, the compound of Formula (IV):

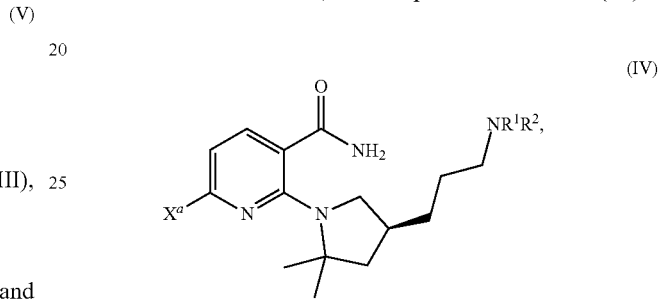

or a salt thereof, is prepared by converting a compound of Formula (VI):

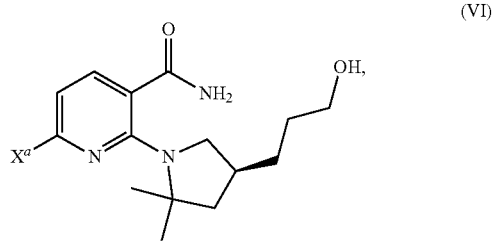

or a salt thereof, into the compound of Formula (IV), or a salt thereof,
wherein in the compound of Formula (VI), or a salt thereof:
$X^a$ is selected from F, Cl, Br, I, and —OSO$_2$R; and
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro.

In some embodiments, the amide of the compound of Formula (IV), or the amide of a salt thereof, is protected with a nitrogen protecting group.

In some embodiments, in the compound of Formula (VI), or a salt thereof, $X^a$ is Br.

In some embodiments, the conversion of the compound of Formula (VI), or a salt thereof, into the compound of Formula (IV), or a salt thereof, comprises the steps of:
1) converting the hydroxy group of the compound of formula (VI), or a salt thereof, into a sulfonate ester (—OSO$_2$R) or Cl; and
2) combining the sulfonate ester or Cl of step 1) with an amine and at least one fifth base to produce the compound of Formula (IV), or a salt thereof.

In some embodiments, the R group of the sulfonate ester (—OSO$_2$R) is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro. In some embodiments, the conversion of the hydroxy group into a sulfonate ester in step 1) is performed in the presence of methanesulfonyl chloride (MsCl) and triethylamine (TEA). In some embodiments, the amine in step 2) is N-phthalimide and the at least one fifth base in step 2) is a carbonate base, such as potassium carbonate (K$_2$CO$_3$) or cesium carbonate (Cs$_2$CO$_3$).

In some embodiments, the compound of Formula (VI):

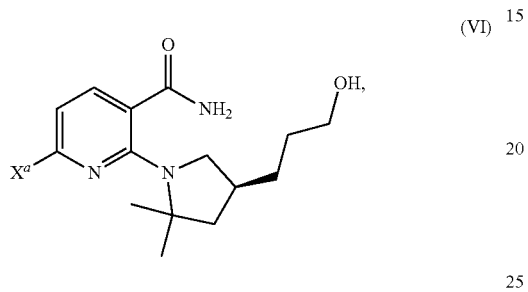

(VI)

or a salt thereof, is prepared by combining compound 2:

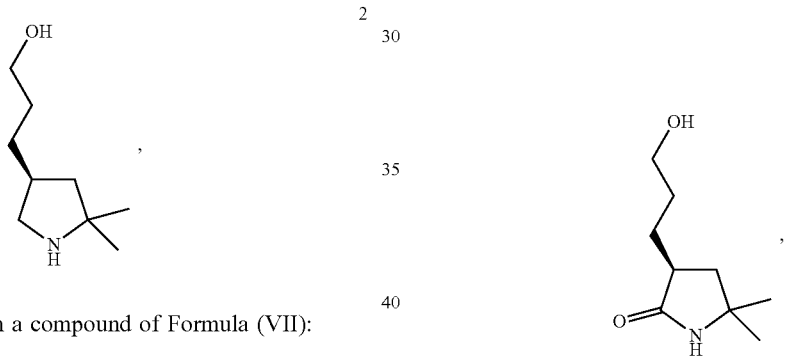

or a salt thereof, with a compound of Formula (VII):

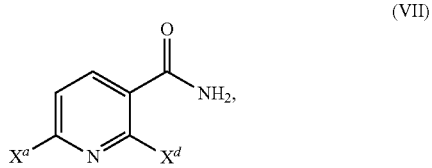

(VII)

or a salt thereof, to produce the compound of Formula (VI), or a salt thereof,
wherein in the compound of Formula (VII), or a salt thereof:
X$^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and
X$^d$ is selected from F, Cl, Br, and I.

In some embodiments, in the compound of Formula (VII), or a salt thereof, X$^a$ is Br and X$^d$ is F.

In some embodiments, the combination of compound 2, or a salt thereof, with the compound of Formula (VII), or a salt thereof, is performed in the presence of at least one sixth base. In some embodiments, the at least one sixth base is selected from potassium t-butoxide (KOt-Bu), lithium hydroxide (LiOH), potassium phosphate tribasic (K$_3$PO$_4$), potassium phosphate dibasic (K$_2$HPO$_4$), cesium carbonate (Cs$_2$CO$_3$), 2,2,6,6-tetramethylpiperidine, 7-methyl-1,5,7-triazabicyclo[4.4.0]dec-5-ene (MTBD), tetramethylguanidine, 1,8-diazabicyclo[5.4.0]undec-7-ene (DBU), triethylamine (TEA), tributylamine (Bu$_3$N), sodium bicarbonate (NaHCO$_3$), potassium bicarbonate (KHCO$_3$), sodium carbonate (Na$_2$CO$_3$) and potassium carbonate (K$_2$CO$_3$). In some embodiments, the combination of compound 2, or a salt thereof, with the compound of Formula (VII), or a salt thereof, is performed in the presence of potassium carbonate (K$_2$CO$_3$) in an aqueous solution in a substrate in 2-MeTHF.

In some embodiments, compound 2:

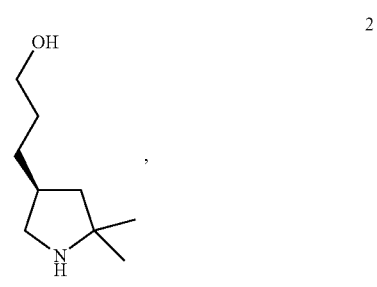

2 or a salt thereof, is prepared by converting compound 3:

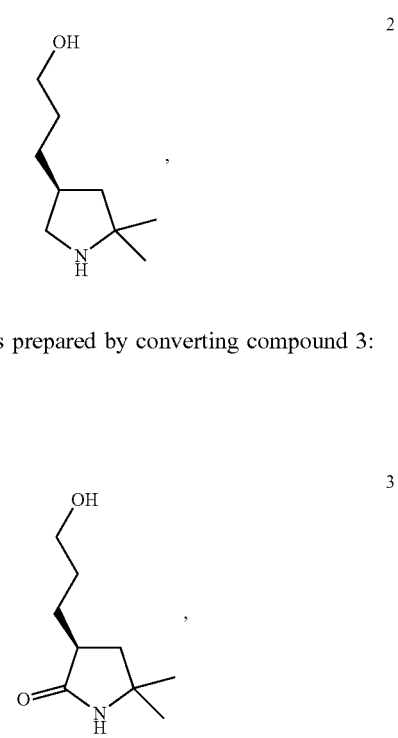

3 or a salt thereof, into compound 2, or a salt thereof.

In some embodiments, the conversion of compound 3, or a salt thereof, into compound 2, or a salt thereof, is performed in the presence of a reducing agent. In some embodiments, the reducing agent is selected from lithium aluminum hydride (LiAlH$_4$), sodium bis(2-methoxyethoxy)aluminum hydride, borane (BH$_3$), and borane-tetrahydrofuran (BH$_3$-THF).

In some embodiments, compound 3:

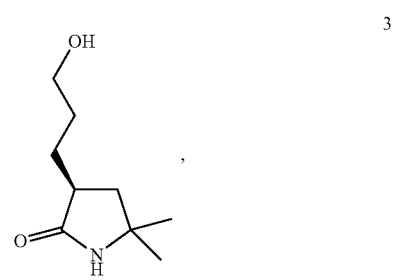

3 or a salt thereof, is prepared by converting compound 4:

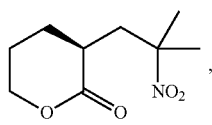
4 or a salt thereof, into compound 3, or a salt thereof.

In some embodiments, the conversion of compound 4, or a salt thereof, into compound 3, or a salt thereof, is performed in the presence of reducing reaction conditions. In some embodiments, the reducing reaction conditions comprise hydrogen gas ($H_2$) and at least one metal catalyst selected from Raney Nickel (Ra—Ni), palladium on carbon (Pd/C), palladium on alumina ($Pd/Al_2O_3$), palladium(II) chloride ($PdCl_2$), platinum oxide ($PtO_2$), palladium/platinum on carbon (Pd/Pt/C), platinum on carbon (Pt/C), and nickel(II) chloride/sodium borohydride ($NiCl_2/NaBH_4$).

In some embodiments, compound 4:

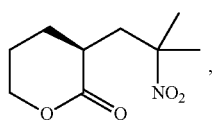
4 or a salt thereof, is prepared by chiral resolution of compound (±)-4:

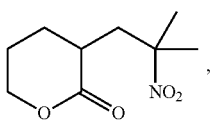
(±)-4 or a salt thereof.

In some embodiments, the chiral resolution of compound (±)-4, or a salt thereof, is performed using a method selected from chiral column chromatography, chiral Simulated Moving Bed (SMB), bioresolution, enzymatic resolution, liquid chromatography, salt resolution, and asymmetric hydrogenation.

The disclosure provides a method of preparing Compound I:

Compound I

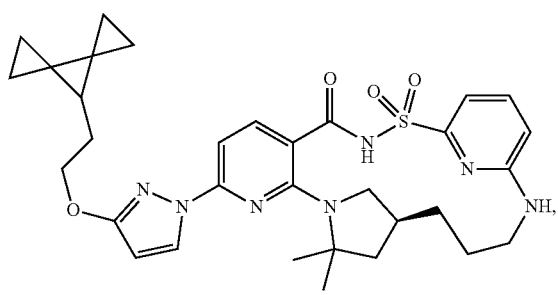

or a pharmaceutically acceptable salt thereof, comprising converting a compound of Formula (VIII):

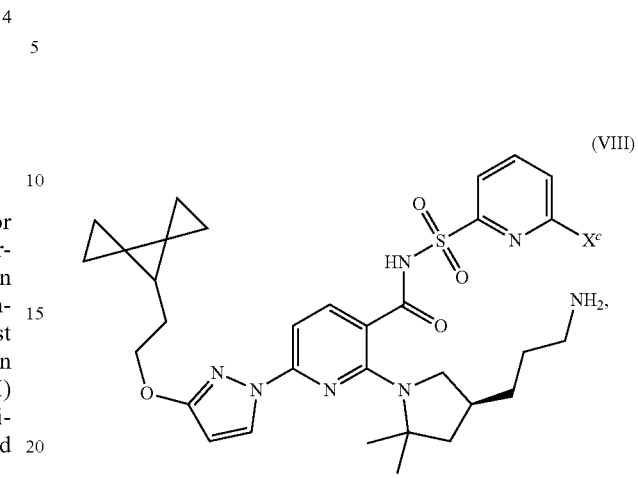
(VIII)

or a salt thereof, into Compound I, or a pharmaceutically acceptable salt thereof, wherein in the compound of Formula (VIII), or a salt thereof, $X^c$ is selected from F, Cl, Br, and I.

In some embodiments, the conversion of the compound of Formula (VIII), or a salt thereof, into Compound I, or a pharmaceutically salt thereof, is performed in the presence of at least one seventh base. In some embodiments, the at least one seventh base is selected from potassium carbonate ($K_2CO_3$), 1,8-diazabicyclo[5.4.0]undec-7-ene (DBU), N,N-diisopropylethylamine (DIPEA), 1,4-diazabicyclo[2.2.2]octane (DABCO), 1,1,3,3-tetramethylguanidine, potassium hydroxide (KOH), potassium hydroxide/Triton B (KOH/Triton B), potassium hydroxide//tetra-n-butylammonium iodide ($KOH/nBu_4NH_4I$), potassium hydroxide/tetra-n-octylammonium bromide ($KOH/n-Oct_4NH_4Br$), lithium hydroxide (LiOH), and lithium carbonate ($Li_2CO_3$). In some embodiments, the conversion of the compound of Formula (VIII), or a salt thereof, into Compound I, or a pharmaceutically salt thereof, further comprises magnesium chloride ($MgCl_2$).

In some embodiments, the compound of Formula (VIII):

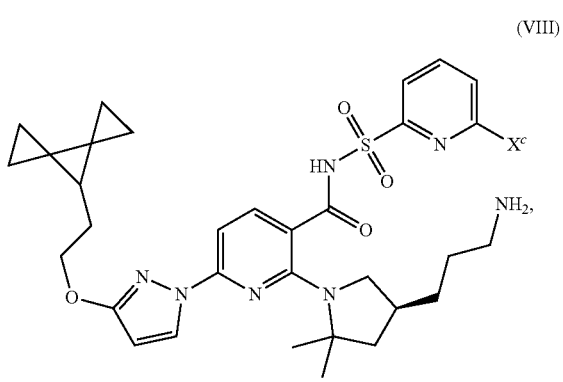
(VIII)

or a salt thereof, is prepared by converting a compound of Formula (IX):

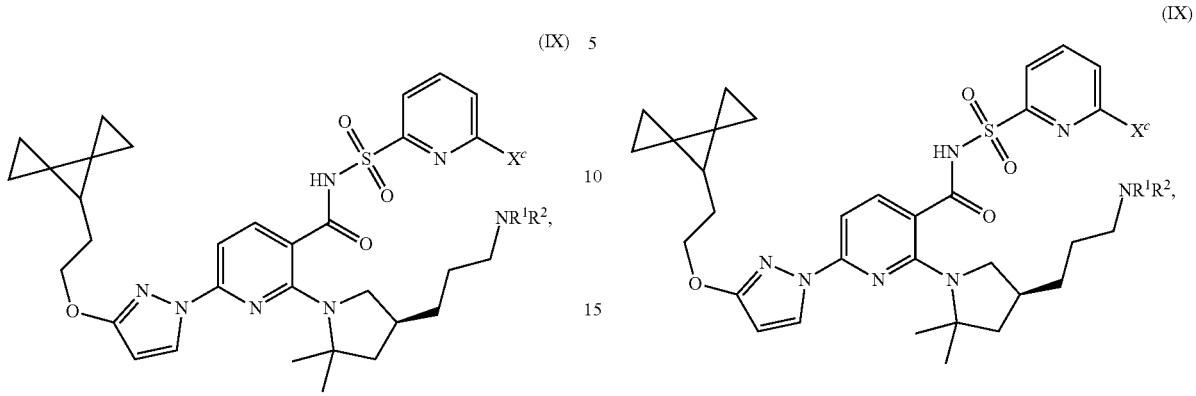

(IX)

or a salt thereof, into the compound of Formula (VIII), or a salt thereof,
wherein in the compound of Formula (IX), or a salt thereof:
$X^c$ is selected from F, Cl, Br, and I; and
wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (IX), or a salt thereof, X is F, $R^1$ is hydrogen, and $R^2$ is benzyloxycarbonyl (Cbz).

In some embodiments, the conversion of the compound of Formula (IX), or a salt thereof, into the compound of Formula (VIII), or a salt thereof, is performed in the presence of reducing reaction conditions. In some embodiments, the reducing reaction conditions are selected from hydrogen gas ($H_2$) and palladium on carbon (Pd/C), $HCO_2H/Et_3N/Pd$ (C), $NH_4HCO_2/K_2CO_3$ and palladium on carbon, $K_2HPO_4$ and Pd/C, $K_3PO_4$ and Pd/C, $NH_2NH_2/Pd(C)$, and 1,4-cyclohexadiene/Pd(C).

In some embodiments, the compound of Formula (IX):

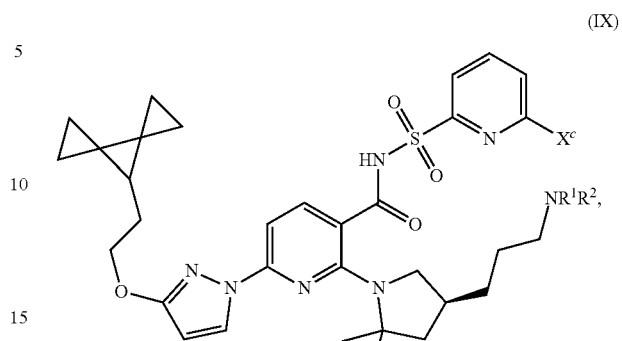

(IX)

or a salt thereof, is prepared by combining a compound of Formula (X):

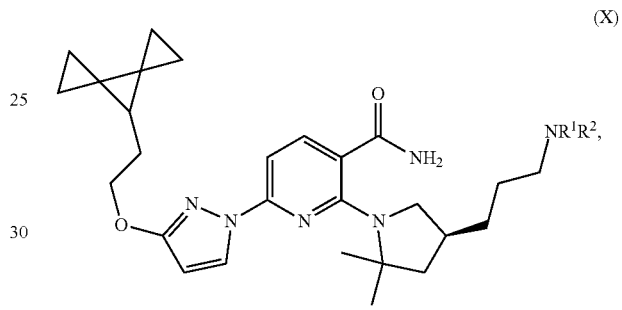

(X)

or a salt thereof, with a compound of Formula (V):

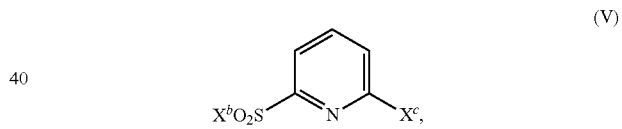

(V)

or a salt thereof, to produce the compound of Formula (IX), or a salt thereof,
wherein in the compound of Formula (X), or a salt thereof:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group; and
wherein in the compound of Formula (V), or a salt thereof:
$X^b$ is selected from Cl, F, —$OC_6F_5$,

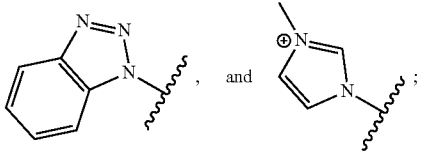

and
$X^c$ is selected from F, Cl, Br, and I.
In some embodiments of the compound of Formula (V) or a salt thereof, $X^b$ is

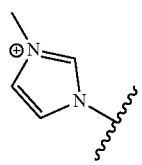 [SMILES: *n1cc[n+](C)c1]

and the salt is the ⁻OTf salt.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (X), or a salt thereof, $R^1$ is hydrogen and $R^2$ is Cbz, or $R^1$ and $R^2$, together with the atoms to which they are attached, form N-phthalimide.

In some embodiments, in the compound of Formula (V), or a salt thereof, $X^b$ is —$OC_6F_5$ and $X^c$ is F.

In some embodiments, the combination of the compound of Formula (X), or a salt thereof, with the compound of Formula (V), or a salt thereof, is performed in the presence of at least one eighth base. In some embodiments, the at least one eighth base is an alkoxy base. In some embodiments, the alkoxy base is selected from lithium t-amylate (t-AmOLi), sodium t-amylate (t-AmONa), potassium t-amylate (t-AmOK), and lithium t-butoxide (LiOt-Bu).

In some embodiments, the compound of Formula (X):

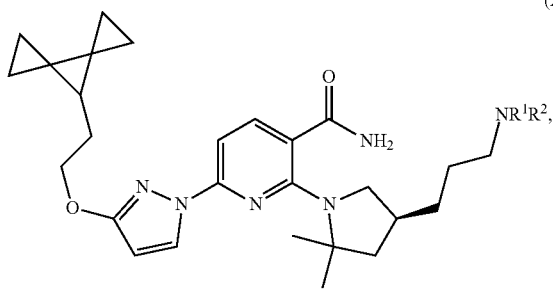

or a salt thereof, is prepared by combining a compound of Formula (IV):

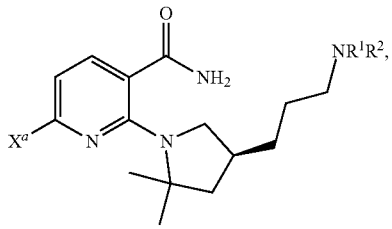

or a salt thereof, with compound 1:

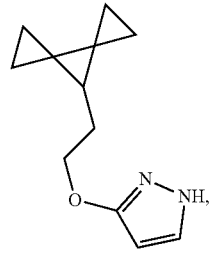

or a salt thereof, to produce the compound of Formula (X), or a salt thereof, wherein in the compound of Formula (IV), or a salt thereof:
$X^a$ is selected from F, Cl, Br, I, and —$OSO_2R$;
R is selected from —$C_{1-10}$ alkyl, —$C_{1-10}$ haloalkyl, and aryl optionally substituted with
—$C_{1-10}$ alkyl, —$C_{1-10}$ haloalkyl, halo, or nitro; and
wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (IV), or a salt thereof, $X^a$ is Br, and $R^1$ and $R^2$, together with the atoms to which they are attached, form N-phthalimide. In some embodiments, in the compound of Formula (IV), or a salt thereof, $X^a$ is Br, $R^1$ is hydrogen, and $R^2$ is benzyloxycarbonyl (Cbz).

In some embodiments, the amide of the compound of Formula (IV), or the amide of a salt thereof, is protected with a nitrogen protecting group.

In some embodiments, the combination of the compound of Formula (IV), or a salt thereof, with compound 1, or a salt thereof, is performed in the presence of at least one ninth base. In some embodiments, the at least one ninth base is selected from carbonate bases, hydroxide bases, alkoxide bases, acetate bases, amine bases, phosphate bases, and sulfate bases. In some embodiments, the at least one ninth base is selected from sodium carbonate ($Na_2CO_3$), potassium carbonate ($K_2CO_3$), cesium carbonate ($Cs_2CO_3$), lithium carbonate ($Li_2CO_3$), sodium hydroxide (NaOH), potassium hydroxide (KOH), sodium tert-butoxide (NaOt-Bu), potassium tert-butoxide (KOt-Bu), pyridine, 2,2,6,6-tetramethylpiperidine, 1,8-diazabicyclo[5.4.0]undec-7-ene (DBU), 7-methyl-1,5,7-triazabicyclo[4.4.0]dec-5-ene (MTBD), t-Bu-tetramethylguanidine, N,N-diisopropylethylamine (DIPEA), potassium bis(trimethylsilyl)amide (KHMDS), pyridine, sodium bicarbonate ($NaHCO_3$), potassium bicarbonate ($KHCO_3$), sodium phosphate tribasic ($Na_3PO_4$), and potassium phosphate tribasic ($K_3PO_4$). In some embodiments, the at least one ninth base is in THF. In some embodiments, the at least one ninth base is in 2-MeTHF. In some embodiments, the at least one ninth base is in IPA.

In some embodiments, the combination of the compound of Formula (II), or a salt thereof, with compound 1, or a salt thereof, further comprises at least one metal catalyst. In some embodiments, the at least one metal catalyst is selected from palladium catalysts and copper catalysts. In some embodiments, the palladium catalyst is selected from [(2-di-tert-butylphosphino-2',4',6'-triisopropyl-1,1'-biphenyl)-2-(2'-amino-1,1'-biphenyl)] palladium(II) methanesulfonate (tBuXPhos Pd G3), [1,1'-bis(di-tert-butylphosphino)ferrocene] dichloropalladium(II), tris(dibenzylideneacetone)dipalladium(0) ($Pd_2dba_3$)/2-di-tert-butylphosphino-2',4',6'-triisopropylbiphenyl)$Pd_2dba_3$/N-phenyl-2-(di-tert-butylphosphino)pyrrole, $Pd_2dba_3$/2-di-tert-butylphosphino-2'-methylbiphenyl, $Pd_2dba_3$/5-(di-tert-butylphosphino)-1',3', 5'-triphenyl-1'H-[1,4']bipyrazole, $Pd_2dba_3$/2-(di-tert-butylphosphino)-1-(2-methoxyphenyl)-1H-pyrrole, $Pd_2dba_3$/2-dicyclohexylphosphino-2',6'-dimethoxybiphenyl, $Pd_2dba_3$/2-(dicyclohexylphosphino)3,6-dimethoxy-2',4',6'-triisopropyl-1,1'-biphenyl ($Pd_2dba_3$/BrettPhos), $Pd_2dba_3$/di-tert-butyl(2,2-diphenyl-1-methyl-1-cyclopropyl)phosphine, $Pd_2dba_3$/1-(dicyclohexylphosphino)-2,2-diphenyl-1-methylcyclopropane, dichloro[1,3-bis(2,6-di-3-pentylphenyl)imidazol-2-ylidene](3-chloropyridyl) palladium(II), $Pd_2dba_3$/1,1'-bis(diphenylphosphino) ferrocene, dichloro[1,1'-bis(dicyclohexylphosphino) ferrocene] palladium(II), (2-dicyclohexylphosphino-2',4',6'-triisopropyl-1,1'-biphenyl)[2-(2'-amino-1,1'-biphenyl)] palladium(II) methanesulfonate (XPhos Pd G3), dichloro[2,2'-bis(diphenylphosphino)-1,1'-binaphthyl]palladium(II) (Pd(BINAP)$Cl_2$), $Pd_2dba_3$/bis[(2-diphenylphosphino)phenyl] ether ($Pd_2dba_3$/DPEPhos), $Pd_2dba_3$/1,2,3,4,5-pentaphenyl-1'-(di-tert-butylphosphino)ferrocene, $Pd_2dba_3$/2-(di-tert-butylphosphino)-2',4',6'-triisopropyl-3,6-dimethoxy-1, 1'-biphenyl, $Pd_2dba_3$/2-dicyclohexylphosphino-2'-(N,N-dimethylamino)biphenyl, $Pd_2dba_3$/1,1'-bis(di-tert-butylphosphino)ferrocene, 2-di-tert-butylphosphino-2',4',6'-triisopropylbiphenyl/$Pd_2dba_3$ (tert-Butyl XPhos/$Pd_2dba_3$); [2-(di-tert-butylphosphino)-2',4',6'-triisopropyl-1,1'-biphenyl][2-(2-aminoethyl)phenyl]palladium(II) chloride (tBuXPhos-Pd-G1), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/$Pd_2dba_3$ (t-BuBrettPhos/$Pd_2dba_3$), trifluoromethanesulfonate allyl[(2-di-tert-butylphosphino-3,6-dimethoxy-2', 4',6'-triisopropyl-1,1'-biphenyl)-2-(2'-amino-1,1'-biphenyl)] palladium(II), (2-dicyclohexylphosphino-2',6'-dimethoxybiphenyl) [2-(2'-amino-1,1'-biphenyl)]palladium(II) methanesulfonate/$Pd_2dba_3$ (SPhos/$Pd_2dba_3$), [1,1'-bis(diphenylphosphino)ferrocene] dichloropalladium(II) (Pd(dppf)$Cl_2$, [1,1'-b(di-tert-butylphosphino)ferrocene] dichloropalladium(II) (Pd(dtbpf)$Cl_2$), dichloro[1,3-bis(2,6-di-3-pentylphenyl)imidazol-2-ylidene](3-chloropyridyl)palladium(II) (PEPSII-pent), di-tert-butyl(2,2-diphenyl-1-methyl-1-cyclopropyl) phosphine/$Pd_2dba_3$ (cBRIDP/$Pd_2dba_3$), and 1-(dicyclohexylphosphino)-2,2-diphenyl-1-methylcyclopropane/$Pd_2dba_3$ (Cy-cBRIDP/$Pd_2dba_3$). The active catalyst, palladium (0) 2-di-tert-butylphosphino-2',4',6'-triisopropylbiphenyl (tBuXPhos, tert-Butyl XPhos) can be generated using palladium (II) tBuXPhos precatalyst (G1-G3) or a combination of a palladium (0) source, for example $Pd_2(dba)_3$ or Pd(PPh$_3$)$_4$, and di-tert-butylphosphino-2',4',6'-triisopropylbiphenyl (tBuXPhos, tert-Butyl XPhos) and finally by using palladium (II) source, such as Pd(OAc)$_2$ or Pd(Cl)$_2$ in the presence of a reducing agent and di-tert-butylphosphino-2',4',6'-triisopropylbiphenyl (tBuXPhos, tert-Butyl XPhos).

In some embodiments, the copper catalyst is selected from copper(II) fluoride, copper(I) bromide (CuBr), copper (I) iodide (CuI), copper(I) thiophene-2-carboxylate, and copper(I) trifluoromethanesulfonate toluene complex, optionally substituted with a ligand such as N,N'-dimethylethylenediamine, N,N'-dimethylcyclohexane-1,2-diamine), 1,10-phenanthroline, 8-hydroxyquinoline, trans-cyclohexane-1,2-diamine, cis-cyclohexane-1,2-diamine, N,N-dimethylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, and N-cyclohexyl-2,6-bis(1-methylethyl)benzenamine. In some embodiments, the copper catalyst is optionally substituted with a ligand selected from N,N-diisopropyl-1,3-propanediamine, trans-1,2-diaminocyclohexane, N,N'-dimethyl-1,3-propanediamine, N,N'-diethylethane-1,2-diamine, 3-(dimethylamino)-propylamine, 1,4-diaminocyclohexane, N,N'-dimethylethane-1, 2-diamine, diethylenetriamine, and trans-N,N-dimethylcyclohexane-1,2-diamine.

In some embodiments, the at least one metal catalyst is [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), bis(dibenzylideneacetone)palladium(0) ($Pd_2dba_3$), copper iodide (CuI), or a combination thereof. In some embodiments, combining a compound of Formula of (IV), or a salt thereof, with compound 1, or a salt thereof, further comprises copper iodide (CuI).

In some embodiments, the combination of the compound of Formula (IV), or a salt thereof, with compound 1, or a salt thereof, further comprises dicyclohexylamine (DMCHDA). In some embodiments, the at least one ninth base is potassium carbonate ($K_2CO_3$).

In some embodiments, the compound of Formula (IV):

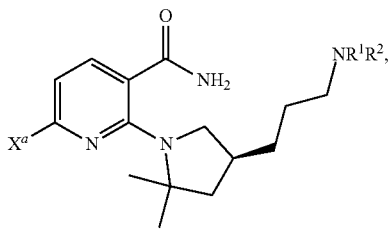

(IV)

or a salt thereof, is prepared by combining a compound of Formula (XI):

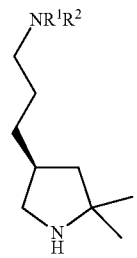

(XI)

or a salt thereof, with a compound of Formula (VII):

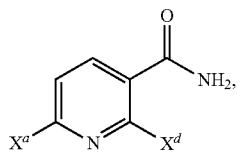

(VII)

or a salt thereof, to produce the compound of Formula (IV), or a salt thereof,
wherein in the compound of Formula (XI), or a salt thereof:
 $R^1$ is hydrogen and $R^2$ is a monovalent nitrogen protecting group;
 $R^1$ and $R^2$ are independently selected from monovalent nitrogen protecting groups; or
 $R^1$ and $R^2$, together with the atoms to which they are attached, form a nitrogen protecting group; and wherein in the compound of Formula (VII), or a salt thereof:
 $X^a$ is selected from F, Cl, Br, I, and —OSO$_2$R;
 R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and
 $X^d$ is selected from F, Cl, Br, and I.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

In some embodiments, in the compound of Formula (XI), or a salt thereof, $R^1$ is hydrogen and $R^2$ is benzyloxycarbonyl (Cbz). In some embodiments, in the compound of Formula (XI), or a salt thereof, $R^1$ and $R^2$, together with the atoms to which they are attached, form N-phthalimide.

In some embodiments, in the compound of Formula (VII), or a salt thereof, $X^a$ is Br and $X^d$ is F.

In some embodiments, the amide of the compound of Formula (IV), or the amide of a salt thereof, is protected with a nitrogen protecting group.

In some embodiments, the combination of the compound of Formula (XI), or a salt thereof, with the compound of Formula (VII), or a salt thereof, is performed in the presence of at least one tenth base. In some embodiments, the at least one tenth base is selected from amine bases, carbonate bases, hydroxide bases, and phosphate bases. In some embodiments, the at least one tenth base is potassium carbonate (K$_2$CO$_3$). In some embodiments, the combination of the compound of Formula (XI), or a salt thereof, with the compound of Formula (VII), or a salt thereof, further comprises zinc chloride (ZnCl$_2$), magnesium chloride (MgCl$_2$), aluminum oxide (Al$_2$O$_3$), cesium fluoride (CsF), indium(III) triflate (In(OTf)$_3$), or indium(III) chloride (InCl$_3$). In some embodiments, the combination of the compound of Formula (XI), or a salt thereof, with the compound of Formula (VII), or a salt thereof, further comprises zinc chloride (ZnCl$_2$).

In some embodiments, the compound of Formula (XI):

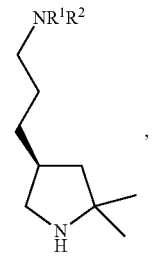

(XI)

or a salt thereof, is prepared by converting a compound of Formula (XII):

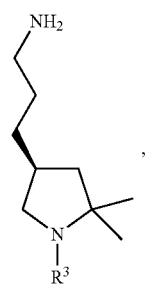

(XII)

or a salt thereof, into the compound of Formula (XI), or a salt thereof, wherein in the compound of Formula (XII), or a salt thereof, R³ is a monovalent nitrogen protecting group. In some embodiments, each monovalent nitrogen protecting group is selected from t-butyloxycarbonyl (Boc), benzyloxycarbonyl (Cbz), and N-phthalimide. In some embodiments, in the compound of Formula (XII), or a salt thereof, R³ is t-butyloxycarbonyl (Boc).

In some embodiments, the conversion of the compound of Formula (XII), or a salt thereof, into the compound of Formula (XI), or a salt thereof, comprises the steps of:

1) converting the primary amine of the compound of Formula (XII), or a salt thereof, into a protected amine —NR¹R²; and 2) deprotecting R³ to produce the compound of Formula (XI), or a salt thereof.

In some embodiments, the conversion in step 1) is performed in the presence of benzyl chloroformate (Cbz-Cl) and potassium carbonate (KOH). In some embodiments, R³ in step 2) is deprotected with hydrochloric acid (HCl), methanesulfonic acid (MsOH), or trifluoroacetic acid.

In some embodiments, the compound of Formula (XII):

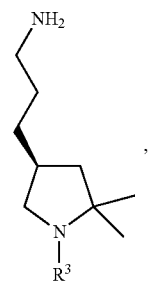

(XII)

or a salt thereof, is prepared by converting the compound of Formula (XV):

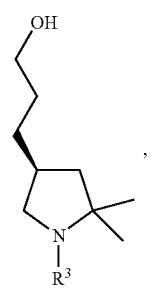

(XV)

or a salt thereof, into the compound of Formula (XII), or a salt thereof, wherein in the compound of Formula (XV), or a salt thereof, R³ is a monovalent nitrogen protecting group. In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, in the compound of Formula (XV), or a salt thereof, R³ is t-butyloxycarbonyl (Boc).

In some embodiments, the conversion of the compound of Formula (XV), or a salt thereof, into the compound of Formula (XII), or a salt thereof, comprises the steps of:

1) converting the compound of Formula (XV):

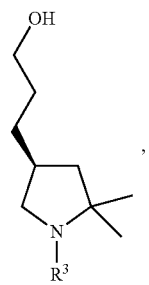

(XV)

or a salt thereof, into the compound of Formula (XIV):

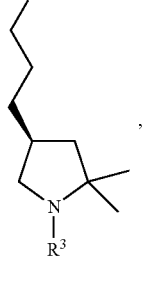

(XIV)

or a salt thereof;

2) converting the compound of Formula (XIV), or a salt thereof, into the compound of Formula (XIII):

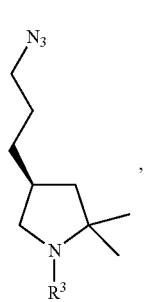

(XIII)

or a salt thereof; and 3) converting the compound of Formula (XIII), or a salt thereof, into the compound of Formula (XII), or a salt thereof, wherein in the compounds of Formulae (XIII)-(XV), or salts thereof, R³ is a monovalent nitrogen protecting group; and wherein in the compound of Formula (XIV), or a salt thereof:

R⁴ is —SO₂R; and

R is selected from —C₁₋₁₀ alkyl, —C₁₋₁₀ haloalkyl, and aryl optionally substituted with —C₁₋₁₀ alkyl, —C₁₋₁₀ haloalkyl, halo, or nitro.

In some embodiments, each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, in the compounds of Formulae (XIII)-(XV), or salts thereof, R³ is t-butyloxycarbonyl (Boc). In some embodiments, in the compound of Formula (XIV), or a salt thereof, R⁴ is 4-nitrobenzylsulfonyl (Ns).

In some embodiments, step 1) of the conversion of the compound of Formula (XV), or a salt thereof, into the compound of Formula (XII), or a salt thereof, is performed in the presence of 4-nitrobenzylsulfonyl chloride (NsCl) and at least one eleventh base. In some embodiments, the at least one eleventh base is an amine base or a carbonate base. In some embodiments, the at least one eleventh base is triethylamine (Et₃N), 1,8-diazabicyclo[5.4.0]undec-7-ene (DBU), 1,5-diazabicyclo[4.3.0]non-5-ene (DBN), N,N-diisopropylethylamine ((iPr)₂NEt). In some embodiments, step 2) of the conversion of the compound of Formula (XV), or a salt thereof, into the compound of Formula (XII), or a salt thereof, is performed in the presence of an azide source. In some embodiments, the azide source is sodium azide (NaN₃). In some embodiments, step 3) of the conversion of the compound of Formula (XV), or a salt thereof, into the compound of Formula (XII), or a salt thereof, is performed in the presence of reducing reaction conditions. In some embodiments, the reducing reaction conditions comprise hydrogen gas (H₂) and platinum dioxide (PtO₂) or palladium on carbon (Pd/C).

In some embodiments, the compound of Formula (XV):

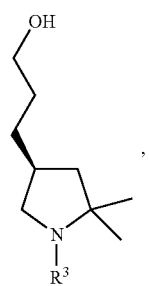

(XV)

or a salt thereof, is prepared by converting compound 2:

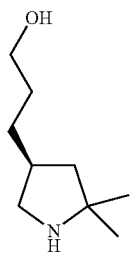

2 or a salt thereof, into the compound of Formula (XV), or a salt thereof.

In some embodiments, the conversion of compound 2, or a salt thereof, into the compound of Formula (XV), or a salt thereof, is performed in the presence of di-tert-butyl dicarbonate (Boc₂O). In some embodiments, the compound of Formula (XV), or a salt thereof, is treated with L-glutamic acid.

In some embodiments, compound 2:

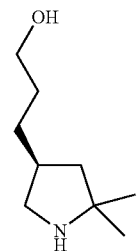

2 or a salt thereof, is prepared by converting compound 3:

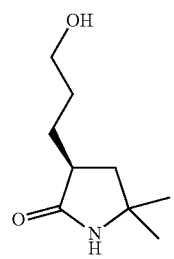

3 or a salt thereof, into compound 2, or a salt thereof.

In some embodiments, the conversion of compound 3, or a salt thereof, into compound 2, or a salt thereof, is performed in the presence of a reducing agent. In some embodiments, the reducing agent is selected from lithium aluminum hydride (LiAlH₄), sodium bis(2-methoxyethoxy)aluminum hydride, borane (BH₃), and borane-tetrahydrofuran (BH₃-THF). In some embodiments, the solvent is 2-methyltetrahydrofuran (2-MeTHF) or tetrahydrofuran (THF).

In some embodiments, compound 3:

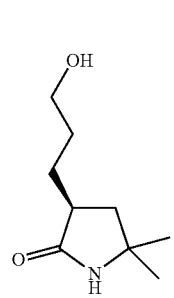

3 or a salt thereof, is prepared by chiral resolution of compound (±)-3:

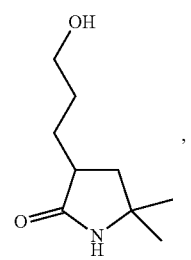

(±)-3 or a salt thereof.

In some embodiments, the chiral resolution of compound (±)-3, or a salt thereof, is performed using a method selected from chiral column chromatography, chiral Simulated Moving Bed (SMB), bioresolution, enzymatic resolution, liquid chromatography, salt resolution, and asymmetric hydrogenation.

In some embodiments, compound (±)-3:

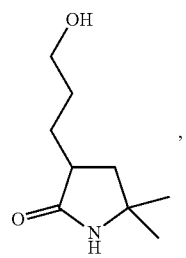

(±)-3 or a salt thereof, is prepared by converting compound (±)-4:

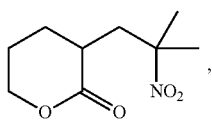

(±)-4 or a salt thereof, into compound (±)-3, or a salt thereof.

In some embodiments, the conversion of compound (±)-4, or a salt thereof, into compound (±)-3, or a salt thereof, is performed in the presence of reducing reaction conditions.

In some embodiments, the reducing reaction conditions comprise hydrogen gas ($H_2$) and Raney Nickel.

In some embodiments, compound (±)-4:

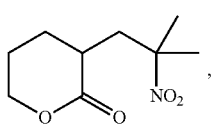

(±)-4 or a salt thereof, is prepared by combining compound 5:

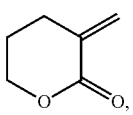

5 or a salt thereof, with 2-nitropropane to produce compound (±)-4, or a salt thereof.

In some embodiments, the combination of compound 5, or a salt thereof, with 2-nitropropane is performed in the presence of 1,8-diazabicyclo[5.4.0]undec-7-ene (DBU).

In some embodiments, compound 5:

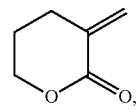

5 or a salt thereof, is prepared by converting δ-valerolactone into compound 5, or a salt thereof.

In some embodiments, the conversion of δ-valerolactone into compound 5, or a salt thereof, comprises the steps of:

1) combining δ-valerolactone with an alkyl formate and at least one twelfth base; and 2) combining the product of step 1) with paraformaldehyde.

In some embodiments, the method further comprises contacting the product of step 2) with $SiO_2$ to produce compound 5, or a salt thereof. In some embodiments, the alkyl formate is ethyl formate and the at least one twelfth base is sodium hydride (NaH).

In some embodiments, compound 1:

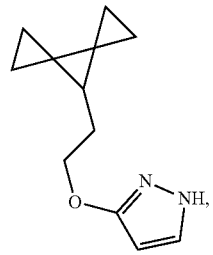

1 or a salt thereof, is prepared by converting compound 6:

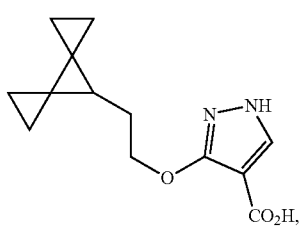

6 or a salt thereof, into compound 1, or a salt thereof. In some embodiments, the conversion of compound 6, or a salt thereof, into compound 1, or a salt thereof, is performed in the presence of 1,8-diazabicyclo[5.4.0]undec-7-ene (DBU).

In some embodiments, compound 6:

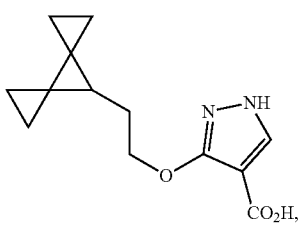

or a salt thereof, is prepared by converting compound 7:

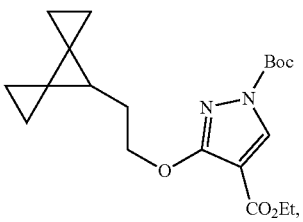

or a salt thereof, into compound 6, or a salt thereof.

In some embodiments, the conversion of compound 7, or a salt thereof, into compound 6, or a salt thereof, is performed in the presence of at least one thirteenth base and at least one solvent. In some embodiments, the at least one thirteenth base is potassium hydroxide (KOH). In some embodiments, the at least one solvent is methanol (MeOH).

In some embodiments, compound 7:

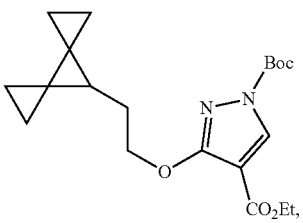

or a salt thereof, is prepared by combining compound 8:

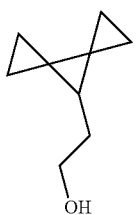

or a salt thereof, with compound 9:

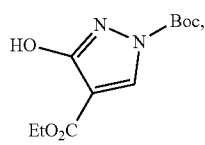

or a salt thereof, to produce compound 7, or a salt thereof.

In some embodiments, the combination of compound 8, or a salt thereof, with compound 9, or a salt thereof, is performed in the presence of a phosphine and an azodicarboxylate. In some embodiments, the phosphine is triphenylphosphine ($PPh_3$). In some embodiments, the azodicarboxylate is diisopropyl azocarboxylate (DIAD). In some embodiments, the combination of compound 8, or a salt thereof, with compound 9, or a salt thereof, is performed in the presence of a sulfonyl chloride and at least one fourteenth base. In some embodiments, the sulfonyl chloride is methanesulfonyl chloride (MsCl) or p-toluenesulfonyl chloride (TsCl). In some embodiments, the at least one fourteenth base is triethylamine ($Et_3N$).

In some embodiments, compound 8:

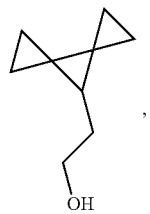

or a salt thereof, is prepared by converting compound 10:

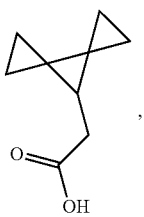

or a salt thereof, into compound 8, or a salt thereof.

In some embodiments, the conversion of compound 10, or a salt thereof, into compound 8, or a salt thereof, is performed in the presence of a reducing agent. In some embodiments, the reducing agent is selected from lithium aluminum hydride ($LiAlH_4$), boron trifluoride/sodium borohydride ($BF_3/NaBH_4$), borane ($BH_3$) and borane complexes such as borane dimethylsulfide ($BH_3SMe_2$) and borane-tetrahydrofuran ($BH_3$-THF), Vitride (sodium bis(2-methoxyethoxy) aluminium hydride), zinc borohydride ($Zn(BH_4)_2$), and diisobutylalum-inui hydride (DIBAL-H).

In some embodiments, compound 10:

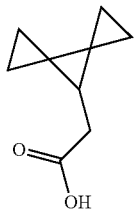

10

, or a salt thereof, is prepared by converting compound 11:

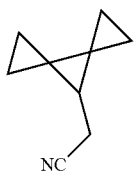

11

, or a salt thereof, into compound 10, or a salt thereof.

In some embodiments, the conversion of compound 11, or a salt thereof, into compound 10, or a salt thereof, is performed in the presence of at least one fifteenth base and at least one solvent. In some embodiments, the at least one fifteenth base is selected from sodium hydroxide (NaOH), potassium hydroxide (KOH), and barium hydroxide (Ba(OH)$_2$). In some embodiments, the at least one solvent is selected from ethanol (EtOH), methanol (MeOH), ethylene glycol, diethylene glycol, and water. In an alternate embodiment the conversion of compound 11, or a salt thereof, into compound 10, or a salt thereof, is performed in acidic hydrolysis conditions, such as hydrochloric acid (HCl), hydrobromic acid (HBr), sulfuric acid (H$_2$SO$_4$), phosphoric acid (H$_3$PO$_4$) in water, and acetic acid (HOAc). In an alternative embodiment, the conversion of compound 11, or a salt thereof, into compound 10, or a salt thereof, is performed in the presence of a nitrilase enzyme.

In some embodiments, compound 11:

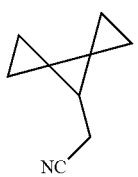

11

, or a salt thereof, is prepared by converting compound 12:

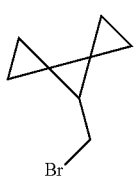

12

, or a salt thereof, into compound 11, or a salt thereof.

In some embodiments, the conversion of compound 12, or a salt thereof, into compound 11, or a salt thereof, is performed in the presence of a cyanide source. In some embodiments, the cyanide source is sodium cyanide (NaCN).

In some embodiments, compound 12:

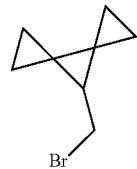

12

, or a salt thereof, is prepared by converting compound 13:

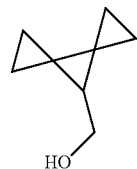

13

, or a salt thereof, into compound 12, or a salt thereof.

In some embodiments, the conversion of compound 13, or a salt thereof, into compound 12, or a salt thereof, is performed in the presence of a phosphine, a source of bromine, and at least one sixteenth base. In some embodiments, the phosphine is triphenylphosphine (PPh$_3$). In some embodiments, the source of bromine is molecular bromine (Br$_2$). In some embodiments, the at least one sixteenth base is pyridine.

In some embodiments, compound 13:

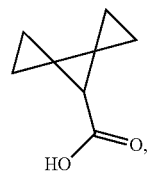

13

, or a salt thereof, is prepared by converting compound 14:

14

, or a salt thereof, into compound 13, or a salt thereof.

In some embodiments, the conversion of compound 14, or a salt thereof, into compound 13, or a salt thereof, is performed in the presence of a reducing agent. In some embodiments, the reducing agent is selected from lithium aluminum hydride (LiAlH$_4$), boron trifluoride/sodium borohydride (BF$_3$/NaBH$_4$), borane (BH$_3$) and borane complexes such as borane dimethylsulfide (BH$_3$SMe$_2$) and borane-tetrahydrofuran (BH₃-THF), Vitride (sodium bis(2-imethoxyethoxy)aluminium hydride), zinc borohydride (Zn(BH₄)₂), and diisobutylaluminum hydride (DIBAL-H).

In some embodiments, compound 14:

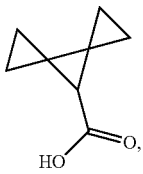

14 or a salt thereof, is prepared by converting compound 15:

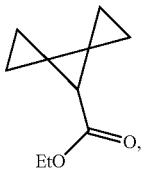

15 or a salt thereof, into compound 14, or a salt thereof.

In some embodiments, the conversion of compound 15, or a salt thereof, into compound 14, or a salt thereof, is performed in the presence of sodium hydroxide (NaOH) in MeOH.

In some embodiments, compound 13:

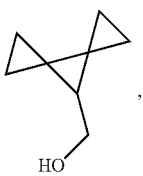

13 or a salt thereof, is prepared by converting compound 15:

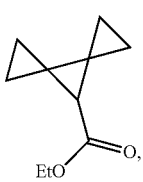

15 or a salt thereof, into compound 13, or a salt thereof.
In some embodiments, compound 15:

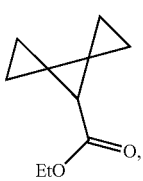

15 or a salt thereof, is prepared by converting compound 16:

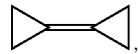

16 or a salt thereof, into compound 15, or a salt thereof.

In some embodiments, the conversion of compound 16, or a salt thereof, into compound 15, or a salt thereof, is performed in the presence of ethyl 2-diazoacetate and copper triflate (Cu(OTf)₂). In some embodiments, the metal catalyst is rhodium (II) acetate dimer (Rh₂(OAc)₄). In some embodiments, the conversion of compound 16, or a salt thereof, into compound 15, or a salt thereof, is performed in the presence of an enzyme.

In some embodiments, compound 16:

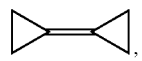

16 or a salt thereof, is prepared by converting compound 17:

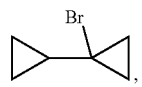

17 or a salt thereof, into compound 16, or a salt thereof.

In some embodiments, the conversion of compound 17, or a salt thereof, into compound 16, or a salt thereof, is performed in the presence of at least one seventeenth base. In some embodiments, the at least one seventeeth base is potassium t-butoxide (KOt-Bu).

In some embodiments, compound 17:

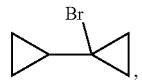

17 or a salt thereof, is prepared by converting compound 18:

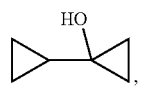

18 or a salt thereof, into compound 17, or a salt thereof.

In some embodiments, the combination of compound 18, or a salt thereof, with compound 17, or a salt thereof, is performed in the presence of a phosphine, a source of bromine, and at least one eighteenth base. In some embodiments, the phosphine is triphenylphosphine (PPh₃). In some embodiments, the source of bromine is molecular bromine (Br₂). In some embodiments, the at least one eighteenth base is pyridine.

In some embodiments, compound 18:

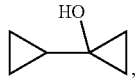

or a salt thereof, is prepared by converting compound 19:

or a salt thereof, into compound 18, or a salt thereof.

In some embodiments, the conversion of compound 19, or a salt thereof, into compound 18, or a salt thereof, is performed in the presence of ethyl magnesium bromine (EtMgBr) and titanium (IV) isopropoxide (Ti(Oi-Pr)$_4$).

In some embodiments, compound 6:

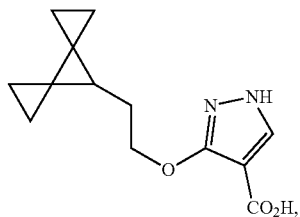

or a salt thereof, is prepared by converting compound 20:

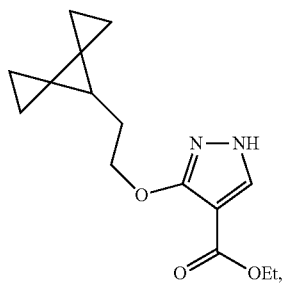

or a salt thereof, into compound 6, or a salt thereof.

In some embodiments, the conversion of compound 20, or a salt thereof, into compound 6, or a salt thereof, is performed in the presence of potassium hydroxide (KOH) in methanol (MeOH).

In some embodiments, compound 20:

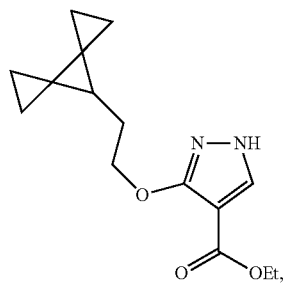

or a salt thereof, is prepared by converting compound 21:

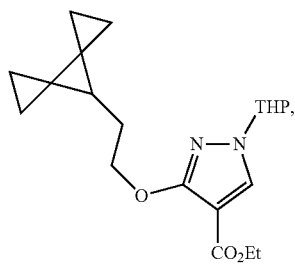

or a salt thereof, into compound 20, or a salt thereof.

In some embodiments, the conversion of compound 21 into compound 20 is performed in the presence of hydrochloric acid (HCl).

In some embodiments, compound 21:

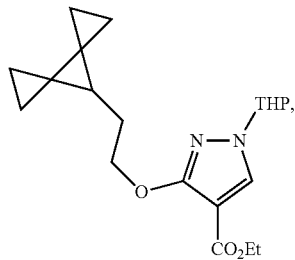

or a salt thereof, is prepared by combining compound 22:

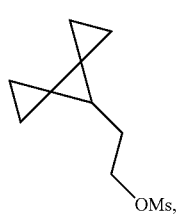

with compound 23:

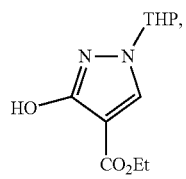

or a salt thereof, to produce compound 21, or a salt thereof.

In some embodiments, the combination of compound 22 with compound 23, or a salt thereof, is performed in the presence of at least one nineteeth base.

In some embodiments, compound 23:

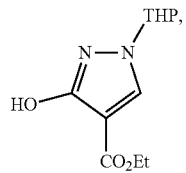

or a salt thereof, is prepared by converting compound 24:

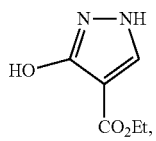

or a salt thereof, into compound 23, or a salt thereof.

In some embodiments, the conversion of compound 24, or a salt thereof, into compound 23, or a salt thereof, is performed in the presence of dihydropyran and p-toluenesulfonic acid (pTsOH).

In some embodiments, compound 24:

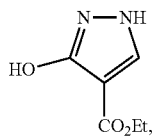

or a salt thereof, is prepared by converting compound 25:

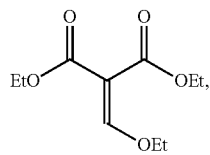

into compound 24, or a salt thereof.

In some embodiments, the conversion of compound 25 into compound 24, or a salt thereof, is performed in the presence of hydrazine.

In some embodiments, compound 15:

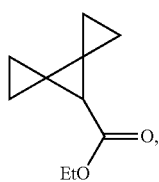

or a salt thereof, is prepared by converting compound 26:

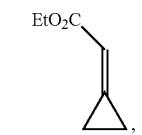

into compound 15, or a salt thereof.

In some embodiments, the conversion of compound 26 into compound 15, or a salt thereof, is performed in the presence of cyclopropyl(diphenyl)sulfonium (tetrafluoroborate) and at least one twentieth base. In some embodiments, the at least one twentieth base is cesium hydroxide hydrate ($Cs(OH)_2 \cdot xH_2O$).

In some embodiments, compound 26:

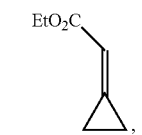

is prepared by converting compound 27:

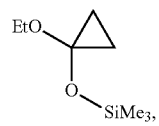

into compound 26.

In some embodiments, the conversion of compound 27 into compound 26 is performed in the presence of ethyl (triphenylphosphoranylidene) acetate.

In some embodiments, compound 10:

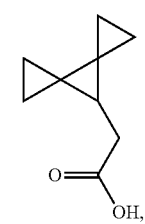

or a salt thereof, is prepared by converting compound 14:

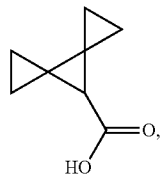
14 or a salt thereof, into compound 10, or a salt thereof.

In some embodiments, the conversion of compound 14, or a salt thereof, into compound 10, or a salt thereof, is performed in the presence of thionyl chloride, followed by diazomethane.

In some embodiments, compound 10:

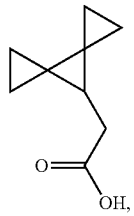
10 or a salt thereof, is prepared by converting compound 28:

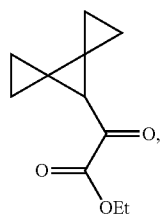
28 or a salt thereof, into compound 10, or a salt thereof.

In some embodiments, the conversion of compound 28, or a salt thereof, into compound 10, or a salt thereof, is performed in the presence of hydrazine.

In some embodiments, compound 28:

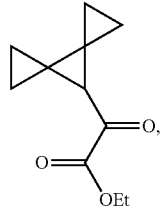
28 or a salt thereof, is prepared by converting compound 16:

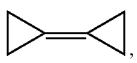
16 into compound 28, or a salt thereof.

In some embodiments, the conversion of compound 16 into compound 28, or a salt thereof, is performed in the presence of rhodium(II) octanoate dimer and compound 28, or a salt thereof.

In some embodiments, the compound of Formula (XI):

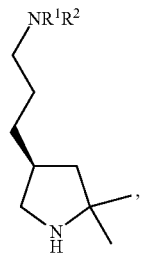
(XI)

or a salt thereof, is compound 30:

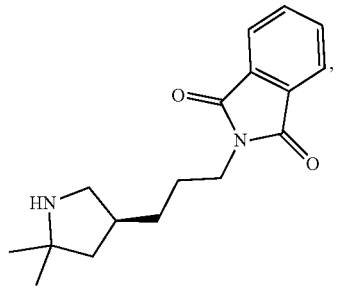
30 or a salt thereof.

In some embodiments, compound 30, or a salt thereof, is prepared by converting compound 31:

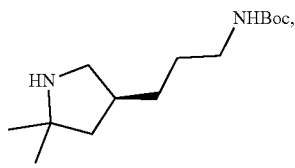
31 or a salt thereof, into compound 30, or a salt thereof.

In some embodiments, the conversion of compound 31, or a salt thereof, into compound 30, or a salt thereof, comprises:
1) reacting compound 31, or a salt thereof, in the presence of trifluoroacetic acid; and
2) combining the product of step 1) with phthalic anhydride to produce compound 30, or a salt thereof.

In some embodiments, compound 31:

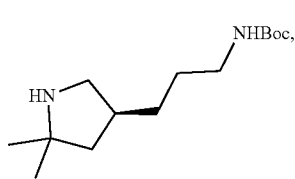
31 or a salt thereof, is prepared by converting compound 32:

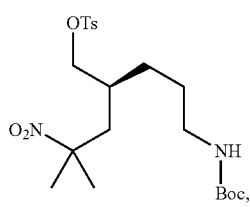

32 or a salt thereof, into compound 31, or a salt thereof.

In some embodiments, the conversion of compound 32, or a salt thereof, into compound 31, or a salt thereof, is performed in the presence of a hydrogen source, a metal catalyst, and at least one twenty-first base. In some embodiments, the source of hydrogen is hydrogen gas. In some embodiments, the metal catalyst is Raney Ni. In some embodiments, the at least one twenty-first base is potassium carbonate ($K_2CO_3$).

In some embodiments, compound 32:

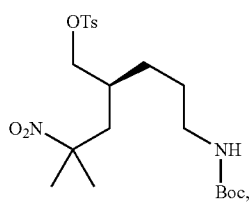

32 or a salt thereof, is prepared by converting compound 33:

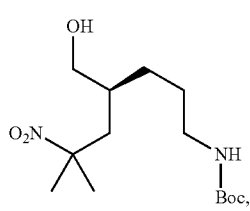

33 or a salt thereof, into compound 32, or a salt thereof.

In some embodiments, the conversion of compound 33, or a salt thereof, into compound 32, or a salt thereof, is performed in the presence of a sulfonyl chloride and at least one twenty-second base. In some embodiments, the sulfonyl chloride is p-toluenesulfonyl chloride. In some embodiments, the at least one twenty-second base is triethylamine ($Et_3N$) and trimethylamine hydrochloride.

In some embodiments, compound 33:

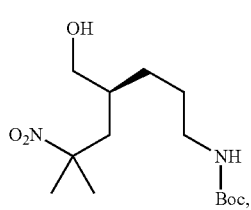

33 or a salt thereof, is prepared by converting compound 34:

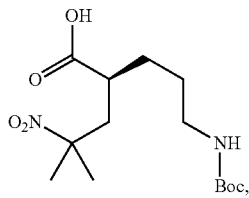

34 or a salt thereof, into compound 33, or a salt thereof.

In some embodiments, the conversion of compound 34, or a salt thereof, into compound 33, or a salt thereof, comprises:

1) reacting compound 34, or a salt thereof, with a carboxylic acid activating agent; and
2) reacting the product of step 1) with a reducing agent.

In some embodiments, the activating agent is carbonyl diimidazole. In some embodiments, the reducing agent is sodium borohydride ($NaBH_4$).

In some embodiments, compound 34:

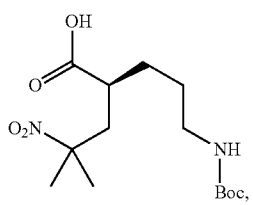

34 or a salt thereof, is prepared by converting compound (f)-34:

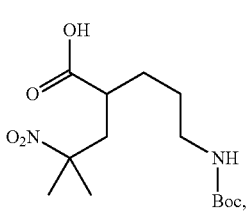

(±)-34 or a salt thereof, into compound 34, or a salt thereof.

In some embodiments, the conversion of compound (f)-34, or a salt thereof, into compound 34, or a salt thereof, comprises:

1) reacting compound (f)-34 with a chiral amine; and
2) reacting the product of step 1) with an acid.

In some embodiments, the chiral amine is (R)-(−)-α-methylbenzylamine. In some embodiments, the acid is hydrochloric acid (HCl).

In some embodiments, compound (f)-34:

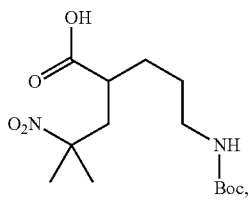

(±)-34 or a salt thereof, is prepared by converting compound 35:

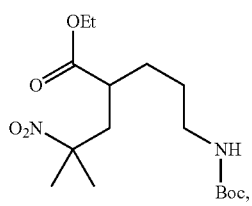

35 or a salt thereof, into compound (f)-34, or a salt thereof.

In some embodiments, the conversion of compound 35, or a salt thereof, into compound (f)-34, or a salt thereof, is performed in the presence of a hydroxide base. In some embodiments, the hydroxide base is sodium hydroxide (NaOH).

In some embodiments, compound 35:

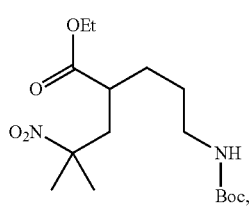

35 or a salt thereof, is prepared by converting compound 36:

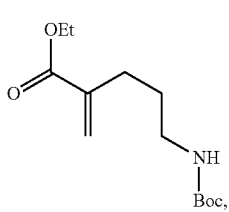

36 or a salt thereof, into compound 35, or a salt thereof.

In some embodiments, compound 36:

OEt
36

NH
Boc, or a salt thereof, is prepared by converting compound 37:

NHBoc,
37 or a salt thereof, into compound 36, or a salt thereof.

In some embodiments, compound 37:

NHBoc,
37 or a salt thereof, is prepared by converting compound 38:

38 or a salt thereof, into compound 37, or a salt thereof.

In some embodiments, the conversion of compound 38, or a salt thereof, into compound 37, or a salt thereof, comprises:

1) reacting compound 38, or a salt thereof, with 3-tert-butoxycarbonylamino-propionic acid and a coupling reagent; and 2) reacting the product of step 1) with a reducing agent.

In some embodiments, the coupling agent is DCC. In some embodiments, step 1) further comprises DMAP. In some embodiments, the reducing agent is sodium borohydride. In some embodiments, step 2) further comprises adding acetic acid.

In some embodiments, compound 3:

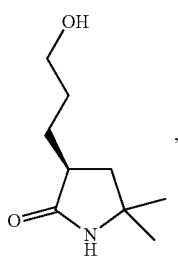

3 or a salt thereof, is prepared by converting compound 39:

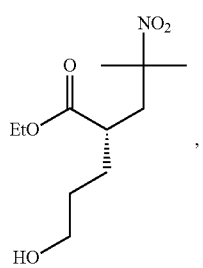

39 or a salt thereof, into compound 3, or a salt thereof.

In some embodiments, the conversion of compound 39, or a salt thereof, into compound 3, or a salt thereof, is performed in the presence of a reducing reaction conditions. In some embodiments, the reducing reaction conditions are a source of hydrogen and a metal catalyst. In some embodiments, the source of hydrogen is hydrogen gas. In some embodiments, the metal catalyst is Raney Ni.

In some embodiments, compound 39:

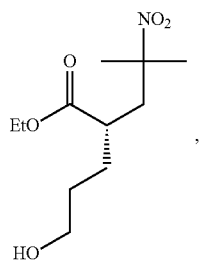

39 or a salt thereof, is prepared by converting compound (±)-39:

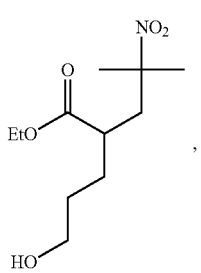

(±)-39 or a salt thereof, into compound 39, or a salt thereof.

In some embodiments, the conversion of compound (±)-39, or a salt thereof, into compound 39, or a salt thereof, is performed in the presence of an enzyme. In some embodiments, the enzyme is palatase enzyme.

In some embodiments, compound (±)-39:

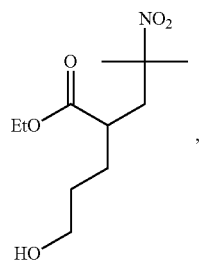

(±)-39 or a salt thereof, is prepared by converting compound (±)-4:

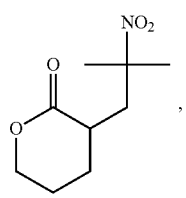

(±)-4 or a salt thereof, into compound (±)-39, or a salt thereof.

In some embodiments, compounds useful for the synthesis of Compound I are chosen from:

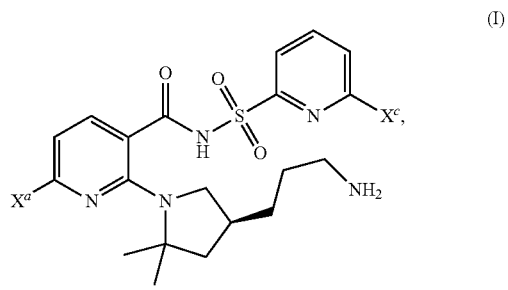

(I)

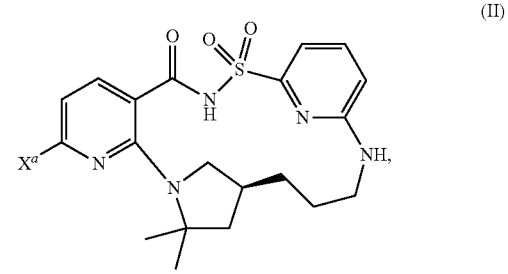

(II)

-continued
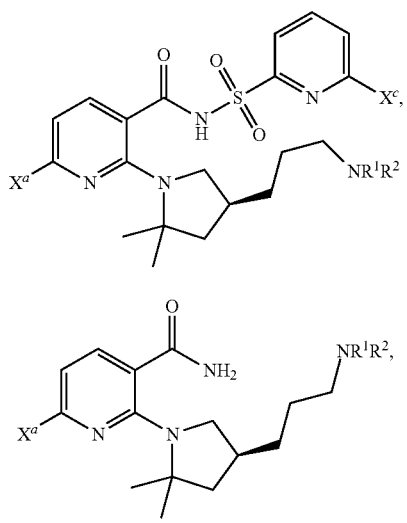
(III)
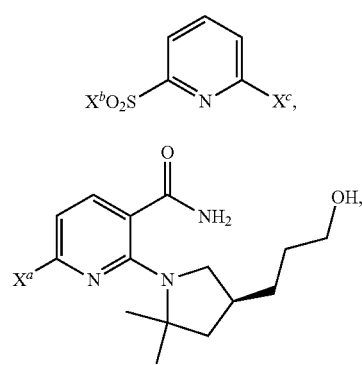
(IV)
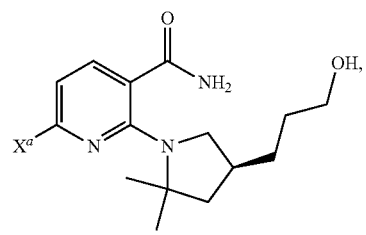
(V)
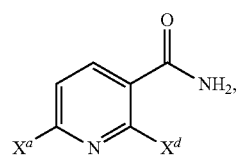
(VI)
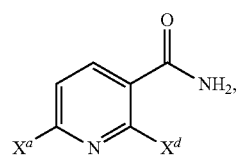
(VI)
(VII)
(VIII)
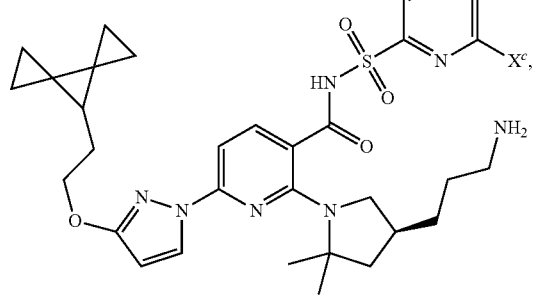
-continued
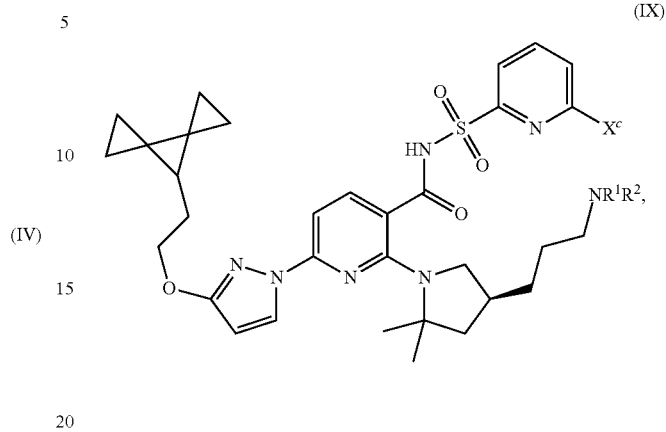
(IX)
(X)
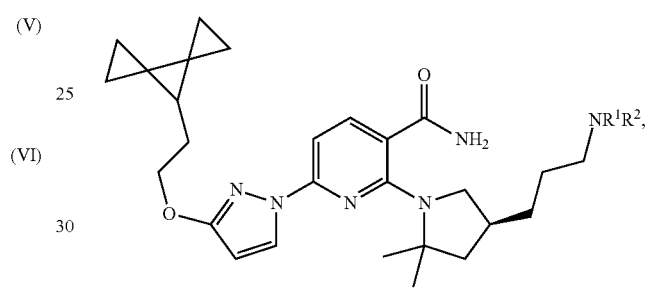
(XI)
(XII)
(XIII)
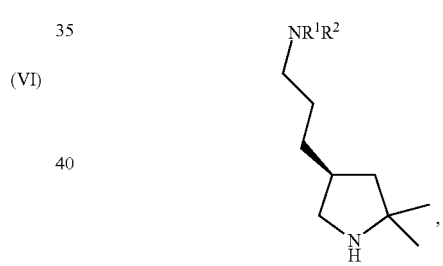

-continued

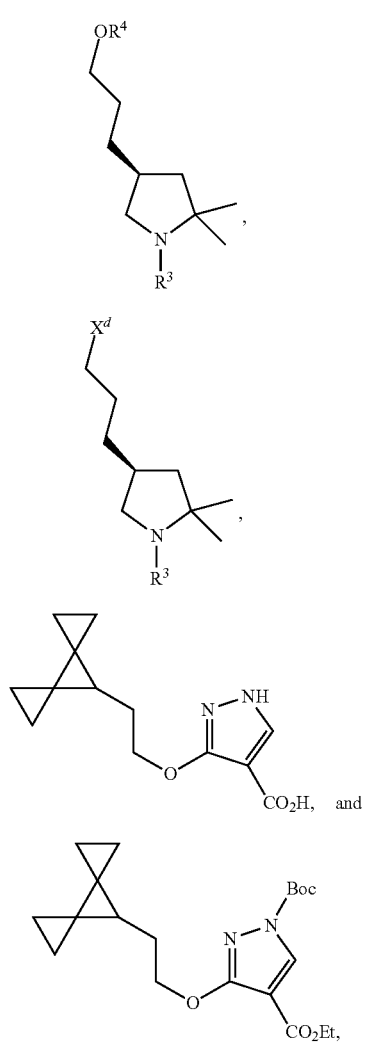

and salts thereof,
wherein:
  $X^a$ is selected from F, Cl, Br, I, and —OSO$_2$R;
  R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro;
  $X^b$ is selected from Cl, F, —OC$_6$F$_5$,

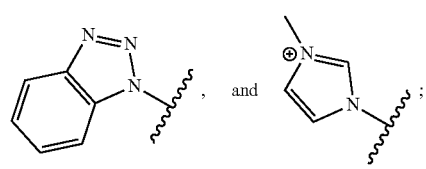

$X^c$ is selected from F, Cl, Br, and I;
  $X^d$ is selected from F, Cl, Br, and I;
  $R^3$ is a monovalent nitrogen protecting group;
  $R^4$ is —SO$_2$R;
  R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and wherein:
  $R^1$ is hydrogen and $R^2$ is a monovalent nitrogen protecting group;

$R^1$ and $R^2$ are independently selected from monovalent nitrogen protecting groups; or
  $R^1$ and $R^2$, together with the atoms to which they are attached, form a nitrogen protecting group; and
wherein the compound is not:

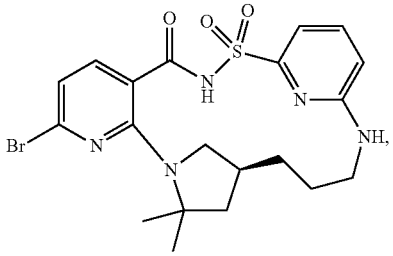

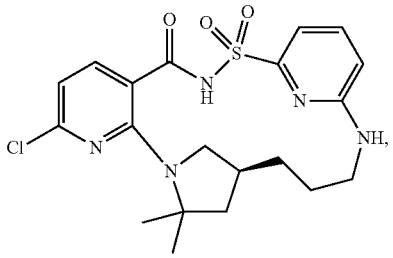

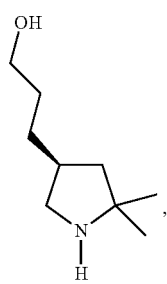

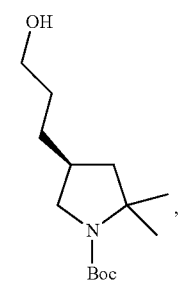

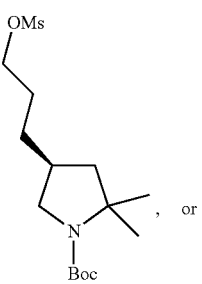

-continued

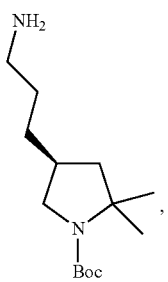

or a salt thereof.

In some embodiments, R is independently selected from methyl and p-tolyl.

In some embodiments, each monovalent nitrogen protecting group is independently selected from t-butyloxycarbonyl (Boc), benzyl (Bn), tetrahydropyranyl (THP), 9-fluorenyl-methyloxycarbonyl (Fmoc), benzyloxycarbonyl (Cbz), formyl, acetyl (Ac), trifluoroacetyl (TFA), trityl (Tr), and p-toluenesulfonyl (Ts). In some embodiments, $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

List of Exemplary Embodiments

1. A method of preparing Compound I:

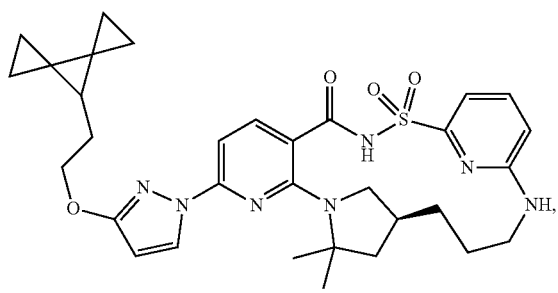

or a pharmaceutically acceptable salt thereof, comprising converting a compound of Formula (I):

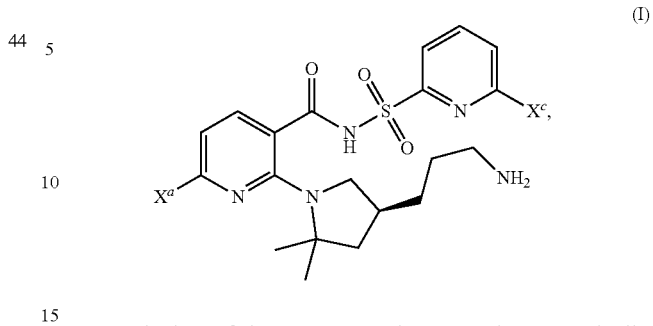

or a salt thereof, into Compound I, or a pharmaceutically acceptable salt thereof, wherein:
  $X^a$ is selected from F, Cl, Br, I, and —$OSO_2R$;
  R is selected from —$C_{1-10}$ alkyl, —$C_{1-10}$ haloalkyl, and aryl optionally substituted with —$C_{1-10}$ alkyl, —$C_{1-10}$ haloalkyl, halo, or nitro; and
  $X^c$ is selected from F, Cl, Br, and I.

2. The method of embodiment 1, wherein $X^a$ is Br and $X^c$ is F.

3. The method of embodiment 1, wherein the conversion of the compound of Formula (I), or a salt thereof, into Compound I, or a pharmaceutically acceptable salt thereof, comprises the steps of:
  1) combining the compound of Formula (I), or a salt thereof, with at least one first base to produce a compound of Formula (II):

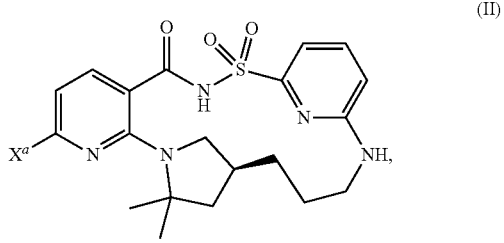

or a salt thereof; and
  2) combining the compound of Formula (II), or a salt thereof, with compound 1:

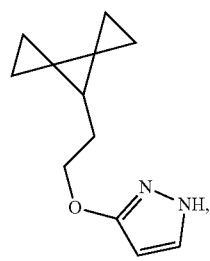

or a salt thereof,
and at least one second base to produce Compound I, or a pharmaceutically acceptable salt thereof,
wherein in the compound of Formula (II), or a salt thereof:
  $X^a$ is selected from F, Cl, Br, I, and —$OSO_2R$; and
  R is selected from —$C_{1-10}$ alkyl, —$C_{1-10}$ haloalkyl, and aryl optionally substituted with —$C_{1-10}$ alkyl, —$C_{1-10}$ haloalkyl, halo, or nitro.

4. The method of embodiment 3, wherein in the compound of Formula (II), or a salt thereof, $X^a$ is Br.

5. The method of embodiment 3 or 4, wherein the at least one first base is selected from carbonate bases, hydroxide bases, alkoxide bases, acetate bases, amine bases, phosphate bases, and sulfate bases.

6. The method of any one of embodiments 3 to 5, wherein the at least one first base is selected from sodium carbonate ($Na_2CO_3$), potassium carbonate ($K_2CO_3$), 2,2,6,6-tetramethylpiperidine, 1,8-diazabicyclo[5.4.0]undec-7-ene (DBU), 7-methyl-1,5,7-triazabicyclo[4.4.0]dec-5-ene (MTBD), t-Bu-tetramethylguanidine, potassium bicarbonate ($KHCO_3$), and potassium phosphate tribasic ($K_3PO_4$).

7. The method of any one of embodiments 3 to 6, wherein the at least one second base is potassium carbonate ($K_2CO_3$).

8. The method of any one of embodiments 3 to 7, wherein the combination of the compound of Formula (II), or a salt thereof, with compound 1, or a salt thereof, further comprises at least one metal catalyst.

9. The method of embodiment 8, wherein the at least one metal catalyst is selected from palladium catalysts and copper catalysts.

10. The method of embodiment 9, wherein the palladium catalyst is selected from [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), [1,1'-bis(di-tertbutylphosphino)ferrocene]dichloropalladium(II), tris(dibenzylideneacetone)dipalladium(0) ($Pd_2dba_3$)/2-di-tert-butylphosphino-2',4',6'-triisopropylbiphenyl)$Pd_2dba_3$/N-phenyl-2-(di-tert-butylphosphino)pyrrole, $Pd_2dba_3$/2-di-tert-butylphosphino-2'-methylbiphenyl, $Pd_2dba_3$/5-(di-tert-butylphosphino)-1', 3', 5'-triphenyl-1'H-[1,4']bipyrazole, $Pd_2dba_3$/2-(di-tert-butylphosphino)-1-(2-methoxyphenyl)-1H-pyrrole, $Pd_2dba_3$/2-dicyclohexylphosphino-2',6'-dimethoxybiphenyl, $Pd_2dba_3$/2-(dicyclohexylphosphino)3,6-dimethoxy-2',4',6'-triisopropyl-1,1'-biphenyl ($Pd_2dba_3$/BrettPhos), $Pd_2dba_3$/di-tert-butyl(2,2-diphenyl-1-methyl-1-cyclopropyl)phosphine, $Pd_2dba_3$/1-(dicyclohexylphosphino)-2,2-diphenyl-1-methylcyclopropane, dichloro[1,3-bis(2,6-di-3-pentylphenyl)imidazol-2-ylidene](3-chloropyridyl)palladium(II), $Pd_2dba_3$/1,1'-bis(diphenylphosphino)ferrocene, dichloro[1,1'-bis(dicyclohexylphosphino)ferrocene]palladium(II), (2-dicyclohexylphosphino-2',4',6'-triisopropyl-1,1'-biphenyl)[2-(2'-amino-1,1'-biphenyl)]palladium(II) methanesulfonate, dichloro[2,2'-bis(diphenylphosphino)-1,1'-binaphthyl]palladium(II) (Pd(BINAP)Cl$_2$), $Pd_2dba_3$/bis[(2-diphenylphosphino)phenyl]ether ($Pd_2dba_3$/DPEPhos), $Pd_2dba_3$/1,2,3,4,5-Pentaphenyl-1'-(di-tert-butylphosphino)ferrocene, $Pd_2dba_3$/2-(di-tert-butylphosphino)-2',4',6'-triisopropyl-3,6-dimethoxy-1,1'-biphenyl, $Pd_2dba_3$/2-dicyclohexylphosphino-2'-(N,N-dimethylamino)biphenyl, $Pd_2dba_3$/1,1'-bis(di-tert-butylphosphino)ferrocene, 2-di-tert-butylphosphino-2',4',6'-triisopropylbiphenyl/$Pd_2dba_3$ (tert-Butyl XPhos/$Pd_2dba_3$), [2-(di-tert-butylphosphino)-2',4',6'-triisopropyl-1,1'-biphenyl][2-(2-aminoethyl)phenyl]palladium(II) chloride (tBuXPhos-Pd-GT), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/$Pd_2dba_3$ (t-BuBrettPhos/$Pd_2dba_3$), trifluoromethanesulfonate allyl[(2-di-tert-butylphosphino-3,6-dimethoxy-2',4',6'-triisopropyl-1,1'-biphenyl)-2-(2'-amino-1,1'-biphenyl)]palladium(II), (2-dicyclohexylphosphino-2',6'-dimethoxybiphenyl) [2-(2'-amino-1,1'-biphenyl)]palladium(II) methanesulfonate/$Pd_2dba_3$ (SPhos/$Pd_2dba_3$), [1,1'-bis(diphenylphosphino)ferrocene]dichloro palladium(II) (Pd(dppf)Cl$_2$, [1,1'-bis(di-tert-butylphosphino)ferrocene]dichloropalladium(II) (Pd(dtbpf)Cl$_2$), dichloro[1,3-bis(2,6-Di-3-pentylphenyl)imidazol-2-ylidene](3-chloropyridyl)palladium(II) (PEPSII-pent), di-tert-butyl(2,2-diphenyl-1-methyl-1-cyclopropyl)phosphine/$Pd_2dba_3$ (cBRIDP/$Pd_2dba_3$), and 1-(dicyclohexylphosphino)-2,2-Diphenyl-1-methylcyclopropane/$Pd_2dba_3$ (Cy-cBRIDP/$Pd_2dba_3$).

11. The method of embodiment 9, wherein the copper catalyst is selected from copper(II) fluoride, copper(I) bromide (CuBr), copper(I) iodide (CuI), copper(I) thiophene-2-carboxylate, and copper(I) trifluoromethanesulfonate toluene complex, optionally substituted with a ligand such as N,N'-dimethylethylenediamine, N,N'-dimethylcyclohexane-1,2-diamine), 1,10-phenanthroline, 8-hydroxyquinoline, trans-cyclohexane-1,2-diamine, cis-cyclohexane-1,2-diamine, N,N-dimethylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, and N-cyclohexyl-2,6-bis(1-methylethyl)benzenamine, N,N-diisopropyl-1,3-propanediamine, trans-1,2-diaminocyclohexane, N,N'-dimethyl-1,3-propanediamine, N,N'-diethylethane-1,2-diamine, 3-(dimethylamino)-propylamine, 1,4-diaminocyclohexane, N,N'-dimethylethane-1,2-diamine, diethylenetriamine, and trans-N,N-dimethylcyclohexane-1,2-diamine.

12. The method of any one of embodiments 8 to 11, wherein the at least one metal catalyst is [(2-di-tert-butylphosphino-2',4',6'-triisopropyl-1,1'-biphenyl)-2-(2'-amino-1,1'-biphenyl)] palladium(II) methanesulfonate (tBuXPhos Pd G3), bis(dibenzylideneacetone)palladium(0) ($Pd_2dba_3$), copper iodide (CuI), or a combination thereof.

13. The method of any one of embodiments 8 to 12, wherein the combination of the compound of Formula (II), or a salt thereof, with compound 1, or a salt thereof, further comprises excess 2-di-tert-butylphosphino-2',4',6'-triisopropyl-biphenyl (tBuXPhos) relative to [(2-di-tert-butylphosphino-2',4',6'-triisopropyl-1,1'-biphenyl)-2-(2'-amino-1,1'-biphenyl)] palladium(II) methanesulfonate (tBuXPhos Pd G3).

14. The method of embodiment 1, wherein the conversion of the compound of Formula (I), or a salt thereof, into Compound I, or a pharmaceutically acceptable salt thereof, comprises combining the compound of Formula (I), or a salt thereof, with compound 1:

or a salt thereof, and at least one third base to produce Compound I, or a pharmaceutically acceptable salt thereof, wherein in the compound of Formula (I), or a salt thereof:

X$^a$ is selected from F, Cl, Br, I, and —OSO$_2$R;

R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and X$^c$ is selected from F, Cl, Br, and I.

15. The method of embodiment 14, wherein in the compound of Formula (I), or a salt thereof, X$^a$ is Br and X$^c$ is F.

16. The method of embodiment 14 or 15, wherein the at least one third base is selected from carbonate bases, hydroxide bases, alkoxide bases, acetate bases, amine bases, phosphate bases, and sulfate bases.

17. The method of any one of embodiments 14 to 16, wherein the at least one third base is selected from sodium carbonate (Na$_2$CO$_3$), potassium carbonate (K$_2$CO$_3$), 2,2,6,6-tetramethylpiperidine, 1,8-diazabicyclo[5.4.0]undec-7-ene (DBU), 7-methyl-1,5,7-triazabicyclo[4.4.0]dec-5-ene (MTBD), t-Bu-tetramethylguanidine, potassium bicarbonate (KHCO$_3$), and potassium phosphate tribasic (K$_3$PO$_4$).

18. The method of any one of embodiments 14 to 17, wherein the at least one third base is potassium carbonate (K$_2$CO$_3$).

19. The method of any one of embodiments 14 to 18, wherein the combination of the compound of Formula (I), or a salt thereof, with compound 1, or a salt thereof, further comprises at least one metal catalyst.

20. The method of embodiment 19, wherein the at least one metal catalyst is selected from palladium catalysts and copper catalysts.

21. The method of embodiment 20, wherein the palladium catalyst is selected from [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), [1,1'-bis(di-tertbutylphosphino)ferrocene]dichloropalladium(II), tris(dibenzylideneacetone)dipalladium(0) (Pd$_2$dba$_3$)/2-di-tert-butylphosphino-2',4',6'-triisopropylbiphenyl)Pd$_2$dba$_3$/N-phenyl-2-(di-tert-butylphosphino)pyrrole, Pd$_2$dba$_3$/2-di-tert-butylphosphino-2'-methylbiphenyl, Pd$_2$dba$_3$/5-(di-tert-butylphosphino)-1', 3', 5'-triphenyl-1'H-[1,4']bipyrazole, Pd$_2$dba$_3$/2-(di-tert-butylphosphino)-1-(2-methoxyphenyl)-1H-pyrrole, Pd$_2$dba$_3$/2-dicyclohexylphosphino-2',6'-dimethoxybiphenyl, Pd$_2$dba$_3$/2-(dicyclohexylphosphino)3,6-dimethoxy-2',4',6'-triisopropyl-1,1'-biphenyl (Pd$_2$dba$_3$/BrettPhos), Pd$_2$dba$_3$/di-tert-butyl(2,2-diphenyl-1-methyl-1-cyclopropyl)phosphine, Pd$_2$dba$_3$/1-(dicyclohexylphosphino)-2,2-diphenyl-1-methylcyclopropane, dichloro[1,3-bis(2,6-di-3-pentylphenyl)imidazol-2-ylidene](3-chloropyridyl)palladium(II), Pd$_2$dba$_3$/1,1'-bis(diphenylphosphino)ferrocene, dichloro[1,1'-bis(dicyclohexylphosphino)ferrocene] palladium(II), (2-dicyclohexylphosphino-2',4',6'-triisopropyl-1,1'-biphenyl)[2-(2'-amino-1,1'-biphenyl)] palladium(II) methanesulfonate, dichloro[2,2'-bis(diphenylphosphino)-1,1'-binaphthyl]palladium(II) (Pd(BINAP)Cl$_2$), Pd$_2$dba$_3$/bis[(2-diphenylphosphino)phenyl] ether (Pd$_2$dba$_3$/DPEPhos), Pd$_2$dba$_3$/1,2,3,4,5-Pentaphenyl-1'-(di-tert-butylphosphino)ferrocene, Pd$_2$dba$_3$/2-(di-tert-butylphosphino)-2',4',6'-triisopropyl-3,6-dimethoxy-1,1'-biphenyl, Pd$_2$dba$_3$/2-dicyclohexylphosphino-2'-(N,N-dimethylamino)biphenyl, Pd$_2$dba$_3$/1,1'-bis(di-tert-butylphosphino)ferrocene, 2-di-tert-butylphosphino-2',4',6'-triisopropylbiphenyl/Pd$_2$dba$_3$ (tert-Butyl XPhos/Pd$_2$dba$_3$), [2-(di-tert-butylphosphino)-2',4',6'-triisopropyl-1,1'-biphenyl][2-(2-aminoethyl)phenyl)]palladium(II) chloride (tBuXPhos-Pd-GT), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/Pd$_2$dba$_3$ (t-BuBrettPhos/Pd$_2$dba$_3$), trifluoromethanesulfonate allyl[(2-di-tert-butylphosphino-3,6-dimethoxy-2',4',6'-triisopropyl-1,1'-biphenyl)-2-(2'-amino-1,1'-biphenyl)] palladium(II), (2-dicyclohexylphosphino-2',6'-dimethoxybiphenyl) [2-(2'-amino-1,1'-biphenyl)]palladium(II) methanesulfonate/Pd$_2$dba$_3$ (SPhos/Pd$_2$dba$_3$), [1,1'-bis(diphenylphosphino)ferrocene]dichloropalladium(II) (Pd(dppf)Cl$_2$, [1,1'-bis(di-tert-butylphosphino)ferrocene]dichloropalladium(II) (Pd(dtbpf)Cl$_2$), dichloro[1,3-bis(2,6-di-3-pentylphenyl)imidazol-2-ylidene](3-chloropyridyl)palladium(II) (PEPSII-pent), di-tert-butyl(2,2-diphenyl-1-methyl-1-cyclopropyl)phosphine/Pd$_2$dba$_3$ (cBRIDP/Pd$_2$dba$_3$), and 1-(dicyclohexylphosphino)-2,2-diphenyl-1-methylcyclopropane/Pd$_2$dba$_3$ (Cy-cBRIDP/Pd$_2$dba$_3$).

22. The method of embodiment 20, wherein the copper catalyst is selected from copper(II) fluoride, copper(I) bromide (CuBr), copper(I) iodide (CuI), copper(I) thiophene-2-carboxylate, and copper(I) trifluoromethanesulfonate toluene complex, optionally substituted with a ligand such as N,N'-dimethylethylenediamine, N,N'-dimethylcyclohexane-1,2-diamine), 1,10-phenanthroline, 8-hydroxyquinoline, trans-cyclohexane-1,2-diamine, cis-cyclohexane-1,2-diamine, N,N-dimethylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, and N-cyclohexyl-2,6-bis(1-methylethyl)benzenamine, N,N-diisopropyl-1,3-propanediamine, trans-1,2-diaminocyclohexane, N,N'-dimethyl-1,3-propanediamine, N,N'-diethylethane-1,2-diamine, 3-(dimethylamino)-propylamine, 1,4-diaminocyclohexane, N,N'-dimethylethane-1,2-diamine, diethylenetriamine, and trans-N,N-dimethylcyclohexane-1,2-diamine.

23. The method of any one of embodiments 19 to 22, wherein the at least one metal catalyst is [(2-di-tert-butylphosphino-2',4',6'-triisopropyl-1,1'-biphenyl)-2-(2'-amino-1,1'-biphenyl)] palladium(II) methanesulfonate (tBuXPhos Pd G3), bis(dibenzylideneacetone)palladium(0) (Pd$_2$dba$_3$), copper iodide (CuI), or a combination thereof.

24. The method of any one of embodiments 19 to 23, wherein the combination of the compound of Formula (I), or a salt thereof, with compound 1, or a salt thereof, further comprises excess 2-di-tert-butylphosphino-2',4',6'-triisopropylbiphenyl (tBuXPhos) relative to [(2-di-tert-butylphosphino-2',4',6'-triisopropyl-1,1'-biphenyl)-2-(2'-amino-1,1'-biphenyl)] palladium(II) methanesulfonate (tBuXPhos Pd G3).

25. The method of any one of embodiments 1 and 3 to 24, wherein the compound of Formula (I):

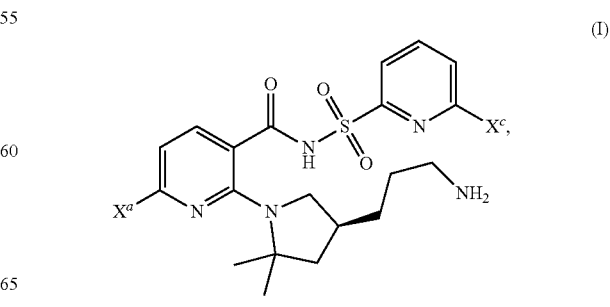

or a salt thereof, is prepared by converting a compound of Formula (III):

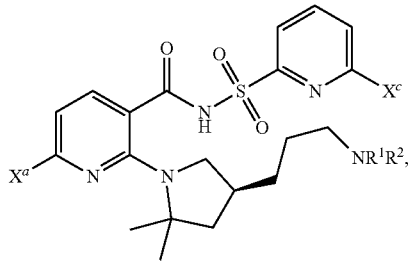

or a salt thereof, into the compound of Formula (I), or a salt thereof,
wherein in the compound of Formula (III), or a salt thereof:
  $X^a$ is selected from F, Cl, Br, I, and —OSO$_2$R;
  R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro;
  $X^c$ is selected from F, Cl, Br, and I; and
wherein:
  $R^1$ is hydrogen and $R^2$ is a monovalent nitrogen protecting group;
  $R^1$ and $R^2$ are independently selected from monovalent nitrogen protecting groups; or
  $R^1$ and $R^2$, together with the atoms to which they are attached, form a nitrogen protecting group.

26. The method of embodiment 25, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

27. The method of embodiment 25, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

28. The method of embodiment 25 or 27, wherein in the compound of Formula (III), or a salt thereof, $X^a$ is Br, $X^c$ is F, and $R^1$ and $R^2$, together with the atoms to which they are attached, form N-phthalimide.

29. The method of embodiment 28, wherein the conversion of the compound of Formula (III), or a salt thereof, into the compound of Formula (I), or a salt thereof, comprises the steps of:
  1) combining the compound of Formula (III), or a salt thereof, in the presence of water and a base selected from lithium hydroxide (LiOH), hydrazine, ethanolamine, and N-methylamine; and
  2) optionally combining the product of step 1) with an acid selected from oxalic acid, hydrochloric acid (HCl), phosphoric acid (H$_3$PO$_4$), and citric acid; then treating the reaction mixture with water and a base selected from potassium carbonate (K$_2$CO$_3$) and cesium carbonate (Cs$_2$CO$_3$) to produce the compound of Formula (I), or a salt thereof.

30. The method of any one of embodiments 25 to 27 and 29, wherein the compound of Formula (III):

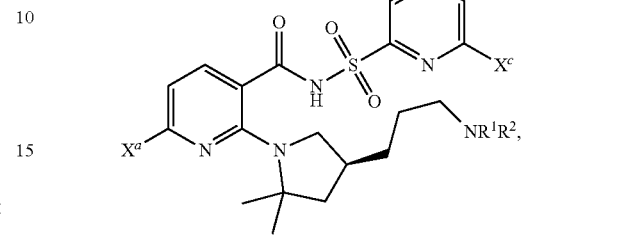

or a salt thereof, is prepared by combining a compound of Formula (IV):

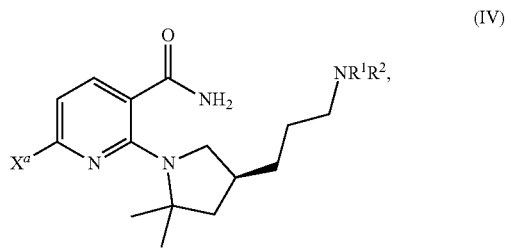

or a salt thereof, with a compound of Formula (V):

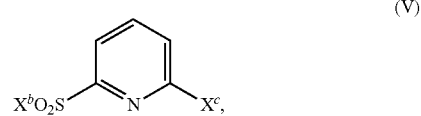

or a salt thereof, to produce the compound of Formula (III), or a salt thereof,
wherein:
  $X^a$ is selected from F, Cl, Br, I, and —OSO$_2$R;
  R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro
  $X^b$ is selected from Cl, F, —OC$_6$F$_5$,

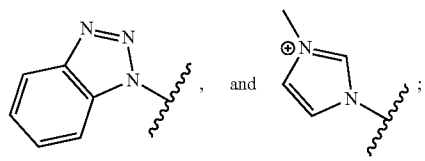

$X^c$ is selected from F, Cl, Br, and I; and
wherein:
  $R^1$ is hydrogen and $R^2$ is a monovalent nitrogen protecting group;
  $R^1$ and $R^2$ are independently selected from monovalent nitrogen protecting groups; or R¹ and R², together with the atoms to which they are attached, form a nitrogen protecting group.

31. The method of embodiment 30, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

32. The method of embodiment 30, wherein R¹ and R², together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

33. The method of embodiment 30 or 32, wherein in the compound of Formula (IV), or a salt thereof, $X^a$ is Br, and R¹ and R², together with the atoms to which they are attached, form N-phthalimide.

34. The method of embodiment 30 or 31, wherein in the compound of Formula (IV), or a salt thereof, $X^a$ is Br, R¹ is hydrogen, and R² is benzyloxycarbonyl (Cbz).

35. The method of any one of embodiments 30 to 34, wherein in the compound of Formula (V), or a salt thereof, $X^b$ is —OC₆F₅ and $X^c$ is F.

36. The method of any one of embodiments 30 to 35, wherein the combination of the compound of Formula (IV), or a salt thereof, with the compound of Formula (V), or a salt thereof, is performed in the presence of at least one fourth base.

37. The method of embodiment 36, wherein the at least one fourth base is an alkoxy base.

38. The method of embodiment 37, wherein the alkoxy base is selected from lithium t-amylate (t-AmOLi), sodium t-amylate (t-AmONa), potassium t-amylate (t-AmOK), and lithium t-butoxide (LiOt-Bu).

39. The method of any one of embodiments 30 to 32 and 35 to 38, wherein the compound of Formula (IV):

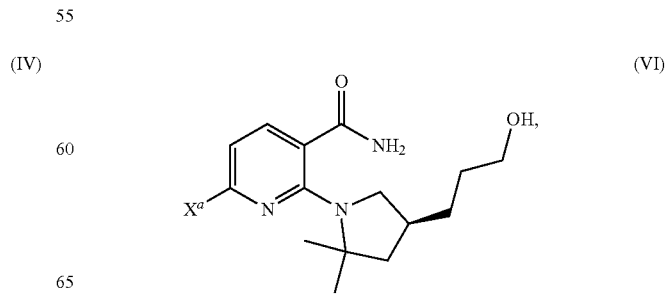

or a salt thereof, is prepared by converting a compound of Formula (VI):

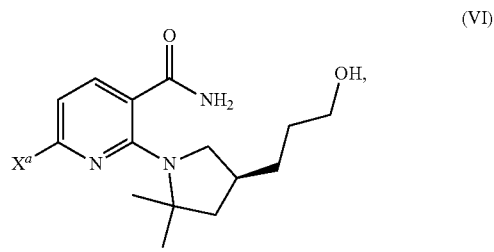

or a salt thereof, into the compound of Formula (IV), or a salt thereof, wherein in the compound of Formula (VI), or a salt thereof:

$X^a$ is selected from F, Cl, Br, I, and —OSO₂R; and

R is selected from —C₁₋₁₀ alkyl, —C₁₋₁₀ haloalkyl, and aryl optionally substituted with —C₁₋₁₀ alkyl, —C₁₋₁₀ haloalkyl, halo, or nitro.

40. The method of embodiment 39, wherein in the compound of Formula (VI), or a salt thereof, $X^a$ is Br.

41. The method of embodiment 39 or 40, wherein the conversion of the compound of Formula (VI), or a salt thereof, into the compound of Formula (IV), or a salt thereof, comprises the steps of:

1) converting the hydroxy group of the compound of formula (VI), or a salt thereof, into a sulfonate ester (—OSO₂R) or Cl; and 2) combining the sulfonate ester or Cl of step 1) with an amine and at least one fifth base to produce the compound of Formula (IV), or a salt thereof.

42. The method of embodiment 41, wherein the R group of the sulfonate ester (—OSO₂R) is selected from —C₁₋₁₀ alkyl, —C₁₋₁₀ haloalkyl, and aryl optionally substituted with —C₁₋₁₀ alkyl, —C₁₋₁₀ haloalkyl, halo, or nitro.

43. The method of embodiment 41, wherein the conversion of the hydroxy group into a sulfonate ester in step 1) is performed in the presence of methanesulfonyl chloride (MsCl) and triethylamine (Et₃N).

44. The method of embodiment 41 or 42, wherein the amine in step 2) is N-phthalimide and the at least one fifth base is potassium carbonate (K₂CO₃).

45. The method of any one of embodiments 39 and 41 to 44, wherein the compound of Formula (VI):

or a salt thereof, is prepared by combining compound 2:

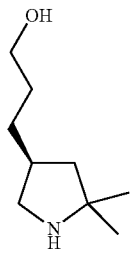

or a salt thereof, with a compound of Formula (VII):

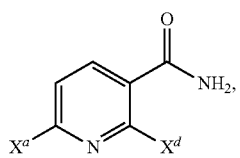

or a salt thereof, to produce the compound of Formula (VI), or a salt thereof, wherein in the compound of Formula (VII), or a salt thereof:

$X^a$ is selected from F, Cl, Br, I, and —OSO$_2$R;

R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and $X^d$ is selected from F, Cl, Br, and I.

46. The method of embodiment 45, wherein in the compound of Formula (VII), or a salt thereof, $X^a$ is Br and $X^d$ is F.

47. The method of any one of embodiments 45 or 46, wherein the combination of compound 2, or a salt thereof, with the compound of Formula (VII), or a salt thereof, is performed in the presence of at least one sixth base.

48. The method of embodiment 47, wherein the at least one sixth base is selected from potassium t-butoxide (KOt-Bu), lithium hydroxide (LiOH), potassium phosphate tribasic (K$_3$PO$_4$), potassium phosphate dibasic (K$_2$HPO$_4$), cesium carbonate (Cs$_2$CO$_3$), 2,2,6,6-tetramethylpiperidine, 7-methyl-1,5,7-triazabicyclo[4.4.0]dec-5-ene (MTBD), tetramethylguanidine, 1,8-diazabicyclo[5.4.0]undec-7-ene (DBU), triethylamine (Et$_3$N), tributylamine (Bu$_3$N), sodium bicarbonate (NaHCO$_3$), potassium bicarbonate (KHCO$_3$), sodium carbonate (Na$_2$CO$_3$) and potassium carbonate (K$_2$CO$_3$).

49. The method of any one of embodiments 45 to 48, wherein the combination of compound 2, or a salt thereof, with the compound of Formula (VII), or a salt thereof, is performed in the presence of potassium carbonate (K$_2$CO$_3$), water, and 2-methyltetrahydrofuran (2-MeTHF).

50. The method of any one of embodiments 45 to 49, wherein compound 2:

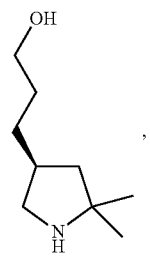

or a salt thereof, is prepared by converting compound 3:

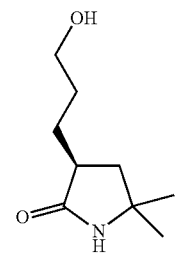

or a salt thereof, into compound 2, or a salt thereof.

51. The method of embodiment 50, wherein the conversion of compound 3, or a salt thereof, into compound 2, or a salt thereof, is performed in the presence of a reducing agent or reducing reaction conditions.

52. The method of embodiment 51, wherein the reducing agent is lithium aluminum hydride (LiAH$_4$).

53. The method of any one of embodiments 50 to 52, wherein compound 3:

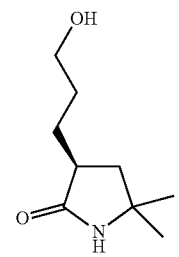

or a salt thereof, is prepared by converting compound 4:

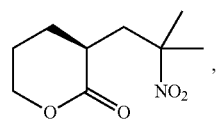

or a salt thereof, into compound 3, or a salt thereof.

54. The method of embodiment 53, wherein the conversion of compound 4, or a salt thereof, into compound 3, or a salt thereof, is performed in the presence of reducing reaction conditions.

55. The method of embodiment 54, wherein the reducing reaction conditions comprise hydrogen gas (H₂) and at least one metal catalyst selected from Raney Nickel (Ra—Ni), palladium on carbon (Pd/C), palladium on alumina (Pd/Al₂O₃), palladium(II) chloride (PdCl₂), platinum oxide (PtO₂), palladium/platinum on carbon (Pd/Pt/C), platinum on carbon (Pt/C), and nickel(II) chloride/sodium borohydride (NiCl₂/NaBH₄).

56. The method of any one of embodiments 53 to 55, wherein compound 4:

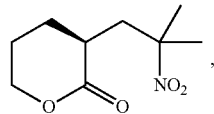

4 or a salt thereof, is prepared by chiral resolution of compound (±)-4:

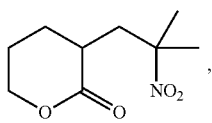

(±)-4 or a salt thereof.

57. The method of embodiment 56, wherein the chiral resolution of compound (±)-4, or a salt thereof, is performed using a method selected from chiral column chromatography, chiral Simulated Moving Bed (SMB) chromatography, bioresolution, enzymatic resolution, liquid chromatography, salt resolution, and asymmetric hydrogenation.

58. A method of preparing Compound I:

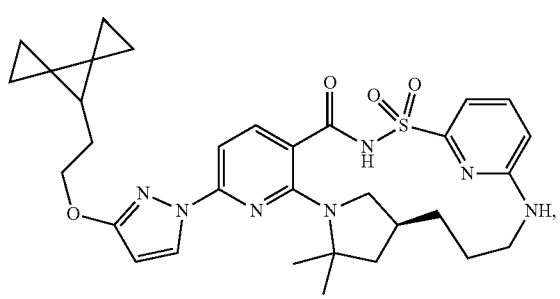

Compound I or a pharmaceutically acceptable salt thereof, comprising converting a compound of Formula (VIII):

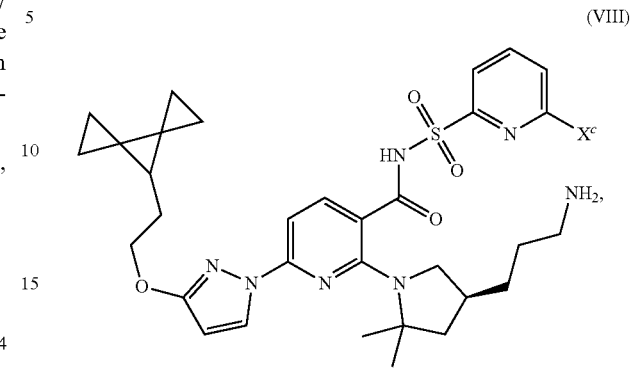

(VIII)

or a salt thereof, into Compound I, or a pharmaceutically acceptable salt thereof, wherein in the compound of Formula (VIII), or a salt thereof, $X^c$ is selected from F, Cl, Br, and I.

59. The method of embodiment 58, wherein the conversion of the compound of Formula (VIII), or a salt thereof, into Compound I, or a pharmaceutically salt thereof, is performed in the presence of at least one seventh base.

60. The method of embodiment 59, wherein the at least one seventh base is selected from potassium carbonate (K₂CO₃), 1,8-diazabicyclo[5.4.0]undec-7-ene (DBU), N,N-diisopropylethylamine (DIPEA), 1,4-diazabicyclo[2.2.2]octane (DABCO), 1,1,3,3-tetramethylguanidine, potassium hydroxide (KOH), potassium hydroxide/Triton B (KOH/Triton B), potassium hydroxide//tetra-n-butylammonium iodide (KOH/nBu₄NH₄I), potassium hydroxide/tetra-n-octylammonium bromide (KOH/n-Oct₄NH₄Br), lithium hydroxide (LiOH), and lithium carbonate (Li₂CO₃).

61. The method of embodiment 59 or 60, wherein the at least one seventh base is potassium carbonate (K₂CO₃).

62. The method of embodiment 61, wherein the conversion of the compound of Formula (VIII), or a salt thereof, into Compound I, or a pharmaceutically acceptable salt thereof, further comprises magnesium chloride (MgCl₂).

63. The method of any one of embodiments 58 to 62, wherein the compound of Formula (VIII):

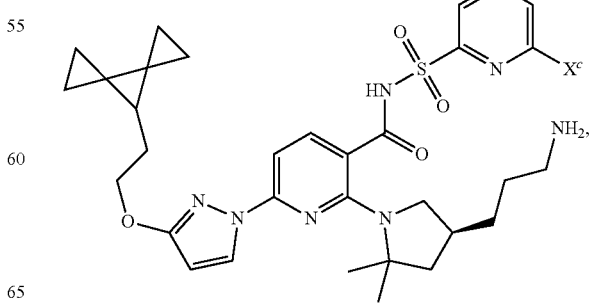

(VIII)

or a salt thereof, is prepared by converting a compound of Formula (IX):

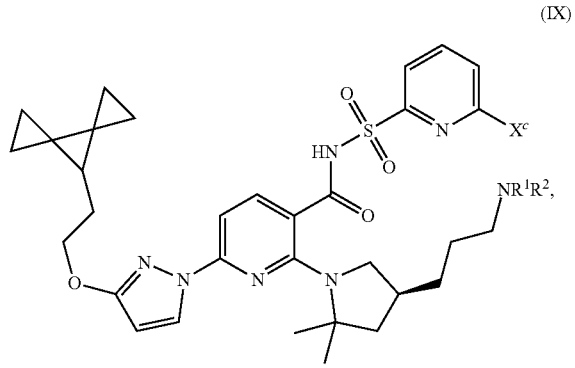
(IX)

or a salt thereof, into the compound of Formula (VIII), or a salt thereof,
wherein in the compound of Formula (IX), or a salt thereof:
$X^c$ is selected from F, Cl, Br, and I; and
wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

64. The method of embodiment 63, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

65. The method of embodiment 63, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

66. The method of embodiment 63 or 64, wherein in the compound of Formula (IX), or a salt thereof, $X^c$ is F, $R^1$ is hydrogen, and $R^2$ is benzyloxycarbonyl (Cbz).

67. The method of any one of embodiments 63 to 66, wherein the conversion of the compound of Formula (IX), or a salt thereof, into the compound of Formula (VIII), or a salt thereof, is performed in the presence of reducing reaction conditions.

68. The method of embodiment 67, wherein the reducing reaction conditions are selected from hydrogen gas ($H_2$) and palladium on carbon (Pd/C), formic acid/triethylamine/palladium on carbon ($HCO_2H/Et_3N$/(Pd/C)), ammonium formate/potassium carbonate and palladium on carbon ($NH_4HCO_2/K_2CO_3$ and Pd/C), potassium phosphate dibasic and palladium on carbon ($K_2HPO_4$ and Pd/C), potassium phosphate and palladium on carbon ($K_3PO_4$ and Pd/C), hydrazine and palladium on carbon ($NH_2NH_2$/(Pd/C)), and 1,4-cyclohexadiene and palladium on carbon.

69. The method of any one of embodiments 63 to 65, 67, and 68, wherein the compound of Formula (IX):

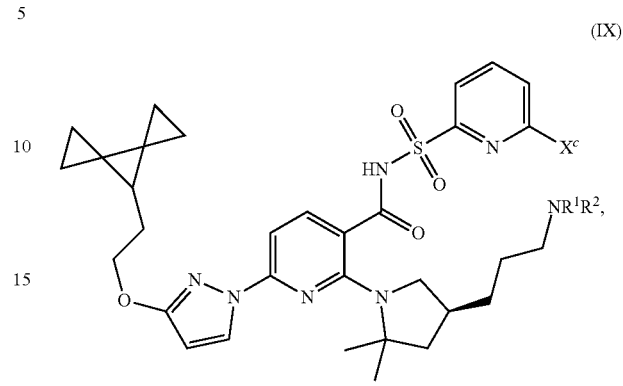
(IX)

or a salt thereof, is prepared by combining a compound of Formula (X):

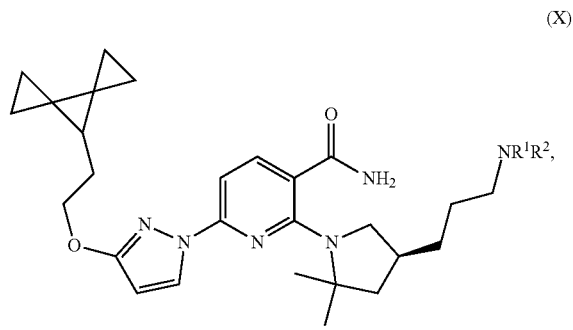
(X)

or a salt thereof, with a compound of Formula (V):

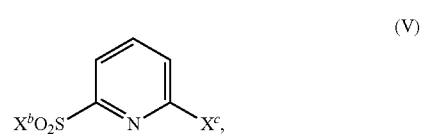
(V)

or a salt thereof, to produce the compound of Formula (IX), or a salt thereof,
wherein in the compound of Formula (X), or a salt thereof:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group; and
wherein in the compound of Formula (V), or a salt thereof:
$X^b$ is selected from Cl, F, —$OC_6F_5$,

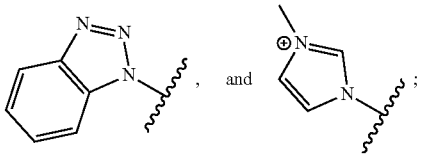

$X^c$ is selected from F, Cl, Br, and I.

70. The method of embodiment 69, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

71. The method of embodiment 69, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

72. The method of any one of embodiments 69 to 71, wherein in the compound of Formula (X), or a salt thereof, $R^1$ is hydrogen and $R^2$ is Cbz, or $R^1$ and $R^2$, together with the atoms to which they are attached, form N-phthalimide.

73. The method of any one of embodiments 69 to 72, wherein in the compound of Formula (V), or a salt thereof, $X^b$ is $-OC_6F_5$ and $X^c$ is F.

74. The method of any one of embodiments 69 to 73, wherein the combination of the compound of Formula (X), or a salt thereof, with the compound of Formula (V), or a salt thereof, is performed in the presence of at least one eighth base.

75. The method of embodiment 74, wherein the at least one eighth base is an alkoxy base.

76. The method of embodiment 75, wherein the alkoxy base is selected from lithium t-amylate (t-AmOLi), sodium t-amylate (t-AmONa), potassium t-amylate (t-AmOK), and lithium t-butoxide (LiOt-Bu).

77. The method of any one of embodiments 69 to 76, wherein the compound of Formula (X):

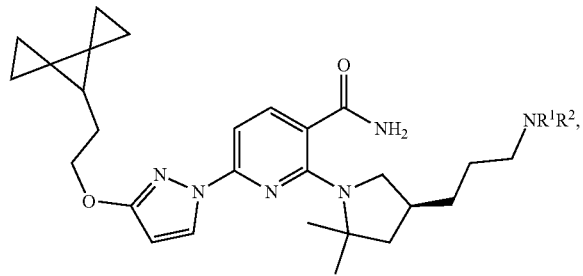

(X)

or a salt thereof, is prepared by combining a compound of Formula (IV):

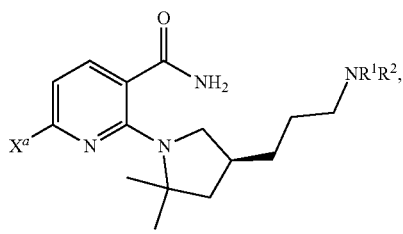

(IV)

or a salt thereof, with compound 1:

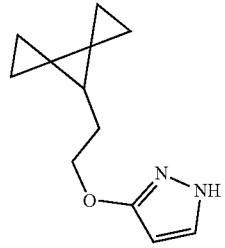

1 or a salt thereof, to produce the compound of Formula (X), or a salt thereof,
wherein in the compound of Formula (IV), or a salt thereof:
$X^a$ is selected from F, Cl, Br, I, and $-OSO_2R$;
R is selected from $-C_{1-10}$ alkyl, $-C_{1-10}$ haloalkyl, and aryl optionally substituted with $-C_{1-10}$ alkyl, $-C_{1-10}$ haloalkyl, halo, or nitro; and wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

78. The method of embodiment 77, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

79. The method of embodiment 77, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

80. The method of embodiment 77 or 79, wherein in the compound of Formula (IV), or a salt thereof, $X^a$ is Br, and $R^1$ and $R^2$, together with the atoms to which they are attached, form N-phthalimide.

81. The method of embodiment 77 or 78, wherein in the compound of Formula (IV), or a salt thereof, $X^a$ is Br, $R^1$ is hydrogen, and $R^2$ is benzyloxycarbonyl (Cbz).

82. The method of any one of embodiments 77 to 81, wherein the combination of the compound of Formula (IV), or a salt thereof, with compound 1, or a salt thereof, is performed in the presence of at least one ninth base.

83. The method of embodiment 82, wherein the at least one ninth base is selected from carbonate bases, hydroxide bases, alkoxide bases, acetate bases, amine bases, phosphate bases, and sulfate bases.

84. The method of embodiment 82 or 83, wherein the at least one ninth base is selected from sodium carbonate ($Na_2CO_3$), potassium carbonate ($K_2CO_3$), cesium carbonate ($Cs_2CO_3$), lithium carbonate ($Li_2CO_3$), sodium hydroxide (NaOH)

optionally in THF, MeTHF, or IPA, potassium hydroxide (KOH), sodium tert-butoxide (NaOt-Bu) optionally in THF, MeTHF, or IPA, potassium tert-butoxide (NaOt-Bu), pyridine, 2,2,6,6-tetramethylpiperidine, 1,8-diazabicyclo[5.4.0]undec-7-ene (DBU) optionally in IPA, 7-methyl-1,5,7-triazabicyclo[4.4.0]dec-5-ene (MTBD), t-Bu-tetramethylguanidine, N,N-diisopropylethylamine (DIPEA), potassium bis(trimethylsilyl)amide (KHMDS), pyridine, sodium bicarbonate ($NaHCO_3$), potassium bicarbonate ($KHCO_3$), sodium phosphate tribasic ($Na_3PO_4$), and potassium phosphate tribasic ($K_3PO_4$).

85. The method of any one of embodiments 82 to 84, wherein the at least one ninth base is potassium carbonate ($K_2CO_3$).

86. The method of any one of embodiments 77 to 85, wherein the combination of the compound of Formula (IV), or a salt thereof, with compound 1, or a salt thereof, further comprises at least one metal catalyst.

87. The method of embodiment 86, wherein the at least one metal catalyst is selected from palladium catalysts and copper catalysts.

88a. The method of embodiment 87, wherein the palladium catalyst is selected from [(2-di-tert-butylphosphino-2',4',6'-triisopropyl-1,1'-biphenyl)-2-(2'-amino-1,1'-biphenyl)]palladium(II) methanesulfonate (tBuXPhos Pd G3), [1,1'-bis(di-tertbutylphosphino)ferrocene]dichloro palladium(II), tris(dibenzylideneacetone)dipalladium(0) ($Pd_2dba_3$)/2-di-tert-butylphosphino-2',4',6'-triisopropylbiphenyl)$Pd_2dba_3$/ N-phenyl-2-(di-tert-butylphosphino)pyrrole, $Pd_2dba_3$/2-di-tert-butylphosphino-2'-methylbiphenyl, $Pd_2dba_3$/5-(di-tert-butylphosphino)-1', 3', 5'-triphenyl-1'H-[1,4']bipyrazole, $Pd_2dba_3$/2-(di-tert-butylphosphino)-1-(2-methoxyphenyl)-1H-pyrrole, $Pd_2dba_3$/2-dicyclohexylphosphino-2',6'-dimethoxybiphenyl, $Pd_2dba_3$/2-(dicyclohexylphosphino)3,6-dimethoxy-2',4',6'-triisopropyl-1,1'-biphenyl ($Pd_2dba_3$/BrettPhos), $Pd_2dba_3$/di-tert-butyl(2,2-diphenyl-1-methyl-1-cyclopropyl)phosphine, $Pd_2dba_3$/1-(dicyclohexylphosphino)-2,2-diphenyl-1-methylcyclopropane, dichloro[1,3-bis(2,6-di-3-pentylphenyl)imidazol-2-ylidene](3-chloropyridyl) palladium(II), $Pd_2dba_3$/1,1'-bis(diphenylphosphino)ferrocene, dichloro[1,1'-bis(dicyclohexylphosphino)ferrocene] palladium(II), (2-dicyclohexylphosphino-2',4',6'-triisopropyl-1,1'-biphenyl)[2-(2'-amino-1,1'-biphenyl)] palladium(II) methanesulfonate (XPhos Pd G3), dichloro[2,2'-bis(diphenylphosphino)-1,1'-binaphthyl]palladium(II) (Pd(BINAP)$Cl_2$, $Pd_2dba_3$/bis[(2-diphenylphosphino)phenyl] ether ($Pd_2dba_3$/DPEPhos), $Pd_2dba_3$/1,2,3,4,5-Pentaphenyl-1'-(di-tert-butylphosphino)ferrocene, $Pd_2dba_3$/2-(di-tertbutylphosphino)-2',4',6'-triisopropyl-3,6-dimethoxy-1,1'-biphenyl, $Pd_2dba_3$/2-dicyclohexylphosphino-2'-(N,N-dimethylamino)biphenyl, $Pd_2dba_3$/1,1'-bis(di-tert-butylphosphino)ferrocene, 2-di-tert-butylphosphino-2',4',6'-triisopropylbiphenyl/$Pd_2dba_3$ (tert-Butyl XPhos/$Pd_2dba_3$), [2-(di-tert-butylphosphino)-2',4',6'-triisopropyl-1,1'-biphenyl][2-(2-aminoethyl)phenyl]palladium(II) chloride (tBuXPhos-Pd-G1), allyl(2-di-tert-butylphosphino-2',4',6'-triisopropyl-1,1'-biphenyl) palladium(II) triflate, [(2-di-tert-butylphosphino-3,6-dimethoxy-2',4',6'-triisopropyl-1,1'-biphenyl)-2-(2'-amino-1,1'-biphenyl)]palladium(II) methanesulfonate (t-BuBrettPhos-Pd-G3), 2-(di-tert-butylphosphino)-2',4',6'-triisopropyl-3,6-dimethoxy-1,1'-biphenyl/$Pd_2dba_3$ (t-BuBrettPhos/$Pd_2dba_3$), trifluoromethanesulfonate allyl[(2-di-tert-butylphosphino-3,6-dimethoxy-2',4',6'-triisopropyl-1,1'-biphenyl)-2-(2'-amino-1,1'-biphenyl)] palladium(II), (2-dicyclohexylphosphino-2',6'-dimethoxybiphenyl) [2-(2'-amino-1,1'-biphenyl)]palladium(II) methanesulfonate/$Pd_2dba_3$ (SPhos/$Pd_2dba_3$), [1,1'-bis(diphenylphosphino)ferrocene]dichloro palladium(II) (Pd(dppf)$Cl_2$, [1,1'-bis(di-tert-butylphosphino)ferrocene]dichloropalladium(II) (Pd(dtbpf)$Cl_2$), dichloro[1,3-bis(2,6-di-3-pentylphenyl)imidazol-2-ylidene](3-chloropyridyl)palladium(II) (PEPSII-pent), di-tert-butyl(2,2-diphenyl-1-methyl-1-cyclopropyl) phosphine/$Pd_2dba_3$ (cBRIDP/$Pd_2dba_3$), and 1-(dicyclohexylphosphino)-2,2-diphenyl-1-methylcyclopropane/$Pd_2dba_3$ (Cy-cBRIDP/$Pd_2dba_3$).

88b. The method of embodiment 87, wherein the active catalyst, palladium (0) 2-di-tert-butylphosphino-2',4',6'-triisopropylbiphenyl (tBuXPhos, tert-Butyl XPhos) is generated using palladium (II) tBuXPhos precatalyst (G1-G3) or a combination of a palladium (0) source, for example $Pd_2(dba)_3$ or Pd($PPh_3$)$_4$, and di-tert-butylphosphino-2',4',6'-triisopropylbiphenyl (tBuXPhos, tert-Butyl XPhos) and finally by using palladium (II) source, such as Pd(OAc)$_2$ or Pd(Cl)$_2$ in the presence of a reducing agent and di-tert-butylphosphino-2',4',6'-triisopropylbiphenyl (tBuXPhos, tert-Butyl XPhos).

89. The method of embodiment 87, wherein the copper catalyst is selected from copper(II) fluoride, copper(I) bromide (CuBr), copper(I) iodide (CuI), copper(I) thiophene-2-carboxylate, and copper(I) trifluoromethanesulfonate toluene complex, optionally substituted with a ligand such as N,N'-dimethylethylenediamine, N,N'-dimethylcyclohexane-1,2-diamine, 1,10-phenanthroline, 8-hydroxyquinoline, trans-cyclohexane-1,2-diamine, cis-cyclohexane-1,2-diamine, N,N-dimethylglycine, 2-picolinic acid, 2,2'-bipyridine, 2-acetylcyclohexanone, 1,3-di-tert-butyl-1,3-propanedione, rac-BINOL, dipivaloylmethane, 2-isobutyrylcyclohexanone, 2-amino-4,6-pyrimidinediol, (1R,2S,4S,5R)-6-methoxycyclohexane-1,2,3,4,5-pentol, salicylaldoxime, glycolic acid, L-proline, 2,2'-dipyridyl, N-cyclohexyl-2,6-bis(1-methylethyl)benzenamine, N,N-diisopropyl-1,3-propanediamine, trans-1,2-diaminocyclohexane, N,N'-dimethyl-1,3-propanediamine, N,N'-diethylethane-1,2-diamine, 3-(dimethylamino)-propylamine, 1,4-diaminocyclohexane, N,N'-dimethylethane-1,2-diamine, diethylenetriamine, and trans-N,N-dimethylcyclohexane-1,2-diamine.

90. The method of any one of embodiments 86 to 89, wherein the at least one metal catalyst is [(2-di-tert-butylphosphino-2',4',6'-triisopropyl-1,1'-biphenyl)-2-(2'-amino-1,1'-biphenyl)] palladium(II) methanesulfonate (tBuXPhos Pd G3), bis(dibenzylideneacetone)palladium(0) ($Pd_2dba_3$), copper iodide (CuI), or a combination thereof.

91. The method of any one of embodiments 77 to 88, wherein the combination of the compound of Formula (IV), or a salt thereof, with compound 1, or a salt thereof, further comprises copper iodide (CuI).

92. The method of embodiment 91, wherein the combination of the compound of Formula (IV), or a salt thereof, with compound 1, or a salt thereof, further comprises dicyclohexylamine (DMCHDA).

93. The method of any one of embodiments 77 to 79 and 82 to 92, wherein the compound of Formula (IV):

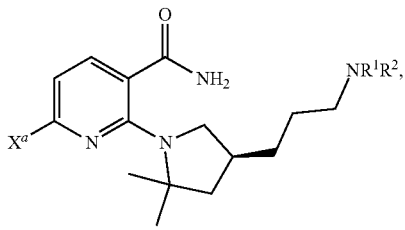

or a salt thereof, is prepared by combining a compound of Formula (XI):

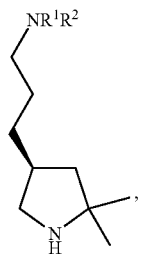

or a salt thereof, with a compound of Formula (VII):

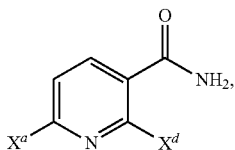

or a salt thereof, to produce the compound of Formula (IV), or a salt thereof,
wherein in the compound of Formula (XI), or a salt thereof:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group; and
wherein in the compound of Formula (VII), or a salt thereof:
$X^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and
$X^d$ is selected from F, Cl, Br, and I.

94. The method of embodiment 93, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

95. The method of embodiment 93, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsiloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

96. The method of embodiment 93 or 94, wherein in the compound of Formula (XI), or a salt thereof, $R^1$ is hydrogen and $R^2$ is benzyloxycarbonyl (Cbz).

97. The method of embodiment 93 or 95, wherein in the compound of Formula (XI), or a salt thereof, $R^1$ and $R^2$, together with the atoms to which they are attached, form N-phthalimide.

98. The method of any one of embodiments 93 to 97, wherein in the compound of Formula (VII), or a salt thereof, $X^a$ is Br and $X^d$ is F.

99. The method of any one of embodiments 93 to 98, wherein the combination of the compound of Formula (XI), or a salt thereof, with the compound of Formula (VII), or a salt thereof, is performed in the presence of at least one tenth base.

100. The method of embodiment 99, wherein the at least one tenth base is a carbonate base.

101. The method of embodiment 99 or 100, wherein the at least one tenth base is potassium carbonate (K$_2$CO$_3$).

102. The method of embodiment 101, wherein the combination of the compound of Formula (XI), or a salt thereof, with the compound of Formula (VII), or a salt thereof, further comprises zinc chloride (ZnCl$_2$).

103. The method of any one of embodiments 93 to 102, wherein the compound of Formula (XI):

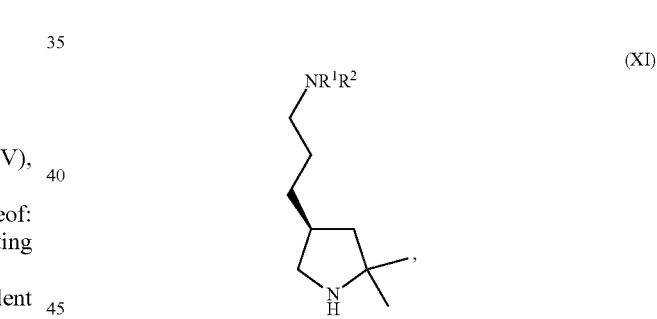

or a salt thereof, is prepared by converting a compound of Formula (XII):

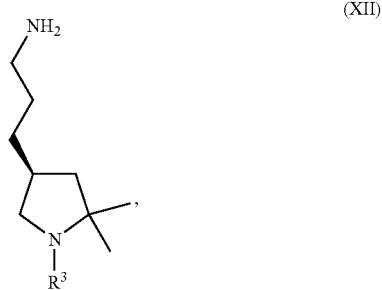

or a salt thereof, into the compound of Formula (XI), or a salt thereof,
wherein in the compound of Formula (XII), or a salt thereof, $R^3$ is a monovalent nitrogen protecting group.

104. The method of embodiment 103, wherein each monovalent nitrogen protecting group is selected from t-butyloxycarbonyl (Boc), benzyloxycarbonyl (Cbz), and N-phthalimide.

105. The method of embodiment 103 or 104, wherein in the compound of Formula (XII), or a salt thereof, $R^3$ is t-butyloxycarbonyl (Boc).

106. The method of any one of embodiments 103 to 105, wherein the conversion of the compound of Formula (XII), or a salt thereof, into the compound of Formula (XI), or a salt thereof, comprises the steps of:
1) converting the primary amine of the compound of Formula (XII), or a salt thereof, into a protected amine —$NR^1R^2$; and
2) deprotecting $R^3$ to produce the compound of Formula (XI), or a salt thereof.

107. The method of embodiment 106, wherein the conversion in step 1) is performed in the presence of benzyl chloroformate (Cbz-Cl) and potassium hydroxide (KOH).

108. The method of embodiment 106 or 107, wherein $R^3$ in step 2) is deprotected with hydrochloric acid (HCl), methanesulfonic acid (MsOH), or trifluoroacetic acid.

109. The method of any one of embodiments 103 to 108, wherein the compound of Formula (XII):

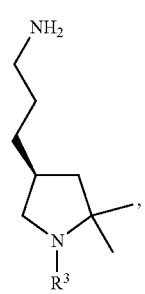

(XII)

or a salt thereof, is prepared by converting the compound of Formula (XV):

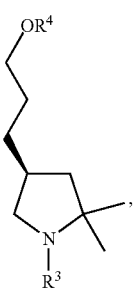

(XV)

or a salt thereof, into the compound of Formula (XII), or a salt thereof,
wherein in the compound of Formula (XV), or a salt thereof, $R^3$ is a monovalent nitrogen protecting group.

110. The method of embodiment 109, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

111. The method of embodiment 109 or 110, wherein in the compound of Formula (XV), or a salt thereof, $R^3$ is t-butyloxycarbonyl (Boc).

112. The method of any one of embodiments 109 to 111, wherein the conversion of the compound of Formula (XV), or a salt thereof, into the compound of Formula (XII), or a salt thereof, comprises the steps of:
1) converting the compound of Formula (XV):

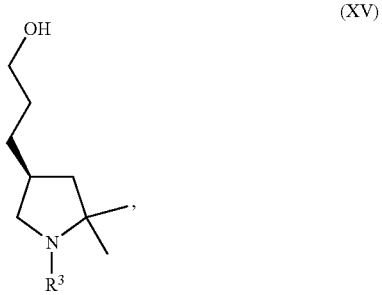

(XV)

or a salt thereof, into the compound of Formula (XIV):

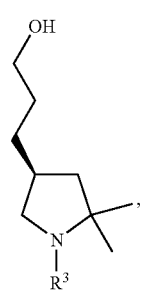

(XIV)

or a salt thereof;
2) converting the compound of Formula (XIV), or a salt thereof, into the compound of Formula (XIII):

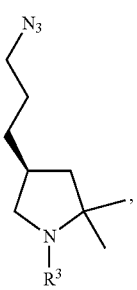

(XIII)

or a salt thereof; and
3) converting the compound of Formula (XIII), or a salt thereof, into the compound of Formula (XII), or a salt thereof,
wherein in the compounds of Formulae (XIII)-(XV), or a salt thereof, $R^3$ is a monovalent nitrogen protecting group; and wherein in the compound of Formula (XIV), or a salt thereof:
$R^4$ is —$SO_2R$; and
R is selected from —$C_{1-10}$ alkyl, —$C_{1-10}$ haloalkyl, and aryl optionally substituted with —$C_{1-10}$ alkyl, —$C_{1-10}$ haloalkyl, halo, or nitro.

113. The method of embodiment 112, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

114. The method of embodiment 112 or 113, wherein in the compounds of Formulae (XIII)-(XV), or a salt thereof, $R^3$ is t-butyloxycarbonyl (Boc).

115. The method of any one of embodiments 112 to 114, wherein in the compound of Formula (XIV), or a salt thereof, $R^4$ is 4-nitrobenzylsulfonyl chloride (NsCl).

116. The method of any one of embodiments 112 to 115, wherein the conversion of the compound of Formula (XV), or a salt thereof, into the compound of Formula (XIV), or a salt thereof, is performed in the presence of 4-nitrobenzylsulfonyl chloride (NsCl) and at least one eleventh base.

117. The method of embodiment 116, wherein the at least one eleventh base is an amine base or carbonate base.

118. The method of any one of embodiments 112 to 117, wherein the conversion of the compound of Formula (XIV), or a salt thereof, into the compound of Formula (XIII), or a salt thereof, is performed in the presence of an azide source.

119. The method of embodiment 118, wherein the azide source is sodium azide ($NaN_3$).

120. The method of any one of embodiments 112 to 119, wherein the conversion of the compound of Formula (XIII), or a salt thereof, into the compound of Formula (XII), or a salt thereof, is performed in the presence of reducing reaction conditions.

121. The method of embodiment 120, wherein the reducing reaction conditions comprise hydrogen gas ($H_2$) and a metal catalyst selected from platinum dioxide ($PtO_2$) and palladium on carbon (Pd/C).

122. The method of any one of embodiments 112 to 121, wherein the compound of Formula (XV):

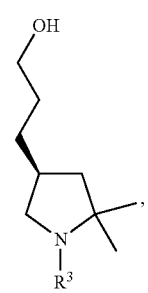

(XV)

or a salt thereof, is prepared by converting compound 2:

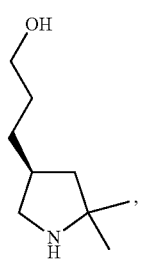

2 or a salt thereof, into the compound of Formula (XV), or a salt thereof.

123. The method of embodiment 122, wherein the conversion of compound 2, or a salt thereof, into the compound of Formula (XV), or a salt thereof, is performed in the presence of di-tert-butyl dicarbonate ($Boc_2O$).

124. The method of embodiment 123, further comprising combining the compound of Formula (XV), or a salt thereof, with L-glutamic acid.

125. The method of embodiment 122 or 124, wherein compound 2:

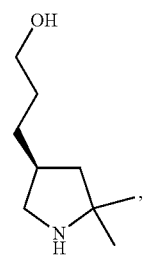

2 or a salt thereof, is prepared by converting compound 3:

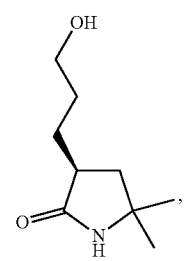

3 or a salt thereof, into compound 2, or a salt thereof.

126. The method of embodiment 125, wherein the conversion of compound 3, or a salt thereof, into compound 2, or a salt thereof, is performed in the presence of a reducing agent and at least one solvent.

127. The method of embodiment 126, wherein the reducing agent is lithium aluminum hydride ($LiAlH_4$).

128. The method of embodiment 127, wherein the at least one solvent is 2-methyltetrahydrofuran (2-MeTHF).

129. The method of any one of embodiments 125 to 128, wherein compound 3:

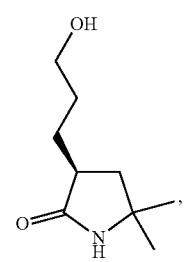

3 or a salt thereof, is prepared by chiral resolution of compound (±)-3:

(±)-3 or a salt thereof.

130. The method of embodiment 129, wherein the chiral resolution of compound (±)-3 is performed using a method selected from chiral column chromatography, chiral Simulated Moving Bed (SMB) chromatography, bioresolution, enzymatic resolution, liquid chromatography, salt resolution, and asymmetric hydrogenation.

131. The method of embodiment 129 or 130, wherein compound (±)-3:

(±)-3 or a salt thereof, is prepared by converting compound (±)-4:

(±)-4 or a salt thereof, into compound (±)-3, or a salt thereof.

132. The method of embodiment 131, wherein the conversion of compound (±)-4, or a salt thereof, into compound (±)-3, or a salt thereof, is performed in the presence of reducing reaction conditions.

133. The method of embodiment 132, wherein the reducing reaction conditions comprise hydrogen gas ($H_2$) and Raney Nickel.

134. The method of any one of embodiments 131 to 133, wherein compound (±)-4:

(±)-4 or a salt thereof, is prepared by combining compound 5:

5 or a salt thereof, with 2-nitropropane to produce compound (±)-4, or a salt thereof.

135. The method of embodiment 134, wherein the combination of compound 5, or a salt thereof, with 2-nitropropane is performed in the presence of 1,8-diazabicyclo[5.4.0]undec-7-ene (DBU).

136. The method of embodiment 134 or 135, wherein compound 5:

5 or a salt thereof, is prepared by converting δ-valerolactone into compound 5, or a salt thereof.

137. The method of embodiment 136, wherein the conversion of δ-valerolactone into compound 5, or a salt thereof, comprises the steps of:
 1) combining δ-valerolactone with an alkyl formate and at least one twelfth base; and
 2) combining the product of step 1) with paraformaldehyde.

138. The method of embodiment 137, wherein the method further comprises contacting the product of step 2) with $SiO_2$ to produce compound 5, or a salt thereof.

139. The method of embodiment 137 or 138, wherein the alkyl formate is ethyl formate and the at least one twelfth base is sodium hydride (NaH).

140. The method of any one of embodiments 3 to 24 and 77 to 92, wherein compound 1:

1 or a salt thereof, is prepared by converting compound 6:

6 or a salt thereof, into compound 1, or a salt thereof.

141. The method of embodiment 140, wherein the conversion of compound 6, or a salt thereof, into compound 1, or a salt thereof, is performed in the presence of 1,8-diazabicyclo[5.4.0]undec-7-ene (DBU).

142. The method of embodiment 140 or 141, wherein compound 6:

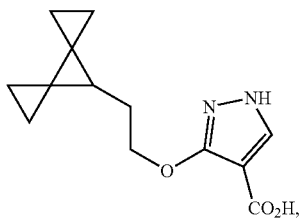

or a salt thereof, is prepared by converting compound 7:

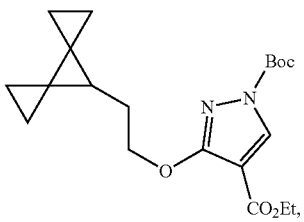

or a salt thereof, into compound 6, or a salt thereof.

143. The method of embodiment 142, wherein the conversion of compound 7, or a salt thereof, into compound 6, or a salt thereof, is performed in the presence of at least one thirteenth base and at least one solvent.

144. The method of embodiment 143, wherein the at least one thirteenth base is potassium hydroxide (KOH).

145. The method of embodiment 143 or 144, wherein the at least one solvent is methanol (MeOH).

146. The method of any one of embodiments 142 to 145, wherein compound 7:

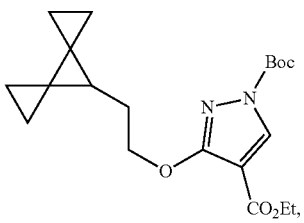

or a salt thereof, is prepared by combining compound 8:

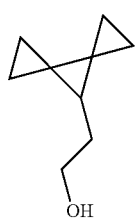

or a salt thereof, with compound 9:

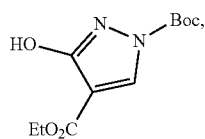

or a salt thereof, to produce compound 7, or a salt thereof.

147. The method of embodiment 146, wherein the combination of compound 8, or a salt thereof, with compound 9, or a salt thereof, is performed in the presence of a phosphine and an azodicarboxylate.

148. The method of embodiment 147, wherein the phosphine is triphenylphosphine (PPh$_3$).

149. The method of embodiment 147 or 148, wherein the azodicarboxylate is diisopropyl azocarboxylate (DIAD).

150. The method of any one of embodiments 146 to 149, wherein the combination of compound 8, or a salt thereof, with compound 9, or a salt thereof, is performed in the presence of a sulfonyl chloride and at least one fourteenth base.

151. The method of embodiment 150, wherein the sulfonyl chloride is methanesulfonyl chloride (MsCl) or p-toluenesulfonyl chloride (TsCl).

152. The method of embodiment 150 or 151, wherein the at least one fourteenth base is triethylamine (Et$_3$N).

153. The method of any one of embodiments 146 to 152, wherein compound 8:

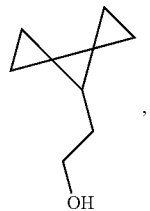

or a salt thereof, is prepared by converting compound 10:

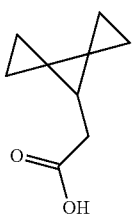

or a salt thereof, into compound 8, or a salt thereof.

154. The method of embodiment 153, wherein the conversion of compound 10, or a salt thereof, into compound 8, or a salt thereof, is performed in the presence of a reducing agent.

155. The method of embodiment 154, wherein the reducing agent is selected from lithium aluminum hydride (LiAlH$_4$), boron trifluoride/sodium borohydride (BF$_3$/NaBH$_4$), borane (BH$_3$) and borane complexes such as borane dimethylsulfide (BH$_3$SMe$_2$) and borane-tetrahydrofuran (BH$_3$-THF), Vitride (sodium bis(2-methoxyethoxy)aluminium hydride), zinc borohydride (Zn(BH$_4$)$_2$), and diisobutylahminum hydride (DIBAL-H).

156. The method of any one of embodiments 153 to 155, wherein compound 10:

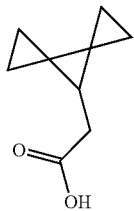

or a salt thereof, is prepared by converting compound 11:

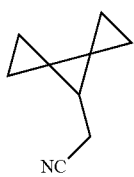

or a salt thereof, into compound 10, or a salt thereof.
157. The method of embodiment 156, wherein the conversion of compound 11, or a salt thereof, into compound 10, or a salt thereof, is performed in the presence of at least one fifteenth base and at least one solvent.
158. The method of embodiment 157, wherein the at least one fifteenth base is selected from sodium hydroxide (NaOH), potassium hydroxide (KOH), and barium hydroxide (Ba(OH)$_2$).
159. The method of embodiment 157 or 158, wherein the at least one solvent is selected from ethanol (EtOH), methanol (MeOH), ethylene glycol, diethylene glycol, and water.
160. The method of any one of embodiments 156 to 159, wherein compound 11:

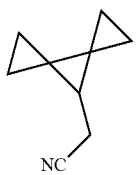

or a salt thereof, is prepared by converting compound 12:

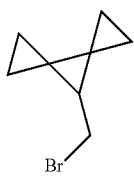

or a salt thereof, into compound 11, or a salt thereof.
161. The method of embodiment 160, wherein the conversion of compound 12, or a salt thereof, into compound 11, or a salt thereof, is performed in the presence of a cyanide source.
162. The method of embodiment 161, wherein the cyanide source is sodium cyanide (NaCN).
163. The method of any one of embodiments 160 or 162, wherein compound 12:

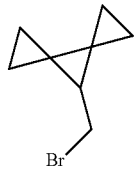

or a salt thereof, is prepared by converting compound 13:

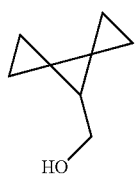

or a salt thereof, into compound 12, or a salt thereof.
164. The method of embodiment 163, wherein the conversion of compound 13, or a salt thereof, into compound 12, or a salt thereof, is performed in the presence of a phosphine, a source of bromine, and at least one sixteenth base.
165. The method of embodiment 164, wherein the phosphine is triphenylphosphine (PPh$_3$).
166. The method of embodiment 164 or 165, wherein the source of bromine is molecular bromine (Br$_2$).
167. The method of any one of embodiments 164 to 166, wherein the at least one sixteenth base is pyridine.
168. The method of any one of embodiments 163 to 167, wherein compound 13:

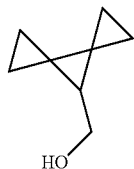

or a salt thereof, is prepared by converting compound 14:

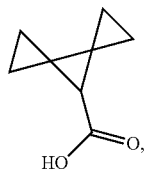

or a salt thereof, into compound 13, or a salt thereof.
169. The method of embodiment 168, wherein the conversion of compound 14, or a salt thereof, into compound 13, or a salt thereof, is performed in the presence of a reducing agent.

170. The method of embodiment 169, wherein the reducing agent is selected from lithium aluminum hydride (LiAH$_4$), boron trifluoride/sodium borohydride (BF$_3$/NaBH$_4$), borane (BH$_3$) and borane complexes such as borane dimethylsulfide (BH$_3$SMe$_2$) and borane-tetrahydrofuran (BH$_3$-THF), Vitride (sodium bis(2-methoxyethoxy)aluminium hydride), zinc borohydride (Zn(BH$_4$)$_2$), and diisobutylailuinum hydride (DIBAL-H).

171. The method of any one of embodiments 168 to 170, wherein compound 14:

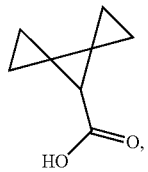

14 or a salt thereof, is prepared by converting compound 15:

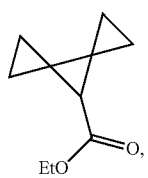

15 or a salt thereof, into compound 14, or a salt thereof.

172. The method of embodiment 171, wherein the conversion of compound 15, or a salt thereof, into compound 14, or a salt thereof, is performed in the presence of sodium hydroxide (NaOH) in methanol (MeOH).

173. The method of embodiment 171 or 172, wherein compound 15:

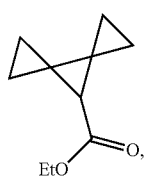

15 or a salt thereof, is prepared by converting compound 16:

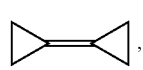

16 or a salt thereof, into compound 15, or a salt thereof.

174. The method of embodiment 173, wherein the conversion of compound 16, or a salt thereof, into compound 15, or a salt thereof, is performed in the presence of ethyl 2-diazoacetate and a metal catalyst.

175. The method of embodiment 174, wherein the metal catalyst is rhodium(II) acetate dimer (Rh$_2$(OAc)$_4$) or copper triflate (Cu(OTf)$_2$).

176. The method of any one of embodiments 173 to 175, wherein compound 16:

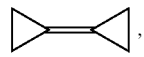

16 or a salt thereof, is prepared by converting compound 17:

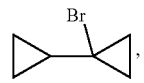

17 or a salt thereof, into compound 16, or a salt thereof.

177. The method of embodiment 176, wherein the conversion of compound 17, or a salt thereof, into compound 16, or a salt thereof, is performed in the presence of at least one seventeeth base.

178. The method of embodiment 177, wherein the at least one seventeenth base is potassium t-butoxide (KOt-Bu).

179. The method of any one of embodiments 176 to 178, wherein compound 17:

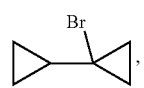

17 or a salt thereof, is prepared by converting compound 18:

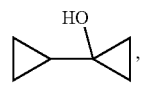

18 or a salt thereof, into compound 17, or a salt thereof.

180. The method of embodiment 179, wherein the combination of compound 18, or a salt thereof, with compound 17, or a salt thereof, is performed in the presence of a phosphine, a source of bromine, and at least one eighteenth base.

181. The method of embodiment 180, wherein the phosphine is triphenylphosphine (PPh$_3$).

182. The method of embodiment 180 or 181, wherein the source of bromine is molecular bromine (Br$_2$).

183. The method of any one of embodiments 180 to 182, wherein the at least one eighteenth base is pyridine.

184. The method of any one of embodiments 179 to 183, wherein compound 18:

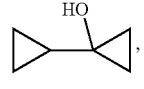

18 or a salt thereof, is prepared by converting compound 19:

19 or a salt thereof, into compound 18, or a salt thereof.

185. The method of embodiment 184, wherein the conversion of compound 19, or a salt thereof, into compound 18, or a salt thereof, is performed in the presence of ethyl magnesium bromine (EtMgBr) and titanium(IV) isopropoxide (Ti(Oi-Pr)$_4$).
186. A compound selected from:
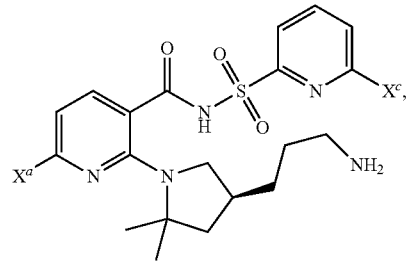
(I)
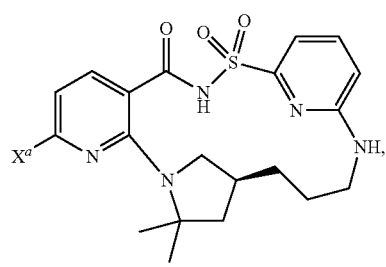
(II)
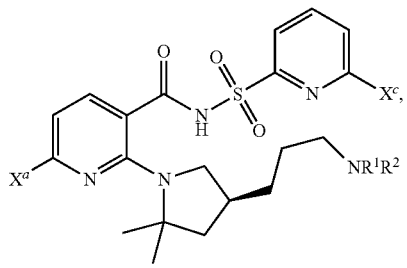
(III)
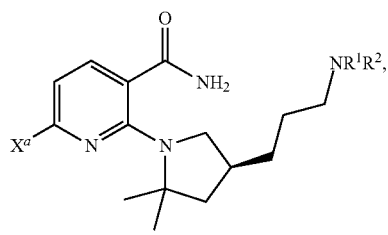
(IV)
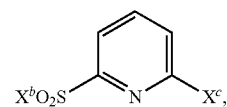
(V)
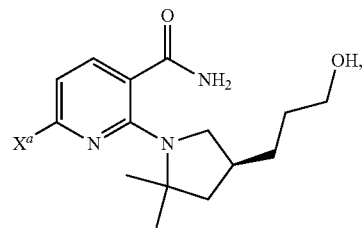
(VI)
-continued
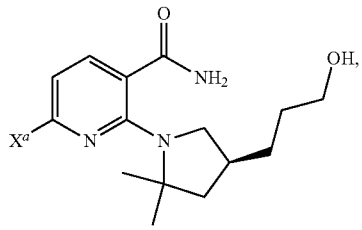
(VI)
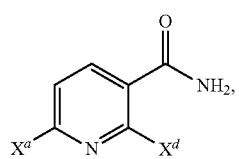
(VII)
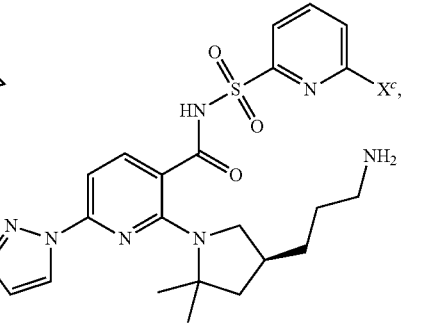
(VIII)
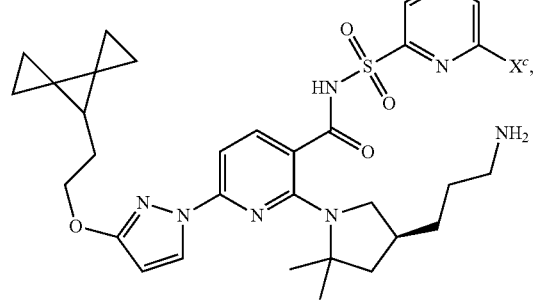
(IX)
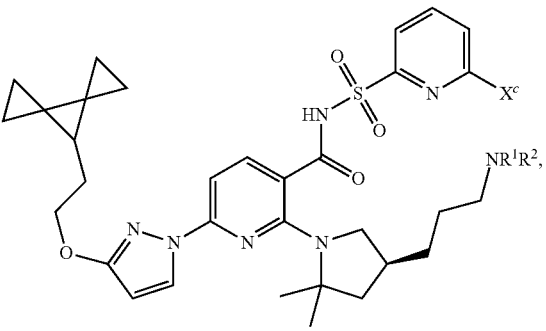
(X)

-continued (XI) 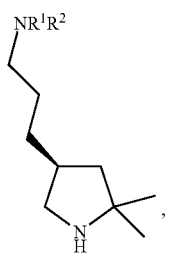

(XII) 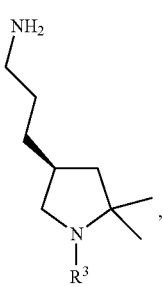

(XIII) 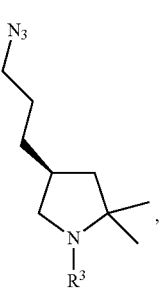

(XIV) 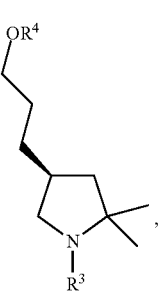

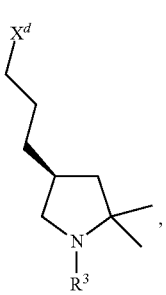

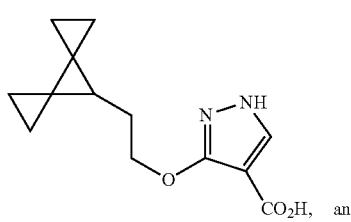

-continued

7

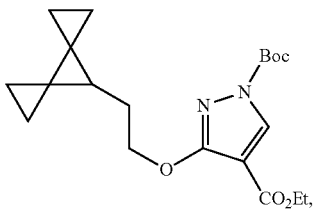

and salts thereof,
wherein:
$X^a$ is selected from F, Cl, Br, I, and —OSO$_2$R;
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro;
$X^b$ is selected from Cl, F, —OC$_6$F$_5$,

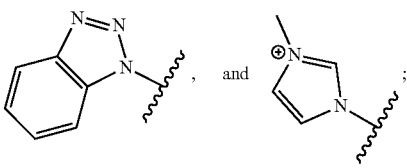

$X^c$ is selected from F, Cl, Br, and I;
$X^d$ is selected from F, Cl, Br, and I;
$R^3$ is a monovalent nitrogen protecting group;
$R^4$ is —SO$_2$R; and
R is selected from —C$_{1-10}$ alkyl, —C$_{1-10}$ haloalkyl, and aryl optionally substituted with —C$_{1-10}$ alkyl, —C$_{1-10}$ haloalkyl, halo, or nitro; and wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group; and
wherein the compound is not:

40
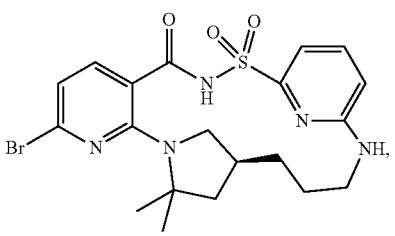

41
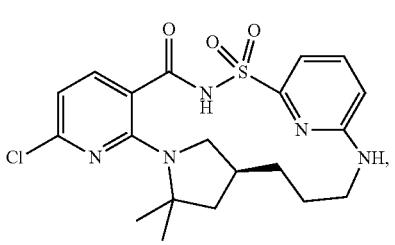

-continued

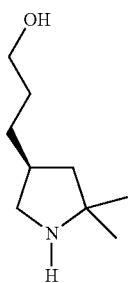
42

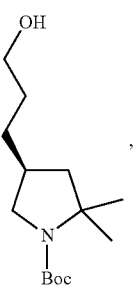
43

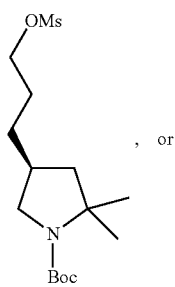
, or

44

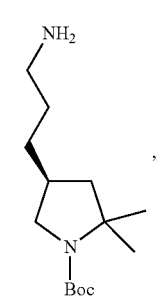

or a salt thereof.

187. The compound of embodiment 186, wherein each monovalent nitrogen protecting group is independently selected from t-butyloxycarbonyl (Boc), benzyl (Bn), tetrahydropyranyl (THP), 9-fluorenylmethyloxycarbonyl (Fmoc), benzyloxycarbonyl (Cbz), formyl, acetyl (Ac), trifluoroacetyl (TFA), trityl (Tr), and p-toluenesulfonyl (Ts).

188. The compound of embodiment 186, wherein $R^1$ and $R^2$, together with the atoms to which they are attached, form a nitrogen protecting group selected from benzylidene, 4,5-diphenyl-3-oxazolin-2-one, N-phthalimide, N-dichlorophthalimide, N-tetrachlorophthalimide, N-4-nitrophthalimide, N-thiodiglycoloyl amine, N-dithiasuccinimide, N-2,3-diphenylmaleimide, N-2,3-dimethylmaleimide, N-2,5-dimethylpyrrole, N-2,5-bis(triisopropylsilyloxy)pyrrole (BIPSOP), N-1,1,4,4-tetramethyldisilylazacyclopentane (STABASE), N-1,1,3,3-tetramethyl-1,3-disilaisoindoline (Benzostabase, BSB), N-diphenylsilyldiethylene, N-5-substituted 1,3-dimethyl-1,3,5-triazacyclohexan-2-one, N-5-substituted 1,3-dibenzyl-1,3,5-triazacyclohexan-2-one, 1-substituted 3,5-dinitro-4-pyridone, and 1,3,5-dioxazine.

General Syntheses

Compound I can be synthesized according to Scheme 1.

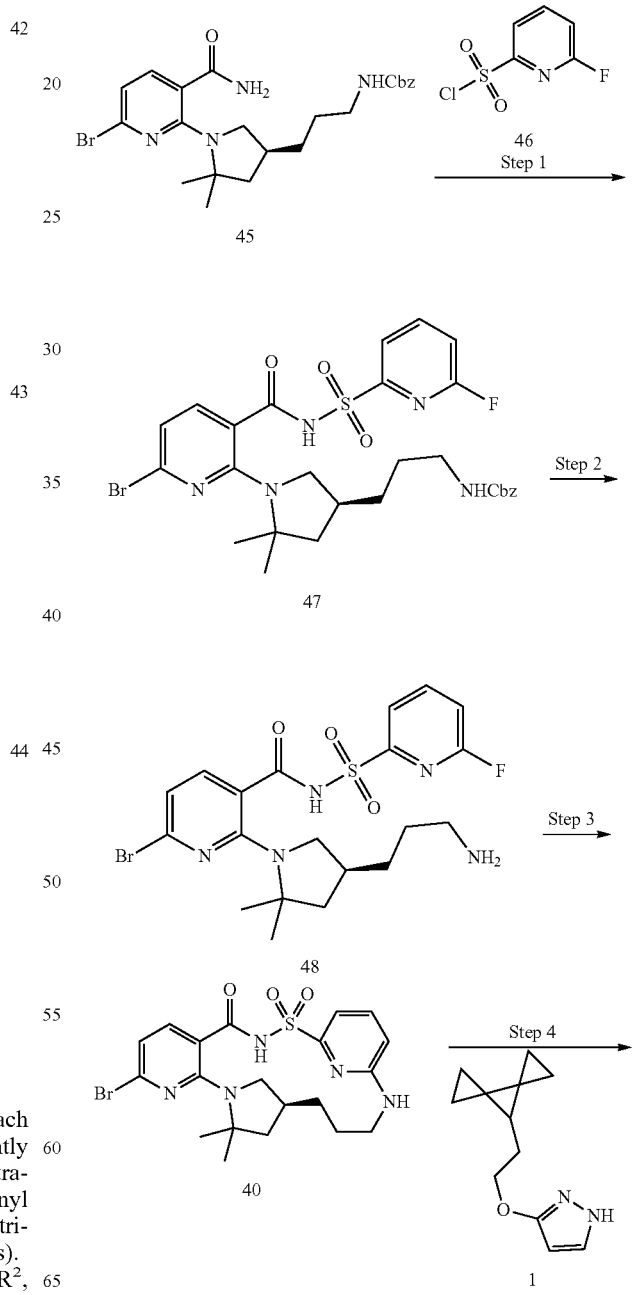

101

-continued

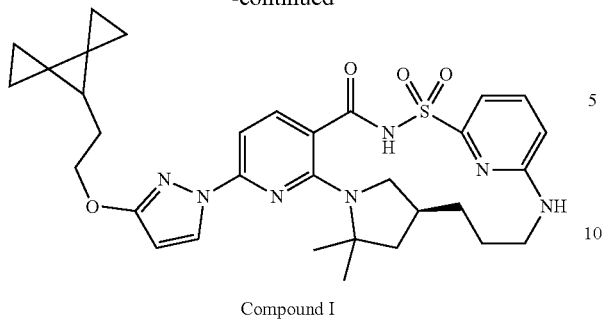

Compound I

In some embodiments, the disclosure is directed to a process comprising one or more of the following steps:

1) combining compound 45 with compound 46 to produce compound 47;

2) converting compound 47 into compound 48;

3) converting compound 48 into compound 40; and 4) combining compound 40 with compound 1 to produce Compound I.

In some embodiments, compound 45 is combined with compound 46 in the presence of an alkoxide base to produce compound 47.

In some embodiments, compound 47 is converted into compound 48 in the presence of an acid.

In some embodiments, compound 48 is converted into compound 40 in the presence of a base.

In some embodiments, compound 40 is combined with compound 1 in the presence of a base and optionally a metal catalyst to produce Compound I.

In some embodiments, compound 40 is combined with compound 1 in the presence of a copper catalyst to produce Compound I.

Compound I can also be synthesized according to Scheme 2.

Scheme 2. Alternative Synthesis of Compound I

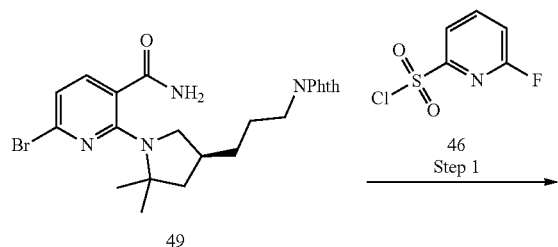

49

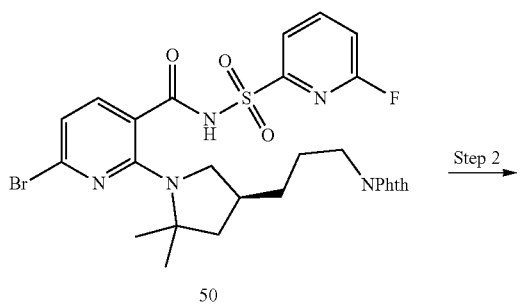

50

102

-continued

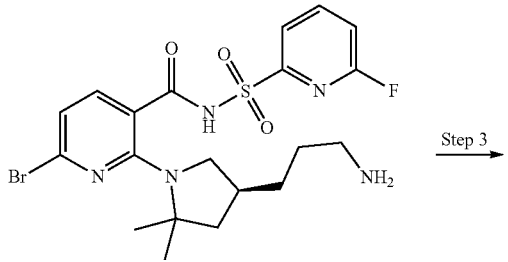

48

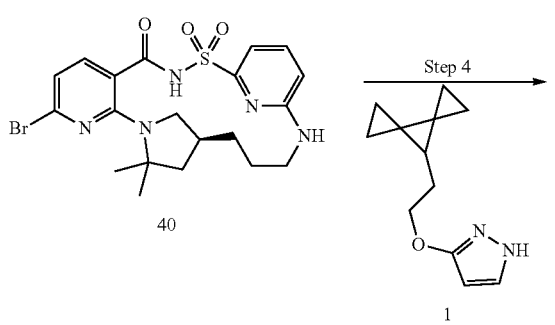

40

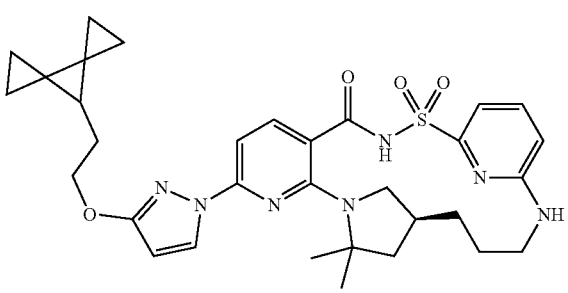

Compound I

In some embodiments, the disclosure is directed to a process comprising one or more of the following steps:

1) combining compound 49 with compound 46 in the presence of an alkoxide base to produce compound 50;

2) converting compound 50 into compound 48;

3) converting compound 48 into compound 40; and 4) combining compound 40 with compound 1 to produce Compound I.

In some embodiments, compound 49 is combined with compound 46 in the presence of an alkoxide base to produce compound 50.

In some embodiments, compound 50 is converted into compound 48 in the presence of aqueous base.

In some embodiments, compound 48 is converted into compound 40 in the presence of a base.

In some embodiments, compound 40 is combined with compound 1 in the presence of a base and optionally at least one metal catalyst to produce Compound I.

Compound I can also be synthesized according to Scheme 3.
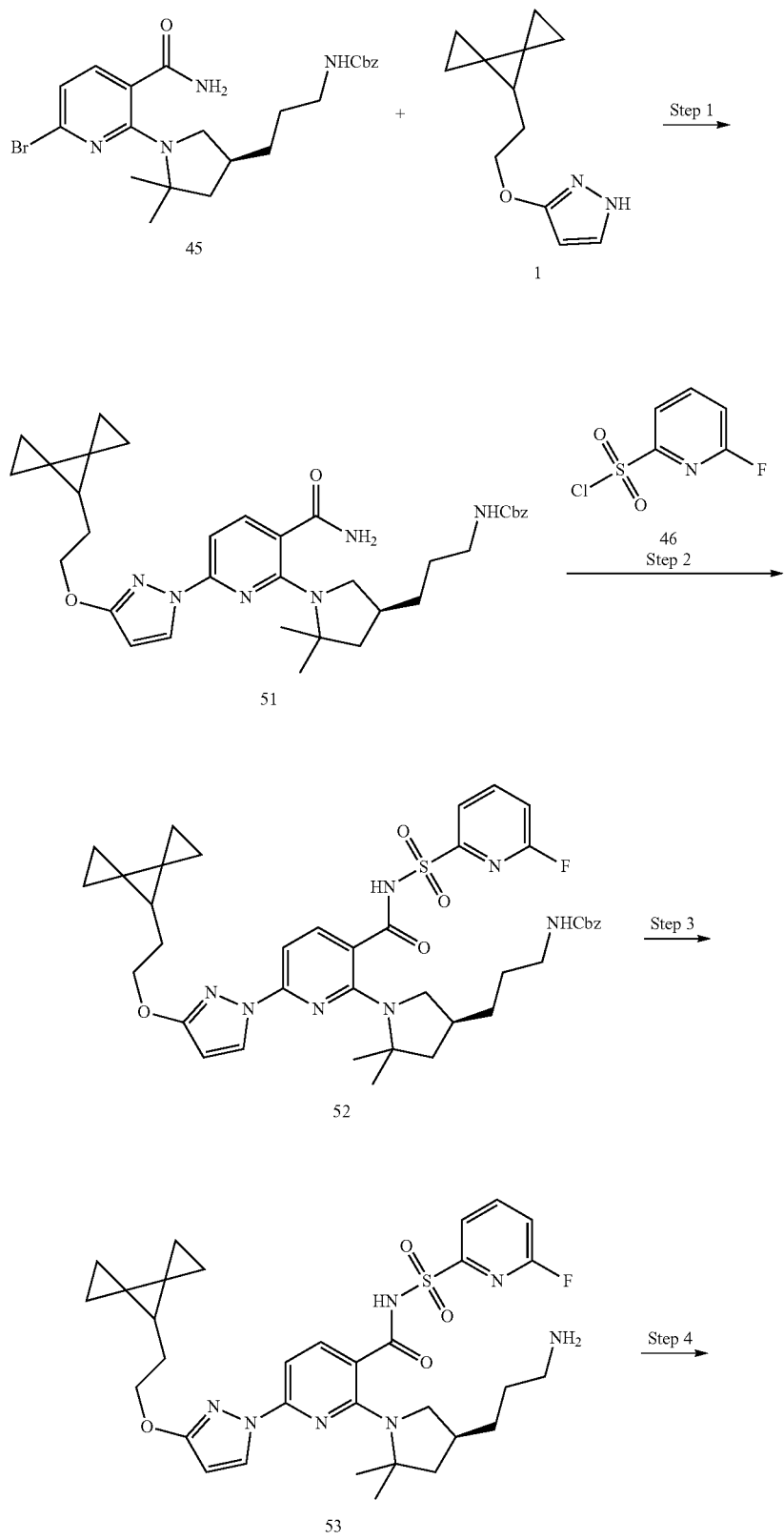
Scheme 3. Alternative Synthesis of Compound I

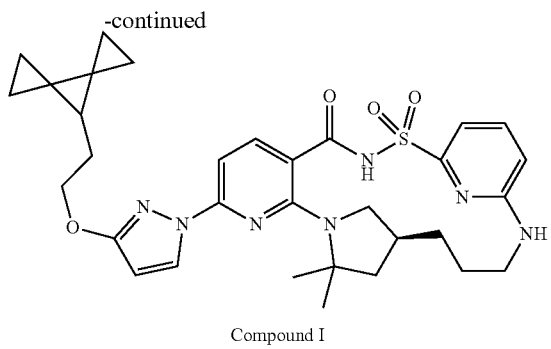

Compound I

In some embodiments, the disclosure is directed to a process comprising one or more of the following steps:

1) combining compound 45 with compound 1 to produce compound 51;
2) combining compound 51 with compound 46 to produce compound 52;
3) converting compound 52 into compound 53; and
4) converting compound 53 into Compound I.

In some embodiments, compound 45 is combined with compound 1 in the presence of a base and optionally at least one metal catalyst to produce compound 51.

In some embodiments, compound 51 is combined with compound 46 in the presence of an alkoxide base to produce compound 52.

In some embodiments, compound 52 is converted into compound 53 in the presence of an acid.

In some embodiments, compound 52 is converted into compound 53 in the presence of palladium on carbon.

In some embodiments, compound 53 is converted into Compound 1 in the presence of a base and optionally a metal catalyst.

Compound I was prepared according to the General Syntheses and Synthetic Examples disclosed herein.

In order that the disclosure described herein may be more fully understood, the following general experimental procedures and examples are set forth. It should be understood that these procedures and examples are for illustrative purposes only and are not to be construed as limiting this disclosure in any manner.

General Experimental Procedures

The definitions of certain abbreviations for the Examples below are summarized below:

| Abbreviation | Chemical Name |
|---|---|
| $Al_2O_3$ | aluminum oxide; alumina |
| t-AmOK | potassium 2-methyl-2-butoxide; potassium tert-amylate; potassium tert-amoxide |
| t-AmOLi | lithium 2-methyl-2-butoxide; lithium tert-amylate; lithium tert-amoxide |
| t-AmONa | sodium 2-methyl-2-butoxide; sodium tert-amylate; sodium tert-amoxide |
| $Ba(OH)_2$ | barium hydroxide |
| $BH_3$ | borane |
| $BH_3SMe_2$ | borane dimethylsulfide |
| $BH_3$—THF | borane-tetrahydrofuran |
| Boc | t-butyloxycarbonyl |
| $Boc_2O$ | di-tert-butyl dicarbonate; Boc anhydride |
| $Br_2$ | bromine |
| $Bu_3N$ | tributylamine |
| $nBu_4NH_4I$ | tetra-n-butylammonium |
| t-BuOK | potassium tert-butoxide |
| t-BuXPhos | 2-di-tert-butylphosphino-2',4',6'-triisopropylbiphenyl |
| t-BuXPhos Pd G3 | [(2-di-tert-butylphosphino-2',4',6'-triisopropyl-1,1'-biphenyl)-2-(2'-amino-1,1'-biphenyl)]palladium(II) methanesulfonate |
| Cbz | benzyloxycarbonyl |
| Cbz—Cl | benzyl chloroformate |
| $Cs_2CO_3$ | cesium carbonate |
| CsF | cesium fluoride |
| CuBr | copper bromide |
| CuI | copper iodide |
| $Cu(OTf)_2$ | copper(II) triflate |
| CDI | 1,1-carbonyl diimidazole |
| DABCO | 1,4-diazabicyclo[2.2.2]octane |
| DBU | 1,8-diazabicyclo[5.4.0]undec-7-ene |
| DBN | 1,5-diazabicyclo[4.3.0]non-5-ene |
| DCM | dichloromethane; methylene chloride |
| DIAD | diisopropyl azodicarboxylate |
| DIEA (DIPEA) | N,N-diisopropylethylamine |
| DMA | N,N-dimethylacetamide |
| DMCHDA | N,N-dimethylcyclohexane-1,2-diamine |
| DMF | N,N-dimethylformamide |
| DMSO | dimethyl sulfoxide |
| EtMgBr | ethylmagnesium bromide |
| $Et_2O$ | diethyl ether |
| EtOH | ethanol |
| $H_2$ | hydrogen gas |
| $H_2O$ | water |
| HATU | 1-[bis(dimethylamino)methylene]-1H-1,2,3-triazolo[4,5-b]pyridinium 3-oxid hexafluorophosphate |
| HCl | hydrochloric acid |
| $HCO_2H$ | formic acid |
| $H_3PO_4$ | phosphoric acid |
| $In(OTf)_3$ | indium(III) triflate |
| $InCl_3$ | indium(III) chloride |
| IPA | isopropanol |
| IPAc | isopropyl acetate |
| $K_2CO_3$ | potassium carbonate |
| $KHCO_3$ | potassium bicarbonate |
| $K_2HPO_4$ | potassium phosphate dibasic |
| KOt-Bu | potassium t-butoxide |
| KOH | potassium hydroxide |
| $K_3PO_4$ | Potassium phosphate |
| $LiAlH_4$ | lithium aluminum hydride |
| $Li_2CO_3$ | lithium carbonate |
| LiOH | lithium hydroxide |
| MeOH | methanol |
| MeCN ($CH_3CN$) | acetonitrile |
| 2-MeTHF | 2-methyltetrahydrofuran |
| $MgCl_2$ | magnesium chloride |
| MTBD | 7-methyl-1,5,7-triazabicyclo[4.4.0]dec-5-ene |
| MsCl | methanesulfonyl chloride; mesyl chloride |
| MsOH | methanesulfonic acid |
| NaCN | sodium cyanide |
| $Na_2CO_3$ | sodium carbonate |
| NaH | sodium hydride |
| $NaHCO_3$ | sodium bicarbonate |
| $NaN_3$ | sodium azide |
| NaOH | sodium hydroxide |

| Abbreviation | Chemical Name |
|---|---|
| NiCl$_2$ | nickel(II) chloride |
| NMP | N-methylpyrrolidone |
| NsCl | 4-nitrobenzenesulfonyl chloride; nosyl chloride |
| MTBE | methyl tert-butyl ether |
| MeTHF | 2-methyltetrahydrofuran |
| n-Oct$_4$NH$_4$Br | tetra-n-octylammonium bromide |
| Pd/Al$_2$O$_3$ | palladium on alumina |
| Pd/C | palladium on carbon |
| PdCl$_2$ | palladium(II) chloride |
| Pd$_2$(dba)$_3$ | bis(dibenzylideneacetone)palladium(0) |
| Phth | N-phthalimide |
| PPh$_3$ | triphenylphosphine |
| Pt/C | platinum on carbon |
| PtO$_2$ | platinum dioxide; Adam's catalyst |
| Raney Ni (Ra-Ni) | Raney Nickel |
| Rh$_2$(OAc)$_4$ | rhodium(II) acetate dimer; dirhodium tetraacetate |
| SiO$_2$ | silicon dioxide; silica |
| SMB | Simulated Moving Bed chromatography |
| TEA (Et$_3$N) | triethylamine |
| THF | tetrahydrofuran |
| Ti(i-PrO)$_4$ | titanium(IV) isopropoxide |
| TsCl | p-toluenesulfonyl chloride; tosyl chloride |
| p-TsOH | p-toluenesulfonic acid; tosylic acid |
| ZnCl$_2$ | zinc chloride |
| Zn(BH$_4$)$_2$ | zinc borohydride |

Reagents and starting materials were obtained from commercial sources unless otherwise stated and were used without purification.

SYNTHETIC EXAMPLES

Should the name of a compound conflict with the structure of the compound anywhere in the present application, the structure supersedes the name and is intended to be controlling.

Example 1: Synthesis of 3-(2-(dispiro[2.0.2$^4$.1$^3$]heptan-7-yl)ethoxy)-1H-pyrazole-4-carboxylic acid (6)

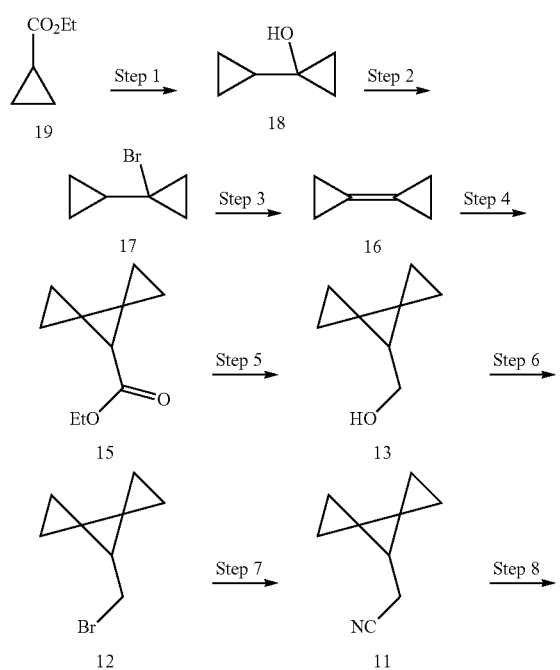

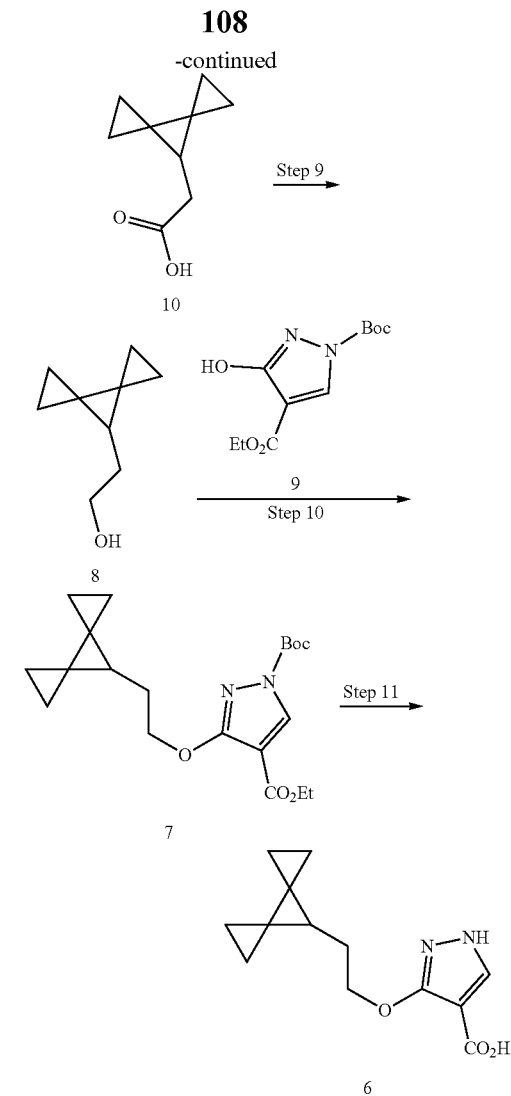

Step 1: Synthesis of [1,1'-bi(cyclopropan)]-1-ol (18)

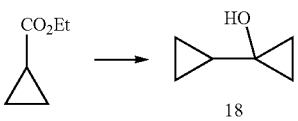

A solution of methyl cyclopropanecarboxylate (109 g, 1.09 mol) in 2-MeTHF (1.31 L) and titanium(IV) isopropoxide (71 mL, 240.6 mmol) was stirred in a Morton flask then cooled to 18° C. Ethylmagnesium bromide (753 mL of 3 M, 2.259 mol) was added dropwise over 2 h to control the temperature between 15 to 20° C. The mixture was stirred for another 2 h then cooled to 5° C. and quenched drop-wise (slowly) with cold (~5-10° C.) NaHSO$_4$ (1.31 L of 20% w/v, 2.182 mol) while keeping the temperature below 10° C. The organic phase was isolated and the aqueous phase was re-extracted with hexanes (500 mL). The aqueous phase was discarded. The organic phases were combined, washed with sat. aq. NaHCO$_3$ (200 mL of 10% w/v, 238 mmol), dried over Na$_2$SO$_4$, and concentrated (30° C./~40 torr) to afford 108.6 g of [1,1'-bi(cyclopropan)]-1-ol as a pale yellow liquid. The sample contained ~8 wt % 2-MeTHF and 2 wt % iPrOH by ¹H NMR, so the corrected yield of the desired product was 91%.

¹H NMR (400 MHz, Chloroform-d) δ 1.99 (s, 1H), 1.35 (tt, J=8.2, 5.1 Hz, 1H), 1.22 (dd, J=9.0, 6.1 Hz, 1H), 0.70-0.65 (m, 2H), 0.52-0.45 (m, 2H), 0.43-0.38 (m, 2H), 0.21-0.15 (m, 2H).

Step 2: Synthesis of 1-bromo-1,1'-bi(cyclopropane) (17)

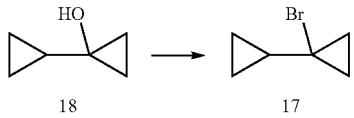 [SMILES: OC1(C2CC2)CC1 ; BrC1(C2CC2)CC1]

A solution of Ph₃P (216 g, 824 mmol) in CH₂Cl₂ (770 mL) was cooled to −10° C. A solution of Br₂ (132 g, 42.6 mL, 824 mmol) in CH₂Cl₂ (154 mL) was added over 15 min. The mixture was stirred for an additional 15 min then cooled further to −20° C. when pyridine (6.21 g, 6.35 mL, 78.5 mmol) was added. A solution of [1,1'-bi(cyclopropan)]-1-ol (77.0 g, 785 mmol), pyridine (65.2 g, 66.7 mL, 824 mmol), and DCM (385 mL) was added dropwise while maintaining the temperature at about −15 to −20° C. The mixture was stirred at −20 to −10° C. for 45 min then heated to reflux (42° C.) until the reaction was completed (~1 h). The mixture was cooled to ambient temperature and concentrated to remove most of the solvent. The mixture was slurried in hexanes (1 L), allowed to stand overnight, then filtered. The filter-cake was washed with hexanes (2×500-mL). Then the combined filtrate and washings were washed with aq HCl (392 mL of 1 M, 392 mmol), then water (200 mL), then dried over Na₂SO₄, and concentrated to afford 82.2 g (65% yield) of 1-bromo-1,1'-bi(cyclopropane) as a yellow liquid.

¹H NMR (400 MHz, Chloroform-d) δ 5.30 (s, 1H), 1.61 (tt, J=8.2, 5.0 Hz, 1H), 1.07-1.02 (m, 2H), 0.78-0.66 (m, 2H), 0.67-0.51 (m, 2H), 0.35-0.21 (m, 2H).

Step 3: Synthesis of 1,1'-bi(cyclopropylidene) (16)

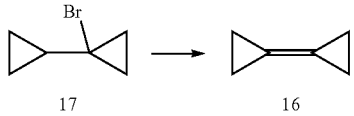 [SMILES: BrC1(C2CC2)CC1 ; C1CC1=C1CC1]

A solution of t-BuOK (62.7 g, 559 mmol) in DMSO (225 mL) was stirred at ambient temperature. Then a solution of crude 1-bromo-1-cyclopropyl-cyclopropane (75.0 g, 465.7 mmol) in DMSO (150 mL) was added dropwise while the temperature was maintained between 10 to 25° C. with an ice-water bath. After 1 h the addition was completed and the mixture was allowed to warm to ambient temperature. After 20 min ¹HNMR showed that the reaction was reasonably clean and nearly completed.

After stirring overnight the product was isolated by flask-to-flask vacuum-distillation with the condenser at −5° C. and the receiver in an ice/i-PrOH bath. Vacuum was applied slowly from 100 to 40 torr. The pot external temperature was increased from 70 to 80° C. The distillate slowly collected (20-30° C. head temperature) in the receiver to afford 40.8 g of a colorless liquid that was a mixture of the desired product, t-BuOH and small amount of DMSO (1.0:1.1:0.15 molar ratio).

The product above was re-distilled using a 14/20 6-inch Vigreaux column at atmospheric pressure under a nitrogen blanket. The condenser was cooled at 2° C. and the receiver was placed in an ice-water bath. The distillate collected (bp 60-62° C.) afforded 28.7 g as a colorless liquid which was again a mixture of desired product, t-BuOH, and DMSO (1.0:1.8:0.15 molar ratio). The calculated yield (¹H NMR) was 10.0 g of 1,1'-bi(cyclopropylidene).

The distillation was continued under reduced pressure (50-30 torr) while the external pot temperature was increased from ambient temperature to 70° C. Additional distillate was collected in a cooled receiver (ice/i-PrOH) to collect an additional 6.9 g of 1,1'-bi(cyclopropylidene) containing trace amounts of t-BuOH and DMSO, for a total yield of 16.9 g (45%).

¹H NMR (400 MHz, Chloroform-d) δ 1.19 (s, 8H).

Step 4: Synthesis of ethyl dispiro[2.0.2⁴.1³]heptane-7-carboxylate (15)

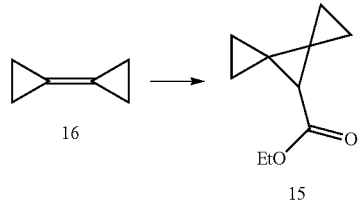 [SMILES: C1CC1=C1CC1 ; CCOC(=O)C1C2(CC2)C12CC2]

A nitrogen-purged, 1-L jacketed reaction vessel was charged with Rh(OAc)₂ (14.43 g, 32.64 mmol), 1,1'-bi(cyclopropylidene) (170 g, 2.122 mol), and DCM (377.7 mL). The jacket was cooled at 0° C. (internal temperature 0.6° C.). A metering pump was used to add ethyl 2-diazoacetate (411.6 g, 379.4 mL, 3.607 mol) at 0.08 mL/min (4.8 mL/h). After 68 h (295 mL added), the addition was stopped (total ethyl 2-diazoacetate added was ~320 mL or 1.3 equivalents). The dark amber reaction mixture was warmed to 20° C. Celite was added (29 g; 2 g/g catalyst) and the reaction mixture was allowed to stand overnight.

A portion of the reaction mixture was filtered using a Celite-packed bed. A DCM-packed SiO₂ (80 g) bed was prepared. The remaining unfiltered suspension was slurried with SiO₂ (40 g) and filtered using the SiO₂ bed under vacuum. The flask/bed were washed with DCM (3×400-mL). The Celite-filtrate and the SiO₂ filtrate/washings were combined and concentrated to afford 409 g (116%) of a dark brown liquid.

A bed of SiO₂ (300 g) was packed with hexanes. The concentrated obtained above was dissolved in heptane/hexanes (~300 mL). The resulting solution was loaded onto the packed SiO₂ bed using hexanes (400 mL). The column was eluted with 10% EtOAc/hexanes, collecting ~400-mL fractions—the eluting solvent turned orange (brown band stayed on the SiO₂ bed): Fraction 1 orange; Fraction 2 yellow; Fraction 3 light yellow; Fraction 4 yellow-tinted. Fractions 1-3 were combined and concentrated to afford 341.6 g of ethyl dispiro[2.0.2⁴.1³]heptane-7-carboxylate (97% yield) as an orange liquid.

¹H NMR (400 MHz, Chloroform-d) δ 4.13 (q, J=7.2 Hz, 2H), 2.24 (s, 1H), 1.24 (t, J=7.1 Hz, 3H), 1.08-0.94 (m, 4H), 0.90-0.82 (m, 2H), 0.78 (ddd, J=8.3, 5.1, 3.6 Hz, 2H).

Step 5: Synthesis of dispiro[2.0.2⁴.1³]heptan-7-ylmethanol (13)

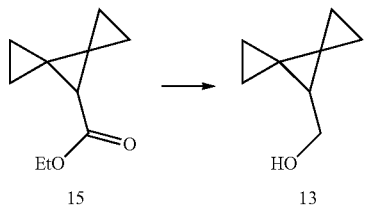 [SMILES: CCOC(=O)C1C2(CC2)C12CC2 ; OCC1C2(CC2)C12CC2]

To a slurry of LiAlH₄ (24 g, 616.0 mmol) in THF (750 mL) was slowly added a solution of ethyl dispiro[2.0.2⁴.1³]heptane-7-carboxylate (100 g, 601.6 mmol) in THF (250 mL) and the mixture came to a gentle reflux. The reaction temperature was controlled with an ice-bath and addition rate. The addition took 90 min and the mixture was stirred at ambient temperature for 16 hr. The mixture was chilled with an ice bath and the reaction was quenched with the addition of water (24 mL, 1.332 mol), followed by NaOH (24 mL of 2 M, 48.00 mmol), and then water (72 mL, 3.997 mol). The slurry was filtered over Celite and the filtrate was concentrated in vacuo. The oil was diluted with 300 mL of DCM and dried over MgSO₄, filtered, and concentrated in vacuo affording dispiro[2.0.2⁴.1³]heptan-7-ylmethanol (58.5 g, 78%) as a light yellow oil.

¹H NMR (400 MHz, Chloroform-d) δ 3.71 (d, J=6.7 Hz, 2H), 1.71 (t, J=6.7 Hz, 1H), 1.51-1.39 (m, 1H), 0.93-0.81 (m, 4H), 0.71-0.61 (m, 2H), 0.61-0.49 (m, 2H).

Step 6: Synthesis of 7-(bromomethyl)dispiro[2.0.2⁴.1³]heptane (12)

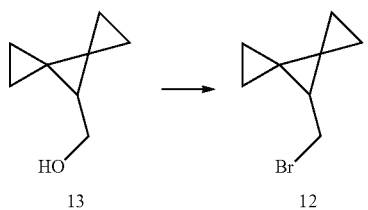 [SMILES: OCC1C2(CC2)C12CC2 ; BrCC1C2(CC2)C12CC2]

To a solution of Ph₃P (98.5 g, 375.5 mmol) in DCM (600 mL) at −15° C. was added dropwise a solution of Br₂ (59.6 g, 372.9 mmol) in DCM (100 mL). The reaction mixture was stirred at −15° C. for 15 min then chilled to −30° C. To the mixture was added dropwise a solution of dispiro[2.0.2⁴.1³]heptan-7-ylmethanol (43.2 g, 347.9 mmol) and pyridine (30 mL, 370.9 mmol) in DCM (100 mL) over 20 min. Following the addition, the reaction was stirred for 1 h at −5° C., at which time analysis by ¹H NMR showed complete reaction. The reaction mixture was concentrated in vacuo (35° C./200 torr) until approximately 100 mL of slurry remained. The slurry was diluted with ~500 mL of 10% Et₂O/hexane and the solid was filtered off. The filtrate was concentrated in vacuo affording more precipitate which was removed by filtration. The filtrate was concentrated again and the slurry was diluted with 250 mL 10% Et₂O/hexanes. The precipitate was removed by filtration and washed with 50 mL of Et₂O. The filtrate was concentrated in vacuo to afford 7-(bromomethyl)dispiro[2.0.2⁴.1³]heptane (65 g, 100%).

¹H NMR (400 MHz, Chloroform-d) δ 3.49 (d, J=7.5 Hz, 2H), 1.90 (t, J=7.5 Hz, 1H), 1.02-0.91 (m, 5H), 0.70 (ddd, J=9.2, 5.1, 4.0 Hz, 2H), 0.54 (dddd, J=8.6, 4.8, 3.7, 1.0 Hz, 2H).

The product was used in the next step without further purification.

Step 7: Synthesis of 2-(dispiro[2.0.2⁴.1³]heptan-7-yl)acetonitrile (11)

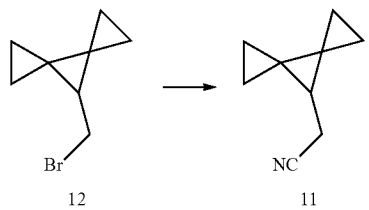 [SMILES: BrCC1C2(CC2)C12CC2 ; N#CCC1C2(CC2)C12CC2]

To a solution of 7-(bromomethyl)dispiro[2.0.2⁴.1³]heptane (65 g, 347.5 mmol) in DMSO (400 mL) was added NaCN (17.5 g, 357.1 mmol). The red mixture was stirred at ambient temperature for 16 h. The reaction was poured into Na₂CO₃ (1,000 mL) and extracted three times with Et₂O (500 mL). The combined organic phases were washed with water (500 mL), brine (500 mL), dried over MgSO₄, filtered, and concentrated in vacuo affording 2-(dispiro[2.0.2⁴.1³]heptan-7-yl)acetonitrile (45.9 g, 99%) as a dark red oil that contained residual Et₂O and PPh₃O.

¹H NMR (400 MHz, Chloroform-d) δ 2.42 (d, J=6.6 Hz, 2H), 1.69 (t, J=6.6 Hz, 1H), 1.03-0.88 (m, 4H), 0.78-0.68 (m, 2H), 0.64-0.55 (m, 2H).

Step 8: Synthesis of 2-(dispiro[2.0.2⁴.1³]heptan-7-yl)acetic acid (10)

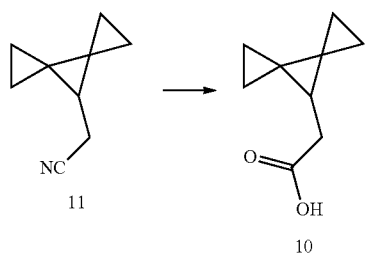 [SMILES: N#CCC1C2(CC2)C12CC2 ; O=C(O)CC1C2(CC2)C12CC2]

To a solution of 2-(dispiro[2.0.2⁴.1³]heptan-7-yl)acetonitrile (45 g, 337.9 mmol) in ethanol (300 mL) and water (100 mL) was added NaOH (100 g of 50% w/w, 1.250 mol). The mixture was stirred at 70° C. for 16 hr. The ethanol was removed in vacuo and the remaining aqueous phase was diluted with water (200 mL) and extracted two times with MTBE (400 mL). The aqueous phase was acidified with 6 M HCl (220 mL, 1.320 mol) and the dark mixture was extracted two times with MTBE (400 mL). The organic phase was washed with brine (400 mL), dried over MgSO₄, filtered, and concentrated in vacuo affording 2-(dispiro[2.0.2⁴.1³]heptan-7-yl)acetic acid (31.8 g, 62%) as a dark yellow solid that contained MTBE and trace amount of PPh₃O.

¹H NMR (400 MHz, Chloroform-d) δ 2.44 (d, J=6.9 Hz, 2H), 1.67 (t, J=6.9 Hz, 1H), 0.91 (ddd, J=9.0, 5.2, 3.9 Hz, 2H), 0.81 (dddd, J=8.9, 5.2, 4.0, 0.6 Hz, 2H), 0.68 (ddd, J=8.9, 5.2, 3.8 Hz, 2H), 0.55-0.45 (m, 2H).

Step 9: Synthesis of 2-(dispiro[2.0.2⁴.1³]heptan-7-yl)ethan-1-ol (8)

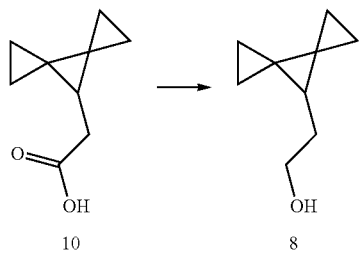 [SMILES: O=C(O)CC1C2(CC2)C12CC2 ; OCCC1C2(CC2)C12CC2]

To a solution of 2-(dispiro[2.0.2⁴.1³]heptan-7-yl)acetic acid (28.4 g, 186.6 mmol) in THF (320 mL) was added LiAlH₄ (8.2 g, 210.5 mmol) (pellets). The mixture was stirred at ambient temperature for 16 h (¹H NMR showed complete reaction). The reaction was quenched with the careful sequential addition of water (8.2 mL, 455.2 mmol), NaOH (8.2 mL of 15% w/w), then water (24.6 mL, 1.366 mol). To the slurry was added MgSO₄, and the slurry was stirred at ambient temperature for 30 min. The light yellow precipitate was filtered off using Celite and washed with MTBE. The filtrate was concentrated in vacuo (35° C., 150 torr) affording 2-(dispiro[2.0.2⁴.1³]heptan-7-yl)ethan-1-ol (24.3 g, 94% yield) as a yellow oil, which contained 9% MTBE.

¹H NMR (400 MHz, Chloroform-d) δ 3.62 (t, J=6.9 Hz, 2H), 1.68 (q, J=6.8 Hz, 2H), 1.39 (t, J=6.6 Hz, 1H), 0.89-0.74 (m, 4H), 0.65 (ddd, J=8.0, 4.7, 3.5 Hz, 2H), 0.53-0.44 (m, 2H).

Step 10: Synthesis of 1-(tert-butyl) 4-ethyl 3-(2-(dispiro[2.0.2⁴.1³]heptan-7-yl)ethoxy)-1H-pyrazole-1,4-dicarboxylate (7)

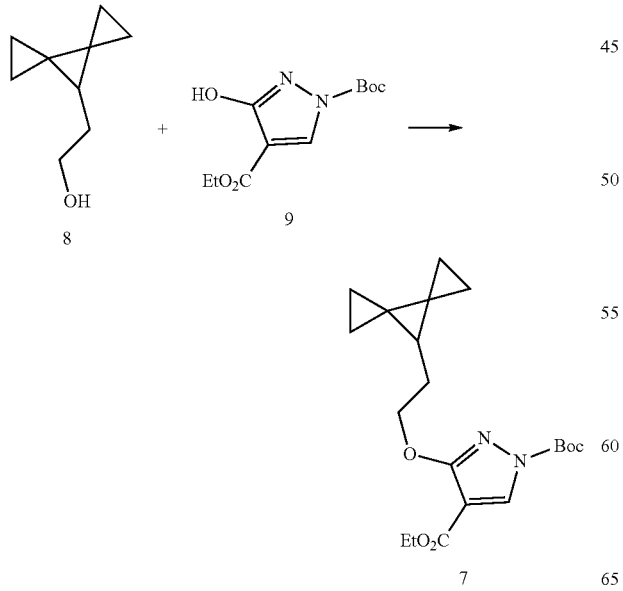

DIAD (490 mL, 2.49 mol, 1.15 equiv) was added to a suspension of 2-(dispiro[2.0.2⁴.1³]heptan-7-yl)ethan-1-ol (85 wt %, 345 g, 2.17 mol, 1 equiv), 1-tert-butyl 4-ethyl 3-hydroxy-1H-pyrazole-1,4-dicarboxylate (555.6 g, 2.17 mol, 1 equiv), and triphenylphosphine (654.6 g, 2.49 mol, 1.15 equiv) in toluene (3 L). After stirring at 40° C. overnight, the reaction was diluted with heptanes (1.2 L) and cooled to 20° C., over 60 min, allowing the bulk of the triphenylphosphine oxide-DIAD complex to crystallize out. Once at ambient temperature, the mixture was filtered, and the cake was washed with heptane (1.5 L) and suction dried. The filtrate was concentrated under reduced pressure to give crude 1-(tert-butyl) 4-ethyl 3-(2-(dispiro[2.0.2⁴.1³]heptan-7-yl)ethoxy)-1H-pyrazole-1,4-dicarboxylate as a viscous yellow oil (1.2 kg). The residue was purified by flash column chromatography, eluting with 20% ethyl acetate in hexanes. The colorless oil was diluted with heptanes (200 mL) and stirred for ~30 min at 0° C. The resulting white solid was filtered to give 1-(tert-butyl) 4-ethyl 3-(2-(dispiro[2.0.2⁴.1³] heptan-7-yl)ethoxy)-1H-pyrazole-1,4-dicarboxylate (603.7 g, 74% yield, >95% purity).

¹H NMR (300 MHz, CDCl₃) δ 8.31 (s, 1H), 4.37-4.26 (m, 4H), 1.92 (d, J=6.9 Hz, 2H), 1.64 (s, 9H), 1.36 (t, 1H), 1.32 (t, J=4.2 Hz, 3H), 0.86-0.82 (m, 4H), 0.64-0.60 (m, 2H), 0.49-0.46 (m, 2H).

Mass Spectrum (positive mode): m/z=377.3 [M+H]⁺.

Step 11: Synthesis of 3-(2-(dispiro[2.0.2⁴.1³]heptan-7-yl)ethoxy)-1H-pyrazole-4-carboxylic acid (6)

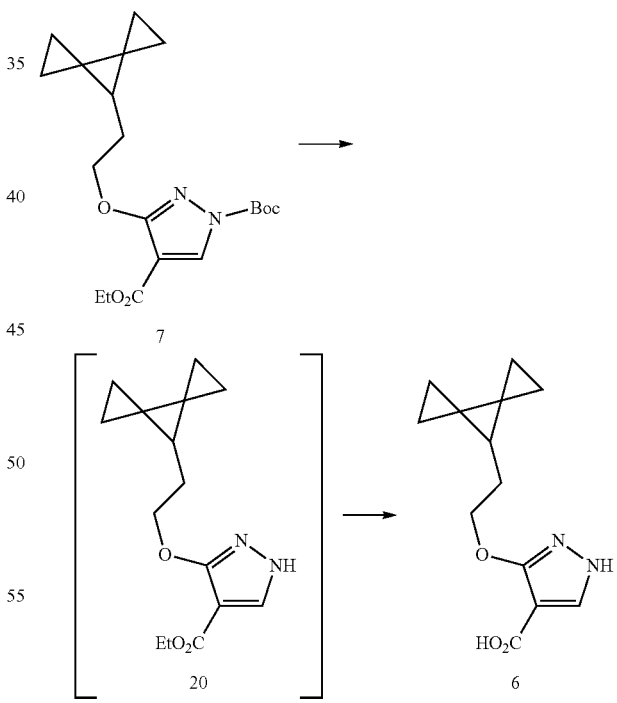

A 45% solution of potassium hydroxide in water (760 mL, 8.8 mol, 10.0 equiv) was added in portions maintaining the internal temperature at <50° C. to a heated solution (40° C.) of 1-(tert-butyl) 4-ethyl 3-(2-(dispiro[2.0.2⁴.1³]heptan-7-yl) ethoxy)-1H-pyrazole-1,4-dicarboxylate (330 g, 877 mmol, 1.0 equiv) in methanol (1 L). The reaction was stirred overnight at 50° C., at which point LCMS indicated the reaction was complete. The reaction was partially concentrated under reduced pressure to remove most of the methanol. The resulting solution was diluted with water (1.65 L) and 2-MeTHF (1 L). The layers were shaken vigorously and separated. The aqueous layer was washed again with 2-MeTHF (660 mL). The aqueous layer was cooled to 5° C. and adjusted to pH 1 with 6M aqueous HCl (2.24 L) portionwise, maintaining the internal temperature between 10 and 30° C. The product began to crystallize close to pH 7 and was accompanied with strong off-gassing. The resulting suspension was diluted with 2-MeTHF (2.7 L) and the product was allowed to dissolve into the organic layer. Stirring was stopped and the layers were separated. The aqueous layer was re-extracted with 2-MeTHF (660 mL). The combined organic layers were washed with saturated brine (660 mL), dried over sodium sulfate, and filtered. The filtrate was concentrated under reduced pressure at 50° C. Heptanes (2 L) were added and the mixture was partially concentrated under reduced pressure to remove most of the 2-MeTHF. The mixture was stirred and cooled to room temperature. The resulting solid was filtered and washed with heptanes (660 mL). The product was dried under vacuum at 35° C. overnight to give 3-(2-(dispiro[2.0.2$^4$.1$^3$]heptan-7-yl)ethoxy)-1H-pyrazole-4-carboxylic acid (200.2 g, 92% yield, >99% purity) as a white solid.

$^1$H NMR (300 MHz, CDCl$_3$) δ 7.96 (s, 1H), 4.13 (t, J=13.0 Hz, 2H), 1.74 (t, J=6.9 Hz, 2H), 1.41 (t, 1H), 0.83-0.77 (m, 4H), 0.62-0.57 (m, 2H), 0.45-0.41 (m, 2H).

Mass Spectrum (positive mode): m/z=497.2 [2M+H]$^+$.

Example 2: Alternative Synthesis of 3-(2-(dispiro[2.0.2$^4$.1$^3$]heptan-7-yl)ethoxy)-H-pyrazole-4-carboxylic acid (6)

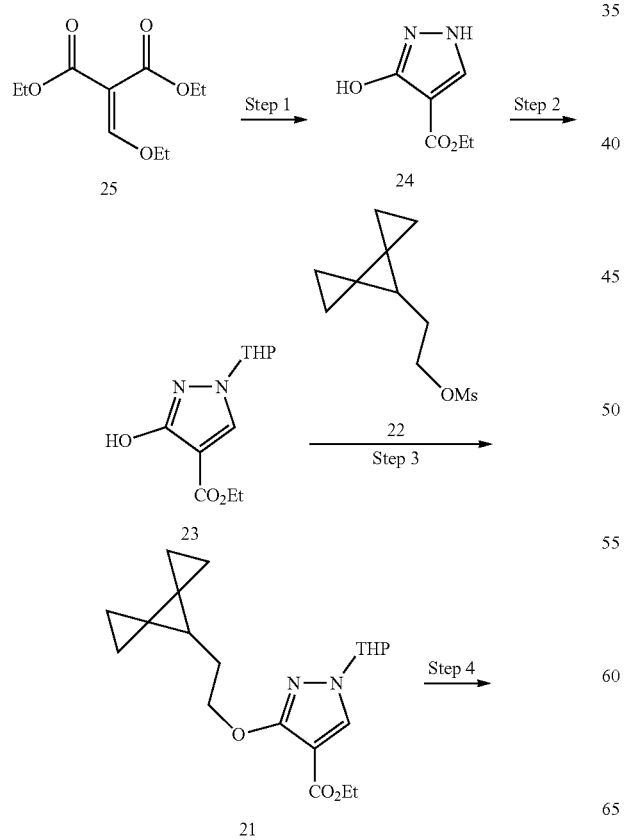

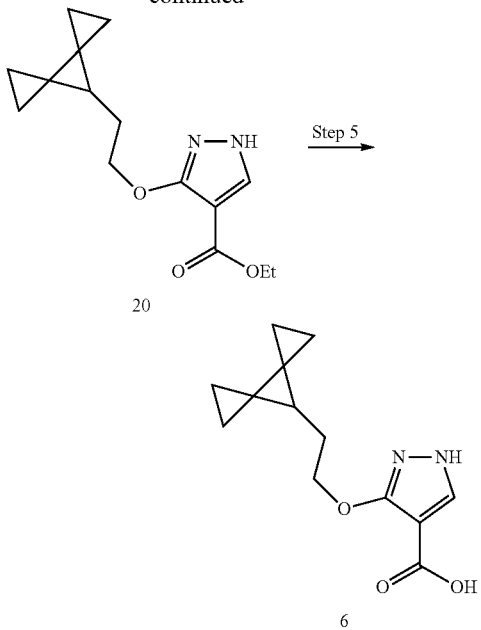

Step 1: Synthesis of ethyl 3-hydroxy-1H-pyrazole-4-carboxylate (24)

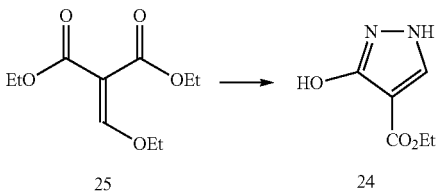 [SMILES: CCOC=C(C(=O)OCC)C(=O)OCC ; CCOC(=O)c1c[nH]nc1O]

55% w/w hydrazine hydrate (29 mL, 515 mmol, 1.03 equiv) was added dropwise to a solution of diethyl 2-(ethoxymethylene)propanedioate (108 g, 500 mmol, 1 equiv) in ethanol (0.45 L). The resulting mixture was heated to reflux for 20 h, after which HPLC indicated complete reaction. The mixture was a slurry upon cooling to ambient temperature. The solid was collected by filtration, washed with EtOH (2×100 mL), and dried in a vacuum oven at 40° C. to afford 46 g (60%) of ethyl 3-hydroxy-1H-pyrazole-4-carboxylate as an off-white solid.

Step 2: Synthesis of ethyl 3-hydroxy-1-(tetrahydro-2H-pyran-2-yl)-1H-pyrazole-4-carboxylate (23)

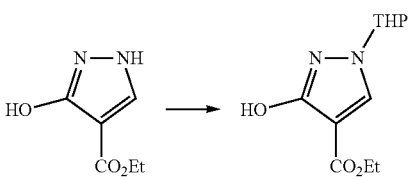

2,3-Dihydropyran (18 mL, 197.2 mmol, 1.03 equiv) was added to a solution of ethyl 3-hydroxy-1H-pyrazole-4-carboxylate (30 g, 192 mmol, 1 equiv) in acetonitrile (180 mL) and the resulting mixture was cooled at 0° C. p-Toluenesulfonic acid hydrate (1.26 g, 6.6 mmol, 0.035 equiv) was added as a solid in one portion. After 2 h the mixture was allowed to warm to 10° C. After 2 h, HPLC indicated complete conversion. The solid was collected by filtration, washed with acetonitrile (2×35 mL), and dried in a vacuum oven at 40° C. to give ethyl 3-hydroxy-1-(tetrahydro-2H-pyran-2-yl)-1H-pyrazole-4-carboxylate (39.2 g, 85%) as an off-white solid.

Step 3: Synthesis of ethyl 3-(2-(dispiro[2.0.2$^4$.1$^3$]heptan-7-yl)ethoxy)-1-(tetrahydro-2H-pyran-2-yl)-1H-pyrazole-4-carboxylate (21)

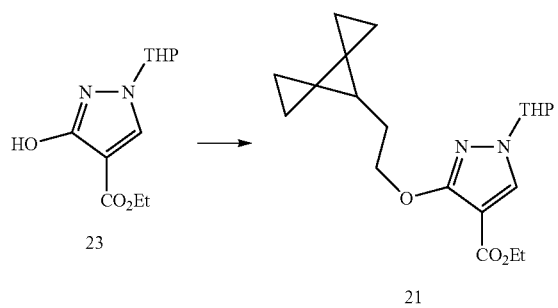

A mixture of 2-(dispiro[2.0.2$^4$.1$^3$]heptan-7-yl)ethyl methanesulfonate (9.2 g, 43.2 mmol, 1.04 equiv) and ethyl 3-hydroxy-1-(tetrahydro-2H-pyran-2-yl)-1H-pyrazole-4-carboxylate (10 g, 41.6 mmol, 1 equiv) in DMF (50 mL) was stirred at room temperature. Then 1,1,3,3-tetramethylguanidine (5.7 mL, 45.7 mmol, 1.1 equiv) was added, and the mixture was heated at 60° C. After heating for 12 h, HPLC showed complete reaction. 100 mL of water was added followed by 75 mL of ethyl acetate. The phases were separated, and the organic layer was washed with 25 ml of water. The organic layer was filtered, concentrated, and dried in a vacuum oven at 40° C. to give ethyl 3-(2-(dispiro[2.0.2$^4$.1$^3$]heptan-7-yl)ethoxy)-1-(tetrahydro-2H-pyran-2-yl)-1H-pyrazole-4-carboxylate (14.3 g) as a light yellow solid, which was used without further purification.

Step 4: Synthesis of ethyl 3-(2-(dispiro[2.0.2$^4$.1$^3$]heptan-7-yl)ethoxy)-1H-pyrazole-4-carboxylate (20)

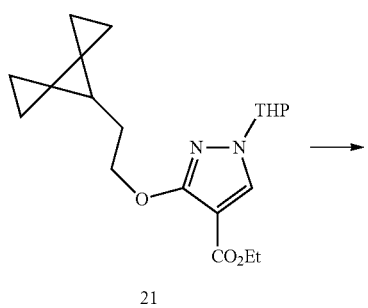

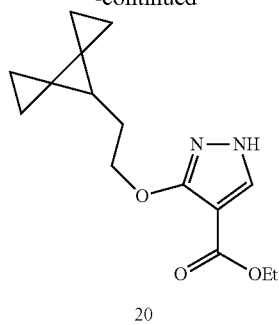

A solution of ethyl 3-(2-(dispiro[2.0.2$^4$.1$^3$]heptan-7-yl)ethoxy)-1-(tetrahydro-2H-pyran-2-yl)-1H-pyrazole-4-carboxylate (7.15 g, 19.7 mmol, 1 equiv) in 4N HCl in 1,4-dioxane (138 mL, 572 mmol, 29 equiv) was stirred at room temperature. A precipitate started forming after about 30 min stirring. After 1 h, heptane (75 mL) was added and the solid was collected by filtration, washed with heptane (2×10 mL), and dried in a vacuum oven at 40° C. to afford ethyl 3-(2-(dispiro[2.0.2$^4$.1$^3$]heptan-7-yl)ethoxy)-1H-pyrazole-4-carboxylate (4.03 g) as a light yellow solid, which was used subsequently.

Step 5: Synthesis of 3-(2-(dispiro[2.0.2$^4$.1$^3$]heptan-7-yl)ethoxy)-1H-pyrazole-4-carboxylic acid (6)

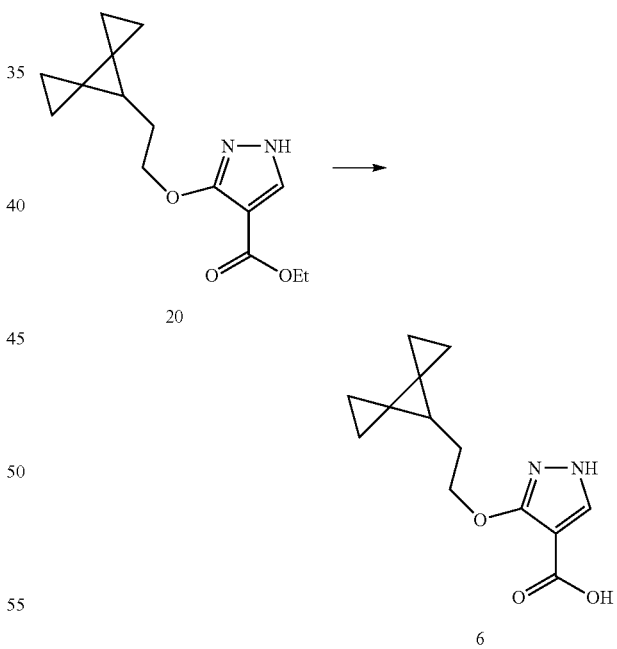

45% Aqueous potassium hydroxide solution (6 g, 106 mmol, 10 equiv) was added to a solution of ethyl 3-(2-(dispiro[2.0.2$^4$.1$^3$]heptan-7-yl)ethoxy)-1H-pyrazole-4-carboxylate (4.03 g, 14.5 mmol, 1.0 equiv) in methanol (12 mL) and the mixture was stirred at 45° C. for 20 h. Water (20 mL) and 2-methyltetrahydrofuran (18 mL) were added and the layers were separated. The water layer was washed with 2-methyltetrahydrofuran (8 mL) and adjusted to pH 1 with 6 N HCl. 2-Methyltetrahydrofuran (35 mL) was added and the layers were separated. The water phase was washed with 2-methyltetrahydrofuran (20 mL). The organic layers were combined and washed with brine (10 mL), dried over sodium sulfate, and concentrated under reduced pressure to give 3-(2-(dispiro[2.0.2⁴.1³]heptan-7-yl)ethoxy)-1H-pyrazole-4-carboxylic acid as a white solid (2.73 g, 95.3% purity, 48% yield over 3 steps from 2-(dispiro[2.0.2⁴.1³]heptan-7-yl)ethyl methanesulfonate).

Example 3: Alternative Synthesis of dispiro [2.0.2⁴.1³]heptane-7-carboxylic acid (14)

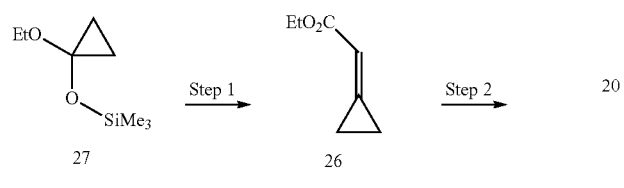

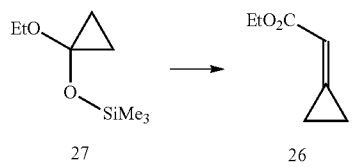 [SMILES: CCOC1(O[Si](C)(C)C)CC1 ; CCOC(=O)C=C1CC1]

Step 1: Synthesis of ethyl 2-cyclopropylideneacetate (26)

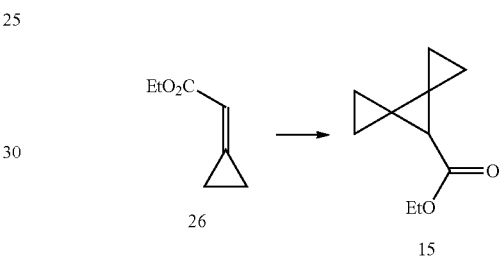

(1-Ethoxycyclopropoxy)trimethylsilane (200 g, 1147 mmol, 1.1 equiv) was added to a 3000 mL round-bottomed flask equipped with a magnetic stir bar. Then methanol (600 mL) was added and the resulting solution was stirred overnight at room temperature. The solvent was evaporated under reduced pressure (water bath at 25° C.). The oil that remained was dissolved in tetraethylene glycol dimethyl ether (700 mL) with a magnetic stir bar. Then benzoic acid (28 g, 229 mmol, 0.22 equiv) was added and the resulting mixture was heated to 100° C. (heat block). Ethyl (triphenylphosphoranylidene) acetate (360 g, 1033 mmol, 1.0 equiv) was dissolved in dichloromethane (550 mL) in a 1000 mL addition funnel and added dropwise to the above solution of cyclopropanone over a 2 h time period. After the addition, the switch of addition funnel was closed to collect condensed dichloromethane. The resulting mixture was heated at 100° C. for another h and then cooled to room temperature. Then the reaction mixture was purified by fractional distillation at 0.54 Torr between 83-100° C. (cooling temperature of fluid in condenser was at −6° C., all distillate under this condition was identified as the product) to give a total of crude ethyl 2-cyclopropylideneacetate (164.19 g, 61% purity by Q-NMR). The crude ethyl 2-cyclopropylideneacetate was dissolved in pentane (400 mL), washed with ice cold saturated sodium carbonate solution (100 mL), dried over sodium sulfate, filtered, and concentrated under reduced pressure (water bath at 25° C.) to give ethyl 2-cyclopropylideneacetate (92.52 g, 80% purity by Q-NMR, 57% yield) as a colorless liquid ¹H NMR (300 MHz, CDCl₃) δ 6.23 (t, J=1.8 Hz, 1H), 4.22 (q, J=7.2 Hz, 2H), 1.49-1.42 (m, 2H), 1.33-1.20 (m, 5H).

Mass Spectrum (positive mode): m/z=125.8 [M]⁺.

Step 2: Synthesis of ethyl dispiro[2.0.2⁴.1³]heptane-7-carboxylate (15)

Cyclopropyl(diphenyl)sulfonium (tetrafluoroborate) (95%, 265 g, 800 mmol, 1.01 equiv) was dissolved in non-anhydrous dimethyl sulfoxide (4000 mL) in a 22 L round-bottomed flask equipped with an overhead stirrer. Room temperature water was added to the secondary container. Ethyl 2-cyclopropylideneacetate (79% purity by Q-NMR, 33.75 g; 80% purity by Q-NMR, 92.52 g, 793 mmol, 1.0 equiv) was added, followed by cesium hydroxide hydrate (containing about 10% H₂O, 133 g, 800 mmol, 1.01 equiv) in one portion. At 120 min, ice was added to the secondary container and the reaction was diluted with ice cold methyl tert-butyl ether (8 L). Ice cold saturated ammonium chloride solution (6 L) was added slowly while keeping the temperature below 25° C. The aqueous layer was extracted with methyl tert-butyl ether (4 L×3), and the combined organic layers were dried over sodium sulfate, filtered, and concentrated under reduced pressure (water bath at 25° C.) to give a total of crude ethyl dispiro [2.0.2⁴.1³]heptane-7-carboxylate (316.67 g) as a pale yellow liquid.

Crude ethyl dispiro[2.0.2⁴.1³]heptane-7-carboxylate with 17% ethyl 2-cyclopropylideneacetate (68.17 g, ~170.7 mmol, 1.0 equiv) was dissolved in non-anhydrous dimethyl sulfoxide (300 mL) at room temperature. Cyclopropyl(diphenyl)sulfonium (tetrafluoroborate) (95%, 19.2 g, 58 mmol, 0.34 equiv) was added, followed by cesium hydroxide hydrate (containing about 10% H₂O, 9.7 g, 58 mmol, 0.34 equiv) in one portion. At 120 min, the reaction was diluted with methyl tert-butyl ether (800 mL). The DMSO layer was separated and cooled to 0° C. with an ice bath. The MTBE layer was washed with saturated ammonium chloride solution (650 mL). This aqueous layer was separated and slowly added to the above DMSO mixture. The resulting aqueous layer was extracted with methyl tert-butyl ether (800 mL), and the combined organic layers were dried over sodium sulfate, filtered, and concentrated under reduced pressure (water bath at 25° C.) to give crude ethyl dispiro [2.0.2$^4$.1$^3$]heptane-7-carboxylate. (Another batch (204.51 g of crude ethyl dispiro[2.0.2$^4$.1$^3$]heptane-7-carboxylate with 17% ethyl 2-cyclopropylideneacetate used) of this reaction was processed in same manner, and both batches were combined for purification. Then this combined mixture was purified by fractional distillation at 0.68 Torr between 68-120° C. (cooling temperature of fluid in condenser was at −6° C., all distillate under this condition was identified as the product) to give crude ethyl dispiro[2.0.2$^4$.1$^3$]heptane-7-carboxylate (83.32 g, 65% purity by Q-NMR, 47% yield) as a colorless liquid.

$^1$H NMR (300 MHz, CDCl$_3$) δ 6.23 (t, J=1.8 Hz, 1H), 4.22 (q, J=7.2 Hz, 2H), 1.49-1.42 (m, 2H), 1.33-1.20 (m, 5H).

Mass Spectrum (positive mode): m/z=165.1 [M−H]$^+$.

Step 3: Synthesis of dispiro[2.0.2$^4$.1$^3$]heptane-7-carboxylic acid (14)

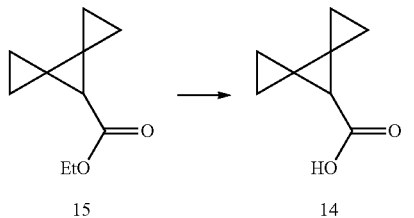 [SMILES: CCOC(=O)C1C2(CC2)C12CC2 ; O=C(O)C1C2(CC2)C12CC2]

To a crude mixture of ethyl dispiro[2.0.2$^4$.1$^3$]heptane-7-carboxylate (5.0 g, 30.0 mmol, 1.0 equiv) and diphenyl sulfide (6.24 g) in methanol/THF (8:1, 126 mL) was added lithium hydroxide (0.72 g, 30.0 mmol, 1.0 equiv) and a solution of sodium hydroxide (21.0 g, 525.0 mmol, 17.5 equiv) in water (30 mL). The resulting mixture was stirred at 40° C. overnight. The solvents were removed under reduced pressure, then the residue was dissolved in water (80 mL) and washed with methyl tert-butyl ether (80 mL). The pH of the aqueous layer was adjusted to 2 using 5N HCl (~110 mL). The precipitate was collected by suction filtration and dried to constant weight to give dispiro[2.0.2$^4$.1$^3$] heptane-7-carboxylic acid (2.98 g, 72% yield, >95% purity) as a white solid.

$^1$H NMR (300 MHz, CDCl$_3$) δ 2.26 (s, 1H), 1.11-1.02 (m, 4H), 0.90-0.80 (m, 4H).

Mass Spectrum (positive mode): m/z=137.0 [M−H]$^+$.

Example 4: Alternative Synthesis of 2-(dispiro [2.0.2$^4$.1$^3$]heptan-7-yl)acetic acid (10)

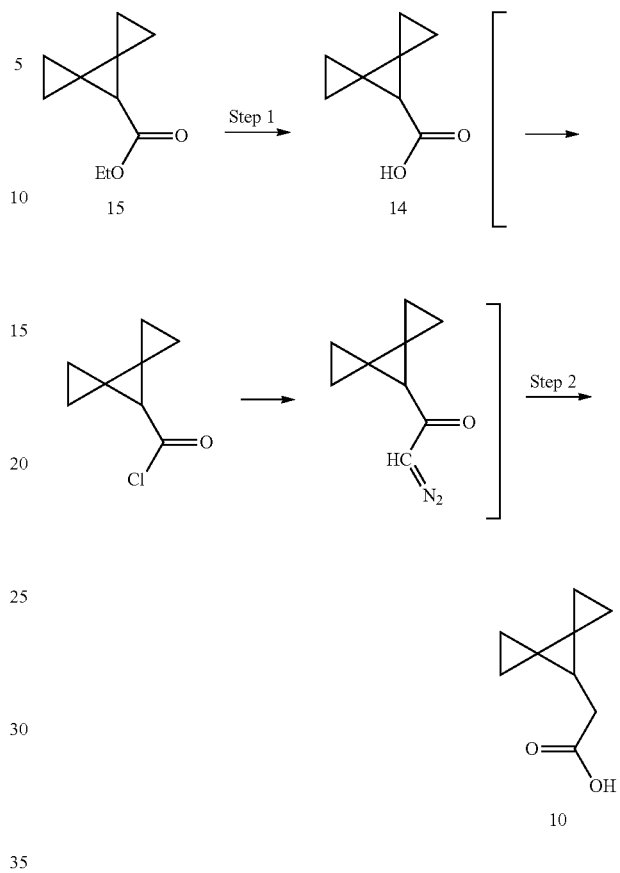

Step 1: Synthesis of dispiro[2.0.2$^4$.1$^3$]heptane-7-carboxylic acid (14)

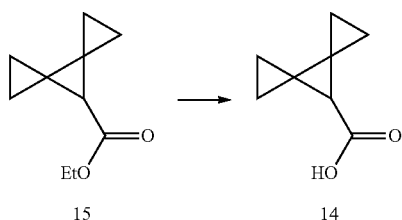 [SMILES: CCOC(=O)C1C2(CC2)C12CC2 ; O=C(O)C1C2(CC2)C12CC2]

Sodium hydroxide (21.5 g, 542 mmol, 2.0 equiv) was added to a solution of ethyl dispiro[2.0.2$^4$.1$^3$]heptane-7-carboxylate (45.0 g, 271 mmol, 1 equiv) in a 4:1 mixture of methanol and water (500 mL) and stirred at 55° C. for 4 h. LC-MS indicated the reaction was complete. Most of solvents were removed under reduced pressure, then the residue was suspended in water (100 mL) and the pH was adjusted to 2 using 5N HCl. The precipitate that formed was collected by suction filtration and dried to constant weight to give dispiro[2.0.2$^4$.1$^3$]heptane-7-carboxylic acid (31 g, 85% yield, >95% purity) as an off-white solid.

$^1$H NMR (300 MHz, CDCl$_3$) δ 2.25 (s, 1H), 1.05 (m, 4H), 0.88-0.96 (m, 4H).

Mass Spectrum (positive mode): m/z=136.9 [M−H]$^+$.

Step 2: Synthesis of 2-(dispiro[2.0.2⁴.1³]heptan-7-yl)acetic acid (10)

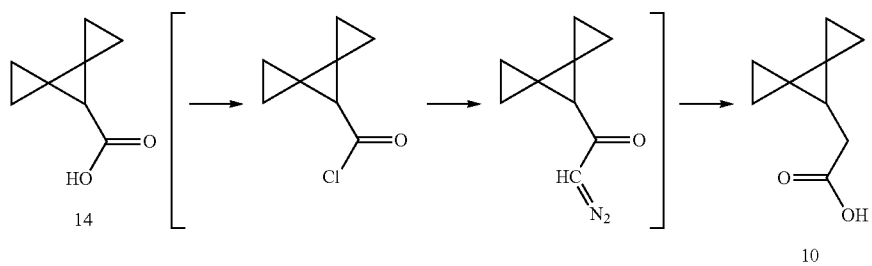

Thionyl chloride (176 mL, 2.4 mol, 9.6 equiv) was added to dispiro[2.0.2⁴.1³]heptane-7-carboxylic acid (35 g, 251 mmol, 1.0 equiv), and the resulting solution was heated at 60° C. for two h. The reaction was cooled to room temperature and concentrated under reduced pressure, and then azeotroped with toluene (2×50 mL) until all the thionyl chloride was removed. The residue was diluted with anhydrous acetonitrile (3 L). Trimethylsilyl diazomethane (2M in hexanes, 190 mL, 380 mmol, 1.5 equiv) was added over 5 min. After stirring for 2 h, silver acetate (64 g, 380 mmol, 1.5 equiv), triethylamine (70 mL, 502 mmol, 2.0 equiv) and water (200 mL) were sequentially added. After stirring overnight, the reaction was filtered through a 2 inch pad of Celite, which was rinsed with acetonitrile (100 mL). The combined filtrates were concentrated under reduced pressure to remove most of the acetonitrile. The resulting semi solid was diluted with 1N HCl (300 mL) and dichloromethane (300 mL). The mixture was filtered again through Celite (1 inch pad), which was washed with additional dichloromethane (100 mL). The layers were separated and the organic layer was dried over sodium sulfate and concentrated under reduced pressure to give 2-(dispiro[2.0.2⁴.1³]heptan-7-yl)acetic acid (28 g, 78% yield, 85% purity by GC-MS) as a yellow solid (containing ~2.3% of dispiro[2.0.2⁴.1³]heptane-7-carboxylic acid).

$^1$H NMR (400 MHz, Chloroform-d) δ 2.44 (d, J=6.9 Hz, 2H), 1.67 (t, J=6.9 Hz, 1H), 0.91 (ddd, J=9.0, 5.2, 3.9 Hz, 2H), 0.81 (dddd, J=8.9, 5.2, 4.0, 0.6 Hz, 2H), 0.68 (ddd, J=8.9, 5.2, 3.8 Hz, 2H), 0.55-0.45 (m, 2H).

Example 5: Alternative Synthesis of 2-(dispiro[2.0.2⁴.1³]heptan-7-yl)acetic acid (10)

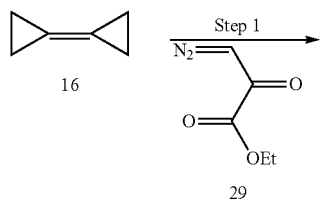

-continued

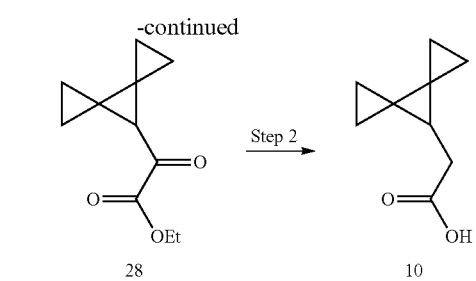

Step 1: Synthesis of ethyl 2-(dispiro[2.0.2⁴.1³]heptan-7-yl)-2-oxoacetate (28)

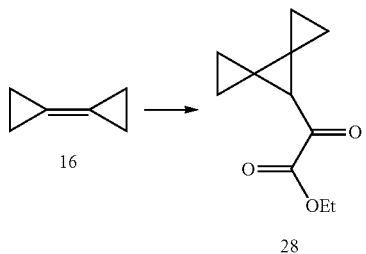 [SMILES: C1CC1=C1CC1 ; CCOC(=O)C(=O)C1C2(CC2)C12CC2]

A solution of ethyl 3-diazo-2-oxopropionate (16.2 g, 125 mmol, 2.0 equiv) in dichloromethane (~48 mL; total volume of solution was 60 mL) was added to a suspension of rhodium octanoate dimer (0.78 g, 1 mmol, 0.016 equiv) and 1,1'-bi(cyclopropylidene) (5 g, 62.5 mmol, 1 equiv) in dichloromethane (10 mL) at 0° C. by a syringe pump at 0.04 mL/min over 24 h, keeping the needle tip under the solvent surface. After 24 h, $^1$H-NMR analysis showed 80% conversion of starting material (including ~10% of homo-coupling by-products). The reaction mixture was allowed to warm up to room temperature, and the solvent was removed under reduced pressure. The residue was purified by flash column chromatography, eluting with a gradient of 0 to 30% ethyl acetate in heptanes (RediSep 2×220 g) to give ethyl 2-(dispiro[2.0.2⁴.1³]heptan-7-yl)-2-oxoacetate (7.1 g, 58% yield, >95% purity by $^1$HNMR) as a light-yellow liquid.

$^1$H NMR (300 MHz, CDCl₃) δ 4.28 (q, J=7.2 Hz, 2H), 3.24 (s, 1H), 1.35 (t, J=7.2 Hz, 3H), 1.15-1.09 (m, 2H), 1.01-0.95 (m, 2H), 0.92-0.80 (m, 4H).

Mass spectrum (positive mode): m/z=195.1 [M+H]⁺.

Step 2: Synthesis of 2-(dispiro[2.0.2⁴.1³]heptan-7-yl)acetic acid (10)

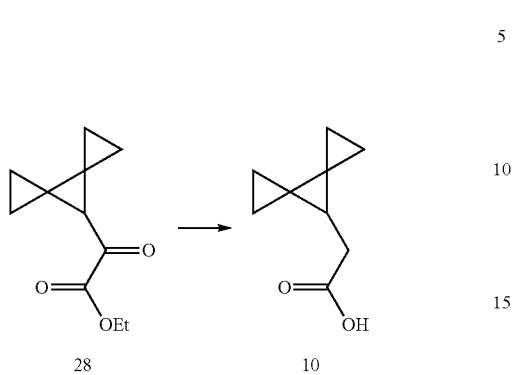

Ethyl 2-(dispiro[2.0.2⁴.1³]heptan-7-yl)-2-oxoacetate (5 g, 25.7 mmol, 1.0 equiv) was added dropwise to a solution of hydrazine hydrate (50-60% in water, 4.95 g, 77 mmol, 3.0 equiv) and water (5 mL) at −20° C. The reaction mixture became a loose solid after addition. The mixture was warmed to room temperature over 30 min and heated to 80° C. for 5 min. After the reaction mixture was cooled to room temperature, potassium hydroxide (3.6 g, 64.4 mmol, 2.5 equiv) was added in three portions while the reaction mixture became a solution. The reaction was stirred at 80° C. for 16 h, after which GC-MS indicated the reaction was complete. The reaction mixture was cooled to room temperature, diluted with water (15 mL), and washed with diethyl ether (30 mL). The aqueous layer was adjusted to pH 1 with concentrated HCl (~6 mL). The aqueous layer was extracted with toluene (4×50 mL). The combined organic layer was washed with brine (50 mL), dried over sodium sulfate, and concentrated under reduced pressure to give 2-(dispiro[2.0.2⁴.1³]heptan-7-yl)acetic acid (3.2 g, 82% yield, 94% purity by $^1$HNMR and GC-MS) as a light yellow solid.

$^1$H NMR (300 MHz, CDCl$_3$) δ 2.44 (d, J=6.9 Hz, 1H), 1.63 (t, 1H), 0.91-0.88 (m, 2H), 0.82-0.80 (m, 2H), 0.68 (m, 2H), 0.52 (m, 2H).

Mass Spectrum (positive mode): m/z=151.1 [M−H]⁺.

Example 6: Alternative Synthesis of 1-(tert-butyl) 4-ethyl 3-(2-(dispiro[2.0.2⁴.1³]heptan-7-yl)ethoxy)-1H-pyrazole-1,4-dicarboxylate (7)

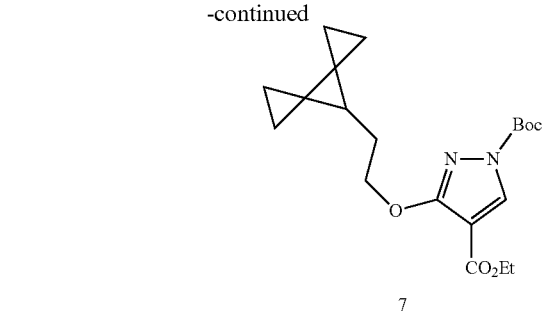

Step 1: Synthesis of 2-(dispiro[2.0.2⁴.1³]heptan-7-yl)ethyl methanesulfonate (22)

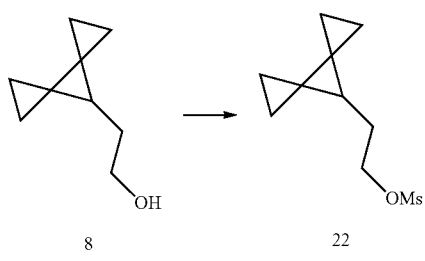 [SMILES: OCCC1C2(CC2)C12CC2 ; CS(=O)(=O)OCCC1C2(CC2)C12CC2]

A mixture of 2-(dispiro[2.0.2⁴.1³]heptan-7-yl)-ethan-1-ol (20 g, 144.6 mmol, 1 equiv) and triethylamine (26.1 mL, 185.8 mmol; 1.28 equiv) in 2-MeTHF (160 mL) was cooled at 0° C. A solution of MsCl (15.1 mL, 193.7 mmol; 1.34 equiv) in 2-MeTHF (90 mL) was added dropwise over 1 h while maintaining the reaction temperature at 0° C. After the addition was completed, the mixture was stirred at 0° C. for an additional 1 h. The mixture was allowed to warm to ambient temperature. The reaction mixture was quenched with water (80 mL) and the phases were separated. The organic phase was washed with saturated aqueous NaHCO$_3$ (80 mL), dried over Na$_2$SO$_4$, filtered, and concentrated under reduced pressure. The residue was vacuum-dried to afford 2-(dispiro[2.0.2⁴.1³]heptan-7-yl)ethyl methanesulfonate (33.1 g) as a brown solid, which was used subsequently.

Step 2: Synthesis of 1-(tert-butyl) 4-ethyl 3-(2-(dispiro[2.0.2⁴.1³]heptan-7-yl)ethoxy)-1H-pyrazole-1,4-dicarboxylate (7)

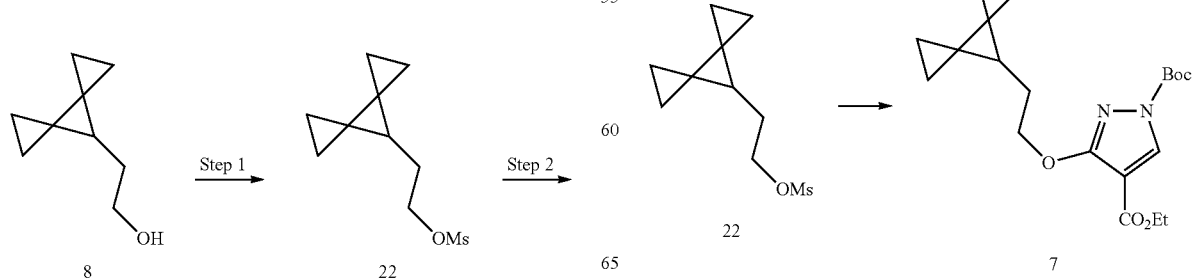

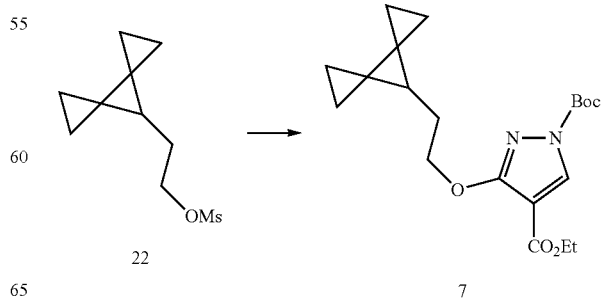

A mixture of 1-tert-butyl 4-ethyl 3-hydroxy-1H-pyrazole-1,4-dicarboxylate (38.7 g, 151.2 mmol, 1 equiv), 2-(dispiro[2.0.2⁴.1³]heptan-7-yl)ethyl methanesulfonate (33.1 g, 152.7 mmol; 1.01 equiv), and Cs$_2$CO$_3$ (55.1 g, 169.3 mmol; 1.12 equiv) in DMF (180 mL) was heated at 50° C. for 24 h. After cooling to room temperature, the reaction mixture was diluted with water (360 mL) and 2-MeTHF (360 mL), and the phases were separated. The aqueous phase was extracted with 2-MeTHF (2×150 mL). The combined organic layers were dried over Na$_2$SO$_4$, filtered, and concentrated under reduced pressure. The residue was purified by flash chromatography system, eluting with a gradient of 0 to 35% ethyl acetate in heptanes (RediSep 220 g) to give compound 1-(tert-butyl) 4-ethyl 3-(2-(dispiro[2.0.2⁴.1³]heptan-7-yl)ethoxy)-1H-pyrazole-1,4-dicarboxylate (34.3 g, 67% yield over 2 steps from 2-(dispiro[2.0.2⁴.1³]heptan-7-yl)-ethan-1-ol, 97% purity) as a white solid.

$^1$H NMR (400 MHz, CDCl$_3$) δ 8.32 (s, 1H), 4.35 (t, J=8.0 Hz, 2H), 4.31 (q, J=8.0 Hz, 2H), 1.93 (q, J=8.0 Hz, 2H), 1.63 (s, 9H), 1.48 (t, J=6.4 Hz, 1H), 1.35 (t, J=8.0 Hz, 3H), 0.90-0.78 (m, 4H), 0.67-0.62 (m, 2H), 0.50-0.47 (m, 2H).

Mass spectrum (positive mode): m/z=377.2 [M+H]$^+$.

Example 7: Synthesis of (S)-6-bromo-2-(4-(3-(1,3-dioxoisoindolin-2-yl)propyl)-2,2-dimethylpyrrolidin-1-yl)nicotinamide (49)

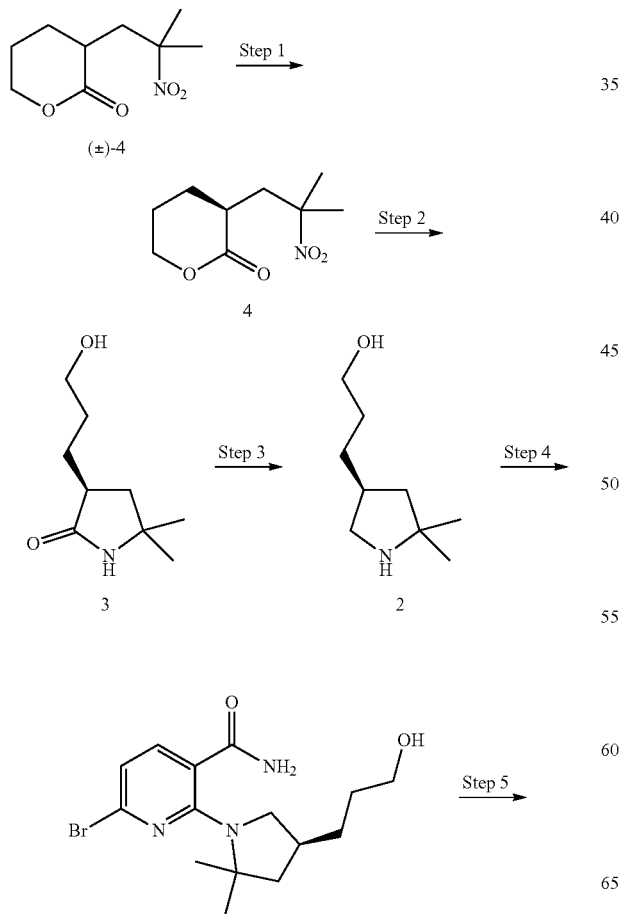

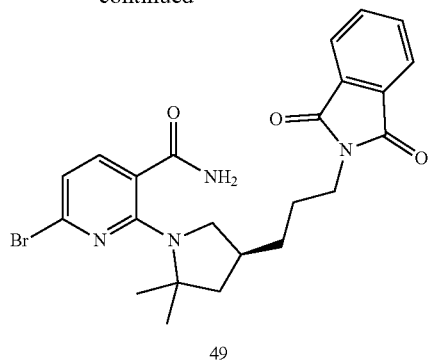

49

Step 1: Preparation of (S)-3-(2-methyl-2-nitropropyl)tetrahydro-2H-pyran-2-one (4)

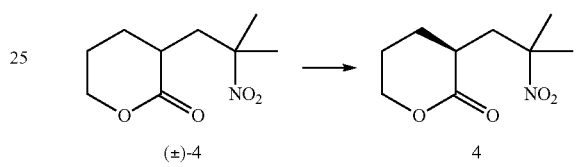

Racemic 3-(2-methyl-2-nitropropyl)tetrahydro-2H-pyran-2-one was dissolved in 80 g/L+/−8 g/L in MeOH/ACN 70/30 v/v (target 80+/−2 g/L) and separated on Chiralpak AD 20 μm as the stationary phase using MeOH/ACN 70/30 v/v as the mobile phase. (S)-3-(2-Methyl-2-nitropropyl)tetrahydro-2H-pyran-2-one is Peak 2. Optional recrystallization of (S)-3-(2-methyl-2-nitropropyl)tetrahydro-2H-pyran-2-one: (S)-3-(2-Methyl-2-nitropropyl)tetrahydro-2H-pyran-2-one (9.5 kg, 1.0 equiv) was stirred in isopropanol (76 L, 8 vol) then heated to >70° C. to dissolve the solid. The mixture was then cooled to 20° C. over 4-5 h, the solid isolated by filtration, and the cake washed with isopropanol (4.75 L, 0.5 vol) and pulled dry. The material was dried under vacuum to afford (S)-3-(2-methyl-2-nitropropyl)tetrahydro-2H-pyran-2-one in 90% recovery.

Step 2: Synthesis of (S)-3-(3-hydroxypropyl)-5,5-dimethylpyrrolidin-2-one (3)

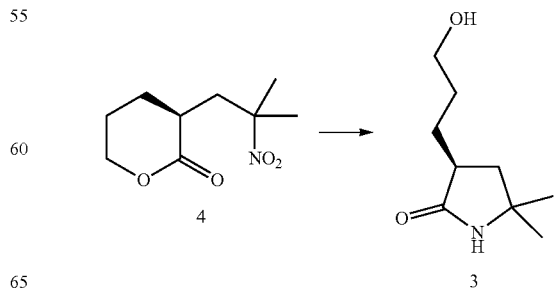

A suspension of Raney Nickel 2400 (77 wt %, 2.8 kg) was allowed to settle for 2 days. The standing liquid was decanted to waste and the remaining catalyst was charged to a reactor with the aide of water (2.6 kg), then degassed with $N_2$. In a second reactor, a mixture of (S)-3-(2-methyl-2-nitropropyl)tetrahydro-2H-pyran-2-one (13.9 kg) and EtOH (170.8 kg) was heated to 30° C., then degassed with $N_2$, then transferred to the reactor containing Raney Nickel. The transfer was completed with the aid of an EtOH (29.8 kg) rinse. The mixture was purged three times with nitrogen and purged three times with hydrogen. The contents of the reactor were heated to 60-65° C. and stirred under $H_2$ (4-8 psi) until the reaction was completed (18 h). The mixture was cooled to 15-20° C., then purged with nitrogen three times, then filtered through a pad of Celite (3.0 kg) wetted with EtOH (3.2 kg). The reactor and Celite cake were washed with EtOH (2×14.0 kg). The filtrate was distilled to a final volume of approx. 25 L then heated to 45° C. MTBE (269.4 kg) was then charged maintaining a temperature of 48-50° C. and then distilled at ambient pressure at 48-55° C. to a final volume of approx. 30 L. Two further portions of MTBE (269.4 kg then 187.4 kg) were sequentially added then concentrated to approx. 30 L volume.

The contents of the reactor were seeded with (S)-3-(3-hydroxypropyl)-5,5-dimethylpyrrolidin-2-one (70.1 g) at 40° C. The seeded crystal slurry was cooled to 15° C. over a period of 3.5 h, then stirred for 16.5 h between 12-15° C. then filtered. The reactor and filter cake were then washed with cold (−2 to −10° C.) MTBE (2×10 kg). The filter-cake was dried to a constant weight which afforded (S)-3-(3-hydroxypropyl)-5,5-dimethylpyrrolidin-2-one (10.4 kg; 88%) as a white, crystalline solid.

Recrystallization of (S)-3-(3-Hydroxypropyl)-5,5-dimethylpyrrolidin-2-one: A mixture of (S)-3-(3-hydroxypropyl)-5,5-dimethylpyrrolidin-2-one (10.3 kg) and DCM (28.2 kg) was stirred and heated to 25° C. for 2 h then transferred to another reactor through an in-line filter (45 um). The initial reactor was rinsed with DCM (6.8 kg) at 21° C. for 10 min then transferred to the reactor through the in-line filter. MTBE (38.1 kg) was charged to the solution at 25-30° C. then the mixture was distilled over a period of 2.5 h at 35-52° C. at atmospheric pressure to a final volume of approx. 30 L. MTBE (38.2 kg) was charged to the reactor at 45-50° C. The resulting suspension was distilled over a period of 3.25 h at 49-55° C. at atmospheric pressure to a final volume of approx. 30 L. The contents of the reactor were cooled to 21° C. over a period of 2.5 h and stirred for 16 h at 20° C. The suspension was filtered. The reactor and filter cake were rinsed with MTBE (7.7 kg, 0.0° C.). The filter cake was dried over a period of 2 days. Yield: 9.1 kg (88.3%) of an off-white solid.

$^1$H NMR (400 MHz, DMSO-d$_6$) δ 7.63 (s, 1H), 4.38 (s, 1H), 3.38 (t, J=6.5 Hz, 2H), 2.37 (qd, J=9.5, 4.4 Hz, 1H), 2.02 (dd, J=12.4, 8.6 Hz, 1H), 1.78-1.63 (m, 1H), 1.50-1.33 (m, 3H), 1.16 (d, J=17.9 Hz, 7H).

ESI-MS m/z calc. 171.12593, found 172.0 [M+1]+.

GCMS:100% (AUC).

Chiral HPLC: 100% (AUC).

Step 3: Synthesis of (S)-3-(5,5-dimethylpyrrolidin-3-yl)propan-1-ol (2)

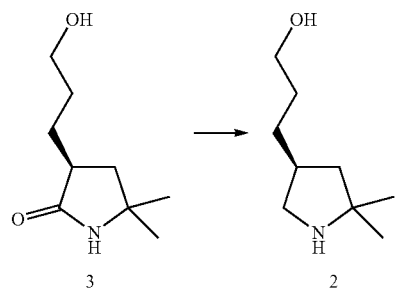

LiAlH$_4$ pellets (332.5 g, 8.760 mol, 1.50 equiv) were slowly added to a reactor with 2-MeTHF (10.00 L, 10 vol) at 30-40° C. The mixture was then heated to 75° C. A mixture of (S)-3-(3-hydroxypropyl)-5,5-dimethylpyrrolidin-2-one (1,000 g, 5.840 mol, 1.00 equiv) and 2-MeTHF (10.00 L, 10 vol) was prepared in a separate reactor and heated to 65° C., which was then carefully transferred to the reactor containing the LiAlH$_4$ mixture over 2 h. The mixture was stirred at 70° C. until the reaction was complete (18-24 h) then cooled to 0-10° C. Water (400.0 mL, 1×LiAlH$_4$ wt) was then carefully added while maintaining the mixture temperature at <30° C. A solution of aq 15% NaOH (400.0 mL, 1×LiAlH$_4$ wt) was then added followed by water (400.0 mL, 1×LiAlH$_4$ wt) while maintaining the mixture temperature at <30° C. The resulting mixture was then heated to 60° C. and held at that temperature for at least 30 min. The mixture was cooled to 20-30° C. then Celite (200 grams, 20 wt %) was added. The mixture was then filtered through a pad of Celite. The reactor and filter cake were rinsed with 2-MeTHF (4.0 L, 4.0 vol). The filtrate was concentrated under vacuum to afford pyrrolidine compound (S)-3-(5,5-dimethylpyrrolidin-3-yl)propan-1-ol (872 g; 94.95% yield) as a clear oil.

$^1$H NMR (400 MHz, dimethyl sulfoxide-d$_6$) δ 3.36 (t, J=6.3 Hz, 3H), 2.95 (dd, J=10.6, 7.6 Hz, 1H), 2.40 (dd, J=10.6, 7.7 Hz, 1H), 2.12-1.97 (m, 1H), 1.69 (dd, J=12.1, 8.2 Hz, 1H), 1.47-1.25 (m, 5H), 1.08 (s, 3H), 1.02 (s, 3H).

Step 4: Synthesis of (S)-6-bromo-2-(4-(3-hydroxypropyl)-2,2-dimethylpyrrolidin-1-yl)nicotinamide

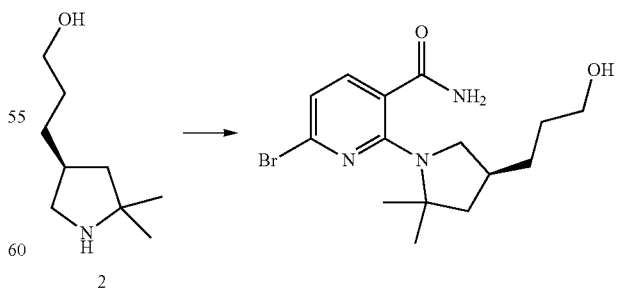

A mixture of (S)-3-(5,5-dimethylpyrrolidin-3-yl)propan-1-ol (2325 g, 14.8 mol) and 6-bromo-2-fluoropyridine-3-carboxamide (3400 g, 15.5 mol) in 2-methyltetrahydrofuran (23 L) was stirred, then potassium carbonate (2650 g, 19.2 mol) and deionized water (7 L) were added. The mixture was stirred at <25° C. until the reaction was complete (≥16 h).

The aqueous phase was removed and the upper organic phase was washed with water (7 L) and 2% aqueous sodium chloride (7 L). The organic layer was concentrated under reduced pressure to about 19 L. 2-Methyltetrahydrofuran was chased from the mixture by two sequential additions and concentrations of acetonitrile (2×20 L) followed by distillation. To the remaining solution was added acetonitrile (20 L) and the reaction was warmed to 85° C. for 2 h and then cooled at 10° C./h to 25° C. The slurry was cooled to 10° C. and stirred for 4 h then filtered. The cake was rinsed two times with acetonitrile (2×3 L) then the solid was dried under vacuum to afford (S)-6-bromo-2-(4-(3-hydroxypropyl)-2,2-dimethylpyrrolidin-1-yl)nicotinamide as a crystalline white solid (3850 g, 73% yield).

$^1$H NMR (400 MHz, DMSO-d$_6$) δ 7.78 (s, 1H), 7.39 (s, 1H), 7.34 (dd, J=7.7, 1.0 Hz, 1H), 6.67 (d, J=7.6 Hz, 1H), 4.42 (t, J=5.1 Hz, 1H), 3.39 (q, J=5.7 Hz, 2H), 3.29-3.12 (m, 2H), 2.19 (dt, J=10.9, 5.8 Hz, 1H), 1.92 (dd, J=11.9, 5.7 Hz, 1H), 1.53 (s, 3H), 1.50 (s, 3H), 1.48-1.29 (m, 5H).

Step 5: Synthesis of (S)-6-bromo-2-(4-(3-(1,3-dioxoisoindolin-2-yl)propyl)-2,2-dimethylpyrrolidin-1-yl)nicotinamide (49)

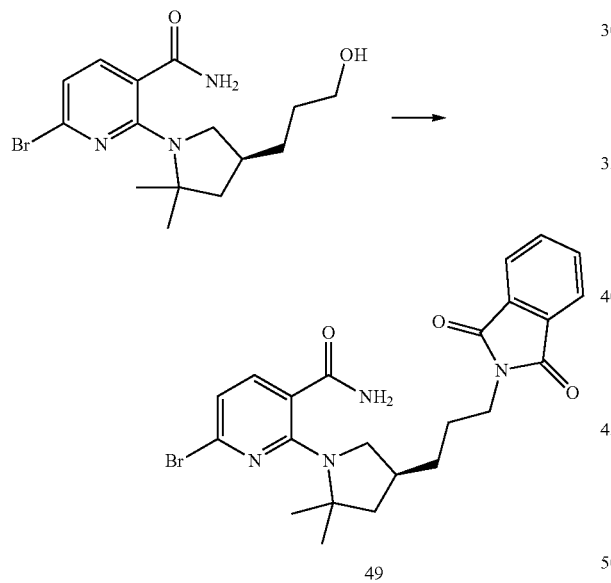

A mixture of (S)-6-bromo-2-(4-(3-hydroxypropyl)-2,2-dimethylpyrrolidin-1-yl)nicotinamide (2.65 kg, 7.4 mol), 2-methyltetrahydrofuran (16 L), and triethylamine (900 g, 8.88 mol) was stirred at 20° C., then methanesulfonyl chloride (933 g, 8.14 mol) was added over 2 h. The mixture was stirred at 20° C. until the reaction was completed (typically 16 h). The resulting mixture was filtered and the filter cake was rinsed with tert-butyl methyl ether (2×4 L). The combined filtrates (containing the mesylate intermediate) were transferred to a reactor and diluted with dimethyl sulfoxide (16 L). To the mixture was added phthalimide (1198 g, 8.14 mol). The mixture was stirred until a solution was obtained, then potassium carbonate (1023 g, 7.4 mol) was added and the mixture was stirred and heated to 70° C. until the reaction was completed (2 h). The mixture was cooled to 20° C. and diluted with 2-methyltetrahydrofuran (16 L), followed by the addition of deionized water (21 L). The phases were separated and the upper organic phase was washed with deionized water (10 L) and saturated aqueous sodium chloride (2×1 L). The organic phase was diluted with toluene (16 L) and concentrated under reduced pressure to approximately 10 L volume. The solid was isolated by filtration and the filter cake was rinsed with toluene (2×2 L). The resulting solid was dried to afford compound (S)-6-bromo-2-(4-(3-(1,3-dioxoisoindolin-2-yl)propyl)-2,2-dimethylpyrrolidin-1-yl)nicotinamide as an off-white solid (3393 g, 6.99 mol, 94% yield).

$^1$H NMR (400 MHz, DMSO-d$_6$) δ 7.91-7.80 (m, 4H), 7.80-7.71 (m, 1H), 7.42-7.36 (m, 1H), 7.34 (d, J=7.7 Hz, 1H), 7.29-7.09 (m, 3H), 6.67 (d, J=7.7 Hz, 1H), 3.59 (t, J=6.9 Hz, 2H), 3.23 (t, J=10.4 Hz, 1H), 3.16 (dd, J=10.2, 7.4 Hz, 1H), 2.30 (s, 2H), 2.28-2.13 (m, 1H), 1.90 (dd, J=12.0, 5.6 Hz, 1H), 1.71-1.53 (m, 2H), 1.51 (s, 3H), 1.48 (s, 3H), 1.47-1.23 (m, 3H).

Example 8: Synthesis of (R)-6-bromo-2-(4-(3-(1,3-dioxoisoindolin-2-yl)propyl)-2,2-dimethylpyrrolidin-1-yl)nicotinamide The reactions in this example provide (R)-6-bromo-2-(4-(3-(1,3-dioxoisoindolin-2-yl)propyl)-2,2-dimethylpyrrolidin-1-yl)nicotinamide, because (S)-(−)-α-methylbenzylamine was used as a reagent. (S)-6-bromo-2-(4-(3-(1,3-dioxoisoindolin-2-yl)propyl)-2,2-dimethylpyrrolidin-1-yl) nicotinamide can be obtained using the same reactions and (R)-(−)-α-methylbenzylamine as a reagent.

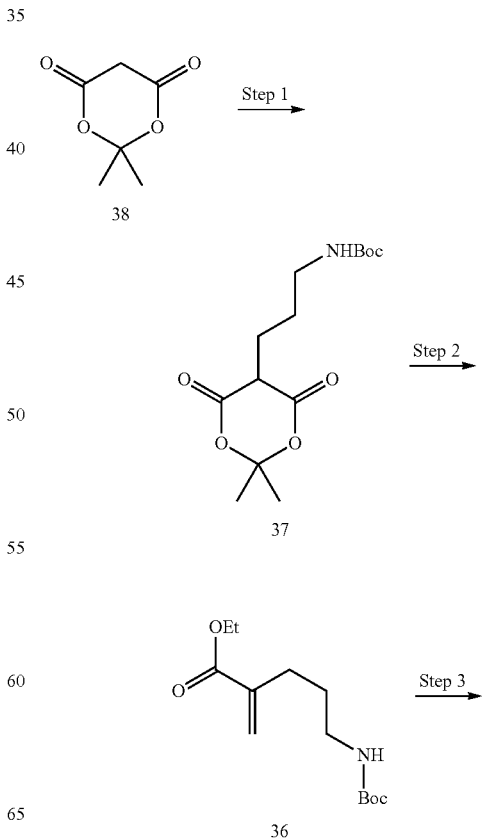

133

-continued

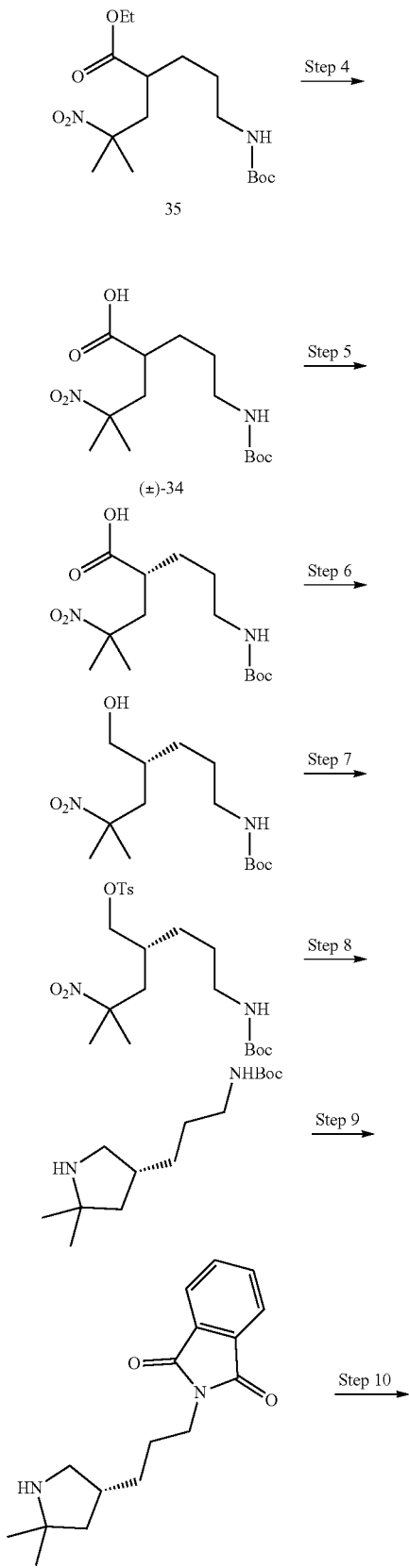

134

-continued

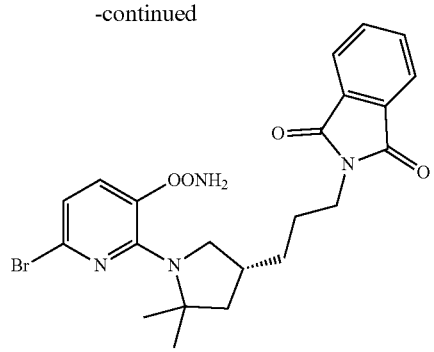

Step 1: Synthesis of tert-butyl (3-(2,2-dimethyl-4,6-dioxo-1,3-dioxan-5-yl)propyl)carbamate (37)

To a stirring solution of 3-tert-butoxycarbonylamino-propionic acid (30.0 g, 158.6 mmol), 2,2-dimethyl-[1,3]dioxane-4,6-dione (27.4 g, 190.3 mmol) and 4-dimethylaminopyridine (31.03 g, 254.0 mmol) in dichloromethane (600 mL) at 0° C. was dropwise added a solution of N,N-dicyclohexylcarbodiimide (39.3 g, 190.3 mmol) in dichloromethane (300 mL). After the addition was complete, the reaction mixture was allowed to warm up to room temperature and stirred for 16 h. The precipitated dicyclohexylurea was filtered off, and the filtrate was washed with 5% aqueous potassium bisulfate solution (3×200 mL) followed by brine (100 mL) and dried over anhydrous magnesium sulfate. The magnesium sulfate was filtered off, and the filtrate was cooled to 0° C. Glacial acetic acid (91 mL, 1.59 mol) was slowly added, followed by a portionwise addition of sodium borohydride (15.0 g, 397.0 mmol). After the addition was complete, the reaction mixture was allowed to warm up to room temperature and stirred for 18 h. The reaction mixture was re-cooled to 0° C. and quenched with water (200 mL). The organic layer was separated, washed with water (2×300 mL) followed by brine (100 mL), dried over anhydrous sodium sulfate, and concentrated to afford crude 2,2-dimethyl-5-(3-tert-butoxycarbonylamino-propyl)-[1,3]dioxane-4,6-dione (49.05 g, 103%, contained ~10% of unreacted 2,2-dimethyl-[1,3]dioxane-4,6-dione) as an off-white solid. The crude product was carried to the next step without further purification.

LCMS Method: Final purity was determined by reverse phase HPLC using a Kinetex C18 column (50×3.0 mm) and a dual gradient run from 5-100% mobile phase B over 12 min. Mobile phase A=water (0.1% $CF_3CO_2H$). Mobile phase B=acetonitrile (0.1% $CF_3CO_2H$). Flow rate=1.5 mL/min, injection volume=10 μL, and column temperature=30° C.

¹H NMR (250 MHz, CDCl₃) δ (ppm): 4.62 (broad s, 1H), 3.74-3.72 (m, 1H), 3.22-3.15 (m, 2H), 2.17-2.08 (m, 2H), 1.81 (s, 3H), 1.75 (s, 3H), 1.70-1.66 (m, 2H), 1.43 (s, 9H).

ESI-MS m/z calc. 301.3, found 302.2 [M+1]+. Retention time: 3.87 min.

Step 2: Synthesis of ethyl 5-((tert-butoxycarbonyl)amino)-2-methylenepentanoate (36)

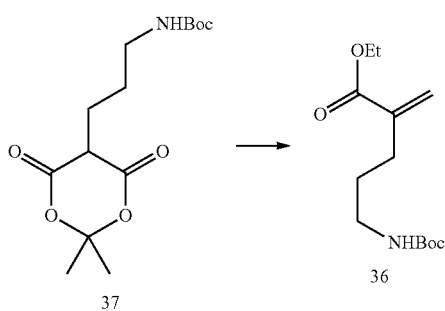 [SMILES: CC(C)(C)OC(=O)NCCCC1C(=O)OC(C)(C)OC1=O ; C=C(CCCNC(=O)OC(C)(C)C)C(=O)OCC]

To a stirring solution of 2,2-dimethyl-5-(3-tert-butoxycarbonylamino-propyl)-[1,3]dioxane-4,6-dione (23.7 g, 78.6 mmol) in anhydrous ethanol (850 mL) under nitrogen atmosphere was added N,N'-dimethylmethyleneiminium iodide (36.5 g, 197.0 mmol). The reaction mixture was heated to 65° C. for 18 h. The reaction mixture was concentrated and the crude product was extracted with ethyl acetate (400 mL). The organic layer was washed with saturated aqueous sodium bicarbonate solution (400 mL), 10% aqueous potassium bisulfate (400 mL), and brine (100 mL), then dried over anhydrous sodium sulfate and concentrated. The product was purified by silica gel column chromatography using 0-15% hexanes-ethyl acetate to afford 5-tert-butoxycarbonylamino-2-methylene-pentanoic acid ethyl ester (14.76 g, 73%) as a colorless oil.

¹H NMR (250 MHz, CDCl₃) δ (ppm): 6.17 (s, 1H), 5.56 (s, 1H), 4.60 (broad s, 1H), 4.24-4.16 (q, J=7.1 Hz, 2H), 3.17-3.10 (m, 2H), 2.30-2.36 (m, 2H), 1.72-1.60 (m, 2H), 1.44 (s, 9H), 1.30 (t, J=7.1 Hz, 3H).

ESI-MS m/z calc. 257.3, found 258.7 [M+1]+. Retention time: 5.12 min.

Step 3: Synthesis of ethyl 2-(3-((tert-butoxycarbonyl)amino)propyl)-4-methyl-4-nitropentanoate (35)

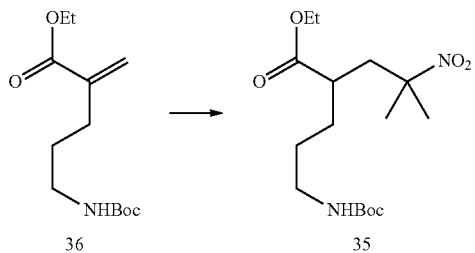 [SMILES: C=C(CCCNC(=O)OC(C)(C)C)C(=O)OCC ; CCOC(=O)C(CCCNC(=O)OC(C)(C)C)CC(C)(C)[N+](=O)[O-]]

To a stirring solution of 5-tert-butoxycarbonylamino-2-methylene-pentanoic acid ethyl ester (16.95 g, 65.87 mmol) and 2-nitropropane (29.4 g, 330.0 mmol) in anhydrous acetonitrile (250 mL) under nitrogen atmosphere was added 1,8-diazabicyclo[5.4.0]undec-7-ene (12.03 g, 79.0 mmol), and the reaction mixture was heated to 90° C. for 2 h. The reaction mixture was concentrated and the residue was extracted with ethyl acetate (400 mL). The organic layer was washed with 5% aqueous potassium bisulfate solution (2×300 mL) followed by brine (100 mL), dried over anhydrous sodium sulfate, and concentrated. The product was purified by silica gel column chromatography using 0-25% hexanes-acetone to afford 2-(3-tert-butoxycarbonylamino-propyl)-4-methyl-4-nitro-pentanoic acid ethyl ester (20.65 g, 90%) as a yellow oil.

¹H NMR (250 MHz, CDCl₃) δ (ppm): 4.51 (broad s, 1H), 4.17-4.08 (q, J=7.1 Hz, 2H), 3.13-3.08 (m, 2H), 2.45-2.29 (m, 2H), 2.17-2.04 (m, 1H), 1.73-1.64 (m, 1H), 1.58-1.36 (m, 18H), 1.25 (t, J=7.1 Hz, 3H).

ESI-MS m/z calc. 346.4, found 347.3 [M+1]. Retention time: 5.65 min.

Step 4: Synthesis of 2-(3-((tert-butoxycarbonyl)amino)propyl)-4-methyl-4-nitropentanoic acid ((f)-34)

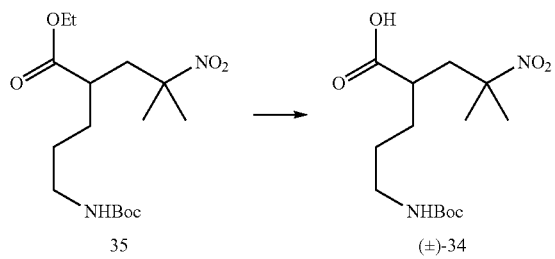 [SMILES: CCOC(=O)C(CCCNC(=O)OC(C)(C)C)CC(C)(C)[N+](=O)[O-] ; CC(C)(C)OC(=O)NCCCC(CC(C)(C)[N+](=O)[O-])C(=O)O]

To a mixture of 2-(3-tert-butoxycarbonylamino-propyl)-4-methyl-4-nitro-pentanoic acid ethyl ester (5 g, 14.43 mmol) in ethanol (20 mL) under nitrogen atmosphere was added 10% w/v NaOH (7 mL, 17.50 mmol), and the reaction mixture was heated to 50° C. After 5 h an additional 0.7 mL of 10% w/v NaOH was added. After heating for an additional 2 h, LC showed complete reaction. 20 mL of water was added to the reaction mixture and the mixture was concentrated to remove EtOH. 15 mL of IPAc was added. After mixing, the layers were separated and the aqueous layer was made acidic with 6 M HCl (pH 2-3). 20 ml of IPAc was added. After mixing, the organic layer was dried over anhydrous sodium sulfate, filtered, and concentrated to afford 2-(3-tert-butoxycarbonylamino-propyl)-4-methyl-4-nitro-pentanoic acid.

The crude product from above was dissolved in 30 mL of IPAc. Dicyclohexylamine (2.6 mL, 13.05 mmol) was added dropwise via addition funnel. Crystallization initiated upon stirring. After stirring the slurry for several h, the solid was collected by filtration and washed with IPAc (2×7 mL). The salt was dried in a vacuum oven at 50° C. with a N₂ bleed to afford 6.37 g of 2-(3-tert-butoxycarbonylamino-propyl)-4-methyl-4-nitro-pentanoic acid dicyclohexylammonium salt (88% for 2 steps).

The salt was then slurried in 40 mL of IPAc. 20 mL of 10% aq w/v citric acid was added. The mixture was stirred vigorously until all solids dissolved. The layers were then separated and the organic layer was dried over anhydrous sodium sulfate, filtered, and concentrated. 50 mL of heptane was added and the mixture was concentrated. 40 mL of heptane was added to the solid and the slurry was stirred at ambient temperature. After stirring the slurry for several hours, the solid was collected by filtration and washed with heptane (2×8 mL). The product was dried in a vacuum oven at 50° C. with a N₂ bleed to afford 3.27 g of 2-(3-tert-butoxycarbonylamino-propyl)-4-methyl-4-nitro-pentanoic acid (71% overall for the process).

Step 5: Synthesis of (R)-2-(3-((tert-butoxycarbonyl)amino)propyl)-4-methyl-4-nitropentanoic acid

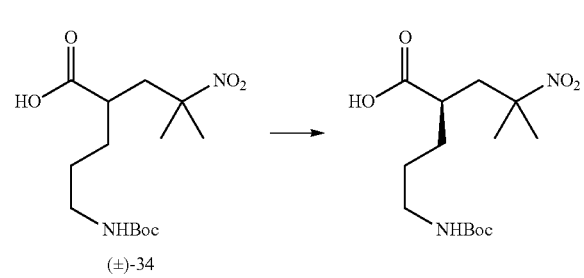 [SMILES: CC(C)(C)OC(=O)NCCCC(CC(C)(C)[N+](=O)[O-])C(=O)O ; CC(C)(C)OC(=O)NCCC[C@H](CC(C)(C)[N+](=O)[O-])C(=O)O]

(±)-34

Initial Crystallization: To a 100 mL flask containing 2-{3-[(tert-butoxycarbonyl)amino]propyl}-4-methyl-4-nitropentanoic acid (5 g, 15.705 mmol, 1 equiv) in CH₃CN (25 mL, 0.628 M, 5 Vols), (S)-(−)-α-methylbenzylamine (0.952 g, 1.012 mL, 7.852 mmol, 0.5 equiv) was added. Stirred at ambient temperature, the mixture initially turned clear and then became a slurry within 5-10 min.

The mixture was heated to 75° C. and held at 71-75° C. for 1 h, then cooled to 60° C. and held at 60° C. for 1 h. Then the mixture was cooled to 50° C., and was seeded with ~25 mg of (R)-2-(3-((tert-butoxycarbonyl)amino)propyl)-4-methyl-4-nitropentanoic acid. The mixture became cloudy, and after 1 hr it was cooled to 40° C., and the resulting slurry was held at 40° C. for 1 hr, then cooled to ambient temperature and stirred overnight. The slurry was collected by filtration, rinsed with ACN (3×3 mL), and dried under vacuum oven at 40° C. overnight with a N₂ bleed. 2.27 g was obtained (TY=3.45 g, 65%). The enantiomer ratio was 95:5 [% (AUC)]. The mother liquor ratio was 26:74.

1st Recrystallization: In a 50 mL of RBF, (1R)-1-phenylethanaminium 2-{3-[(tert-butoxycarbonyl)amino]propyl}-4-methyl-4-nitropentanoate (2.22 g, 5.051 mmol, 1 equiv) in CH₃CN (15.54 mL, 0.325 M, 7 Vols). Mixture heated to 75° C., mixture became homogeneous at 66° C., hold at 71-75° C. for 1 h. Then cool to 60° C., slurry formed. Hold at 60° C. for 1 h. Cool to 50° C. and hold for 1 h. Cool to 40° C. Hold at 40° C. for 1 hr and then cool to ambient stirring overnight. Solid was collected by filtration and dried over the vacuum oven at 40° C. with N₂ bleed overnight to afford 2.056 g of product as white solid (92%). The enantiomer ratio was 97:3 [% (AUC)]. The mother liquor ratio was 25:75.

2nd Recrystallization: To a 100 mL round-bottomed flask was added (1R)-1-phenylethanaminium 2-{3-[(tert-butoxycarbonyl)amino]propyl}-4-methyl-4-nitropentanoate (2 g, 4.55 mmol, 1 equiv) in CH₃CN (16 mL, 0.284 M, 8 Vols). The mixture was heated to 75° C. The mixture became homogeneous at >66° C., then was held at 71-75° C. for 1 h. The mixture was then allowed to cool to 65° C. A slurry formed and was held for 1 h. Then it was cooled to 60° C. and held for 1 h, then cooled to 55° C. and held for 1 h, then cooled to 50° C. and held for 1 h, then cooled to 45° C. and held for 1 h, then cooled to ambient and stirred overnight. The solid was collected by filtration and dried in a vacuum oven at 40° C. with a N₂ bleed overnight to afford 1.92 g of product as white solid (96%, 57% overall). The enantiomer ratio was 99:1 [% (AUC)]. The mother liquor ratio was 53:47.

Step 6: Synthesis of tert-butyl (R)-(4-(hydroxymethyl)-6-methyl-6-nitroheptyl)carbamate

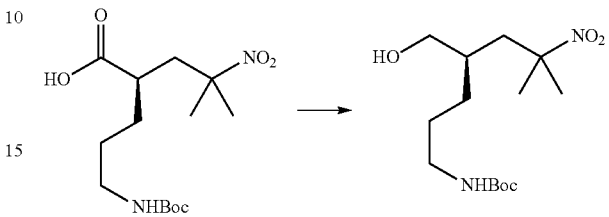

CDI (305.7 mg, 1.885 mmol) was added to a solution of (R)-2-[3-(tert-butoxycarbonylamino)propyl]-4-methyl-4-nitro-pentanoic acid (500 mg, 1.571 mmol) in THF (1.500 mL) at room temperature. The mixture was stirred at ambient temperature. CDI activation of carboxylic acid was checked using n-butylamine in ACN. UPLC was checked at 80 min, 3 h, and 4 h.

This reaction mixture was then transferred over 15 min to a solution of NaBH₄ (178.3 mg, 188.7 µL, 4.713 mmol) in a mixture of THF (1.000 mL) and H₂O (625.0 µL) at 0-5° C. The addition was exothermic. The mixture was stirred for 90 min at ambient temperature. UPLC showed the starting material was fully consumed.

EtOAc (2.5 mL) and aqueous citric acid (approximately 2.415 g, 1.450 mL, 12.57 mmol) (in 2.5 mL of water) was added to quench the reaction. The layers were separated. The pH of the aqueous layer was 3. The organic layer was dried over Na₂SO₄ and concentrated by rotary evaporation (80 mbar, 20° C. bath temp.) MTBE (5 mL) was added to the crude product and was washed with 1.5 mL of Sat. bicarb/water (1:1), at which point the aqueous layer pH was 5. The wash was repeated, at which point the aqueous layer pH became 7. The MTBE layer was dried over Na₂SO₄ and concentrated by rotary evaporation (300-150 mbar, 20° C. bath temp.) and used for the next step reaction without further purification.

Step 7: Synthesis of (R)-2-(3-((tert-butoxycarbonyl)amino)propyl)-4-methyl-4-nitropentyl 4-methylbenzenesulfonate

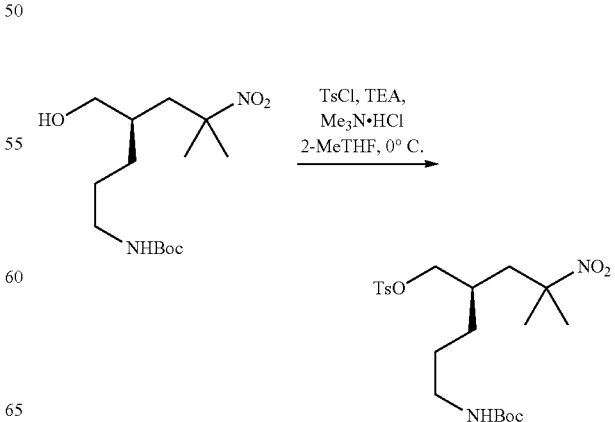

To the mixture of (R)-tert-buty N-[5-hydroxy-4-(2-methyl-2-nitropropyl)pentyl]carbamate (480 mg, 1.577 mmol, 1 equiv), triethylamine (0.319 g, 0.443 mL, 3.154 mmol, 2 equiv) and trimethylamine hydrochloride (0.154 g, 1.608 mmol, 1.02 equiv) in 2-MeTHF (3.5 mL, 0.451 M, 7.292 Vols), was added p-toluenesulfonyl chloride (0.451 g, 2.365 mmol, 1.5 equiv) at 0-5° C. The reaction was stirred at this temperature for 1 h, then warmed to ambient temperature and stirred at ambient temperature for another 3 h. By UPLC, the starting material was fully consumed. The reaction mixture was washed with water and brine, dried over $Na_2SO_4$, and concentrated. The crude was purified by column chromatography eluting with EtOAc/Hexane.

Step 8: Synthesis of tert-butyl (R)-(3-(5,5-dimethylpyrrolidin-3-yl)propyl)carbamate

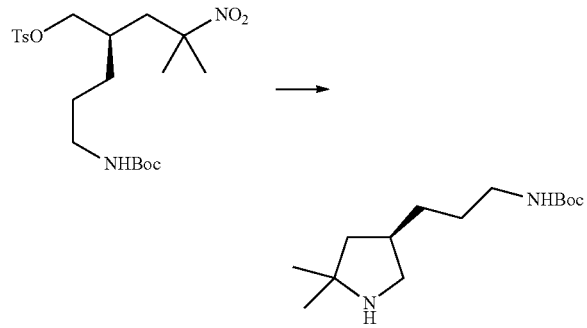

To the solution of (R)-tert-butyl N-(6-methyl-4-{1[(4-methylbenzenesulfonyl)oxy]methyl}-6-nitroheptyl)carbamate (0.55 g, 1.103 mmol, 1 equiv) in MeTHF (9 mL, 0.123 M, 16.364 Vols) was added potassium carbonate (0.153 g, 1.103 mmol, 1 equiv) and Raney nickel (0.13 g, 1.103 mmol, 1 equiv). The mixture was degassed (vacuum) then purged with a hydrogen balloon (3 times). The reaction was heated to 78° C. The reaction mixture was cooled to room temperature and filtered through celite, and the cake was washed with MeTHF (50 mL). The filtered solution was washed with water, some product went to water layer (pH 5-6), the water layer was re-extracted with MeTHF. The combined MeTHF layer was dried over $Na_2SO_4$ and concentrated on rotovap. After drying under house vacuum overnight, 640 mg of crude product was obtained as an oil and was used without further purification.

Step 9: Synthesis of (R)-2-(3-(5,5-dimethylpyrrolidin-3-yl)propyl)isoindoline-1,3-dione

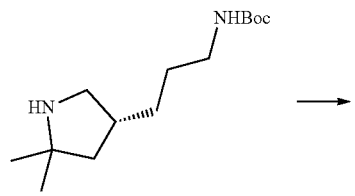

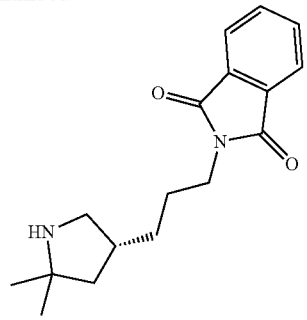

A method for preparing (R)-2-(3-(5,5-dimethylpyrrolidin-3-yl)propyl)isoindoline-1,3-dione from tert-butyl (R)-(3-(5,5-dimethylpyrrolidin-3-yl)propyl)carbamate is shown in the scheme above.

Step 10: Synthesis of (R)-6-bromo-2-(4-(3-(1,3-dioxoisoindolin-2-yl)propyl)-2,2-dimethylpyrrolidin-1-yl)nicotinamide

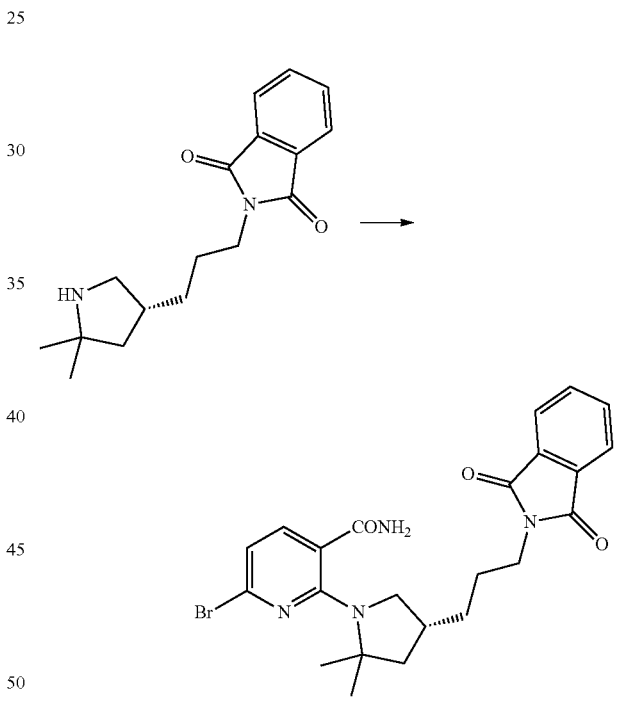

In a 3 necked 1 L round bottom flask, (R)-2-(3-(5,5-dimethylpyrrolidin-3-yl)propyl)isoindoline-1,3-dione (38.98 g, 136.1 mmol, 1.03 equiv), 6-bromo-2-fluoronicotinamide (28.91 g, 132.0 mmol, 1 equiv), and MeCN (202 mL, 7 vol) were added followed by $K_2CO_3$ (−325 mesh, 21.16 g, 153.1 mmol, 1.16 equiv). The mixture was heated to 40° C. and the reaction was monitored by LC analysis. The reaction went to completion after 17 h. The reaction mixture was cooled down to ambient temperature. 300 mL (10.3 vol) of water was added through an addition funnel to afford a slurry. The resulting solid was collected by filtration. The solid was washed with water/MeCN (½, 2×40 mL, 1.4 vol) then dried by vacuum oven at 45° C. to afford (R)-6-bromo-2-(4-(3-(1,3-dioxoisoindolin-2-yl)propyl)-2,2-dimethylpyrrolidin-1-yl)nicotinamide (56.5 g 88%).

Example 9: Synthesis of (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide (50)

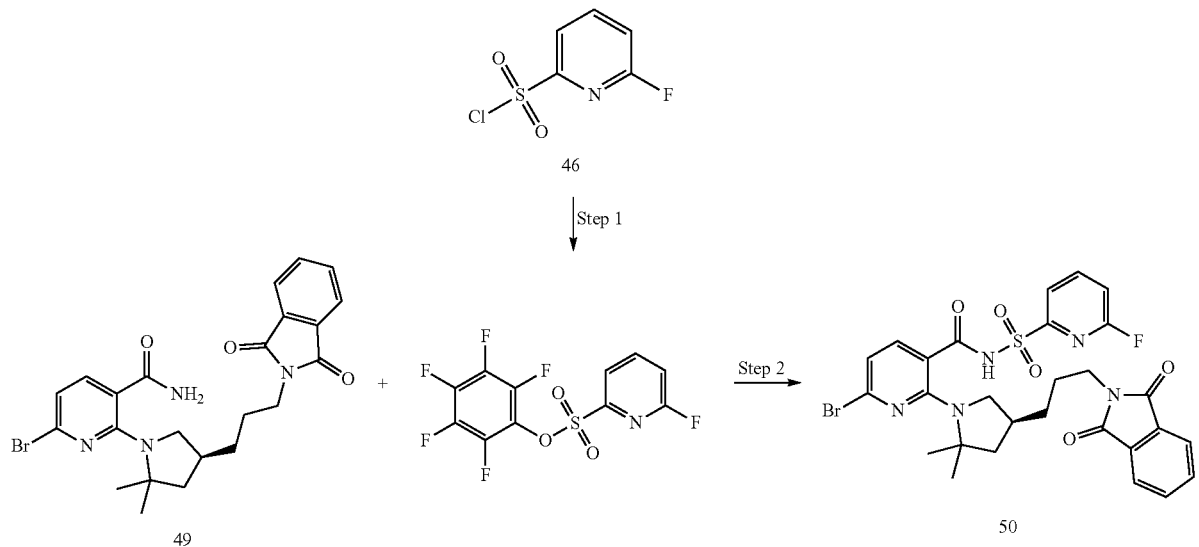

Step 1: Synthesis of perfluorophenyl 6-fluoropyridine-2-sulfonate

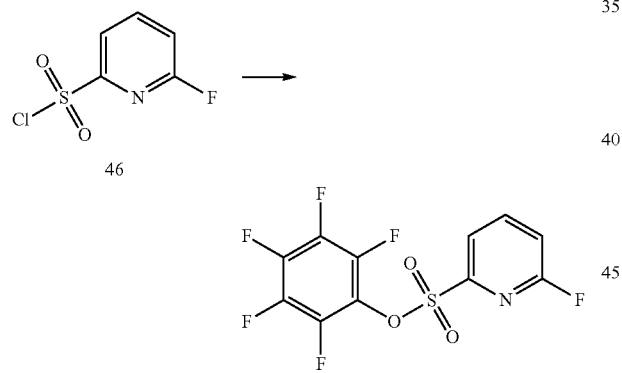

To a solution of 2,3,4,5,6-pentafluorophenol (33.21 g, 180.4 mmol) in iPrOAc (175 mL) was added aq KHCO$_3$ (approximately 90.30 mL of 20% w/v, 180.4 mmol). The mixture was stirred at ambient temperature for 10 min. A solution of 6-fluoropyridine-2-sulfonyl chloride (35.29 g, 180.4 mmol) in iPrOAc (25 mL) was then added while keeping the temperature below 20° C. The reaction mixture was allowed to stir at ambient temperature for 1 hr to complete the reaction. The aqueous layer was removed, and the organic layer was washed with water (50 mL), dried over Na$_2$SO$_4$, then concentrated by rotary evaporation to remove most of solvent and precipitate a white solid. Heptane (70 mL) was added and the slurry was stirred at ambient temperature. The solid was collected by filtration, rinsed with heptane (30 mL), and dried under vacuum to give 58.76 g of perfluorophenyl 6-fluoropyridine-2-sulfonate as a white solid. The mother liquor was concentrated by rotary evaporation, then 1 mL (iPrOAc)/20 mL (Heptane) was added and stirred at ambient temperature overnight. The resulting solid was collected and dried under vacuum oven at ambient temperature overnight with a N$_2$ bleed to give 0.87 g as a second crop. In total, 59.63 g (96% yield) of perfluorophenyl 6-fluoropyridine-2-sulfonate was obtained.

$^1$H NMR (400 MHz, DMSO-d$_6$) δ 8.46 (q, J=7.7 Hz, 1H), 8.20 (dd, J=7.5, 2.0 Hz, 1H), 7.84 (dd, J=8.3, 2.2 Hz, 1H).
$^{19}$F NMR (376 MHz, DMSO-d$_6$) δ −64.25 (s, 1F), −152.20--152.69 (m, 2F), −154.84 (t, J=23.3 Hz, 2F), −161.00--161.74 (m, 1F).

Step 2: Synthesis of (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide (50)

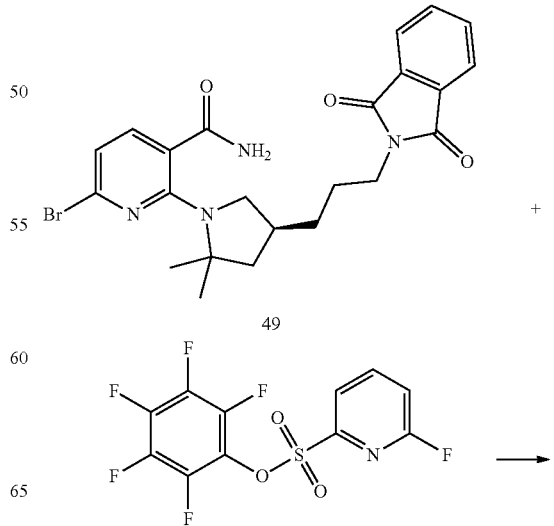

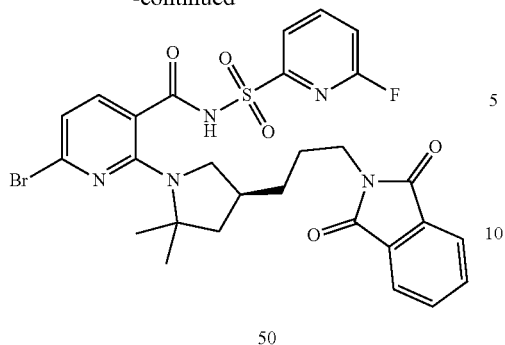

50

A solution of lithium tert-butoxide (1,905.13 g, 2.20 equiv, 20% w/w in THF) was added to a mixture of (S)-6-bromo-2-(4-(3-(1,3-dioxoisoindolin-2-yl)propyl)-2,2-dimethylpyrrolidin-1-yl)nicotinamide (1,050 g, 1.00 equiv) and perfluorophenyl 6-fluoropyridine-2-sulfonate (890.93 g, 1.20 equiv) in 2-MeTHF (10.5 L, 10.0 vol), keeping the internal temperature below −2° C. The mixture was stirred at −10° C. until the reaction was complete (typically 0.5 h). A solution of aq HCl (5.25 L, 5 vol, 1 N) was added while keeping the internal temperature <20° C. 2-MeTHF (5.0 L, 5 vol) was then added to the reactor at ambient temperature and then the phases were allowed to separate. The lower aqueous layer was discarded. The organic phase was washed with water (5 vol) then concentrated to 5 volumes under vacuum keeping the temperature below 50° C. 2-MeTHF (10.0 L, 10 vol) was added and again the mixture concentrated to 5 volumes. 2-MeTHF (5 vol) was added and the heterogenous mixture was heated to 70° C. with agitation until complete dissolution occurred. The mixture was then cooled linearly to 45° C. over 6 h then held at 45° C. for 6 h. The mixture was then cooled to 25° C. over 2 h then heptane (10.0 L, 10 vol) was added to the mixture over 3 h. The mixture was drained from the reactor and the solids were isolated. The reactor and filter cake were then washed twice with a mixture of 2-MeTHF (2.0 L, 2 vol) and heptane (2.0 L, 2 vol). The solids were dried under vacuum at 45° C. to afford (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide.

$^1$H NMR (400 MHz, DMSO-$d_6$) δ 13.05 (s, 1H), 8.37 (q, J=7.8 Hz, 1H), 8.11 (dd, J=7.4, 1.9 Hz, 1H), 7.95-7.88 (m, 2H), 7.88-7.81 (m, 2H), 7.59 (dd, J=8.1, 2.4 Hz, 2H), 6.78 (d, J=7.9 Hz, 1H), 3.59 (t, J=6.8 Hz, 2H), 2.45 (dd, J=8.8, 3.9 Hz, 2H), 2.17 (s, 1H), 1.87 (dd, J=11.9, 5.5 Hz, 1H), 1.56 (dddd, J=22.3, 16.7, 8.9, 4.1 Hz, 2H), 1.47 (s, 3H), 1.44 (s, 3H), 1.35 (t, J=12.1 Hz, 1H), 1.21 (ddd, J=13.3, 10.5, 5.4 Hz, 1H), 1.00 (dtd, J=14.1, 9.4, 5.7 Hz, 1H).

Example 10: Synthesis of (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (40)

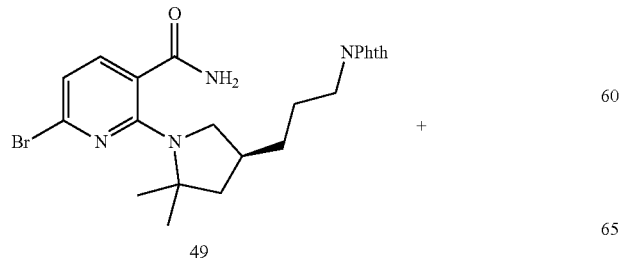

49

46

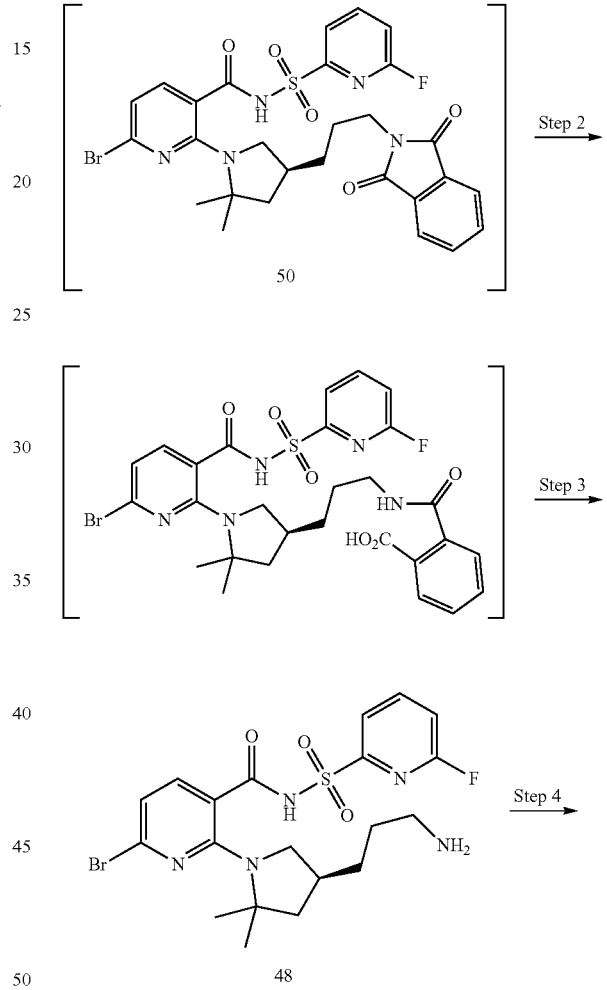

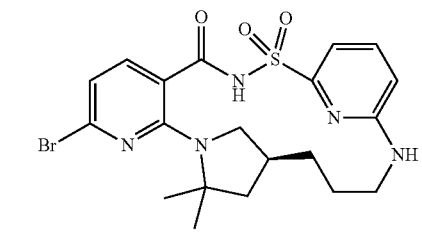

40

Step 1: Alternative Synthesis of (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide (50)

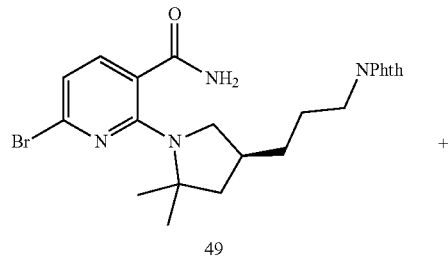

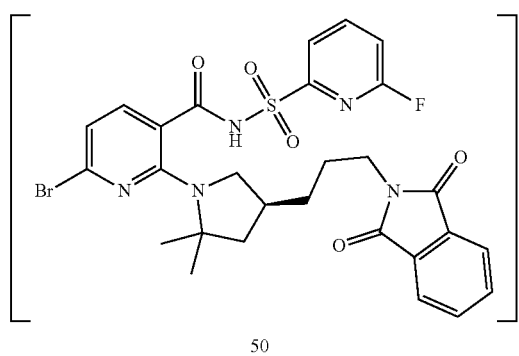

6-Fluoropyridine-2-sulfonyl chloride (529 g, 340 mL, 2.71 mol) was added to a solution of a 2:1 ratio of (S)-6-bromo-2-(4-(3-(1,3-dioxoisoindolin-2-yl)propyl)-2,2-dimethylpyrrolidin-1-yl)nicotinamide in toluene (1.20 kg, 2.26 mol; 91.2% potency) in 2-MeTHF (6.56 L; 6 VolEq) at 0-5° C. then lithium 2-methylbutan-2-olate (t-OAmLi; 1.22 kg of 40% w/w, 1.67 L of 40% w/w, 5.19 mol; 2.3 equiv) was added while maintaining the reaction temperature between 5-10° C. After the addition was completed, the reaction solution was stirred at 0-10° C. until the reaction is complete (HPLC shows <1% AUC (S)-6-bromo-2-(4-(3-(1,3-dioxoisoindolin-2-yl)propyl)-2,2-dimethylpyrrolidin-1-yl)nicotinamide remains). The reaction solution was advanced to the next step without any further processing.

Step 2: Synthesis of (S)-2-((3-(1-(6-bromo-3-(((6-fluoropyridin-2-yl)sulfonyl)carbamoyl)pyridin-2-yl)-5,5-dimethylpyrrolidin-3-yl)propyl)carbamoyl)benzoic acid

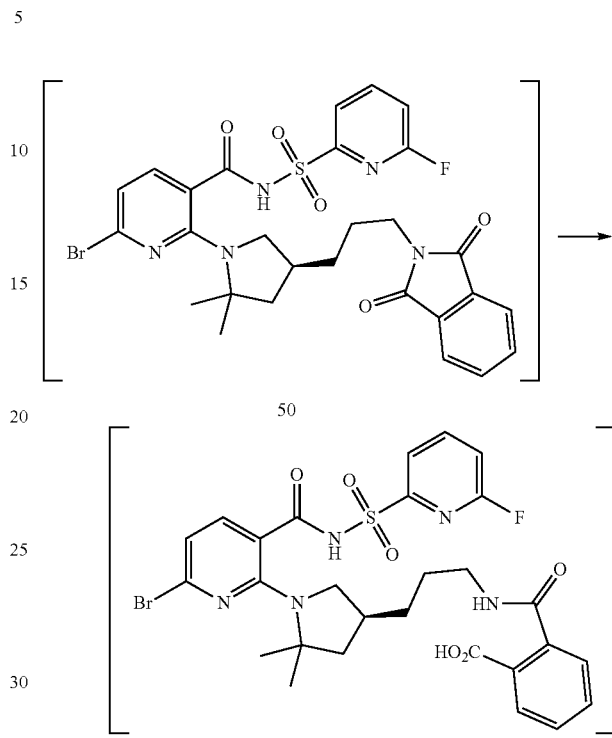

The reaction solution containing (S)-6-bromo-2-(4-(3-(1,3-dioxoisoindolin-2-yl)propyl)-2,2-dimethylpyrrolidin-1-yl)-N-((6-fluoropyridin-2-yl)sulfonyl)nicotinamide from the preceding step was cooled and maintained below 10° C. when a solution of LiOH.H$_2$O (284 g, 6.77 mol; 3 equiv) in water (2.19 L; 2 VolEq) was added. The biphasic mixture was stirred at 5-15° C. until the reaction was completed (about 2 h). While maintaining the reaction temperature below 10° C., 2 M HCl (5.64 L, 11.3 mol; 5 equiv) was added dropwise over ~1 h. The pH of the aqueous phase was about 2. The phases were separated then the organic phase was concentrated to a minimum volume removing most of the 2-MeTHF (40° C./150-70 torr). The reaction mixture was advanced to the next step without any further processing.

Step 3: Synthesis of (S)-2-(4-(3-aminopropyl)-2,2-dimethylpyrrolidin-1-yl)-6-bromo-N-((6-fluoropyridin-2-yl)sulfonyl)nicotinamide (48)

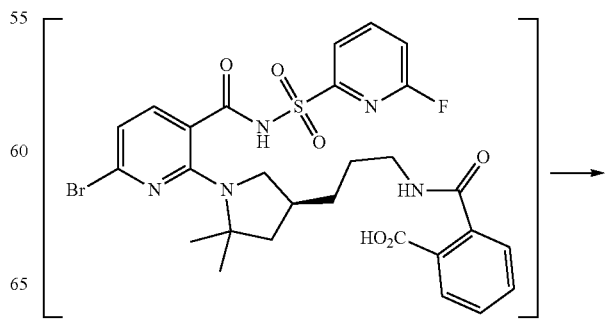

-continued

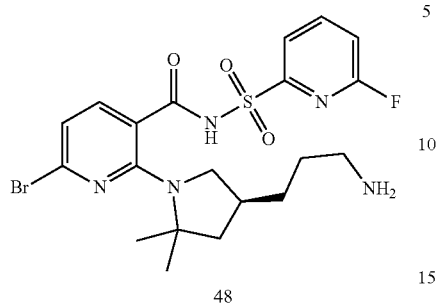

48

The concentrate containing (S)-2-((3-(1-(6-bromo-3-(((6-fluoropyridin-2-yl)sulfonyl)carbamoyl)pyridin-2-yl)-5,5-dimethylpyrrolidin-3-yl)propyl)carbamoyl)benzoic acid from the preceding step was diluted with CH$_3$CN (6.56 L; 6 VolEq) and water (3.83 L; 2 VolEq) then oxalic acid (508 g, 5.64 mol; 2.5 equiv) was added and the resultant solution was heated at 60° C. until the reaction was complete (about at least 4 h). The solution was cooled to 0-10° C. then a solution of K$_2$CO$_3$ (2.18 kg, 15.8 mol; 7 equiv) in water (3.83 L; 3.5 VolEq) was added dropwise while maintaining the reaction temperature below 10° C. The solid was collected by filtration. The damp filter-cake was washed consecutively with water (2×2.2 L; 2 VolEq) and then i-PrOH (2×600 mL; 0.5 VolEq), air-dried with suction, and vacuum-dried (50° C./30 torr) to afford (S)-2-(4-(3-aminopropyl)-2,2-dimethylpyrrolidin-1-yl)-6-bromo-N-((6-fluoropyridin-2-yl)sulfonyl)nicotinamide (959 g; 83% for 3 steps; >98% AUC) as a fine, white powder.

$^1$H NMR (400 MHz, DMSO-d$_6$) δ 8.09 (q, J=7.9 Hz, 1H), 7.83 (dd, J=7.5, 2.2 Hz, 1H), 7.67 (s, 3H), 7.39 (d, J=7.6 Hz, 1H), 7.23 (dd, J=8.2, 2.4 Hz, 1H), 6.58 (d, J=7.6 Hz, 1H), 3.20-2.99 (m, 2H), 2.81 (td, J=7.2, 4.7 Hz, 2H), 2.08 (dh, J=15.3, 7.0 Hz, 1H), 1.84 (dd, J=11.8, 5.7 Hz, 1H), 1.54 (q, J=7.6 Hz, 2H), 1.48 (s, 3H), 1.47 (s, 3H), 1.37 (t, J=11.9 Hz, 1H), 1.26 (ddd, J=29.1, 13.8, 7.4 Hz, 2H).

Step 4: Synthesis of (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione (40)

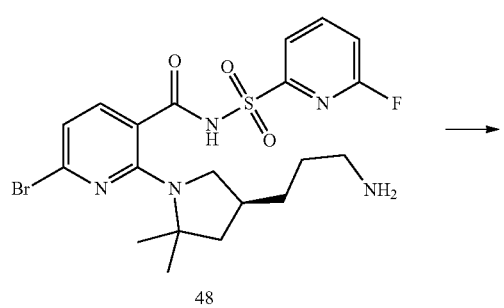

48

-continued

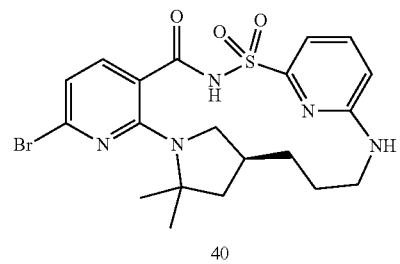

40

A mixture of (S)-2-(4-(3-aminopropyl)-2,2-dimethylpyrrolidin-1-yl)-6-bromo-N-((6-fluoropyridin-2-yl)sulfonyl)nicotinamide (950 g, 1.85 mol) and Na$_2$CO$_3$ (392 g, 3.69 mol; 2 equiv) in DMSO (7.60 L; 8 VolEq) was heated at 85° C. until the reaction was completed (~6 h). The suspension was cooled to <15° C. and diluted with MeTHF (19.0 L; 20 VolEq). Water (13.3 L) was added slowly while maintaining the reaction temperature <15° C. While maintaining the reaction temperature <15° C., 2 M HCl (4.62 L, 9.24 mol; 5 equiv) was added (pH ~2). The phases were separated and the organic phase was washed twice with water (9.50 L; 10 VolEq) containing NaCl (190 g; 2 wt %). The organic phase was concentrated to a minimum volume (45° C./180 torr) and chased with i-PrOAc (2-3×500 mL) to remove the MeTHF. The concentrate was backfilled with i-PrOAc (3.800 L; 4 VolEq) and agitated at 45° C. until crystallization occurred. (The mixture may be seeded with (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione if necessary). The suspension was aged with agitation for at least 30 min and then allowed to cool to 20° C. After aging at 20° C. for at least 2 h, the solid was collected by filtration. The filter-cake was washed with 1:1 i-PrOAc/MTBE (500-mL), air-dried with suction, and vacuum-dried (40-55° C./<100 torr/N$_2$ bleed) to afford (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione.0.8 i-PrOAc (830 g; 78% yield corrected for i-PrOAc solvate) as a white powder with a slight yellow tint.

A second crop was obtained by concentrating the filtrate to ~400 mL total volume. The mixture was then seeded and aged at 15-20° C. The solid was collected by filtration. The filter-cake was washed successively with 1:1 i-PrOAc/MTBE (200 mL) and MTBE (100 mL), air-dried with suction, and vacuum-dried (55° C./<100 torr/N$_2$ bleed) to afford (14S)-8-bromo-12,12-dimethyl-2λ$^6$-thia-3,9,11,18,23-pentaazatetracyclo[17.3.1.1$^{11,14}$.0$^{5,10}$]tetracosa-1(23),5,7,9,19,21-hexaene-2,2,4-trione.0.67 i-PrOAc (113 g; 11% corrected yield) as a pale yellow solid.

$^1$H NMR (400 MHz, Chloroform-d) δ 9.13 (s, 1H), 7.66 (d, J=7.9 Hz, 1H), 7.54 (dd, J=8.4, 7.3 Hz, 1H), 7.43 (d, J=7.3 Hz, 1H), 6.79 (d, J=7.9 Hz, 1H), 6.56 (d, J=8.4 Hz, 1H), 4.99 (hept, J=6.3 Hz, 1H), 4.57 (d, J=8.8 Hz, 1H), 4.02-3.85 (m, 1H), 3.27-3.09 (m, 2H), 2.96 (t, J=10.2 Hz, 1H), 2.35 (p, J=9.5 Hz, 1H), 2.02 (s, 3H), 1.95 (dd, J=12.1, 6.7 Hz, 1H), 1.72-1.59 (m, 6H), 1.58 (s, 3H), 1.55 (s, 3H), 1.43 (d, J=40.1 Hz, 1H), 1.23 (d, J=6.3 Hz, 5H).

Example 11: Synthesis of (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (40)

Example 12A: Synthesis of (14S)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I)

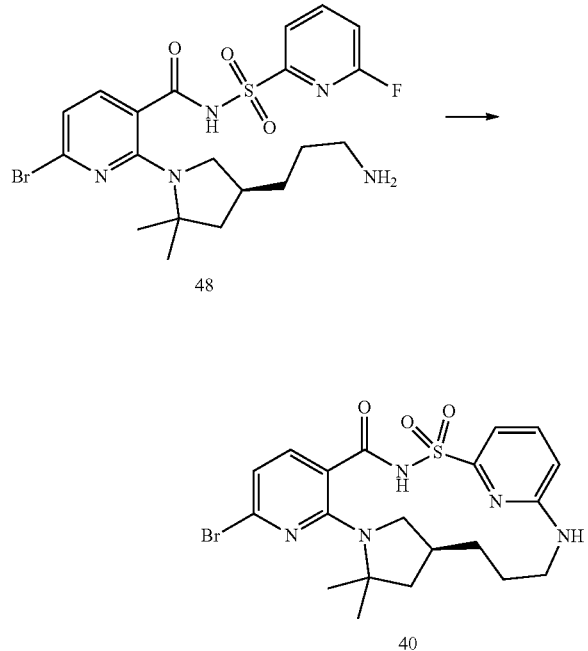 [SMILES: CC1(C)C[C@H](CCCN)CN1c1nc(Br)ccc1C(=O)NS(=O)(=O)c1cccc(F)n1 ; CC1(C)C[C@@H]2CCCNc3cccc(n3)S(=O)(=O)NC(=O)c3ccc(Br)nc3N1C2]

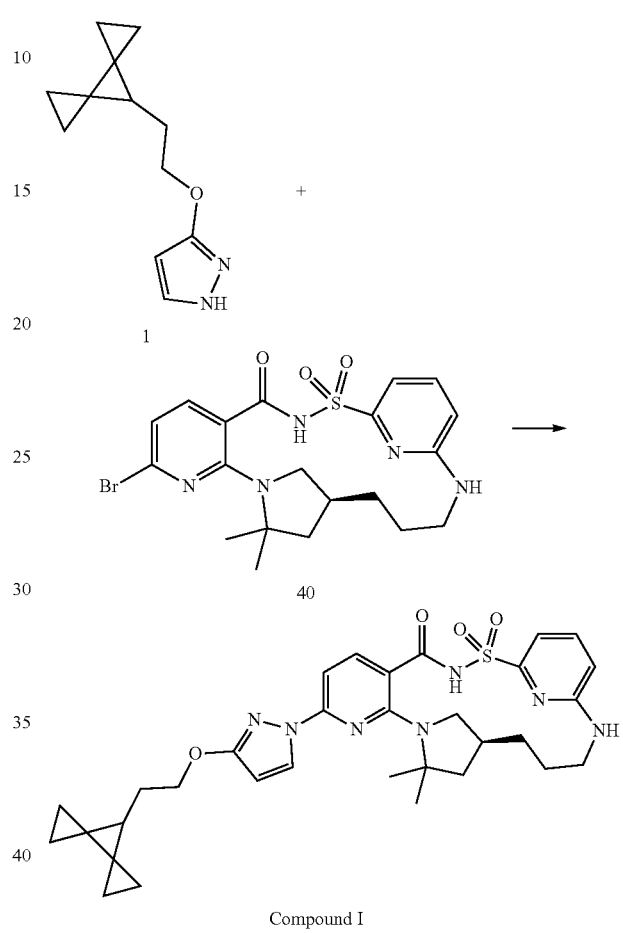

A mixture of (S)-2-(4-(3-aminopropyl)-2,2-dimethylpyrrolidin-1-yl)-6-bromo-N-((6-fluoropyridin-2-yl)sulfonyl)nicotinamide (40.2 g, 78.2 mmol) and K$_2$CO$_3$ (−325 mesh, 27.0 g, 195.5 mmol; 2.5 equiv) in DMSO (0.4 L; 10 VolEq) was heated at 70° C. until the reaction was completed. The suspension was cooled to <15° C. and diluted with IPAc (0.3 L; 7.5 VolEq). While maintaining the reaction temperature <15° C., 1 M HCl (0.41 L, 406.8 mmol; 4.3 equiv) was added (pH ~2).

After aging at 20° C. for at least 2 h, the solid was collected by filtration. The filter-cake was washed with water (4×50-mL) followed by IPAc (2×75 mL), air-dried with suction, and vacuum-dried (45° C./<100 torr/N$_2$ bleed) to afford (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione.1 DMSO (29 g; 73% yield corrected for DMSO solvate).

¹H NMR (400 MHz, Chloroform-d) δ 9.13 (s, 1H), 7.66 (d, J=7.9 Hz, 1H), 7.54 (dd, J=8.4, 7.3 Hz, 1H), 7.43 (d, J=7.3 Hz, 1H), 6.79 (d, J=7.9 Hz, 1H), 6.56 (d, J=8.4 Hz, 1H), 4.99 (hept, J=6.3 Hz, 1H), 4.57 (d, J=8.8 Hz, 1H), 4.02-3.85 (m, 1H), 3.27-3.09 (m, 2H), 2.96 (t, J=10.2 Hz, 1H), 2.5 (s, 6H, DMSO), 2.35 (p, J=9.5 Hz, 1H), 2.02 (s, 3H), 1.95 (dd, J=12.1, 6.7 Hz, 1H), 1.72-1.59 (m, 6H), 1.58 (s, 3H), 1.55 (s, 3H), 1.43 (d, J=40.1 Hz, 1H), 1.23 (d, J=6.3 Hz, 5H).

A mixture of (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (120 g of 86% w/w with IPAc [103.2 g (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione], 0.21 mol, 1 equiv), 3-(2-(dispiro[2.0.2⁴.1³]heptan-7-yl)ethoxy)-1H-pyrazole (42.6 g, 0.21 mol, 1 equiv), K$_2$CO$_3$ (325 mesh, 63.4 g, 0.46 mol, 2.2 equiv), CuI (3.3 g, 17.2 mmol, 0.083 equiv) and BuOAc (740 mL, 7.2 vol based on active (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione) was stirred at ambient temperature. DMF (300 mL, 2.9 vol) and N,N'-dimethylcyclohexane-1,2-diamine (14.6 g or 16.2 ml, 0.1 mol, 0.49 equiv) were then added and the reactor contents purged with N$_2$. The mixture was then heated to 120° C. until the reaction is completed (~4 h).

The mixture was allowed to cool to ambient then 10% aq w/v oxalic acid (860 mL, 0.96 mol, 4.6 equiv) was added dropwise. The mixture was stirred for at least 1 h then the solids were removed by filtration. The removed solids were washed with IPAc (2×120 mL). The organic layer was isolated then washed with 8% aq w/v trisodium citrate (600 mL) then 1:1 v/v water/brine (400 mL). The organic layer was filtered through a pad of Celite. The filter pad was washed with IPAc (150 mL) and the filtrate concentrated. 1-PrOH (800 mL of 7.8 vol) was added and the mixture concentrated. This step was repeated one more time then toluene (800 mL) was added and the mixture concentrated. This step is repeated one more time to afford a thick slurry. The crude mixture was concentrated to volume of 300 mL (2.9 vol) of toluene. (The mixture was seeded with Compound I Form A if the mixture is homogeneous). After stirring the slurry overnight, the solid was collected by filtration washing the solid with toluene (2×100 mL, 0.97 vol). The solid is dried under vacuum to afford Compound I Form A as a white/off-white solid (107.0 g, 83%, 94.5% (AUC) HPLC purity).

Compound I Form A [22.2 g, 94.6% (AUC)] was suspended in toluene (440 mL, 20 vol based on Compound I) and the mixture heated to reflux for at least 2 h. The mixture was cooled over 8 h to ambient temperature then stirred overnight. The solid was collected by filtration washing the solid with toluene (40 mL, 1.8 vol). The solid was dried under vacuum with a nitrogen bleed at 50° C. until the loss on drying is NMT 1.0% to afford Compound I Form A as a white/off-white solid (18.8 g, 84%, 96.8% (AUC) HPLC purity).

Compound I Form A [17.5 g, 97.0% (AUC)] was suspended in toluene (350 mL, 20 vol) and the mixture heated to reflux. After holding at reflux for at least 2 h, the mixture was cooled over 8 h to ambient temperature then stirred at ambient temperature overnight. The solid was collected by filtration washing the solid with toluene (40 mL, 1.8 vol) then dried under vacuum to afford Compound I Form A as a white/off-white solid (15.7 g, 89%, 98.4% (AUC) HPLC purity).

$^1$H NMR (500 MHz, DMSO-$d_6$) δ 12.52 (s, 1H), 8.21 (d, J=2.9 Hz, 1H), 7.83 (d, J=8.2 Hz, 1H), 7.59 (t, J=7.9 Hz, 1H), 7.12-6.83 (m, 3H), 6.72 (d, J=8.5 Hz, 1H), 6.09 (d, J=2.8 Hz, 1H), 4.22 (td, J=6.8, 2.3 Hz, 2H), 4.04-3.84 (m, 1H), 3.16 (s, 1H), 2.96 (d, J=13.1 Hz, 1H), 2.70 (d, J=11.3 Hz, 1H), 2.13 (s, 1H), 1.84 (dq, J=20.2, 6.6, 5.9 Hz, 4H), 1.70-1.40 (m, 10H), 1.32 (q, J=12.2 Hz, 1H), 0.90-0.75 (m, 4H), 0.65 (dd, J=8.6, 4.2 Hz, 2H), 0.51 (dd, J=8.5, 4.2 Hz, 2H).

Example 12B: Alternative Synthesis of (14S)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I)

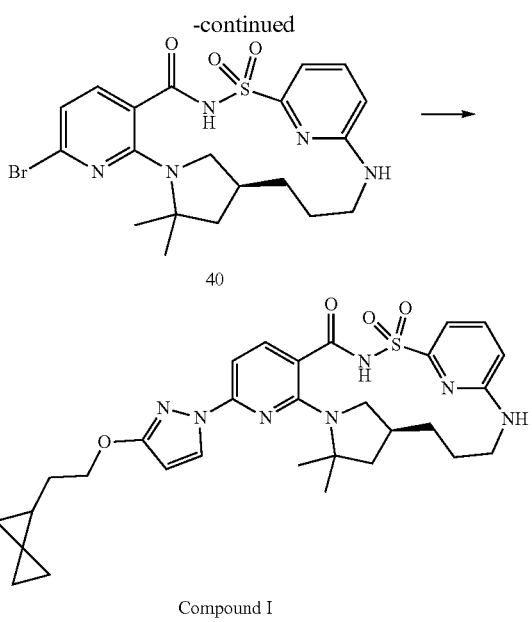

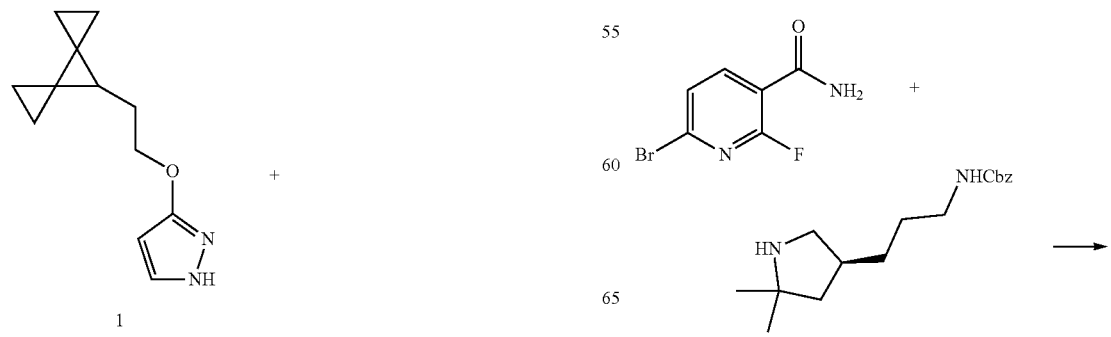

Compound I

A mixture of (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (110 g, 182.441 mmol, 1.00 equiv, iPrOAc solvate), 3-(2-(dispiro[2.0.2⁴.1³]heptan-7-yl)ethoxy)-1H-pyrazole (48.447 g, 237.174 mmol, 1.3 equiv) and MEK (8 volumes) was heated to 40° C. then degassed with N₂. tBuXphos Pd G3 (1.922 g, 2.372 mmol, 1.25 mol %) was then added to the mixture. A degassed solution of MTBD (67.034 g, 428.737 mmol, 2.35 equiv) in MEK (2.00 vol) was then added to the reactor over 1 h while maintaining 40° C. The reaction was then stirred at 40° C. until completed (about 2 h) then cooled to 20° C. An aqueous work-up was then performed with 1M HCl then the organic layer was stirred with Silia Met S Thiol (66 g, 60% w/w relative to (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione) at 50° C. for 6 h. The mixture was cooled to 20° C. then filtered through Celite then concentrated under vacuum. The solvent was swapped by vacuum distillation to toluene (3 vol) then cooled to 20° C. and stirred for at least 3 h. The solid was isolated by filtration then dried under vacuum to afford Compound I Form A (92 g, 81% yield).

Example 13: Synthesis of benzyl (S)-(3-(1-(6-bromo-3-carbamoylpyridin-2-yl)-5,5-dimethylpyrrolidin-3-yl)propyl)carbamate (45)

153

-continued

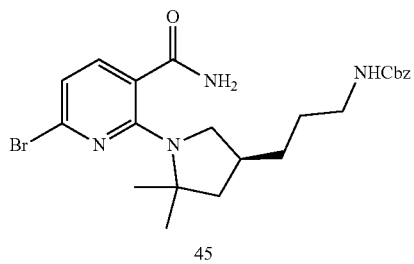
45

A stirred suspension of 6-bromo-2-fluoronicotinamide (40.0 g, 183 mmol), benzyl (S)-(3-(5,5-dimethylpyrrolidin-3-yl)propyl)carbamate•HCl (65.7 g, 201 mmol; 1.1 equiv), and K$_2$CO$_3$ (30.3 g, 219 mmol) in acetonitrile (260 mL) was warmed at 40° C. until the reaction was complete (~20 h) then cooled to ambient temperature. Water (480 mL) was slowly added and the resulting solid was collected by filtration. The filter-cake was washed with 2:1 water:CH$_3$CN (2×120 mL), then dried to afford benzyl (S)-(3-(1-(6-bromo-3-carbamoylpyridin-2-yl)-5,5-dimethylpyrrolidin-3-yl)propyl)carbamate (86.8 g; 97%; 99.0% AUC) as an off-white powder.

$^1$H NMR (400 MHz, DMSO-d$_6$) δ 7.80 (d, J=2.3 Hz, 1H), 7.40 (d, J=2.2 Hz, 1H), 7.39-7.25 (m, 7H), 6.68 (d, J=7.7 Hz, 1H), 5.01 (s, 2H), 3.29-3.10 (m, 2H), 3.00 (q, J=6.6 Hz, 2H), 2.19 (s, 1H), 1.90 (dd, J=11.8, 5.6 Hz, 1H), 1.53 (s, 3H), 1.49 (s, 3H), 1.47-1.24 (m, 5H).

UPLC-MS: M+1=489/491 (conforms).

Example 14: Alternative Synthesis of (14S)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I)

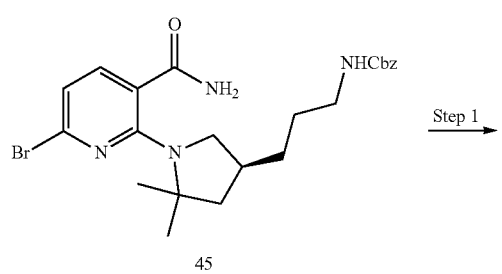
51

154

-continued

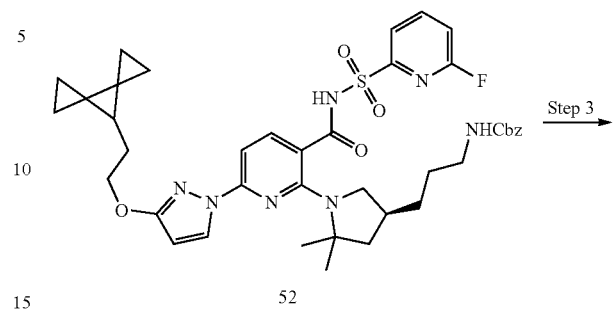
52

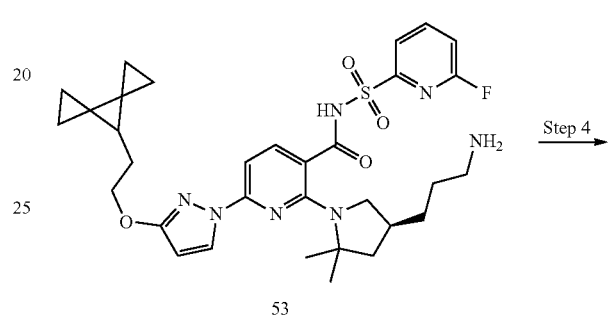
53

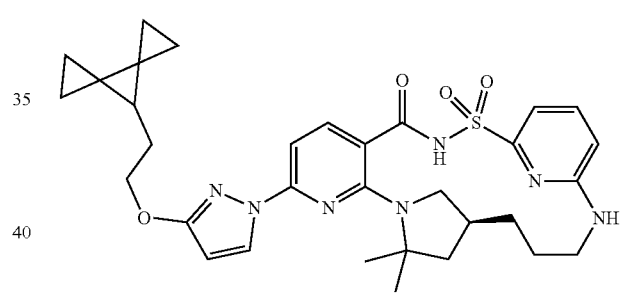
Compound I

Step 1: Synthesis of benzyl (S)-(3-(1-(3-carbamoyl-6-(3-(2-(dispiro[2.0.2⁴.1³]heptan-7-yl)ethoxy)-1H-pyrazol-1-yl)pyridin-2-yl)-5,5-dimethylpyrrolidin-3-yl)propyl)carbamate (51)

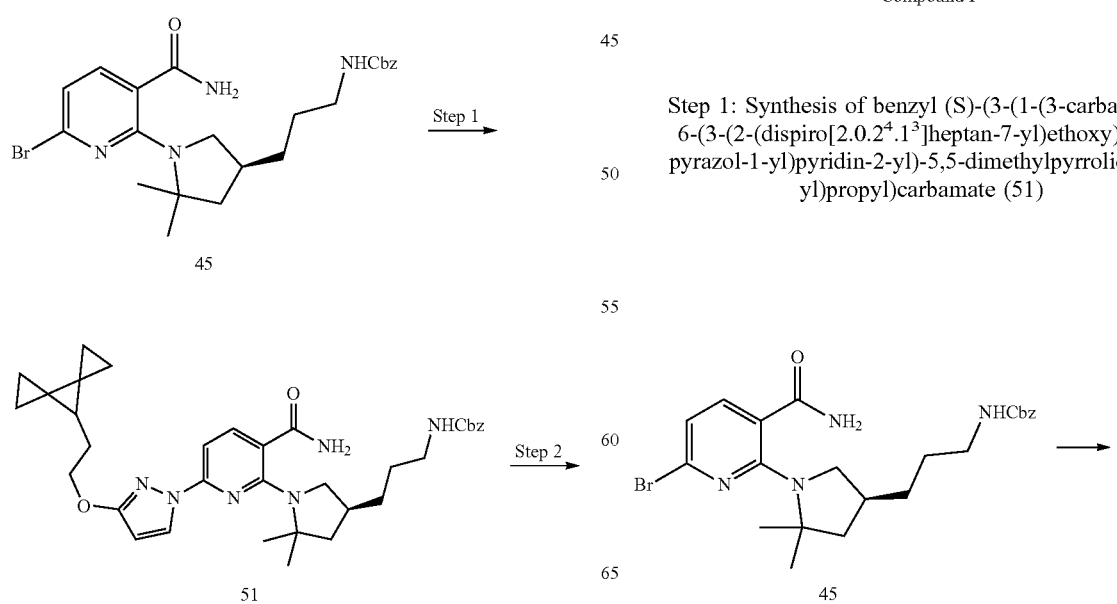

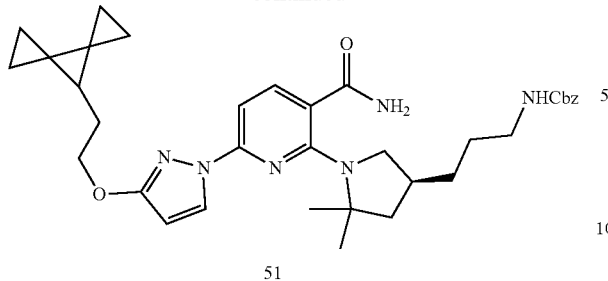

51

A suspension of benzyl (S)-(3-(1-(6-bromo-3-carbamoylpyridin-2-yl)-5,5-dimethylpyrrolidin-3-yl)propyl)carbamate (85.0 g, 174 mmol), 3-(2-(dispiro[2.0.2$^4$.1$^3$]heptan-7-yl)ethoxy)-1H-pyrazole (42.57 g, 208.4 mmol, 1.2 equiv), K$_2$CO$_3$ (52.8 g, 382 mmol, 2.2 equiv), and (1R,2R)-N$^1$,N$^2$-dimethylcyclohexane-1,2-diamine (19.8 g, 21.9 mL, 139 mmol, 0.8 equiv) in DMF (425 mL) was purged with N$_2$ for 20 min. CuI (3.3 g, 17 mmol, 0.1 equiv) was added and the mixture purged for an additional 5 min, then heated at 90° C. until the reaction was completed (~3.5 h). Next the reaction was cooled at ambient temperature. 2-MeTHF (850 mL) and 0.5 M NH$_4$OH (452 mL, 226 mmol) were added and the uppermost organic phase was isolated then washed successively with 0.5 M NH$_4$OH (2×174 mL, 86.8 mmol), 0.5 M HCl (347 mL, 174 mmol), water (150 mL)/brine (50 mL), and sat. NaHCO$_3$ (50 mL). The solution was dried (Na$_2$SO$_4$) then concentrated to an oil. CH$_3$CN (255 mL) was added then removed under vacuum to afford a tan solid. The solid was slurried with CH$_3$CN (255 mL) at 40° C. for 20 min to give a suspension, which was then cooled to room temperature and stirred. The solid was isolated by filtration then dried to afford benzyl (S)-(3-(1-(3-carbamoyl-6-(3-(2-(dispiro[2.0.2$^4$.1$^3$]heptan-7-yl)ethoxy)-1H-pyrazol-1-yl)pyridin-2-yl)-5,5-dimethylpyrrolidin-3-yl)propyl)carbamate (70.4 g; 66%; 95.8% AUC) as a white powder.

$^1$H NMR (400 MHz, DMSO-d$_6$) δ 8.19 (d, J=2.7 Hz, 1H), 7.73 (s, 1H), 7.61 (d, J=8.0 Hz, 1H), 7.42-7.20 (m, 7H), 6.84 (d, J=8.0 Hz, 1H), 6.05 (d, J=2.7 Hz, 1H), 5.01 (s, 2H), 4.20 (t, J=6.7 Hz, 2H), 3.32 (t, J=10.4 Hz, 1H), 3.19 (t, J=8.8 Hz, 1H), 3.01 (q, J=6.5 Hz, 2H), 2.21 (s, 1H), 1.94 (dd, J=11.9, 5.6 Hz, 1H), 1.81 (q, J=6.6 Hz, 2H), 1.61 (s, 3H), 1.57 (s, 3H), 1.53-1.23 (m, 6H), 0.90-0.77 (m, 4H), 0.67-0.60 (m, 2H), 0.53-0.46 (m, 2H).

Step 2: Synthesis of benzyl (S)-(3-(1-(6-(3-(2-(dispiro[2.0.2$^4$.1$^3$]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate (52)

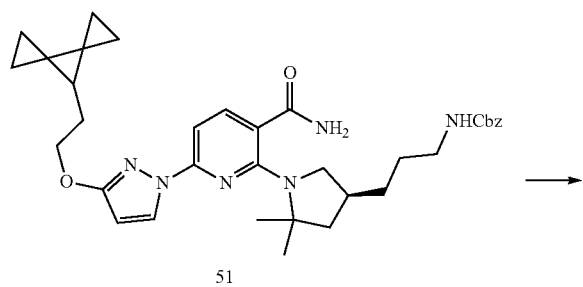

51

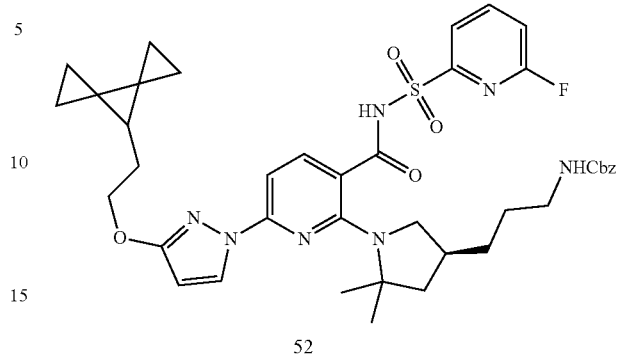

52

A solution of benzyl (S)-(3-(1-(3-carbamoyl-6-(3-(2-(dispiro[2.0.2$^4$.1$^3$]heptan-7-yl)ethoxy)-1H-pyrazol-1-yl)pyridin-2-yl)-5,5-dimethylpyrrolidin-3-yl)propyl)carbamate (68.0 g, 111 mmol) in 2-MeTHF (408 mL, 6 VolEq) was cooled to 0-5° C., then 6-fluoropyridine-2-sulfonyl chloride (29.2 g of 92.9% w/w, 139 mmol; 1.25 equiv) in 2-MeTHF (136 mL, 2 VolEq) was added. A 40% w/w heptane solution of lithium 2-methylbutan-2-olate (82.3, 255 mmol; 2.3 equiv) was added slowly, maintaining the reaction temperature between 0-5° C. The solution was stirred until the reaction was complete (30 min), then EtOAc (408 mL, 6 VolEq) and a solution of NaHSO$_4$ (32.0 g, 266 mmol, 2.4 equiv) in water (272 mL; 4 VolEq) were added. The organic phase was isolated then washed with water (272 mL; 4 VolEq), dried (Na$_2$SO$_4$), and concentrated to a brown semi-solid. MIBK (238 mL; 3.5 VolEq) was added and the mixture was heated to 70° C., then seeded with crystalline benzyl (S)-(3-(1-(6-(3-(2-(dispiro[2.0.2$^4$.1$^3$]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate, then allowed to cool to ambient temperature, then stirred for 2 h. The solid was collected by filtration then dried to afford benzyl (S)-(3-(1-(6-(3-(2-(dispiro[2.0.2$^4$.1$^3$]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate (53.7 g, 63%; 97.5% AUC) as a white powder.

Additional product was obtained as a 2$^{nd}$ crop after a SiO$_2$ plug filtration followed by crystallization from i-PrOH/MIBK to afford benzyl (S)-(3-(1-(6-(3-(2-(dispiro[2.0.2$^4$.1$^3$]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate (14.4 g; 17%; 92.5% AUC) as an off-white powder.

$^1$H NMR (400 MHz, DMSO-d$_6$) δ 8.34 (q, J=7.8 Hz, 1H), 8.13 (dd, J=7.4, 2.0 Hz, 1H), 7.88 (d, J=8.3 Hz, 1H), 7.59 (dd, J=8.3, 2.3 Hz, 1H), 7.37 (d, J=4.2 Hz, 4H), 7.34-7.21 (m, 2H), 6.94 (d, J=8.3 Hz, 1H), 6.10 (d, J=2.8 Hz, 1H), 5.05 (s, 2H), 4.22 (t, J=6.7 Hz, 2H), 3.01 (hept, J=6.7 Hz, 2H), 2.46 (dd, J=10.4, 7.0 Hz, 1H), 2.13 (s, 1H), 1.89 (dd, J=11.8, 5.5 Hz, 1H), 1.81 (q, J=6.6 Hz, 2H), 1.54 (s, 6H), 1.47 (t, J=6.5 Hz, 1H), 1.34 (td, J=13.1, 12.6, 6.7 Hz, 3H), 1.17 (dt, J=16.1, 5.2 Hz, 1H), 0.97 (dt, J=13.4, 8.8 Hz, 1H), 0.89-0.75 (m, 4H), 0.71-0.57 (m, 2H), 0.56-0.41 (m, 2H).

$^{19}$F NMR (376 MHz, DMSO-d$_6$) δ −65.73.

Step 3: Synthesis of (S)-2-(4-(3-aminopropyl)-2,2-dimethylpyrrolidin-1-yl)-6-(3-(2-(dispiro[2.0.2⁴.1³]heptan-7-yl)ethoxy)-1H-pyrazol-1-yl)-N-((6-fluoropyridin-2-yl)sulfonyl)nicotinamide((S)-53)

Step 4: Synthesis of (14S)-8-[3-(2-{dispiro[2.0.2⁴.1³]heptan-7-yl}ethoxy)-H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I)

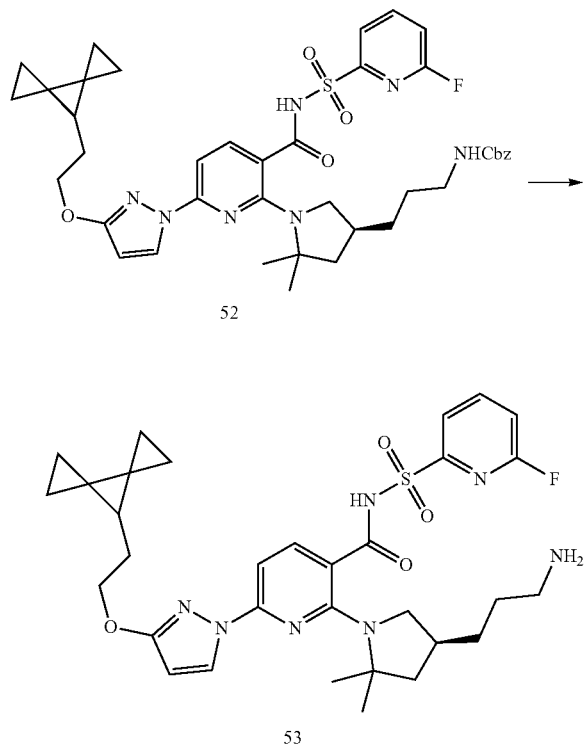

52

53

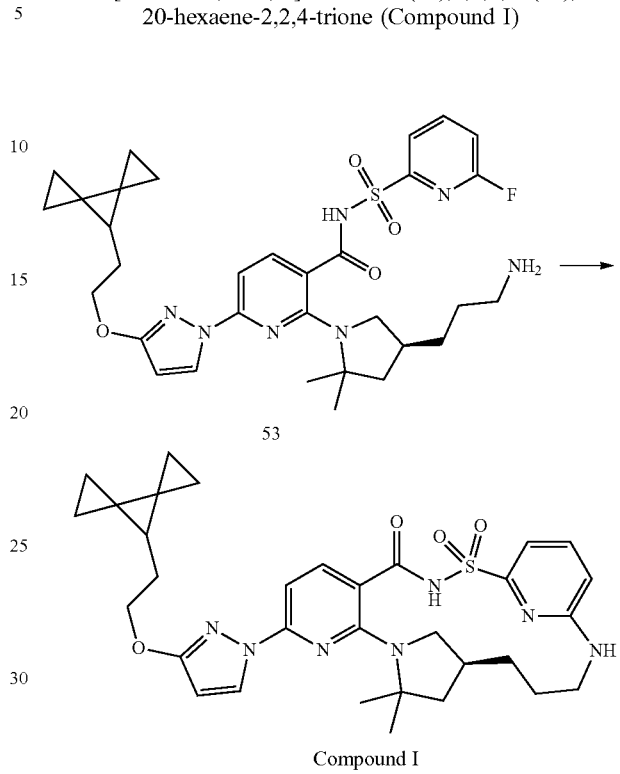

53

Compound I

A suspension of benzyl (S)-(3-(1-(6-(3-(2-(dispiro[2.0.2⁴.1³]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate (40.0 g, 51.8 mmol), ammonium formate (26.1 g, 415 mmol; 8 equiv), DABCO (116 mg, 1.03 mmol; 0.02 equiv), and 10% Pd on carbon (1.0 g, 0.94 mmol; 0.02 equiv) in MeOH (240 mL; 6 VolEq) was stirred at ambient temperature until the reaction was complete (~70 min). The catalyst was removed by filtration and the filtrate concentrated under vacuum to an oil. The mixture was slurried in MeTHF (200 mL) and EtOAc (200 mL) at 40° C. then the solid was removed by filtration. The filter-cake was rinsed with 2-MeTHF (3×30 mL) then the combined filtrate and washings were concentrated under vacuum to afford (S)-2-(4-(3-aminopropyl)-2,2-dimethylpyrrolidin-1-yl)-6-(3-(2-(dispiro[2.0.2⁴.1³]heptan-7-yl)ethoxy)-1H-pyrazol-1-yl)-N-((6-fluoropyridin-2-yl)sulfonyl)nicotinamide (36.0 g; 102% of HCO₂H salt; 96.2% AUC) as a white, granular powder which was used without further purification.

¹H NMR (500 MHz, DMSO-d₆) δ 8.15 (d, J=2.7 Hz, 1H), 8.11 (q, J=7.9 Hz, 1H), 7.86 (dd, J=7.4, 2.2 Hz, 1H), 7.70 (d, J=7.9 Hz, 1H), 7.24 (dd, J=8.3, 2.4 Hz, 1H), 6.79 (d, J=7.9 Hz, 1H), 6.01 (d, J=2.7 Hz, 1H), 4.20 (t, J=6.7 Hz, 2H), 3.15 (t, J=10.6 Hz, 1H), 3.06 (dd, J=10.9, 7.3 Hz, 2H), 2.82 (hept, J=7.2, 6.3 Hz, 2H), 2.08 (s, 1H), 1.81 (q, J=6.5 Hz, 2H), 1.55 (s, 5H), 1.51 (s, 3H), 1.47 (t, J=6.5 Hz, 1H), 1.42-1.27 (m, 3H), 1.26-1.15 (m, 1H), 0.83 (d, J=5.5 Hz, 4H), 0.64 (dd, J=8.5, 4.2 Hz, 2H), 0.50 (dd, J=8.5, 4.0 Hz, 2H).

A mixture of (S)-2-(4-(3-aminopropyl)-2,2-dimethylpyrrolidin-1-yl)-6-(3-(2-(dispiro[2.0.2⁴.1³]heptan-7-yl)ethoxy)-1H-pyrazol-1-yl)-N-((6-fluoropyridin-2-yl)sulfonyl)nicotinamide•HCO₂H (35.0 g, 51.2 mmol) and K₂CO₃ (21.2 g, 154 mmol; 3 equiv) in DMSO (350 mL; 10 VolEq) was heated at 90° C. under a N₂ blanket for 6 h and then allowed to cool to RT. The suspension was diluted with EtOAc (525 mL; 15 VolEq) and water (280 mL; 8 VolEq). The phases were separated, and the aqueous phase extracted with EtOAc (210 mL). The combined organic phases were washed with a 20% w/v solution of citric acid (49.2 mL, 51.2 mmol) diluted in water (280 mL); the aqueous pH was 3-4. The organic phase was then washed with water (2×280 mL), dried (Na₂SO₄), and concentrated (40° C./30 torr) to afford crude Compound I (35.9 g; 114% theoretical yield; 94.9% AUC) as a pale orange foam.

The crude product was dissolved in hot (105° C.) PhMe (210 mL; 6 VolEq); a yellow solution resulted at ~40° C. The solution self-nucleated at ~80° C. and gradual crystallization occurred. The reaction mixture remained a suspension at 105° C. The suspension was cooled to 20° C. at 10° C./h and allowed to stir overnight. The solid was collected by filtration and the filter-cake was washed with PhMe (2×20 mL). The damp solid was air-dried with suction and then vacuum-dried (50° C./300 torr/N₂ bleed) to afford crystalline Compound I (25.3 g; 80%; 98.7% AUC) as a bright, white powder.

¹H NMR (500 MHz, DMSO-d₆) 12.52 (s, 1H), 8.21 (d, J=2.9 Hz, 1H), 7.83 (d, J=8.2 Hz, 1H), 7.59 (t, J=7.9 Hz, 1H), 7.12-6.83 (m, 3H), 6.72 (d, J=8.5 Hz, 1H), 6.09 (d, J=2.8 Hz, 1H), 4.22 (td, J=6.8, 2.3 Hz, 2H), 4.04-3.84 (m, 1H), 3.16 (s, 1H), 2.96 (d, J=13.1 Hz, 1H), 2.70 (d, J=11.3

Hz, 1H), 2.13 (s, 1H), 1.84 (dq, J=20.2, 6.6, 5.9 Hz, 4H), 1.70-1.40 (m, 10H), 1.32 (q, J=12.2 Hz, 1H), 0.90-0.75 (m, 4H), 0.65 (dd, J=8.6, 4.2 Hz, 2H), 0.51 (dd, J=8.5, 4.2 Hz, 2H).

UPLC-MS: [M+1]=618.5 (conforms).

Example 15: Alternative Synthesis of (14S)-8-[3-(2-{dispiro[2.0.2$^4$.1$^3$]heptan-7-yl}ethoxy)-1H-pyrazol-1-yl]-12,12-dimethyl-2λ$^6$-thia-3,9,11,18,23-pentaazatetracyclo[17.3.1.1$^{11,14}$.0$^{5,10}$]tetracosa-1(22),5,7,9,19(23),20-hexaene-2,2,4-trione (Compound I)

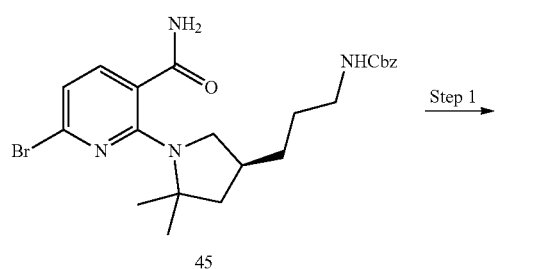

45

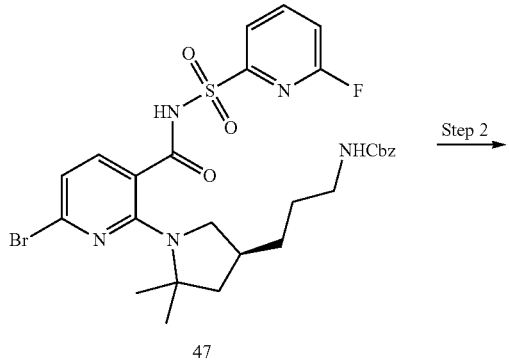

47

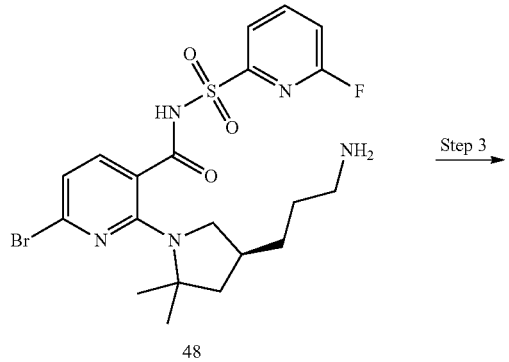

48

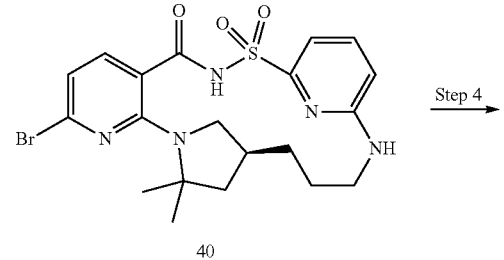

40

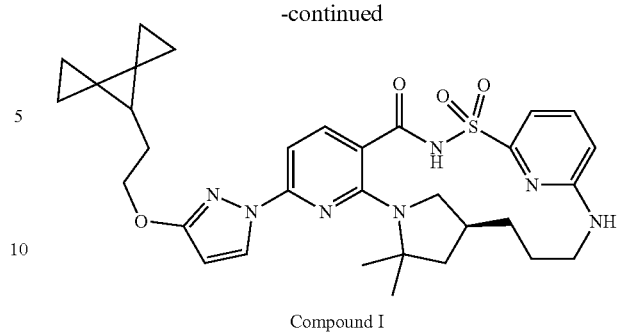

Compound I

Step 1: Synthesis of benzyl (S)-(3-(1-(6-bromo-3-(((6-fluoropyridin-2-yl)sulfonyl)carbamoyl)pyridin-2-yl)-5,5-dimethylpyrrolidin-3-yl)propyl)carbamate (47)

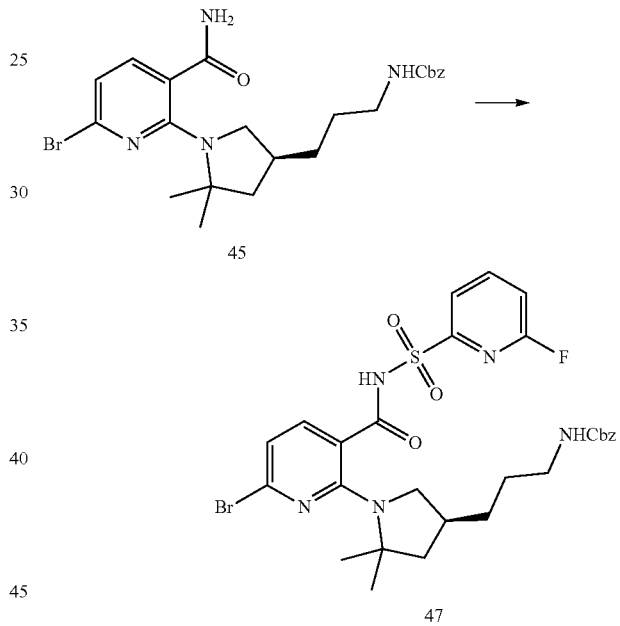

A reaction solution containing 6-fluoropyridine-2-sulfonyl chloride (459.5 mg, 2.349 mmol, 1.15 equiv), was diluted with 2-MeTHF (10 mL, 10 VolEq), and benzyl (S)-(3-(1-(6-bromo-3-(((6-fluoropyridin-2-yl)sulfonyl)carbamoyl)pyridin-2-yl)-5,5-dimethylpyrrolidin-3-yl)propyl) carbamate (1.00 g, 2.043 mmol, 1.0 equiv) was added, then the mixture was cooled to 5° C. and lithium t-amoxide (40 w/w % solution in heptane, 1.20 g, 5.108 mmol, 2.5 equiv) slowly added via syringe in order to maintain an internal temperature of <7° C. Once the addition was complete, the reaction mixture was stirred and allowed to warm to room temperature and held until reaction was complete (~1 h). The reaction mixture was cooled to <10° C. and aq 1M HCl solution (8.172 mL, 8.172 mmol, 4.0 equiv) was added, to bring the mixture to pH=1. The phases were separated and the organic phase was washed with water (5.000 mL, 5.0 VolEq), then washed with brine (3.000 mL, 3.0 VolEq). The organic phase was transferred to a flask and concentrated to solid benzyl (S)-(3-(1-(6-bromo-3-(((6-fluoropyridin-2-yl)

sulfonyl)carbamoyl)pyridin-2-yl)-5,5-dimethylpyrrolidin-3-yl)propyl)carbamate (1.38 g, 104.2% yield, not corrected for residual solvent).

$^{1}$H NMR (400 MHz, DMSO-d$_{6}$) δ 13.09 (s, 1H), 8.44-8.31 (m, 1H), 8.12 (d, J=7.2 Hz, 1H), 7.59 (d, J=8.0 Hz, 2H), 7.41-7.22 (m, 5H), 6.78 (d, J=8.0 Hz, 1H), 5.04 (s, 2H), 3.87-3.71 (m, 2H), 3.52 (q, 1H), 3.09-2.91 (m, 2H), 2.11 (s, 1H), 2.01-1.68 (m, 1H), 1.46 (d, J=8.4 Hz, 6H), 1.39-1.24 (m, 4H).

Step 2: Alternative Synthesis of (S)-2-(4-(3-aminopropyl)-2,2-dimethylpyrrolidin-1-yl)-6-bromo-N-((6-fluoropyridin-2-yl)sulfonyl)nicotinamide (48)

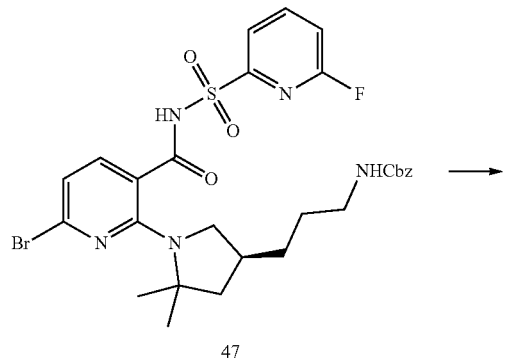

47

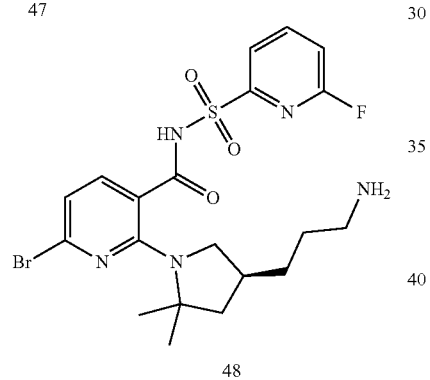

48

To a reaction vessel stirring at room temperature was added water followed by sulfuric acid to prepare aqueous 9M H$_{2}$SO$_{4}$ (41.14 mL, 9.0 M, 370.2 mmol). To the resulting solution was added benzyl (S)-(3-(1-(6-bromo-3-(((6-fluoropyridin-2-yl)sulfonyl)carbamoyl)164yridine-2-yl)-5,5-dimethylpyrrolidin-3-yl)propyl)carbamate (8.0 g, 12.34 mmol, 1.0 equiv) and the resulting reaction mixture was stirred at 30° C. until the reaction was deemed complete. The reaction mixture was cooled >10° C. and basified with aq NaOH (aq 4M solution, aprox 100 mL, 400 mmol) and diluted with 2-MeTHF (160.0 mL, 20.0 VolEq), stirred at 20-25° C., and separated. The aqueous phase was re-extracted with 2-MeTHF (80.0 mL, 10.0 VolEq). The organic phases were combined and partially concentrated (4-8 VolEq) allowing product to crystallize out of solution. The mixture was then filtered the solid rinsed with 2-MeTHF (16.0 mL, 2.0 VolEq), and the solid dried in vacuo to afford (S)-2-(4-(3-aminopropyl)-2,2-dimethylpyrrolidin-1-yl)-6-bromo-N-((6-fluoropyridin-2-yl)sulfonyl)nicotinamide (2.96 g, 45%), as off-white crystalline solid.

$^{1}$H NMR (400 MHz, DMSO-d$_{6}$) δ 8.08 (q, J=8.0 Hz, 1H), 7.83 (dd, J=7.3, 2.4 Hz, 1H), 7.39 (d, J=7.7 Hz, 1H), 7.32 (d, J=5.1 Hz, 1H), 6.56 (d, J=7.6 Hz, 1H), 3.86-3.79 (m, 0H), 3.77-3.68 (m, 0H), 3.55 (td, J=8.0, 6.4 Hz, 0H), 3.03-2.87 (m, 2H), 1.97-1.89 (m, 0H), 1.86-1.77 (m, 1H), 1.46 (s, 6H), 1.30 (ddt, J=12.9, 5.3, 3.8 Hz, 2H), 1.14-1.07 (m, 2H).

Step 3: Alternative Synthesis of (14S)-8-bromo-12,12-dimethyl-2λ$^{6}$-thia-3,9,11,18,23-pentaazatetracyclo[17.3.1.1$^{11,14}$.0$^{5,10}$]tetracosa-1(23),5,7,9,19,21-hexaene-2,2,4-trione (40)

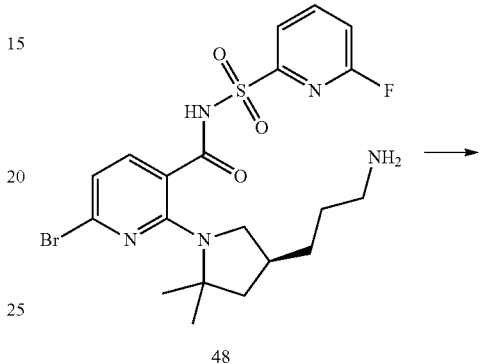

48

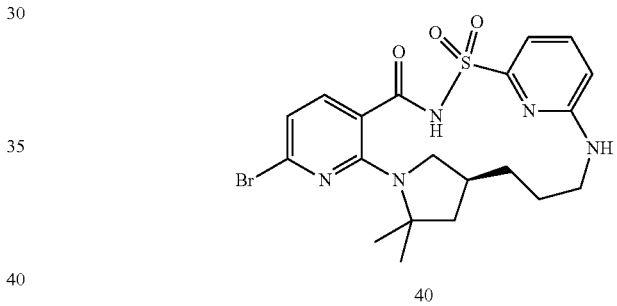

40

A mixture of (S)-2-(4-(3-aminopropyl)-2,2-dimethylpyrrolidin-1-yl)-6-bromo-N-((6-fluoropyridin-2-yl)sulfonyl)nicotinamide (2.80 g, 5.443 mmol, 1.0 equiv) in DMSO (28.00 mL, 10.0 VolEq) was stirred and added MgCl$_{2}$ (518.2 mg, 5.443 mmol, 1.0 equiv) followed by addition of K$_{2}$CO$_{3}$ (1.881 g, 13.61 mmol, 2.50 equiv, 325 mesh) and stirred at 80° C. until complete (20 h). The mixture was cooled to 10° C., diluted with EtOAc (42.00 mL, 15.0 VolEq) and acidified with aq 1M HCl (32.66 mL, 32.66 mmol, 6.0 equiv), The aqueous phase was re-extracted with EtOAc (22.40 mL, 8.0 VolEq) and the organic phases combined and washed with water (22.40 mL, 8.0 VolEq), then twice with brine (8.400 mL, 3.0 VolEq). The solution was concentrated to afford 2.59 g (yield=96%) of (14S)-8-bromo-12,12-dimethyl-2λ$^{6}$-thia-3,9,11,18,23-pentaazatetracyclo[17.3.1.1$^{11,14}$.0$^{5,10}$]tetracosa-1(23),5,7,9,19,21-hexaene-2,2,4-trione, as amber foam.

$^{1}$H NMR (400 MHz, DMSO-d$_{6}$) δ 12.63 (s, 1H), 7.67-7.44 (m, 2H), 7.06 (d, J=7.2 Hz, 1H), 6.73 (dd, J=17.6, 8.2 Hz, 2H), 4.86 (p, J=6.3 Hz, 1H), 3.87 (s, 1H), 3.09 (s, 1H), 2.94 (d, J=13.5 Hz, 1H), 2.61 (d, J=10.6 Hz, 1H), 2.11 (s, 1H), 1.90-1.68 (m, 1H), 1.55 (s, 2H), 1.42 (s, 2H), 1.36-1.23 (m, 1H), 1.17 (d, J=6.3 Hz, 6H).

Step 4: Alternative Synthesis of (14S)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound I)

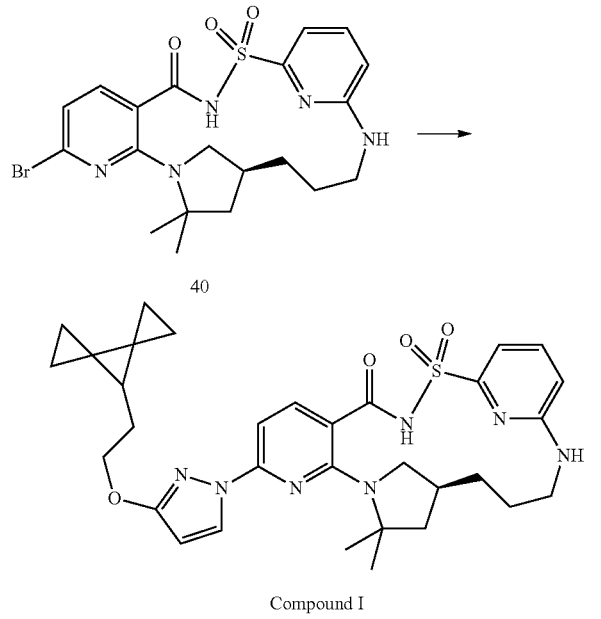

Compound I

To a vessel was loaded DMF (17,500 mL, 7.0 VolEq), butyl acetate (17,500 mL, 7.0 VolEq), (14S)-8-bromo-12,12-dimethyl-2λ⁶-thia-3,9,11,18,23-pentaazatetracyclo[17.3.1.1¹¹,¹⁴.0⁵,¹⁰]tetracosa-1(23),5,7,9,19,21-hexaene-2,2,4-trione (2,500 g, 5,056.58 mmol, 1.00 equiv), and 3-(2-(dispiro[2.0.2⁴.1³]heptan-7-yl)ethoxy)-1H-pyrazole (1,122.716 g, 5,056.58 mmol, 1.00 equiv). The mixture was stirred at room temperature. then added K₂CO₃ (325 mesh, 1,537.514 g, 11,124.477 mol, 2.2 equiv), CuI (79.931 g, 419.696 mmol, 0.083 equiv) and trans-cyclohexane-1,2-diamine (238.794 g, 1,678.785 mmol, 0.332 equiv). The mixture was heated to 120° C. until complete. then the mixture was cooled >30° C. and aq oxalic acid (27.0 L of 0.8 M aqueous solution prepared by mixing 2,094.236 g oxalic acid into 25,0000 mL water) was added to adjust the pH to >3. The resulting mixture was diluted by addition of isopropyl acetate (7,500 mL, 3.0 VolEq) and filtered through Celite washing with isopropyl acetate (2,500 mL, 1.0 VolEq). The filtrate layers were allowed to separate (slow). The organic phase was then washed with aqueous sodium citrate (8% solution, made from trisodium citrate 1,150.963 g, 4,459.904 mmol, 5.0 equiv dissolved in 15.0 L, 6.0 VolEq water), the organic phase was washed with brine (5.0 L, 2.0 VolEq of 10% w/w NaCl in water solution), the organic phase was filtered through Celite, and the Celite cake rinsed with isopropyl acetate (2.5 L, 1.0 VolEq). The organic phase was concentrated to a thick oil, that was diluted with toluene (50,000 mL, 20.0 VolEq), transferred to a reactor (reactor jacket at 60° C.) and stirred, then heated to reflux, held at reflux for 2 h, then cooled to 20° C. over 8 h, then filtered. The filter cake was washed with toluene (5.0 L, 2.0 VolEq) and dried in vacuo (50-55° C., vacuum) to afford Compound I (1,290 g, 41.296% yield) as a crystalline solid.

¹H NMR (400 MHz, DMSO-d₆) δ 12.49 (s, 1H), 8.20 (d, J=2.8 Hz, 1H), 7.82 (d, J=8.2 Hz, 1H), 7.58 (dd, J=8.5, 7.2 Hz, 1H), 7.06 (d, J=7.1 Hz, 1H), 6.97 (d, J=9.2 Hz, 1H), 6.92 (d, J=8.2 Hz, 1H), 6.71 (d, J=8.5 Hz, 1H), 6.08 (d, J=2.7 Hz, 1H), 4.21 (td, J=6.6, 1.4 Hz, 2H), 3.92 (d, J=12.0 Hz, 1H), 3.15 (d, J=9.1 Hz, 1H), 2.95 (d, J=13.4 Hz, 1H), 2.71 (t, J=10.5 Hz, 1H), 2.12 (s, 1H), 1.83 (tq, J=14.8, 8.1, 6.7 Hz, 4H), 1.66-1.43 (m, 11H), 1.39-1.24 (m, 1H), 0.88-0.79 (m, 4H), 0.69-0.58 (m, 2H), 0.54-0.44 (m, 2H).

Example 16: Synthesis of (S)-3-(3-hydroxypropyl)-5,5-dimethylpyrrolidin-2-one (3)

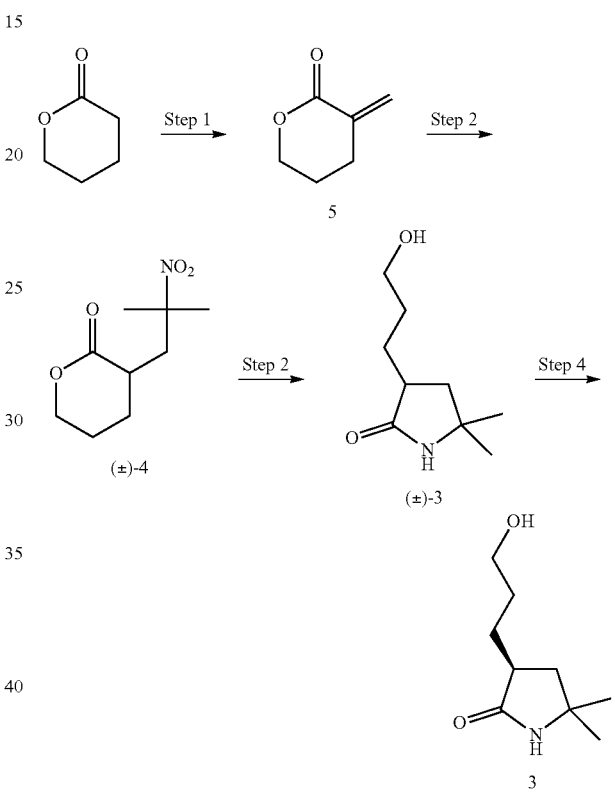

Step 1: Synthesis of 3-methylenetetrahydro-2H-pyran-2-one (5)

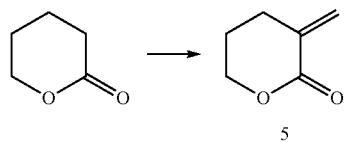

Step 1a: A 5 L 3-neck round bottom flask was fitted with a mechanical stirrer, a heating mantle, an addition funnel, a J-Kem temperature probe/controller and a nitrogen inlet/outlet. The vessel was charged under a nitrogen atmosphere with sodium hydride (59.91 g of 60% w/w, 1.498 mol) followed by heptane (1.5 L) which provided a grey suspension. Stirring was commenced and the internal temperature was recorded at 19° C. The vessel was then charged with ethyl alcohol (3.451 g, 74.91 mmol) added via syringe, which resulted in gas evolution. The addition funnel was charged with a clear pale yellow solution of tetrahydropyran-2-one (150 g, 1.498 mol) and ethyl formate (111 g, 1.50 mol). The solution was added dropwise over 1 h, which resulted in gas evolution and a gradual exotherm to 45° C. The resulting thick white suspension was then heated to 65° C. for 2 h and then allowed to cool to room temperature. The mixture continued to stir at room temperature overnight (about 10 h). The reaction mixture was vacuum filtered through a glass frit Buchner funnel (Medium porosity) under a stream of nitrogen. The filter cake was displaced and washed with heptane (2×250 ml) and pulled for a few minutes. The slightly heptane wet cake was transferred to a glass tray and dried in a vacuum oven at 45° C. for 15 h to provide a white solid (205 g, 1.36 mol, 91% yield) as the desired product (E)-(2-oxotetrahydropyran-3-ylidene)methanolate.

$^1$H NMR (400 MHz, DMSO-$d_6$) δ 8.99 (s, 1H), 3.90-3.83 (m, 2H), 2.09 (t, J=6.3 Hz, 2H), 1.57 (qd, J=6.4, 4.7 Hz, 2H).

Step 1b: A 5 L 3-neck round bottom flask was fitted with a mechanical stirrer, a heating mantle, an addition funnel, a J-Kem temperature probe/controller and a nitrogen inlet/outlet. The vessel was charged under a nitrogen atmosphere with (E)-(2-oxotetrahydropyran-3-ylidene)methanolate-Na salt (205 g, 1.366 mol) and tetrahydrofuran (1640 mL) which provided a white suspension. Stirring was commenced and the pot temperature was recorded at 19° C. The vessel was then charged with paraformaldehyde (136.6 g, 4.549 mol) added as a solid in one portion. The resulting suspension was heated to 63° C. and the condition was maintained for 15 h. The resulting white gelatinous mixture was concentrated under reduced pressure to remove most of the tetrahydrofuran. The remaining residue was partitioned with ethyl acetate (1000 ml), saturated sodium chloride (500 ml) and saturated sodium hydrogen carbonate (500 ml) in a separatory funnel. The organic phase was removed and the residual aqueous phase was extracted with ethyl acetate (5×300 ml). The combined organic phases were dried over sodium sulfate (500 g) and then vacuum filtered through a glass frit Buchner funnel with a 20 mm layer of Celite. The filter cake was displacement washed with ethyl acetate (250 ml). The clear filtrate was concentrated under reduced pressure to provide a clear pale yellow oil (135 g), as the desired crude product. The material was purified by flash column chromatography eluting with a gradient of 100% hexane to 60% ethyl acetate in hexane over 1 h collecting 450 ml fractions. Note: The product can be detected by TLC analysis on silica gel eluting with 3:1 Hex/EtOAc and visualized under UV. The product fractions were combined and concentrated under reduced pressure to provide a clear colorless oil (132 g, 1.18 mol, 86% yield) as the desired product 3-methylenetetrahydropyran-2-one.

$^1$H NMR (400 MHz, DMSO-$d_6$) δ 6.18 (q, J=1.9 Hz, 1H), 5.60 (q, J=1.9 Hz, 1H), 4.40-4.26 (m, 2H), 2.61 (ddt, J=7.0, 6.3, 2.0 Hz, 2H), 1.90-1.75 (m, 2H). The proton NMR indicates about 16 wt % residual ethyl acetate. The corrected yield would then be: (100-16=84) 0.84 (132)=110.9 g (72% yield).

Preparation of this compound in a one-pot procedure has been reported; see *J. Org. Chem.* 2016, 81, 11235-11249. Distillation of this compound has been reported at 52° C. and 0.2 Torr in *Synthesis* 1985, (1), 35-38.

Step 2: Synthesis of 3-(2-methyl-2-nitropropyl)tetrahydro-2H-pyran-2-one ((±)-4)

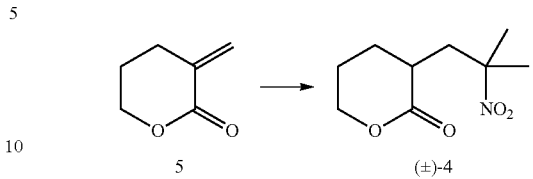

A 5 L 3-neck round bottom flask was fitted with a mechanical stirrer, a cooling bath used as secondary containment, a J-Kem temperature probe, an addition funnel and a nitrogen inlet/outlet. The vessel was charged under a nitrogen atmosphere with 2-nitropropane (104.9 g, 1.177 mol). Stirring was commenced and the pot temperature was recorded at 19° C. The vessel was then charged with 1,8-diazabicyclo[5.4.0]undec-7-ene (22.41 g, 147.2 mmol) added neat in one portion, which resulted in a clear light yellow solution. No exotherm was observed. The addition funnel was charged with a solution of 3-methylenetetrahydropyran-2-one (110 g, 981.0 mmol) in acetonitrile (1100 mL), which was added dropwise over 1 h resulting in a clear light yellow solution and a gradual exotherm to 24° C. The reaction mixture continued to stir at room temperature for 3.5 h and then concentrated under reduced pressure. The remaining residue was dissolved in dichloromethane (1000 ml) and partitioned with 500 ml of a 3:2 mixture of 1 M citric acid solution/saturated sodium chloride solution. Note: The resulting organic phase is a clear pale blue solution and the aqueous phase is a slightly cloudy very pale blue solution. The organic phase was removed and the residual aqueous was extracted with dichloromethane (300 ml). The combined organic phases were washed with saturated sodium chloride solution (300 ml), dried over sodium sulfate (250 g) and then filtered through a glass frit Buchner funnel. The filtrate was concentrated under reduced pressure to a volume of about 200 ml. The clear pale blue dichloromethane solution was diluted with methyl tert-butyl ether (1500 ml) and the cloudy solution was concentrated under reduced pressure to a volume of about 200 ml which provided a suspension. The mixture was diluted with methyl tert-butyl ether (1500 ml) and concentrated under reduced pressure to a volume of about 250 ml. The resulting suspension was allowed to stand at ambient temperature overnight (about 12 h). The solid was collected by vacuum filtration in a glass frit Buchner funnel and the filter cake was displacement washed with cold methyl tert-butyl ether (2×150 ml) and then pulled for 30 min. The material was further dried in a vacuum oven at 45° C. for 5 h to provide the desired product 3-(2-methyl-2-nitro-propyl)tetrahydropyran-2-one (160 g, 0.795 mol, 81% yield), as a white solid.

$^1$H NMR (400 MHz, DMSO-$d_6$) δ 4.34 (ddd, J=11.1, 9.3, 4.3 Hz, 1H), 4.20 (dt, J=11.1, 5.1 Hz, 1H), 2.75-2.62 (m, 1H), 2.56 (dd, J=14.9, 5.2 Hz, 1H), 2.01-1.89 (m, 2H), 1.89-1.67 (m, 2H), 1.55 (d, J=6.0 Hz, 6H), 1.44 (dddd, J=12.8, 11.5, 8.1, 6.6 Hz, 1H). ESI-MS m/z calc. 201.10011, found 202.0 [M+1].

Retention time: 0.97 min as an off white solid.

Step 3: Synthesis of 3-(3-hydroxypropyl)-5,5-dimethylpyrrolidin-2-one ((f)-3)

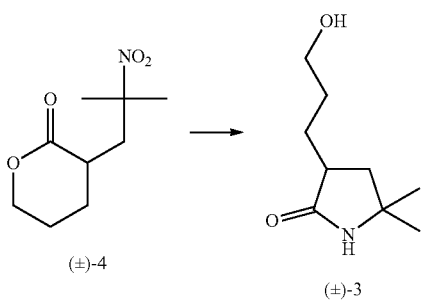

A solution of 3-(2-methyl-2-nitro-propyl)tetrahydropyran-2-one (122 g, 606.3 mmol) in ethanol (2000 mL) purged with nitrogen then Raney Ni (40 g of 50% w/w, 340 mmol) (washed twice with water and once with ethanol, by mixing and decantation) was added. The mixture was purged with nitrogen then hydrogen. The suspension was stirred vigorously and heated at 60° C. for 20 h under hydrogen (1 atm). The reaction was cooled to room temperature, then purged with nitrogen, filtered over celite and carefully washed with ethanol to prevent the residual catalyst from drying out. The clear colorless filtrate was evaporated and the solid residue (105 g) was suspended in MTBE (~1.5 L) and concentrated at reflux to a thick suspension (~200 mL MTBE). The solid was collected by filtration and washed with dry ice-cold MTBE. This solid was dissolved in DCM (~300 mL) under warming and slowly diluted with MTBE (~1 L) with seeding to give a colorless suspension. The colorless suspension was concentrated at 45° C. under reduced pressure to ~500 mL and the suspension was left stirring at room temperature overnight. The colorless suspension was filtered, washed with dry ice-cold MTBE and dried to give 3-(3-hydroxypropyl)-5,5-dimethyl-pyrrolidin-2-one (94.1 g, 88%)

$^1$H NMR (400 MHz, DMSO-$d_6$) δ 7.63 (s, 1H), 4.38 (s, 1H), 3.38 (t, J=6.5 Hz, 2H), 2.37 (qd, J=9.5, 4.4 Hz, 1H), 2.02 (dd, J=12.4, 8.6 Hz, 1H), 1.78-1.63 (m, 1H), 1.50-1.33 (m, 3H), 1.16 (d, J=17.9 Hz, 7H). ESI-MS m/z calc. 171.12593, found 172.0 [M+1]+.

Step 4: Synthesis of (S)-3-(3-hydroxypropyl)-5,5-dimethylpyrrolidin-2-one (3)

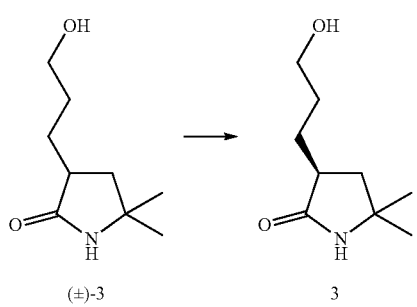

3-(3-Hydroxypropyl)-5,5-dimethyl-pyrrolidin-2-one (1813 g) was separated using a Chiralpak® AZ column eluted with a isocratic mixture of hexane:ethanol (85:15) at ambient temperature to afford (S)-3-(3-hydroxypropyl)-5,5-dimethylpyrrolidin-2-one (810 g) as a colorless solid after removal of the solvent.

98.6% enantiomeric excess (Chiralpak® AZ column, 210 nm); The (S)-enantiomer elutes at 13.1 min. The (R)-enantiomer elutes at 22.5 min.

Example 17: Alternative Synthesis of (S)-3-(3-hydroxypropyl)-5,5-dimethylpyrrolidin-2-one (3)

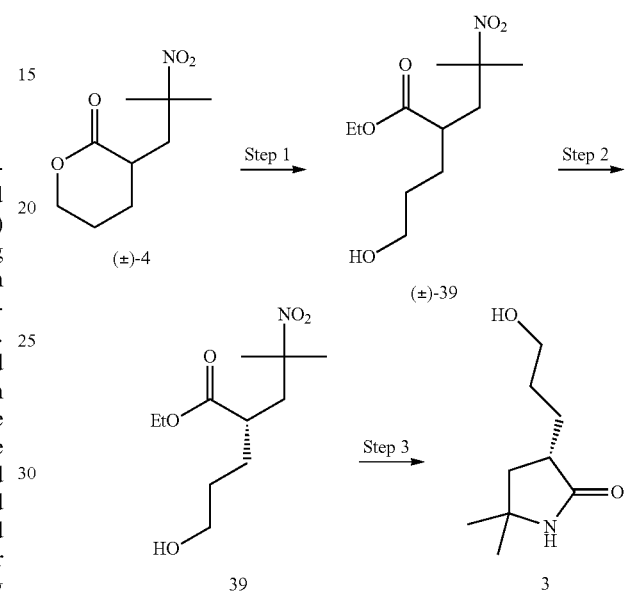

Step 1: Synthesis of ethyl 2-(3-hydroxypropyl)-4-methyl-4-nitropentanoate ((f)-39)

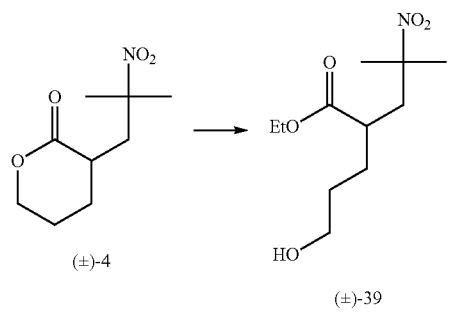 [SMILES: CC(C)(CC1CCCOC1=O)[N+](=O)[O-] ; CCOC(=O)C(CCCO)CC(C)(C)[N+](=O)[O-]]

A 500-mL jacketed reactor, equipped with a reflux condenser, nitrogen purge, stirrer at 450 rpm, and jacket at 20° C., was loaded with 3-(2-methyl-2-nitro-propyl)tetrahydropyran-2-one (55.0 g, 273.3 mmol, 1.0 equiv) and EtOH (440.0 mL, 8.0 vol), and stirred. The starting material did not dissolve. To the reaction mixture was added HCl, 4M Dioxane (13.67 mL of 4 M, 54.66 mmol, 0.20 equiv) causing a 2° C. temperature increase, followed by endotherm and drop in temperature to 19° C. Starting material did not dissolve. The reaction progress was followed by HPLC and deemed complete after 2 h (>98.0% conversion). The reaction solution was neutralized with aqueous 20% $KHCO_3$ and the resulting mixture was then partially concentrated to remove bulk EtOH (75-85% of EtOH removed). The mixture was diluted with 2-MeTHF (550.0 mL, 10.0 vol) and water (275.0 mL, 5.0 vol), then transferred back to the 500 mL reactor, stirred, then stopped and layers allowed to separate, and the aqueous layer drained. The organic layer was washed with brine (165.0 mL, 3.0 vol). The organic layer was dried over $Na_2SO_4$, filtered through celite and cake washed with 2-MeTHF (110.0 mL, 2.0 vol). The clear, light amber filtrate was concentrated to provide the desired product ethyl 2-(3-hydroxypropyl)-4-methyl-4-nitro-pentanoate (62.98 g, 93%) as light amber oil.

$^1$H NMR (400 MHz, DMSO-$d_6$) δ 4.43 (br s, 1H), 4.04 (q, J=7.1 Hz, 2H), 3.35 (t, J=6.3 Hz, 2H), 2.38-2.24 (m, 2H), 2.07-1.96 (m, 1H), 1.50 (m, 7H), 1.46-1.28 (m, 1H), 1.18 (t, J=7.1 Hz, 3H).

Step 2: Synthesis of ethyl (S)-2-(3-hydroxypropyl)-4-methyl-4-nitropentanoate (39)

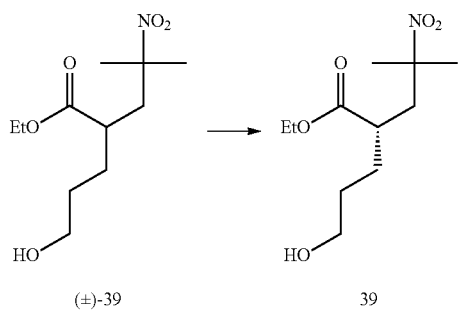 [SMILES: CCOC(=O)C(CCCO)CC(C)(C)[N+](=O)[O-] ; CCOC(=O)[C@@H](CCCO)CC(C)(C)[N+](=O)[O-]]

(±)-39    39

A 500 ml jacketed reactor, equipped with reflux condenser and nitrogen purge, stirrer at 450 rpm, jacket at 35° C. was loaded with pH 7.93 Phosphate buffer, 0.8M (250.0 mL) and ethyl 2-(3-hydroxypropyl)-4-methyl-4-nitro-pentanoate (5 g, 20.22 mmol, 1.0 equiv) and stirred to produce a suspension. Enzyme Lipase from *Rhizomucor miehei* (125.0 mL, 25.0 vol, Palatase® 20,000 L) was added. The resulting reaction mixture was sampled and had a starting pH of 7.63. Reaction allowed to run at 35° C. The reaction progress was followed by chiral GC, and deemed complete after two days (>99.0% of desired ester remains). Once complete, the reaction was cooled to 20° C. and the product extracted into MTBE (250.0 mL, 50 vol), resulting in a large emulsion in the organic layer, that was separated from the aqueous layer. The aqueous layer was re-extracted with MTBE (125.0 mL, 25.0 vol). The emulsified organic layers were combined and filtered through Celite to break up the emulsion, returned to the rinsed reactor, and the aqueous phase was separated from the organic layer. The organic (product) layer was washed with 20% aq $Na_2CO_3$ (50.00 mL, 10.0 vol), 20% aq $Na_2CO_3$ (25.00 mL, 5.0 vol), 20% aq $Na_2CO_3$ (25.00 mL, 5.0 vol), and lastly with 20% aq $Na_2CO_3$ (25.00 mL, 5.0 vol). The organic layer was then washed with water (25.00 mL, 5.0 vol), then with 10% brine (25.00 mL, 5.0 vol). The washed organic layer was concentrated in a rotovap (45° C., vacuum) to provide 2.01 g of ethyl (S)-2-(3-hydroxypropyl)-4-methyl-4-nitropentanoate as light amber oil, enriched to 99.7% of desired enantiomer.

Step 3: Synthesis of (S)-3-(3-hydroxypropyl)-5,5-dimethylpyrrolidin-2-one (3)

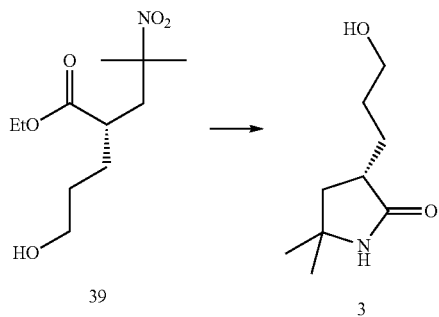 [SMILES: CCOC(=O)[C@@H](CCCO)CC(C)(C)[N+](=O)[O-] ; CC1(C)C[C@H](CCCO)C(=O)N1]

39    3

Ethyl (S)-2-(3-hydroxypropyl)-4-methyl-4-nitropentanoate (5 g, 20.22 mmol) in ethanol (250 mL) was cycled three times with vacuum/nitrogen and Raney Ni (2.374 g of 50% w/w, 20.22 mmol) (washed twice with water and once with ethanol, by mixing and decantation) was added. The mixture was cycled three times vacuum/nitrogen and then three times vacuum/hydrogen. The suspension was stirred vigorously and heated at 60° C. under hydrogen (2 bar) until the reaction was completed.

The reaction was cooled to room temperature, cycled 3 times with vacuum/nitrogen, filtered over Celite and washed with ethanol (50 mL). The solvent was removed from the filtrate then MeCN (50 mL) was added then the solvent was removed to afford (S)-3-(3-hydroxypropyl)-5,5-dimethylpyrrolidin-2-one (2.88 g, 83%) as off-white solid.

$^1$H NMR (400 MHz, DMSO-$d_6$) δ 7.63 (s, 1H), 4.38 (s, 1H), 3.38 (t, J=6.5 Hz, 2H), 2.37 (qd, J=9.5, 4.4 Hz, 1H), 2.02 (dd, J=12.4, 8.6 Hz, 1H), 1.78-1.63 (m, 1H), 1.50-1.33 (m, 3H), 1.16 (d, J=17.9 Hz, 7H).

ESI-MS m/z calc. 171.12593, found 172.0 [M+1]+.

Example 18: Synthesis of tert-butyl (S)-2,2-dimethyl-4-(3-(((6-sulfamoylpyridin-2-yl)amino)propyl) pyrrolidine-1-carboxylate

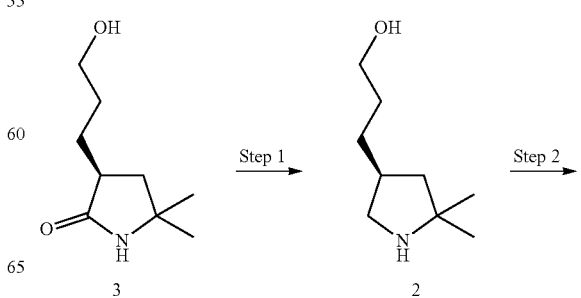

3    2

-continued

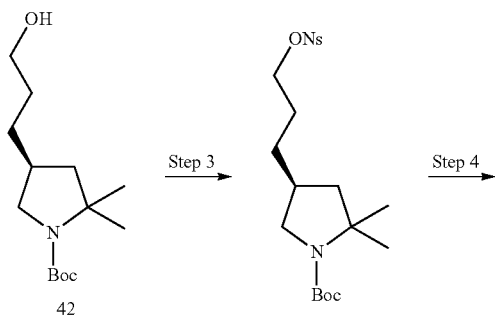

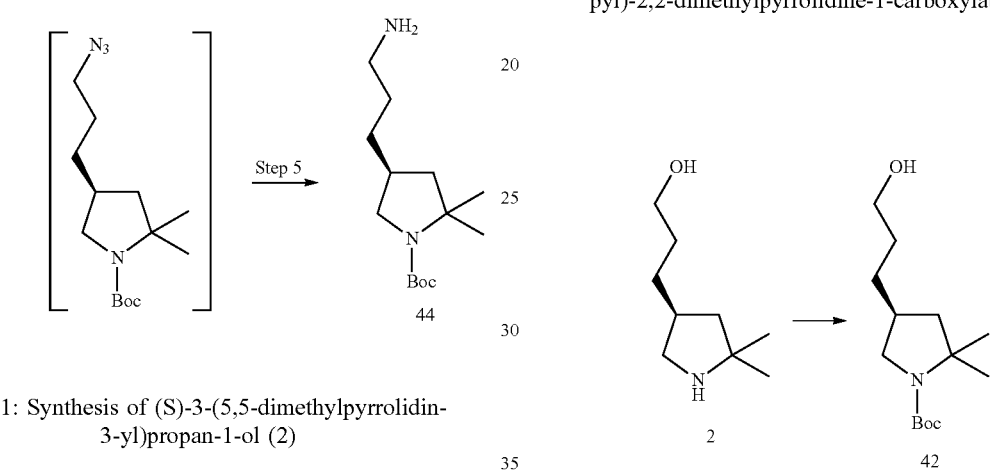

Step 1: Synthesis of (S)-3-(5,5-dimethylpyrrolidin-3-yl)propan-1-ol (2)

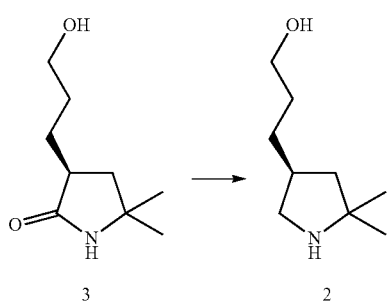

To a 50 L reactor, stirring at 150 rpm, equipped with a jacket set to 40° C. and reflux condenser (10° C.) with nitrogen purge, was added 2-MeTHF (10.00 L, 10 vol) followed by portion-wise addition of LAH pellets (332.5 g, 8.760 mol, 1.50 equiv). After pellet addition, the internal temperature was recorded at 38° C. The stirrer speed was then adjusted to 175 rpm, and the mixture was heated to 75° C. internal temperature. To a 20 L RBF was added (S)-3-(3-hydroxypropyl)-5,5-dimethylpyrrolidin-2-one (1,000 g, 5.840 mol, 1.00 equiv) and 2-MeTHF (10.00 L, 10 vol). The resulting mixture was stirred and heated in a water bath at 65° C. The resulting mixture was added over the course of 2 h into the reactor containing the LAH mixture via an addition funnel, which was heated. The mixture was stirred and then quenched using the Fieser method. Water was added drop-wise (400.0 mL, 1×LAH wt), at 3.5° C., jacket at −2° C., using reactor temperature control, maintaining internal temperature control <30° C. Sodium hydroxide (aqueous, 15%; 400.0 mL, 1×LAH wt) was added, followed by portion-wise addition of water (400.0 mL, 1×LAH wt). The resulting mixture was heated to 60° C. for at least 30 min, and then cooled to 25±5° C. Celite (200 grams, 20 wt %) was added, stirred, and then packed a 12-inch diameter QVF filter with a half-inch layer of Celite and filtered the mixture from the reactor. The reactor was rinsed with 2-MeTHF (4.0 L, 4.0 vol) and the resulting mixture was filtered. The filtrate (clear, light amber) was concentrated in vacuo (50° C. bath, vacuum) to afford a clear oil (872 grams, 94.95% yield).

Step 2: Synthesis of tert-butyl (S)-4-(3-hydroxypropyl)-2,2-dimethylpyrrolidine-1-carboxylate (42)

To a 50 L glass, jacketed reactor, with the jacket set to 20° C., stirring at 175 rpm, and condenser set at 20° C., with $N_2$ purge, was added water (3.480 L, 4.0 vol) and potassium carbonate (1.914 kg, 13.85 mol, 2.5 equiv). To the resulting mixture was then added a solution of (S)-3-(5,5-dimethylpyrrolidin-3-yl)propan-1-ol (870 g, 5.532 mol, 1.0 equiv) in 2-MeTHF (3.480 L, 4.0 vol). 2-MeTHF (3.480 L, 4.0 vol) and $Boc_2O$ (1.096 kg, 5.023 mol, 0.90 equiv) were combined in a glass container. The reactor temperature was set to maintain 20° C. before addition of mixture of 2-MeTHF and $Boc_2O$ via addition funnel over the course of 35 min. The resulting mixture was stirred for 30 min.

To the resulting emulsion was added L-glutamic acid (203.5 g, 1.383 mol, 0.25 equiv) and the emulsion was stirred overnight at room temp. The stirrer was stopped and layers allowed to separate. Water (2.610 L, 3.0 vol) was added, and the mixture stirred. The organic layer was isolated, and the aqueous layer was extracted with 2-MeTHF (2.610 L, 3.0 vol). The combined organic layers were washed with aqueous sodium bisulfate (0.5 M, 1.740 L, 2.0 vol), aq layer pH acidic, then washed with aq 0.5M $NaHSO_4$ (870.0 mL, 1.0 vol). The organic layer was then washed with Aq 0.5M $K_2CO_3$ (1.740 L, 2.0 vol) (pH 12 with pH strip), and aq 0.5M $K_2CO_3$ (1.740 L, 2.0 vol). The organic layer was then washed with brine (870.0 mL, 1.0 vol), then dried over $Na_2SO_4$, and filtered through Celite. The filter cake was rinsed with 2-MeTHF (870.0 mL, 1.0 vol). The filtrate was concentrated in vacuo to afford tert-butyl (S)-4-(3-hydroxypropyl)-2,2-dimethylpyrrolidine-1-carboxylate (1,336 g, 94%) as a clear, viscous oil.

Step 3: Synthesis of tert-butyl (S)-2,2-dimethyl-4-(3-(((4-nitrophenyl)sulfonyl)oxy)propyl)pyrrolidine-1-carboxylate

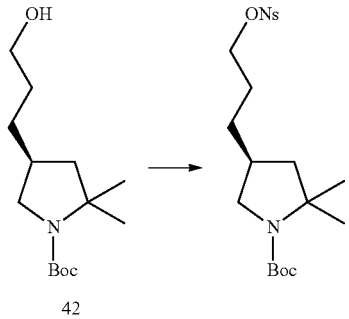

42

To a 50 L jacketed reactor, with jacket set to 20° C., stirring at 175 rpm, a reflux condenser (10° C.), and a nitrogen purge was added tert-butyl (S)-4-(3-hydroxypropyl)-2,2-dimethylpyrrolidine-1-carboxylate (1,330 g, 5.168 mol, 1.0 equiv), DCM (7.980 L, 6.0 vol) and 4-nitrobenzenesulfonyl chloride (1.753 kg, 7.752 mol, 1.50 equiv). The resulting mixture was stirred with a reactor internal temperature of 5° C. Triethylamine (1.046 kg, 10.34 mol, 2.0 equiv) was added via addition funnel at a rate to maintain a reaction temperature of less than 15° C.

The resulting mixture was stirred for approximately 30 min before water (3.990 L, 3.0 vol) and saturated aqueous sodium bicarbonate (2.660 L, 2.0 vol) were added. The resulting mixture was stirred and warmed to room temperature. Addition exotherm went from 5° C. to 12° C. at this scale, jacket then set to 20° C. Stirring was then stopped, the organic was isolated and washed with saturated aqueous sodium bicarbonate (3.990 L, 3.0 vol). The amber organic solution was dried over sodium sulfate, and filtered through Celite. The filter cake was washed with DCM (1.330 L, 1.0 vol). The filtrate was partially concentrated in vacuo, and then IPA (5.320 L, 4.0 vol) was added. Partially concentrated in vacuo and added seed material (tert-butyl (S)-2,2-dimethyl-4-(3-(((4-nitrophenyl)sulfonyl)oxy)propyl)pyrrolidine-1-carboxylate, 250 mg), returned flask to rotovap, stirred at room temp overnight, then added ice-water bath, continued stirring, cooling for 1-2 h. The mixture was filtered through a QVF filter (12-inch diameter). The filter cake was washed with cold IPA (1.330 L, 1.0 vol), and the filter cake was scooped into a rotovap flask and dried in vacuo (50° C., rotovap, vacuum). The solid was dried to 2,091 grams (91.43% yield) as beige colored fine solid.

Step 4: Synthesis of tert-butyl (S)-4-(3-aminopropyl)-2,2-dimethylpyrrolidine-1-carboxylate (44)

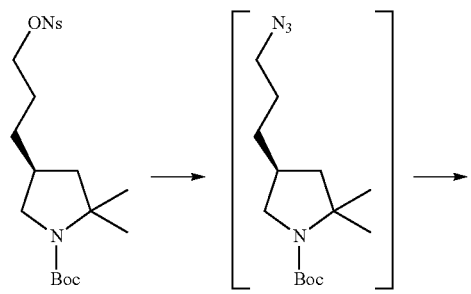

44

Step 4a: To a 50 L jacketed reactor with a jacket set to 20° C., stirring at 175 rpm, and a reflux condenser (10° C.) with nitrogen purge was added tert-butyl (S)-2,2-dimethyl-4-(3-(((4-nitrophenyl)sulfonyl)oxy)propyl)pyrrolidine-1-carboxylate (2090 g, 4.723 mol, 1.00 equiv) and NMP (10.45 L, 5.0 vol). The system was set to maintain an internal temperature of 20° C. while stirring. Sodium azide (307.0 g, 4.723 mol, 1.00 equiv) was added in two portions into the reactor and rinsed in with NMP (2.090 L, 1.0 vol). The resulting mixture was stirred for 1 h before diluting with 2-MeTHF (25.08 L). The organic layer was isolated, washed with 1:1 water, saturated NaHCO₃ solution (16.72 L, 8.0 vol). Additional water was added (4.180 L, 2.0 vol), stirred, and then allowed to separate. The aqueous layer was extracted with 2-MeTHF (6.270 L, 3.0 vol). The organic layers were combined and washed with 2:1 water/sodium bicarbonate (6.270 L, 3.0 vol total, 2 vol water:1 vol bicarb), and then washed with 2:1 water/brine (6.270 L, 3.0 vol), 1:1 water/brine (4.180 L, 2.0 vol), and with brine (4.180 L, 2.0 vol). The organic layer was dried over sodium sulfate then filtered through Celite. The filter cake was washed with 2-MeTHF (2.090 L, 1.0 vol), and the filtrate was partially concentrated in the rotovap to 5+/−1 volumes. Concentrated to 3.02 kg as clear amber solution. Estimate 75% yield that was used without further purification.

Step 4b: To a Buchi 1 L pressure system with a jacket at 20° C., purging with nitrogen was added tert-butyl (4S)-4-(3-azidopropyl)-2,2-dimethyl-pyrrolidine-1-carboxylate (200 g, 708.3 mmol) solution in 2-MeTHF (~700 mL), followed by addition of platinum oxide (2.0 g, 8.85 mmol, 1.0 wt %), and rinsed in with 2-MeTHF (50.00 mL, 0.25 vol). The resulting mixture was stirred at 400 rpm and the reaction chamber was degassed with three cycles of N₂/vacuum, followed with three cycles of H₂/vacuum. The H₂ pressure was set to 2.0 bar and system set for automatic H₂ feed, maintaining 2.0 bar, stirring increased to 900 rpm at 21.1° C. Then, with the jacket set to 20° C., the headspace was evacuated by cycling nitrogen/vacuum times. The reaction mixture was filtered through Celite. The filter cake was rinsed with 2-MeTHF (100.0 mL, 0.5 vol), and the filtrate transferred to a stirred vessel and diluted with 2-MeTHF (2000.0 mL, 10.0 vol), followed by addition of cold aqueous 1N HCl (1.062 L of 1 M, 1.062 mol, 5.0 vol) while stirring. The stirring was stopped, the pH was measured with indicating strips, and the layers separated. The organic layer was extracted with cold aqueous 1 N HCl (354.1 mL of 1 M, 354.2 mmol, 0.5 equiv). The aqueous layers were combined in the reactor and stirred at room temp. 2-MeTHF (1.600 L, 8.0 vol) was added and the mixture was basified by adding aqueous (4 M) NaOH (approximately 354.2 mL of 4 M, 1.417 mol) as needed. The layers were separated, then drained into clean container. The aqueous layer was isolated and extracted with 2-MeTHF (400.0 mL, 2.0 vol). The organic layers were combined and added to the reactor, then washed with brine (600.0 mL, 3.0 vol) then dried over sodium sulfate then filtered through celite. The filter cake was rinsed with 2-MeTHF (400.0 mL, 2.0 vol). The filtrate was concentrated in vacuo (50° C., vacuum) to afford an oil. The material was used without further purification.

Step 4c: The crude amine oil (990 grams, 3.87 mol) was diluted with 2-MeTHF (25.0 L, 25 vol) transferred into a 50 L reactor, and stirred at 25° C. Measured the required amount of oxalic acid (208.9 grams, 425.0 mmol, 0.60 equiv) and dispensed into a glass carboy, then added 2-MeTHF (5.0 L, 5.0 vol) and stirred to dissolve the acid. Began slow addition of the oxalic acid solution to the amine solution. Note that salts start forming on addition and may require slow addition to prevent large chunks of solid from forming. Salts appeared to form a gel that slowly changed. The mixture was stirred at room temp overnight. Appearance of the solid changed from a gel to a mixture containing fine solids. The mixture was filtered (slow filtration), cake then washed with 2-MeTHF (4.00 L, 4.0 vol) and pulled dry in the filter. The cake was scooped out of the filter and dried in vacuo (50° C., vacuum, rotovap). Obtained 1,057 grams of tert-butyl (S)-4-(3-aminopropyl)-2,2-dimethylpyrrolidine-1-carboxylate hemi-oxalate salt, as an off-white solid. The crude amine oil (990 grams, 3.87 mol) was diluted with 2-MeTHF (25.0 L, 25 vol) transferred into a 50 L reactor, and stirred at 25° C. Oxalic acid (208.9 grams, 425.0 mmol, 0.60 equiv) was measured and dispensed into a glass carboy, then dissolved in 2-MeTHF (5.0 L, 5.0 vol) with stirring to dissolve the acid. Slow addition of the oxalic acid solution to the amine solution was carried out. Note that salts start forming on addition and may require slow addition to prevent large chunks of solid from forming. Salts appeared to form a gel that slowly changed. The mixture was stirred at room temp overnight. The appearance of the solid changed from a gel to a mixture containing fine solids. The mixture was filtered (slow filtration), cake then washed with 2-MeTHF (4.00 L, 4.0 vol) and pulled dry in the filter. The cake was scooped out of the filter and dried in vacuo (50° C., vacuum, rotovap). Obtained 1,057 grams of tert-butyl (S)-4-(3-aminopropyl)-2,2-dimethylpyrrolidine-1-carboxylate hemi-oxalate salt as an off-white solid.

Example 19: Synthesis of 2-chloro-6-(3-(2-(dispiro[2.0.2$^4$.1$^3$]heptan-7-yl)ethoxy)-1H-pyrazol-1-yl)nicotinic acid

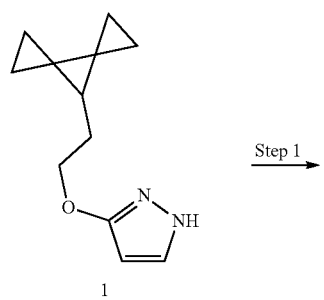

Step 1: Synthesis of ethyl 2-chloro-6-(3-(2-(dispiro[2.0.2$^4$.1$^3$]heptan-7-yl)ethoxy)-1H-pyrazol-1-yl)nicotinate

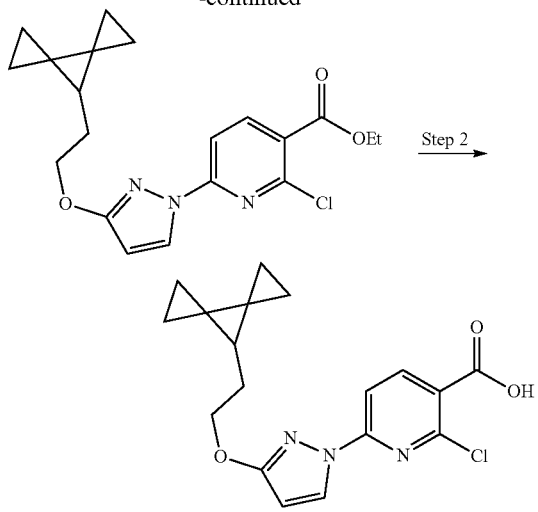

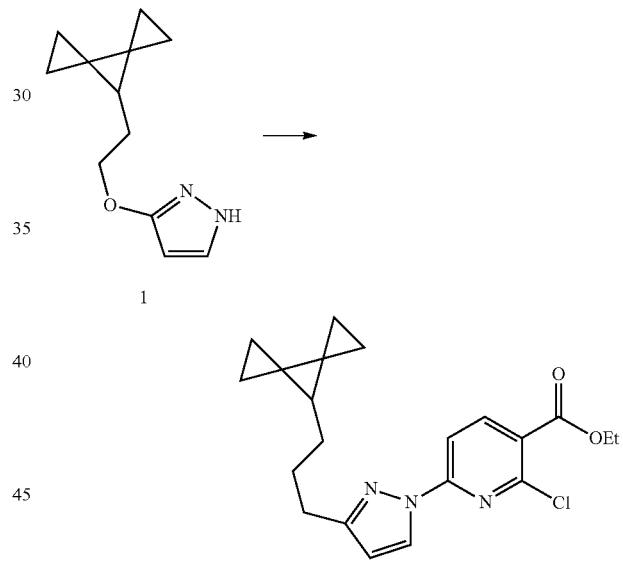

A suspension of 3-(2-(dispiro[2.0.2$^4$.1$^3$]heptan-7-yl)ethoxy)-1H-pyrazole (40.0 g, 196 mmol), ethyl 2,6-dichloronicotinate (43.1 g, 196 mmol), and K$_2$CO$_3$ (35.2 g, 255 mmol) in DMF (240 mL) was stirred at RT. Dissolution resulted in an endotherm from 22 to 16° C. In one portion, DABCO (3.3 g, 29 mmol) was added. The addition was mildly exothermic and raised the reaction temperature from 17 to 23° C. over 20 min. The reaction temperature was maintained at 20-30° C. After ~20 h, HPLC analysis showed the reaction was completed (no ethyl 2,6-dichloronicotinate remained; 90% AUC). The mixture was diluted with dropwise addition of water (400 mL)-white solid formed and the temperature gradually rose from 22 to 32° C. The mixture was re-cooled to maintain the temperature at 15-25° C. After an unsuccessful filtration (solid blinded the filter) the suspension was diluted with EtOAc (480 mL) and the phases were separated. The organic phase was washed with water (200 mL)/brine (50 mL) (2×); the organic phase was dried (Na$_2$SO$_4$) and concentrated (40° C./30 torr) to afford crude ethyl 2-chloro-6-(3-(2-(dispiro[2.0.2⁴.1³]heptan-7-yl)ethoxy)-1H-pyrazol-1-yl)nicotinate (73.1 g; 96%) as an amber oil which became crystalline.

The crude solid was dissolved in warm (80° C.) i-PrOH (200 mL) and allowed to cool to RT over 2 h. The solution was seeded at 38-40° C. for a slow nucleation/crystallization event. At 35-34° C. much crystallization was observed. The suspension was allowed to stir at RT overnight.

The resultant suspension was very thick (oatmeal consistency). The solid was collected by filtration (sintered-glass/paper); the filter-cake was washed with i-PrOH (50 mL), air-dried with suction and then vacuum-dried (55° C./300 torr/N₂ bleed) to afford ethyl 2-chloro-6-(3-(2-(dispiro[2.0.2⁴.1³]heptan-7-yl)ethoxy)-1H-pyrazol-1-yl)nicotinate (60.2 g; 79%; 98.6% AUC) as a white powder. The filtrate was cooled to 3° C. and a 2$^{nd}$ crop was collected (5.8 g; 8%) as a white powder of acceptable purity (98% AUC). Total Yield: 60.2+5.8=66.0 g (87%).

$^1$H NMR (400 MHz, DMSO-d₆) δ 8.45-8.36 (m, 2H), 7.73 (d, J=8.3 Hz, 1H), 6.19 (d, J=2.8 Hz, 1H), 4.34 (q, J=7.1 Hz, 2H), 4.25 (t, J=6.7 Hz, 2H), 1.82 (q, J=6.7 Hz, 2H), 1.47 (t, J=6.6 Hz, 1H), 1.34 (t, J=7.1 Hz, 4H), 0.89-0.77 (m, 1H), 0.83 (s, 4H), 0.71-0.60 (m, 3H), 0.54-0.44 (m, 2H).

Step 2: Synthesis of 2-chloro-6-(3-(2-(dispiro[2.0.2⁴.1³]heptan-7-yl)ethoxy)-1H-pyrazol-1-yl)nicotinic acid

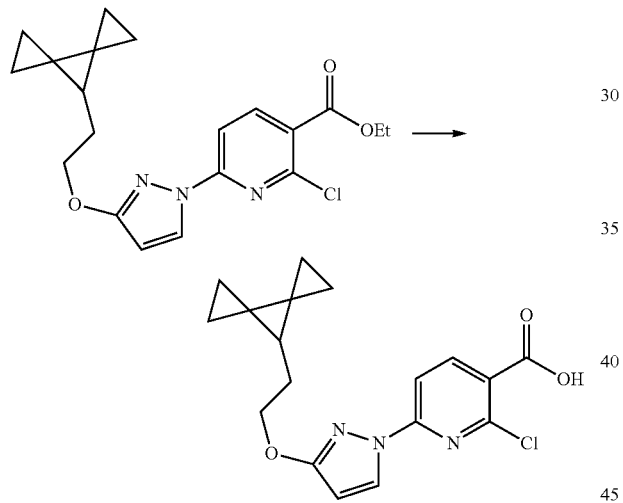

A solution of ethyl 2-chloro-6-(3-(2-(dispiro[2.0.2⁴.1³]heptan-7-yl)ethoxy)-1H-pyrazol-1-yl)nicotinate (62.0 g, 160 mmol) in THF (248 mL) and EtOH (186 mL) was stirred at ambient temperature (13° C.). A 2 M aqueous solution of NaOH (approximately 96 mL; 192 mmol) was added in one portion; an exotherm from 13 to 20° C. was observed. After 1 h, UPLC-MS analysis showed reaction completion. The reaction solution was concentrated (40° C./50 torr) to remove most of the organic solvent. The concentrate was diluted with water (248 mL) and 2-MeTHF (750 mL) and then 2 M HCl (100 mL, 200 mmol) was added while maintaining the internal temperature below 20° C. The phases were separated and the organic phase was washed with water (2×200-mL); dried (Na₂SO₄), and concentrated to afford crude 2-chloro-6-(3-(2-(dispiro[2.0.2⁴.1³]heptan-7-yl)ethoxy)-1H-pyrazol-1-yl)nicotinic acid (62.4 g (109% of theory) as a white powder. The product contains some residual solvent(s).

The crude product was recrystallized from warm (106° C.) PhMe (5 VolEq), seeded at ~95° C. and cooled to RT over 2 h and then further to 10° C. The solid was collected by filtration, washed with cold PhMe (1 VolEq), and the filter-cake was dried with suction and then in a vacuum oven (40° C./100 torr) to afford 2-chloro-6-(3-(2-(dispiro[2.0.2⁴.1³]heptan-7-yl)ethoxy)-1H-pyrazol-1-yl)nicotinic acid (88% yield) as a white powder.

$^1$H NMR (400 MHz, DMSO-d₆) δ 13.61 (s, 1H), 8.44-8.36 (m, 2H), 7.72 (d, J=8.4 Hz, 1H), 6.17 (d, J=2.9 Hz, 1H), 4.24 (t, J=6.7 Hz, 2H), 1.82 (q, J=6.7 Hz, 2H), 1.47 (t, J=6.5 Hz, 1H), 0.89-0.77 (m, 2H), 0.83 (s, 2H), 0.71-0.60 (m, 2H), 0.50 (ddd, J=8.2, 4.5, 2.2 Hz, 2H).

Example 20: Synthesis of (14R)-8-[3-(2-{dispiro[2.0.2⁴.1³]heptan-7-yl}ethoxy)-H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione

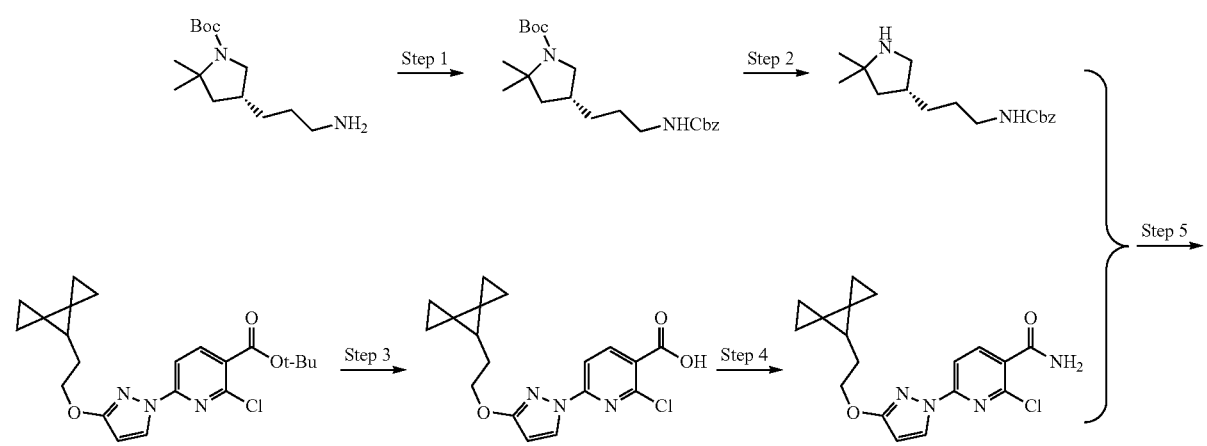

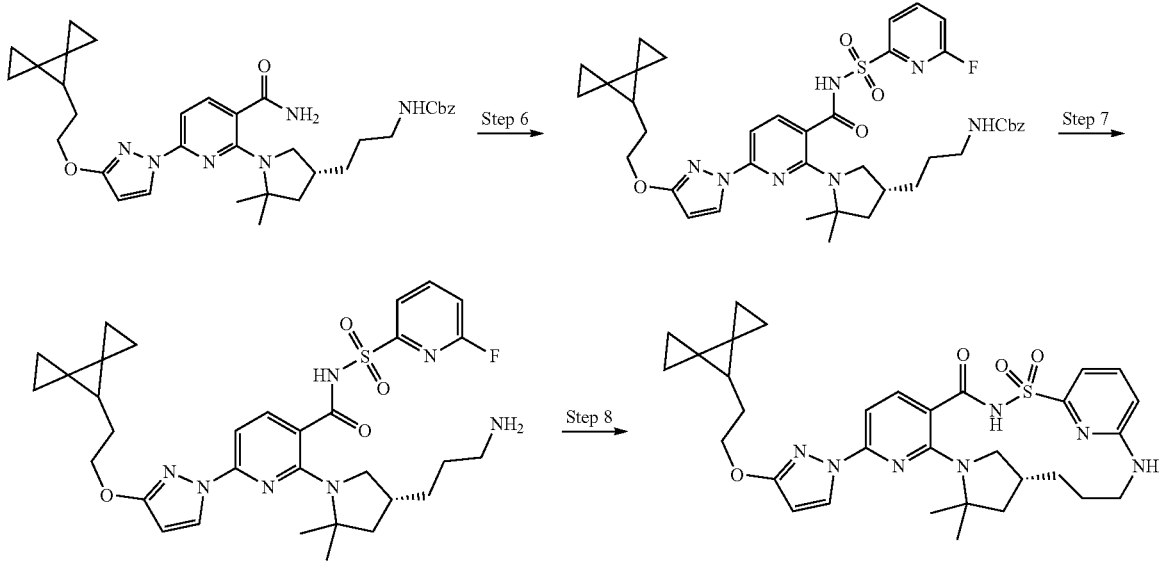

Step 1: Synthesis of tert-butyl (R)-4-(3-(((benzyloxy)carbonyl)amino)propyl)-2,2-dimethylpyrrolidine-1-carboxylate Step 2: Synthesis of benzyl (R)-(3-(5,5-dimethylpyrrolidin-3-yl)propyl)carbamate

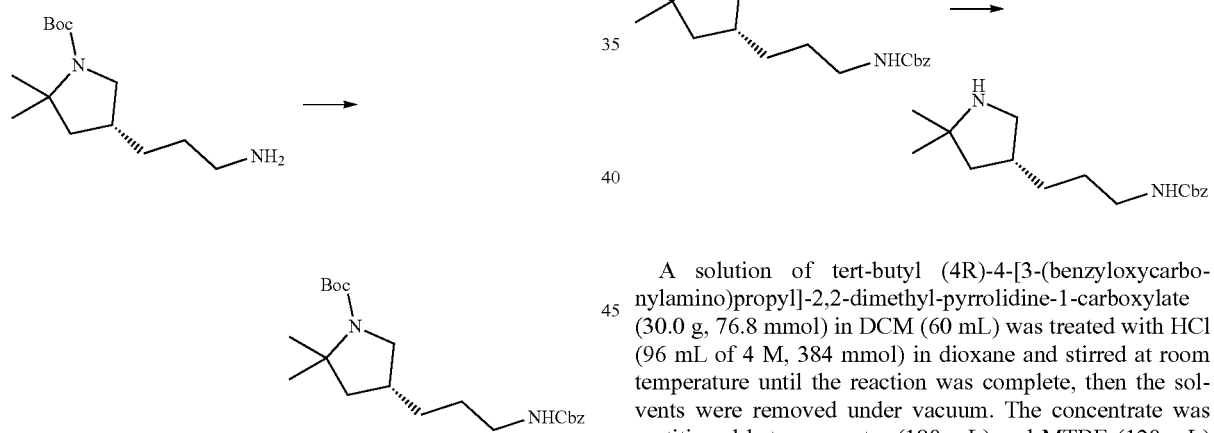

A biphasic mixture of tert-butyl (4R)-4-(3-aminopropyl)-2,2-dimethyl-pyrrolidine-1-carboxylate (22.0 g, 85.8 mmol) in PhMe (132 mL) and NaOH (86 mL of 2 M, 172 mmol) was cooled at 0-10° C., then a solution of Cbz-Cl (22.0 g, 18.4 mL, 129 mmol) in PhMe (44 mL) was added over 15 min while maintaining the reaction temperature below 10° C. Once the reaction was complete, the biphasic mixture was warmed to room temperature and the phases were separated. The aqueous phase was extracted with PhMe (44.00 mL) then the combined organic phases were washed with water (88 mL), dried ($Na_2SO_4$), and concentrated to afford tert-butyl (4R)-4-[3-(benzyloxycarbonylamino)propyl]-2,2-dimethyl-pyrrolidine-1-carboxylate (36.1 g; 108%) as a colorless oil.

A solution of tert-butyl (4R)-4-[3-(benzyloxycarbonylamino)propyl]-2,2-dimethyl-pyrrolidine-1-carboxylate (30.0 g, 76.8 mmol) in DCM (60 mL) was treated with HCl (96 mL of 4 M, 384 mmol) in dioxane and stirred at room temperature until the reaction was complete, then the solvents were removed under vacuum. The concentrate was partitioned between water (180 mL) and MTBE (120 mL) and the phases were separated. The aqueous phase was washed with MTBE (120 mL). The aqueous phase was diluted with MTBE (180 mL) and basified with NaOH (46 mL of 2 M, 92 mmol) (pH ~14). The phases were separated and the aqueous phase was extracted with MTBE (120 mL). The combined organic phases were dried ($Na_2SO_4$) and concentrated (40° C./20 torr) to afford benzyl N-[3-[(3R)-5,5-dimethylpyrrolidin-3-yl]propyl]carbamate (15.2 g, 68%) as a colorless liquid.

UPLC-MS analysis: tR=0.99 min/M+1=291 (conforms to structure).

$^1$H NMR (400 MHz, Chloroform-d) δ 7.43-7.23 (m, 5H), 5.09 (s, 2H), 4.79 (s, 1H), 3.26-3.05 (m, 3H), 2.55 (dd, J=11.0, 8.0 Hz, 1H), 2.13 (dq, J=15.5, 7.8 Hz, 1H), 1.79 (dd, J=12.5, 8.0 Hz, 2H), 1.48 (q, J=7.3 Hz, 2H), 1.37 (ddd, J=9.8, 7.2, 3.3 Hz, 2H), 1.18 (s, 3H), 1.12 (s, 4H).

Step 3: Synthesis of 2-chloro-6-(3-(2-(dispiro [2.0.2⁴.1³]heptan-7-yl)ethoxy)-1H-pyrazol-1-yl) nicotinic acid

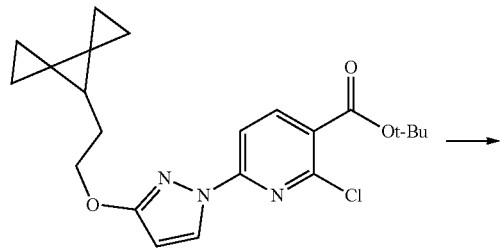

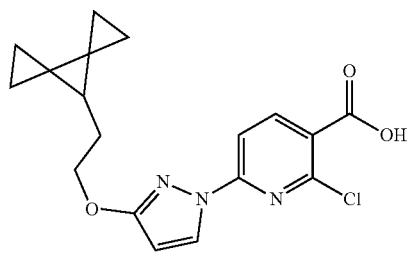

To a solution of tert-butyl 2-chloro-6-[3-(2-dispiro [2.0.2⁴.1³]heptan-7-ylethoxy)pyrazol-1-yl]pyridine-3-carboxylate (10.0 g, 24.0 mmol) in DCM (100 mL) was added trifluoroacetic acid (26 mL, 338 mmol). The reaction stirred under nitrogen gas at room temperature for 16 h. The reaction mixture was concentrated to afford a white solid. To the white solid was added MTBE and the mixture was concentrated three times to give 2-chloro-6-[3-(2-dispiro [2.0.2⁴.1³]heptan-7-ylethoxy)pyrazol-1-yl]pyridine-3-carboxylic acid (9.00 g, 96%). The crude NMR showed MTBE and some baseline impurities.

¹H NMR (400 MHz, DMSO-d₆) δ 13.61 (s, 1H), 8.50-8.32 (m, 2H), 7.72 (d, J=8.4 Hz, 1H), 6.17 (d, J=2.9 Hz, 1H), 4.24 (t, J=6.7 Hz, 2H), 1.82 (q, J=6.7 Hz, 2H), 1.47 (t, J=6.5 Hz, 1H), 0.88-0.78 (m, 4H), 0.68-0.61 (m, 2H), 0.50 (ddd, J=8.2, 4.5, 2.2 Hz, 2H).

Step 4: Synthesis of 2-chloro-6-(3-(2-(dispiro [2.0.2⁴.1³]heptan-7-yl)ethoxy)-H-pyrazol-1-yl)nicotinamide

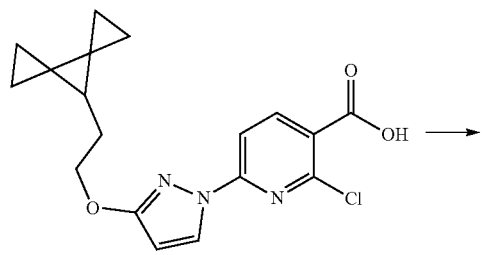

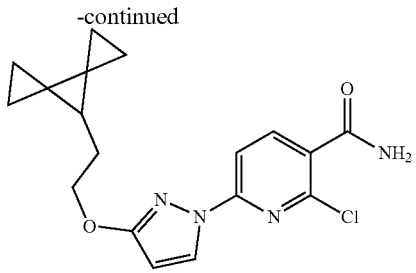

A suspension of 2-chloro-6-[3-(2-dispiro[2.0.2⁴.1³]heptan-7-ylethoxy)pyrazol-1-yl]pyridine-3-carboxylic acid (7.5 g, 20.8 mmol) in 2-MeTHF (45 mL) and DMF (152 mg, 161 μL, 2.1 mmol) was stirred at room temperature then SOCl₂ (3.35 g, 2.05 mL, 28.1 mmol) was added and heated at 40° C. Once the reaction was completed, the reaction was added to a separate flask containing a cooled solution of NH₄OH (approximately 28 mL of 14.8 M, 417 mmol) in water (26 mL) while maintaining the internal temperature below 15° C. Once the reaction was completed (20 min) the mixture was diluted with MTBE (120 mL) and water (60 mL) then EtOAc (180 mL). The phases were separated then the organic phase was dried (Na₂SO₄) and concentrated to afford a beige powder. The powder was stirred with MTBE (50 mL; 7 VolEq) and warmed to form a slurry then cooled to room temperature. The solid was collected by filtration then rinsed with MTBE (2×5-mL) and dried to afford 2-chloro-6-[3-(2-dispiro[2.0.2⁴.1³]heptan-7-ylethoxy)pyrazol-1-yl]pyridine-3-carboxamide (6.70 g; 90%) as an off-white powder.

HPLC analysis: 98.6% AUC (272 nm)

¹H NMR (400 MHz, DMSO-d₆) δ 8.38 (d, J=2.8 Hz, 1H), 8.04 (d, J=8.3 Hz, 1H), 8.00 (s, 1H), 7.73 (s, 1H), 7.68 (d, J=8.2 Hz, 1H), 6.13 (d, J=3.0 Hz, 1H), 4.24 (t, J=6.7 Hz, 2H), 1.82 (q, J=6.7 Hz, 2H), 1.47 (t, J=6.5 Hz, 1H), 0.90-0.76 (m, 4H), 0.69-0.58 (m, 2H), 0.56-0.45 (m, 2H).

Step 5: Synthesis of benzyl (R)-(3-(1-(3-carbamoyl-6-(3-(2-(dispiro[2.0.2⁴.1³]heptan-7-yl)ethoxy)-1H-pyrazol-1-yl)pyridin-2-yl)-5,5-dimethylpyrrolidin-3-yl)propyl)carbamate

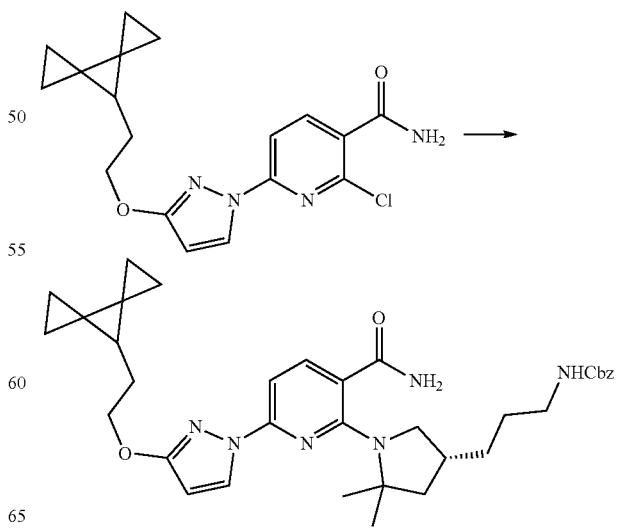

A suspension of 2-chloro-6-[3-(2-dispiro[2.0.2⁴.1³]heptan-7-ylethoxy)pyrazol-1-yl]pyridine-3-carboxamide (5.0 g, 13.9 mmol), benzyl N-[3-[(3R)-5,5-dimethylpyrrolidin-3-yl]propyl]carbamate (4.86 g, 16.7 mmol), K₂CO₃ (approximately 5.8 g, 42 mmol), and ZnCl₂ (approximately 1.9 g, 14 mmol) in n-BuOAc (40 mL) was heated at 120° C. until the reaction was complete (~2.5 days).

The suspension was diluted with EtOAc (60 mL) and acidified with HCl (approximately 42 mL of 2 M, 84 mmol); $C_{O2}$ degassing; pH ~1. The phases were separated and the aqueous phase was extracted with EtOAc (60 mL); combined organic phases and washed with water (60 mL), dried (Na₂SO4), and concentrated to afford 14.0 g (164%) of a dark amber liquid (residual n-BuOAc remained).

Diluted with DCM and purified by flash column chromatography eluting with EtOAc/hexanes. The fractions containing the desired product were combined and concentrated to afford benzyl N-[3-[(3R)-1-[3-carbamoyl-6-[3-(2-dispiro[2.0.2⁴.1³]heptan-7-ylethoxy)pyrazol-1-yl]-2-pyridyl]-5,5-dimethyl-pyrrolidin-3-yl]propyl]carbamate (3.05 g; 36%) as a yellow foam.

¹H NMR (400 MHz, DMSO-d₆) δ 8.19 (d, J=2.7 Hz, 1H), 7.73 (s, 1H), 7.61 (d, J=8.0 Hz, 1H), 7.42-7.20 (m, 7H), 6.84 (d, J=8.0 Hz, 1H), 6.05 (d, J=2.7 Hz, 1H), 5.01 (s, 2H), 4.20 (t, J=6.7 Hz, 2H), 3.32 (t, J=10.4 Hz, 1H), 3.19 (t, J=8.8 Hz, 1H), 3.01 (q, J=6.5 Hz, 2H), 2.21 (s, 1H), 1.94 (dd, J=11.9, 5.6 Hz, 1H), 1.81 (q, J=6.6 Hz, 2H), 1.61 (s, 3H), 1.57 (s, 3H), 1.53-1.23 (m, 6H), 0.90-0.77 (m, 4H), 0.67-0.60 (m, 2H), 0.53-0.46 (m, 2H).

Step 6: Synthesis of benzyl (R)-(3-(1-(6-(3-(2-(dispiro[2.0.2⁴.1³]heptan-7-yl)ethoxy)-1H-pyrazol-1-yl)-3-(((6-fluoropyridin-2-yl)sulfonyl)carbamoyl)pyridin-2-yl)-5,5-dimethylpyrrolidin-3-yl)propyl)carbamate

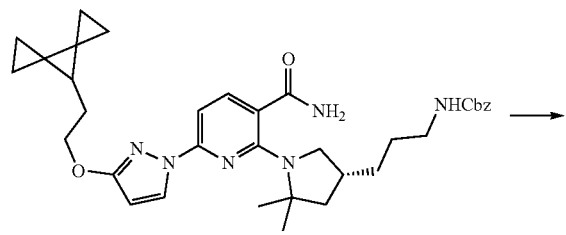

A solution of benzyl N-[3-[(3R)-1-[3-carbamoyl-6-[3-(2-dispiro[2.0.2⁴.1³]heptan-7-ylethoxy)pyrazol-1-yl]-2-pyridyl]-5,5-dimethyl-pyrrolidin-3-yl]propyl]carbamate (2.50 g, 4.08 mmol) in 2-MeTHF (15 mL) was cooled at 0-5° C. then a solution of 6-fluoropyridine-2-sulfonyl chloride (approximately 1.19 g, 6.12 mmol) in 2-MeTHF (5 mL) was added, followed by lithium 2-methylbutan-2-olate (3.3 mL of 40% w/w, 10.2 mmol) over 15 min while maintaining the reaction temperature below 5° C. Analysis showed 10-15% of unreacted starting material, so an additional portion of 6-fluoropyridine-2-sulfonyl chloride (0.20 g, 1.0 mmol), followed by lithium 2-methylbutan-2-olate (330 µL of 40% w/w, 1.0 mmol), were added. The mixture was stirred until the reaction was complete (~20 min) then partitioned between EtOAc (20 mL) and HCl (12 mL of 1 M, 12 mmol). The phases were separated and the organic phase was washed with water (10 mL), then dried (Na₂SO₄) and concentrated to afford a brown taffy/foam. Purification by normal phase column chromatography (gradient EtOAc/hexanes) followed by reversed-phase column chromatography (gradient CH₃CN/H₂O) afforded benzyl N-[3-[(3R)-1-[6-[3-(2-dispiro[2.0.2⁴.1³]heptan-7-ylethoxy)pyrazol-1-yl]-3-[(6-fluoro-2-pyridyl)sulfonylcarbamoyl]-2-pyridyl]-5,5-dimethyl-pyrrolidin-3-yl]propyl]carbamate (1.10 g; 35%; 97+% AUC) as a white powder.

A less pure fraction (0.80 g; 84% AUC) was dissolved in warm EtOH (~10 mL), stirred, and allowed to cool to RT. After ~10 min crystallization occurred. The suspension was stirred for ~1 h and the solids were collected by filtration (fritted syringe). The filter-cake was rinsed with EtOH (3 mL) and the solid air-dried/vacuum dried (55° C.) to afford additional benzyl N-[3-[(3R)-1-[6-[3-(2-dispiro[2.0.2⁴.1³]heptan-7-ylethoxy)pyrazol-1-yl]-3-[(6-fluoro-2-pyridyl)sulfonylcarbamoyl]-2-pyridyl]-5,5-dimethyl-pyrrolidin-3-yl]propyl]carbamate (0.61 g; 76% recovery) of a free-flowing, white powder.

HPLC analysis: 95.2% AUC (272 nm).

Total yield=1.10 g+0.61 g=1.71 g (54%).

¹H NMR (400 MHz, DMSO-d₆) δ 8.34 (q, J=7.8 Hz, 1H), 8.13 (dd, J=7.4, 2.0 Hz, 1H), 7.88 (d, J=8.3 Hz, 1H), 7.59 (dd, J=8.3, 2.3 Hz, 1H), 7.37 (d, J=4.2 Hz, 4H), 7.34-7.21 (m, 2H), 6.94 (d, J=8.3 Hz, 1H), 6.10 (d, J=2.8 Hz, 1H), 5.05 (s, 2H), 4.22 (t, J=6.7 Hz, 2H), 3.01 (hept, J=6.7 Hz, 2H), 2.46 (dd, J=10.4, 7.0 Hz, 1H), 2.13 (s, 1H), 1.89 (dd, J=11.8, 5.5 Hz, 1H), 1.81 (q, J=6.6 Hz, 2H), 1.54 (s, 6H), 1.47 (t, J=6.5 Hz, 1H), 1.34 (td, J=13.1, 12.6, 6.7 Hz, 3H), 1.17 (dt, J=16.1, 5.2 Hz, 1H), 0.97 (dt, J=13.4, 8.8 Hz, 1H), 0.89-0.75 (m, 4H), 0.71-0.57 (m, 2H), 0.56-0.41 (m, 2H).

¹⁹FNMR (376 MHz, DMSO) δ −65.73.

Step 7: Synthesis of (R)-2-(4-(3-aminopropyl)-2,2-dimethylpyrrolidin-1-yl)-6-(3-(2-(dispiro[2.0.2⁴.1³]heptan-7-yl)ethoxy)-1H-pyrazol-1-yl)-N-((6-fluoropyridin-2-yl)sulfonyl)nicotinamide ((R)-53)

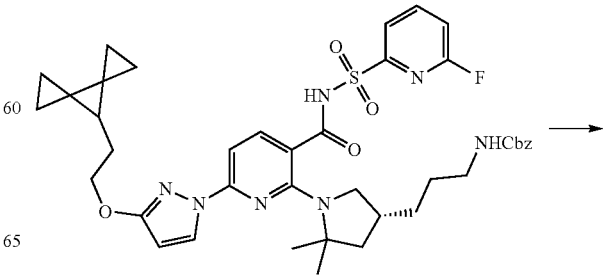

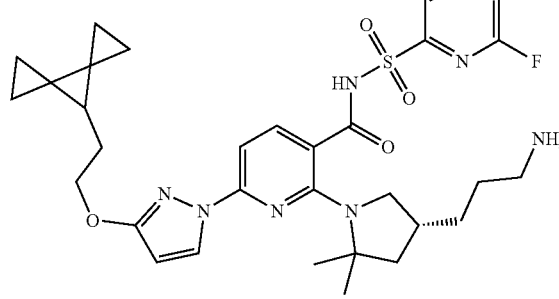

A mixture of benzyl N-[3-[(3R)-1-[6-[3-(2-dispiro[2.0.2⁴.1³]heptan-7-ylethoxy)pyrazol-1-yl]-3-[(6-fluoro-2-pyridyl)sulfonylcarbamoyl]-2-pyridyl]-5,5-dimethyl-pyrrolidin-3-yl]propyl]carbamate (1.00 g, 1.30 mmol) and Pd on carbon (69 mg of 10% w/w) in MeOH (8 mL) was stirred under an atmosphere of H$_2$ (1 bar) at ~40° C. until the reaction was completed (2.5 h). The catalyst was removed the catalyst by filtration and the filtrate was concentrated to afford crude as a white taffy/solid. Purification by reversed-phase flash column (gradient CH$_3$CN/H$_2$O) followed by slurrying in MTBE (10 mL) afforded 2-[(4R)-4-(3-aminopropyl)-2,2-dimethyl-pyrrolidin-1-yl]-6-[3-(2-dispiro[2.0.2⁴.1³]heptan-7-ylethoxy)pyrazol-1-yl]-N-[(6-fluoro-2-pyridyl)sulfonyl]pyridine-3-carboxamide (190 mg; 23%; 95.0% AUC) as a white powder.

$^1$H NMR (500 MHz, DMSO-d$_6$) δ 8.15 (d, J=2.7 Hz, 1H), 8.11 (q, J=7.9 Hz, 1H), 7.86 (dd, J=7.4, 2.2 Hz, 1H), 7.70 (d, J=7.9 Hz, 1H), 7.24 (dd, J=8.3, 2.4 Hz, 1H), 6.79 (d, J=7.9 Hz, 1H), 6.01 (d, J=2.7 Hz, 1H), 4.20 (t, J=6.7 Hz, 2H), 3.15 (t, J=10.6 Hz, 1H), 3.06 (dd, J=10.9, 7.3 Hz, 1H), 2.82 (hept, J=7.2, 6.3 Hz, 2H), 2.08 (s, 1H), 1.81 (q, J=6.5 Hz, 2H), 1.55 (s, 5H), 1.51 (s, 3H), 1.47 (t, J=6.5 Hz, 1H), 1.42-1.27 (m, 3H), 1.26-1.15 (m, 1H), 0.83 (d, J=5.5 Hz, 4H), 0.64 (dd, J=8.5, 4.2 Hz, 2H), 0.50 (dd, J=8.5, 4.0 Hz, 2H).

Step 8: Synthesis of (14R)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione

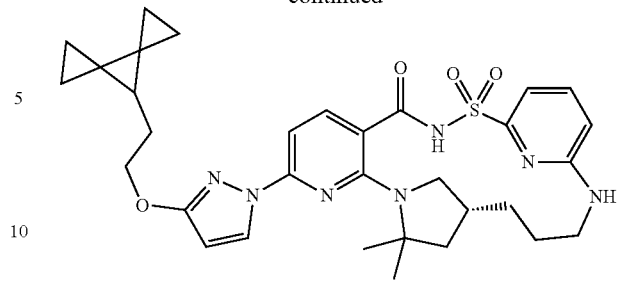

A suspension of 2-[(4R)-4-(3-aminopropyl)-2,2-dimethyl-pyrrolidin-1-yl]-6-[3-(2-dispiro[2.0.2⁴.1³]heptan-7-ylethoxy)pyrazol-1-yl]-N-[(6-fluoro-2-pyridyl)sulfonyl]pyridine-3-carboxamide (300 mg, 0.4704 mmol), K$_2$CO$_3$ (162.5 mg, 1.176 mmol), and MgCl$_2$ (44.79 mg, 0.4704 mmol) in DMSO (2.400 mL) was heated at 80° C. for ~6 h until the starting material was consumed. The suspension was partitioned between EtOAc (12 mL) and 0.5 M HCl (4.7 mL, 2.35 mmol). The phases were separated and the aqueous phase extracted with EtOAc (6 mL). The combined organic phases were washed with water (3×2-mL), dried (Na$_2$SO$_4$), and concentrated to afford (14R)-8-[3-(2-{dispiro[2.0.2⁴.1³]heptan-7-yl}ethoxy)-1H-pyrazol-1-yl]-12,12-dimethyl-2λ⁶-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (262 mg; 90%) as an amber solid.

HPLC analysis showed 94.8% AUC with a trace (0.2%) of unreacted starting material.

UPLC-MS analysis: M+1=618 (conforms to structure).

$^1$H NMR (500 MHz, DMSO-d$_6$) δ 12.52 (s, 1H), 8.21 (d, J=2.9 Hz, 1H), 7.83 (d, J=8.2 Hz, 1H), 7.59 (t, J=7.9 Hz, 1H), 7.12-6.83 (m, 3H), 6.72 (d, J=8.5 Hz, 1H), 6.09 (d, J=2.8 Hz, 1H), 4.22 (td, J=6.8, 2.3 Hz, 2H), 4.04-3.84 (m, 1H), 3.16 (s, 1H), 2.96 (d, J=13.1 Hz, 1H), 2.70 (d, J=11.3 Hz, 1H), 2.13 (s, 1H), 1.84 (dq, J=20.2, 6.6, 5.9 Hz, 4H), 1.70-1.40 (m, 10H), 1.32 (q, J=12.2 Hz, 1H), 0.90-0.75 (m, 4H), 0.65 (dd, J=8.6, 4.2 Hz, 2H), 0.51 (dd, J=8.5, 4.2 Hz, 2H).

Example 21: Synthesis of tert-butyl (S)-(3-(1-(6-bromo-3-(((6-fluoropyridin-2-yl)sulfonyl)carbamoyl)pyridin-2-yl)-5,5-dimethylpyrrolidin-3-yl)propyl)carbamate

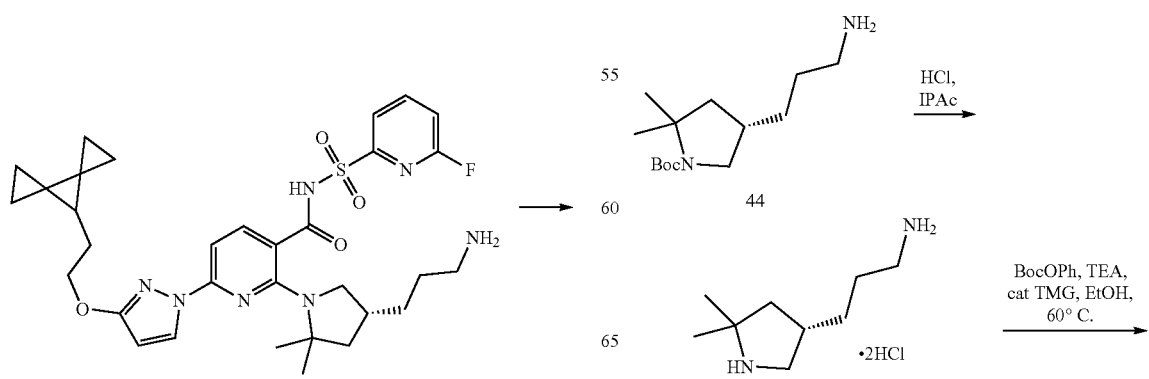

-continued

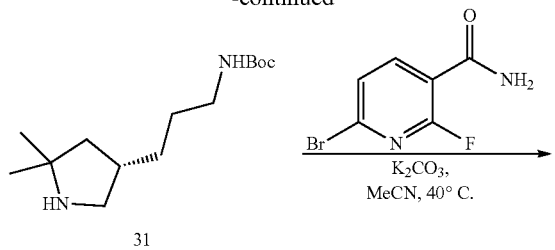

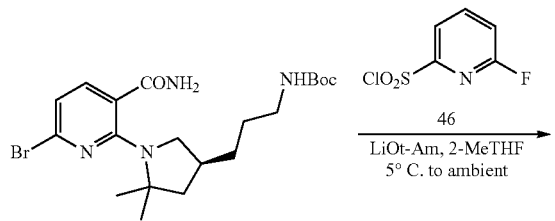

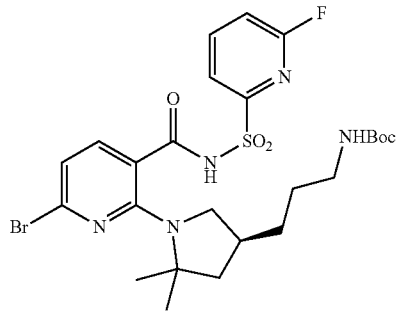

A method for preparing tert-butyl (S)-(3-(1-(6-bromo-3-((((6-fluoropyridin-2-yl)sulfonyl)carbamoyl)pyridin-2-yl)-5,5-dimethylpyrrolidin-3-yl)propyl)carbamate is shown in the above scheme. In some embodiments, N and O may have one or more protecting groups selected from a range of protecting groups disclosed herein.

Example 22: Synthesis of (S)-6-bromo-2-(4-(3-(bis-Boc-amino)propyl)-2,2-dimethylpyrrolidin-1-yl)-N-((6-fluoropyridin-2-yl)sulfonyl)nicotinamide

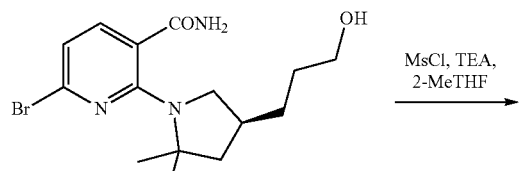

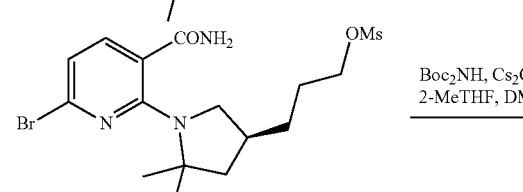

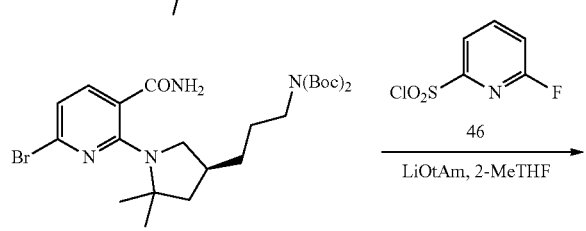

-continued

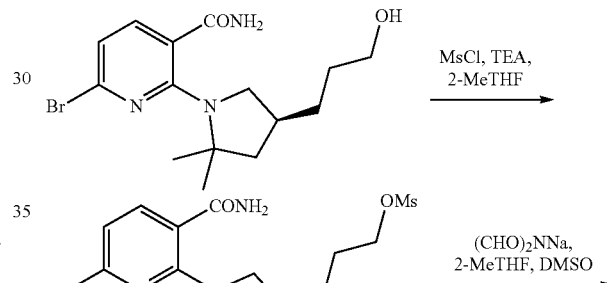

A method for preparing (S)-6-bromo-2-(4-(3-(bis-Boc-amino)propyl)-2,2-dimethylpyrrolidin-1-yl)-N-((6-fluoropyridin-2-yl)sulfonyl)nicotinamide is shown in the above scheme. In some embodiments, N and O may have one or more protecting groups selected from a range of protecting groups disclosed herein.

Example 23: Synthesis of benzyl (S)-(3-(1-(6-bromo-3-carbamoylpyridin-2-yl)-5,5-dimethylpyrrolidin-3-yl)propyl)carbamate (45)

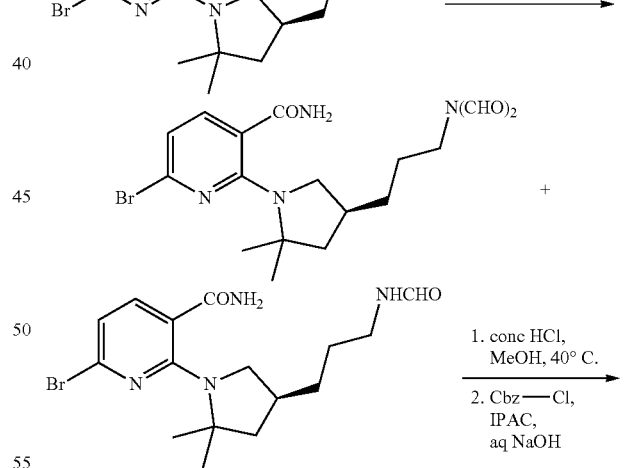

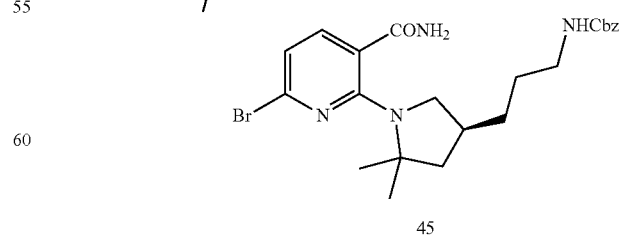

An alternative method for preparing compound 45 is shown in the above scheme. In some embodiments, N and O may have one or more protecting groups selected from a range of protecting groups disclosed herein.

Example 24: Synthesis of (13S)-26-chloro-15,15-dimethyl-5-thia-4,7-diaza-2(2,3),6(2,6)-dipyridina-1(1,3)-pyrrolidinacyclodecaphan-3-one 5,5-dioxide (41)

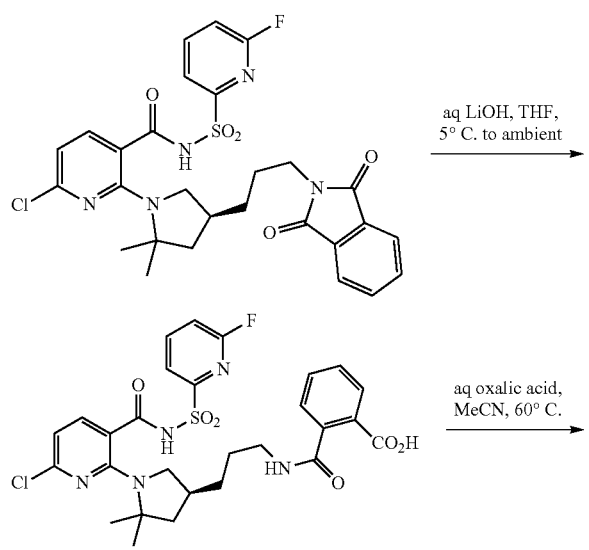

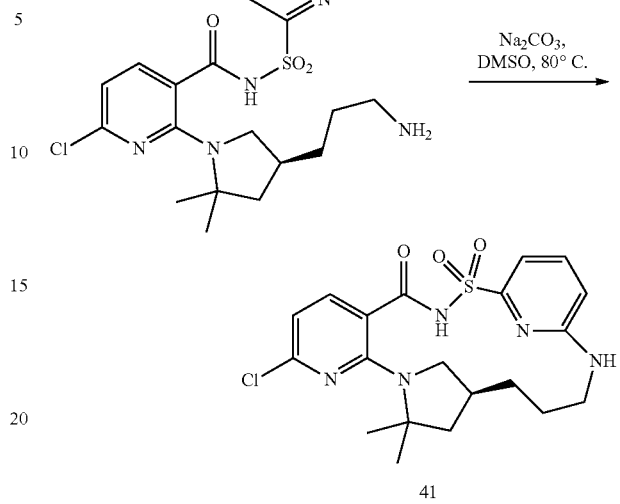

A method for preparing compound 41 is shown in the above scheme. In some embodiments, N and O may have one or more protecting groups selected from a range of protecting groups disclosed herein.

Example 25: Synthesis of (R)-2-(4-(3-aminopropyl)-2,2-dimethylpyrrolidin-1-yl)-6-chloro-N-((6-fluoropyridin-2-yl)sulfonyl)nicotinamide

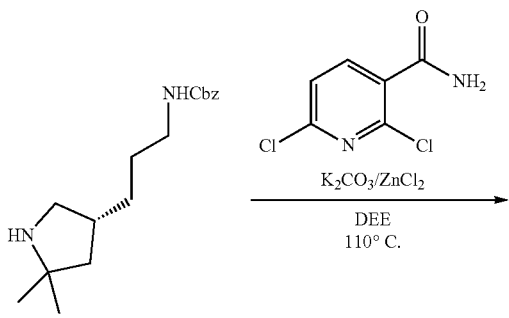

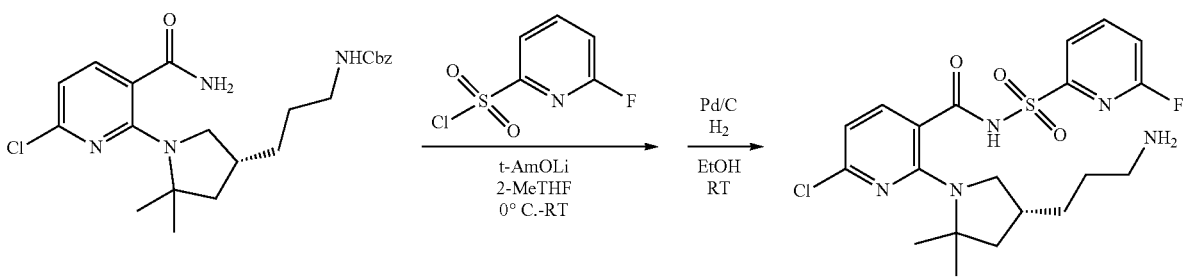

A method for preparing (R)-2-(4-(3-aminopropyl)-2,2-dimethylpyrrolidin-1-yl)-6-chloro-N-((6-fluoropyridin-2-yl)sulfonyl)nicotinamide is shown in the above scheme. In some embodiments, N and O may have one or more protecting groups selected from a range of protecting groups disclosed herein.

Example 26: Diester enzymatic resolution of diethyl 2-(2-methyl-2-nitropropyl)pentanedioate

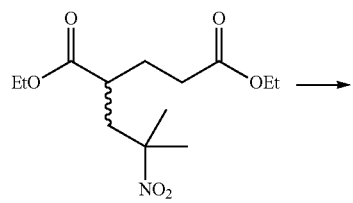

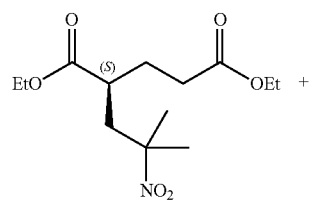

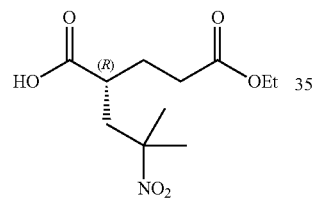

A method for the chiral resolution of diethyl 2-(2-methyl-2-nitropropyl)pentanedioate is shown in the above scheme. In some embodiments, O may have one or more protecting groups selected from a range of protecting groups disclosed herein.

Example 27: Dinitrile enzymatic resolution of 2-(2-methyl-2-nitropropyl)pentanedinitrile

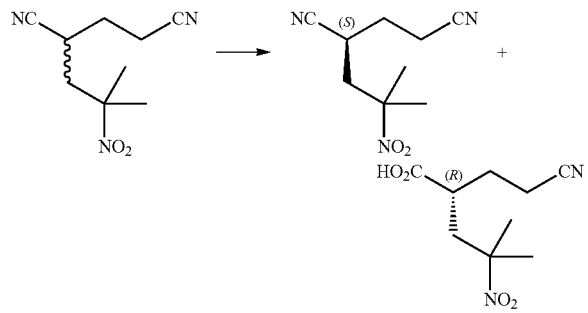

A method for the chiral resolution of 2-(2-methyl-2-nitropropyl)pentanedinitrile is shown in the above scheme.

Example 28: Ester Enzymatic Resolution of Ethyl 2-(3-((tert-butoxycarbonyl)amino)propyl)-4-methyl-4-nitropentanoate (35)

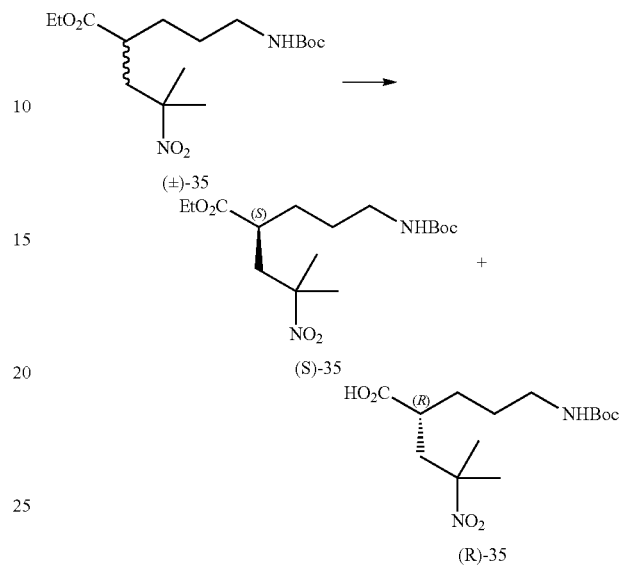

A method for the chiral resolution of compound 35 is shown in the above scheme. In some embodiments, N and O may have one or more protecting groups selected from a range of protecting groups disclosed herein.

Example 29: Ester enzymatic resolution of ethyl 2-(3-(1,3-dioxoisoindolin-2-yl)propyl)-4-methyl-4-nitropentanoate

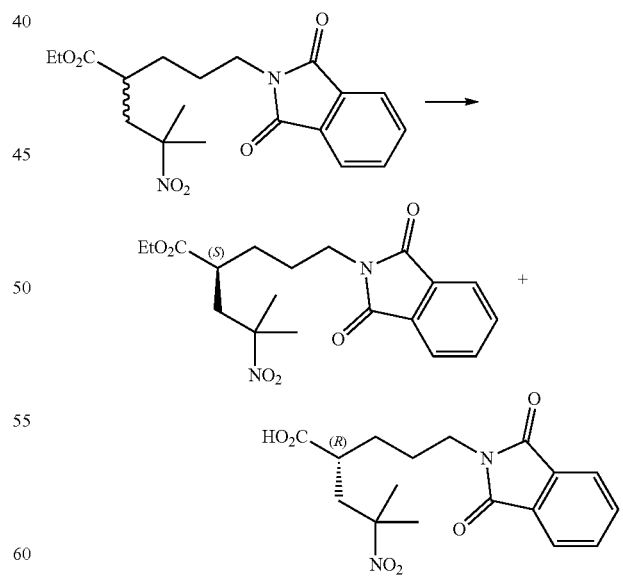

A method for the chiral resolution of ethyl 2-(3-(1,3-dioxoisoindolin-2-yl)propyl)-4-methyl-4-nitropentanoate shown in the above scheme. In some embodiments, N and O may have one or more protecting groups selected from a range of protecting groups disclosed herein.

Example 30: Enantioselective ring opening of ethyl 4-cyano-6,6-dimethyl-2-oxotetrahydro-2H-pyran-3-carboxylate

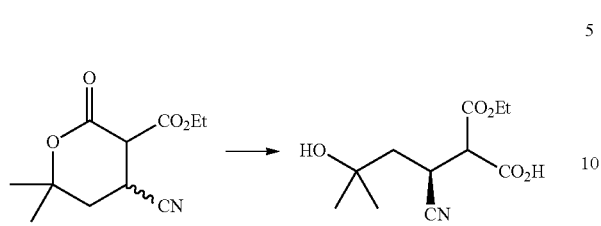

A method for the chiral resolution of ethyl 4-cyano-6,6-dimethyl-2-oxotetrahydro-2H-pyran-3-carboxylate is shown in the above scheme. In some embodiments, O may have one or more protecting groups selected from a range of protecting groups disclosed herein.

Example 31: Synthesis of 3-(5,5-dimethylpyrrolidin-3-yl)propan-1-ol ((f)-42)

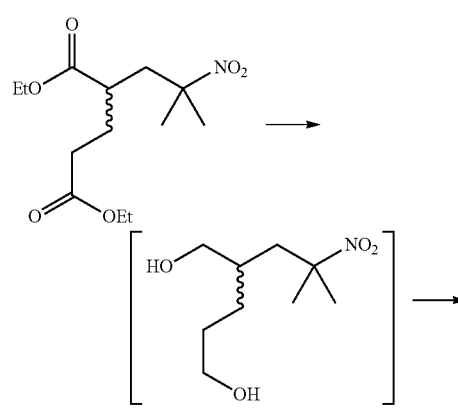

(±)-42

A method for the chiral resolution of diethyl 2-(2-methyl-2-nitropropyl)pentanedioate is shown in the above scheme. In some embodiments, N and O may have one or more protecting groups selected from a range of protecting groups disclosed herein.

Example 32: Synthesis of 2-(3-(5,5-dimethylpyrrolidin-3-yl)propyl)isoindoline-1,3-dione

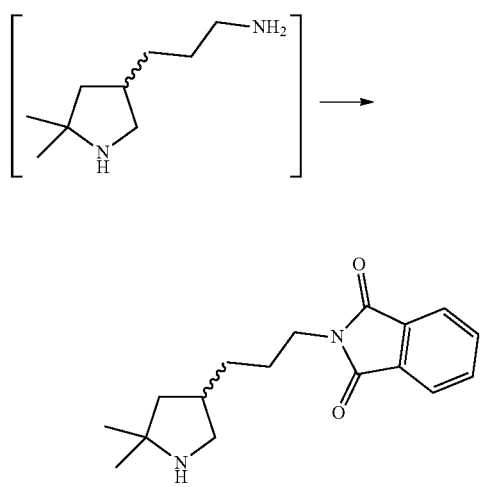

A method for the chiral resolution of 2-(2-methyl-2-nitropropyl)pentanedinitrile is shown in the above scheme. In some embodiments, N and O may have one or more protecting groups selected from a range of protecting groups disclosed herein.

Example 33: Synthesis of tert-butyl (3-(5,5-dimethyl-2-oxopyrrolidin-3-ylidene)propyl)carbamate

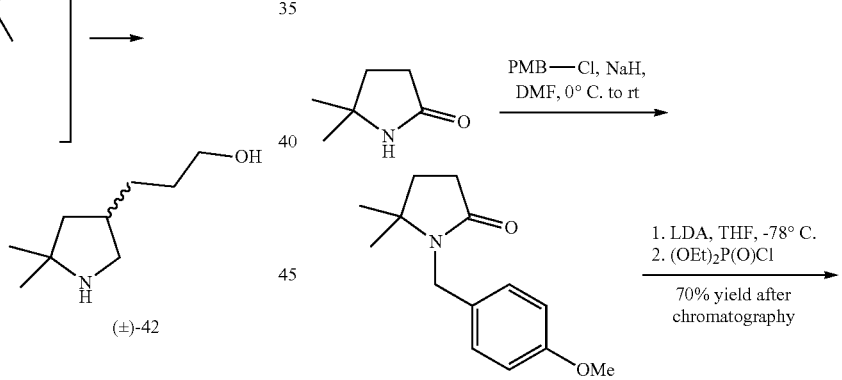

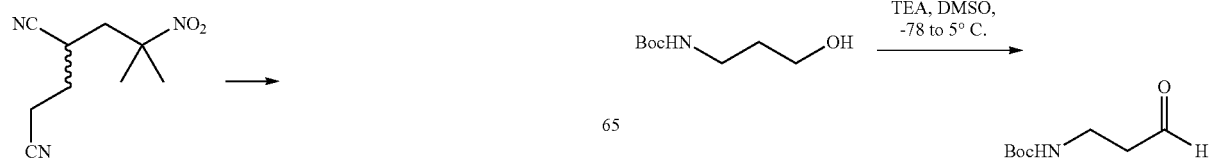

-continued

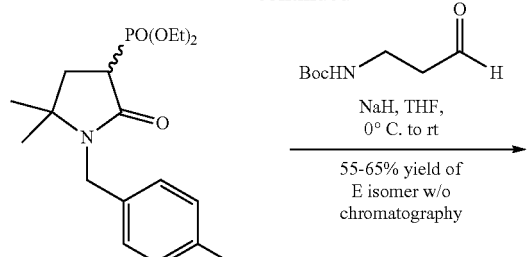

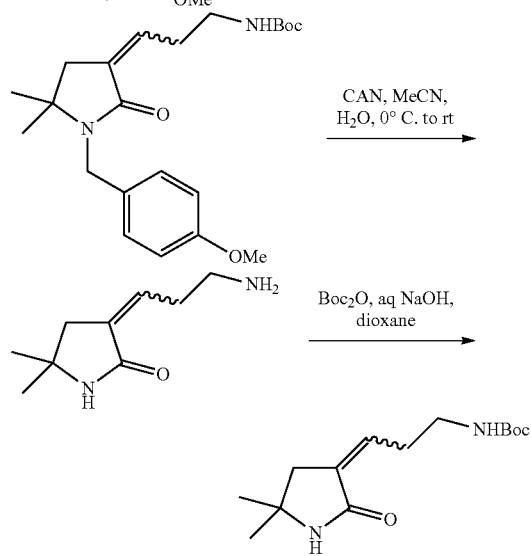

A method for preparing tert-butyl (3-(5,5-dimethyl-2-oxopyrrolidin-3-ylidene)propyl)carbamate is shown in the above scheme. In some embodiments, N and O may have one or more protecting groups selected from a range of protecting groups disclosed herein.

Example 34: Synthesis of tert-butyl (S)-(3-(5,5-dimethyl-2-oxopyrrolidin-3-yl)propyl)carbamate

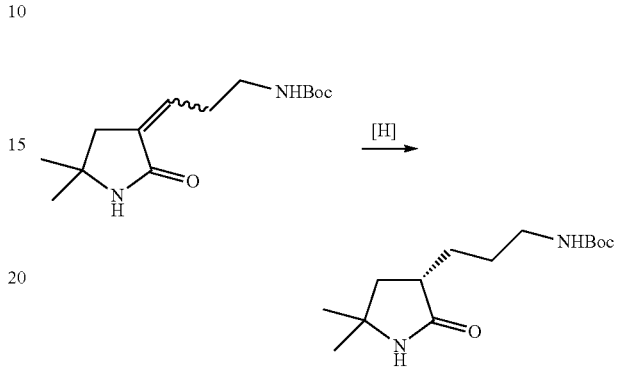

A method for preparing tert-butyl (S)-(3-(5,5-dimethyl-2-oxopyrrolidin-3-yl)propyl)carbamate is shown in the above scheme. In some embodiments, N and O may have one or more protecting groups selected from a range of protecting groups disclosed herein.

Example 35: Synthesis of tert-butyl (S)-(3-(5,5-dimethylpyrrolidin-3-yl)propyl)carbamate (31)

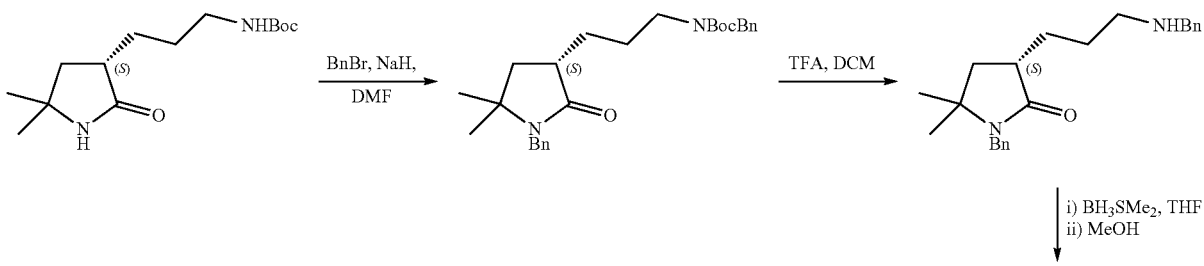

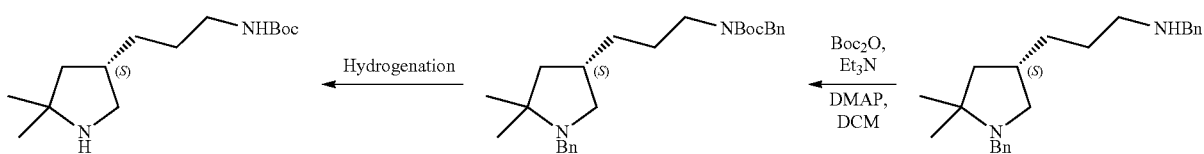

31

A method for preparing compound 31 is shown in the above scheme. In some embodiments, N and O may have one or more protecting groups selected from a range of protecting groups disclosed herein.

Example 36: Synthesis of tert-butyl (3-(5,5-dimethyl-2-oxopyrrolidin-3-ylidene)propyl)carbamate

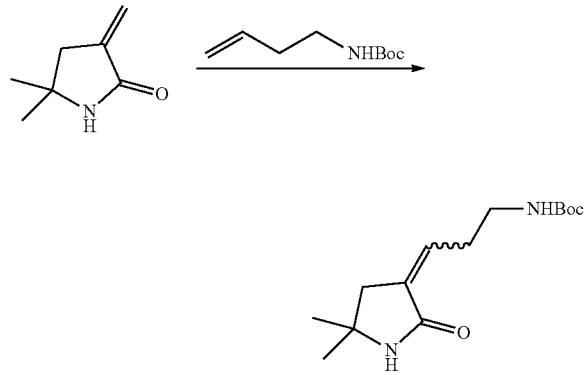

A method for preparing tert-butyl (3-(5,5-dimethyl-2-oxopyrrolidin-3-ylidene)propyl)carbamate is shown in the above scheme. In some embodiments, N and O may have one or more protecting groups selected from a range of protecting groups disclosed herein.

Example 37: Synthesis of 3-(5,5-dimethyl-2-oxopyrrolidin-3-yl)propyl benzoate

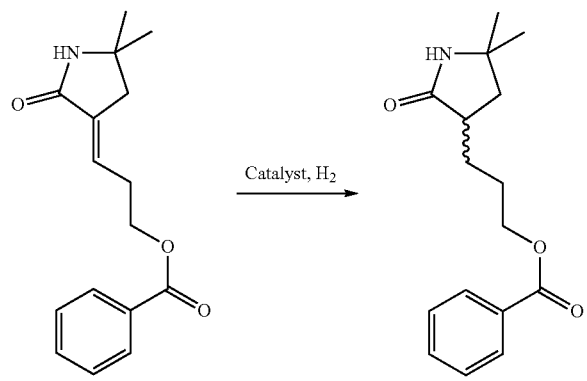 [SMILES: CC1(C)C/C(=C\CCOC(=O)c2ccccc2)C(=O)N1 ; CC1(C)CC(CCCOC(=O)c2ccccc2)C(=O)N1]

A method for preparing 3-(5,5-dimethyl-2-oxopyrrolidin-3-yl)propyl benzoate is shown in the above scheme. In some embodiments, N and O may have one or more protecting groups selected from a range of protecting groups disclosed herein.

Example 38: Synthesis of tert-butyl 4-(3-((tert-butyldimethylsilyl)oxy)propyl)-2,2-dimethyl-5-oxopyrrolidine-1-carboxylate

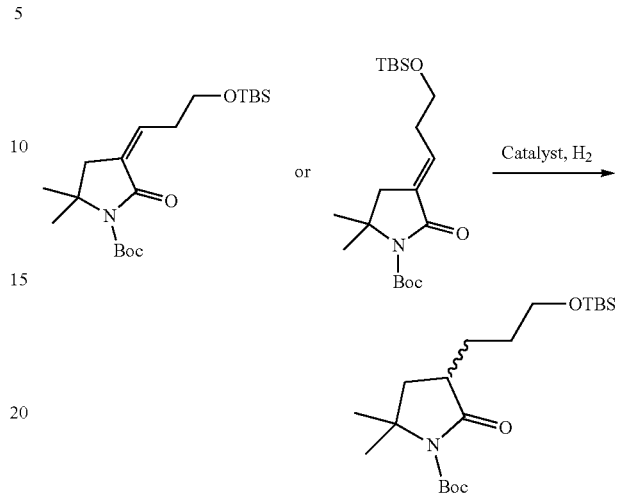

A method for preparing tert-butyl 4-(3-((tert-butyldimethylsilyl)oxy)propyl)-2,2-dimethyl-5-oxopyrrolidine-1-carboxylate is shown in the above scheme. In some embodiments, N and O may have one or more protecting groups selected from a range of protecting groups disclosed herein.

Example 39: Synthesis of 1-benzyl-3-(3-(benzyloxy)propyl)-5,5-dimethyl-1,5-dihydro-2H-pyrrol-2-one

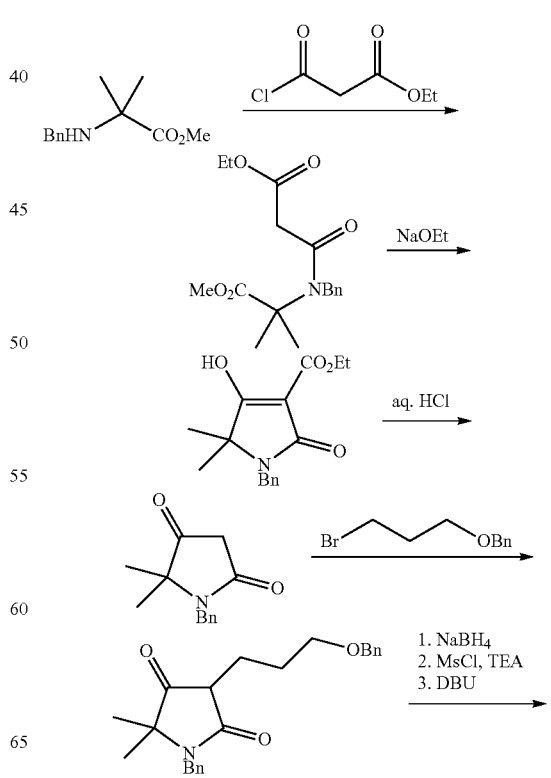

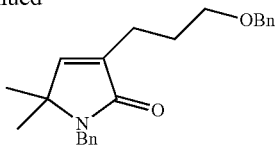

A method for preparing 1-benzyl-3-(3-(benzyloxy)propyl)-5,5-dimethyl-1,5-dihydro-2H-pyrrol-2-one is shown in the above scheme. In some embodiments, N and O may have one or more protecting groups selected from a range of protecting groups disclosed herein.

Example 40: Synthesis of Pyrroline

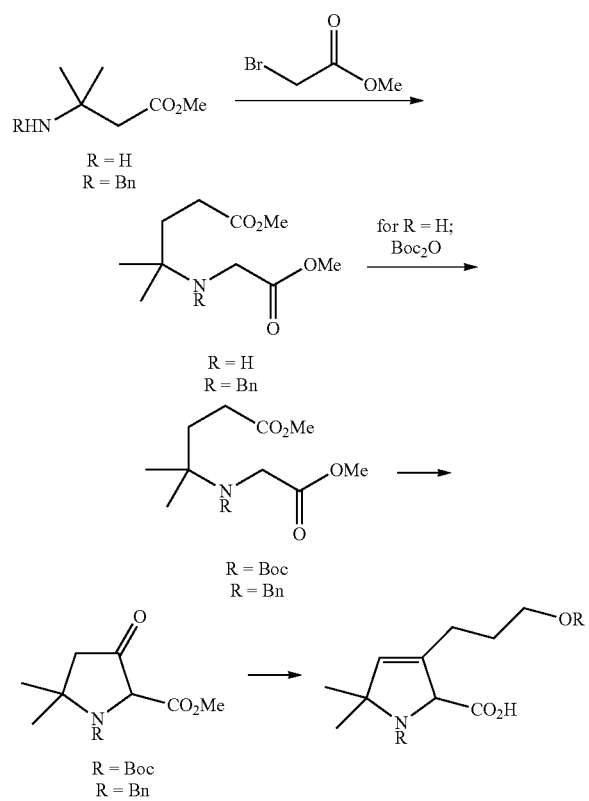

A method for preparing the pyrroline is shown in the above scheme. In some embodiments, N and O may have one or more protecting groups selected from a range of protecting groups disclosed herein.

Example 41: Synthesis of 7,7-dibromodispiro [2.0.2⁴.1³]heptane (54)

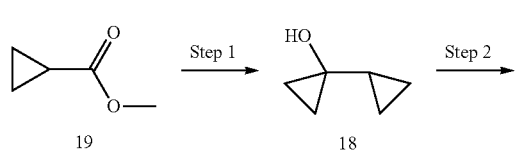

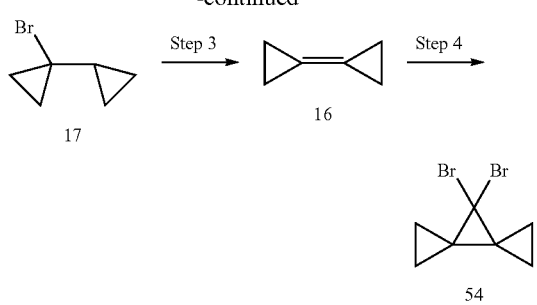

Compound 18 was prepared by reacting compound 19 with Ti(Oi-Pr)$_4$ and EtMgBr in the presence of MTBE at 20° C. to 25° C. for 14 h. Compound 17 was prepared by reacting compound 18 with PPh$_3$, Br$_2$, and pyridine in the presence of DCM at −30° C. to 15° C. for 14 h, then distilling the reaction mixture. Compound 16 was prepared by reacting compound 17 with KOt-Bu in the presence of DMSO at 20° C. to 25° C. for 16 h. Compound 54 was prepared by reacting compound 16 with KOt-Bu and CHBr$_3$ in the presence of heptane at 0° C. to rt for 17-72 h.

Example 42: Alternative Synthesis of 2-(dispiro [2.0.2⁴.1³]heptan-7-yl)ethan-1-ol (8)

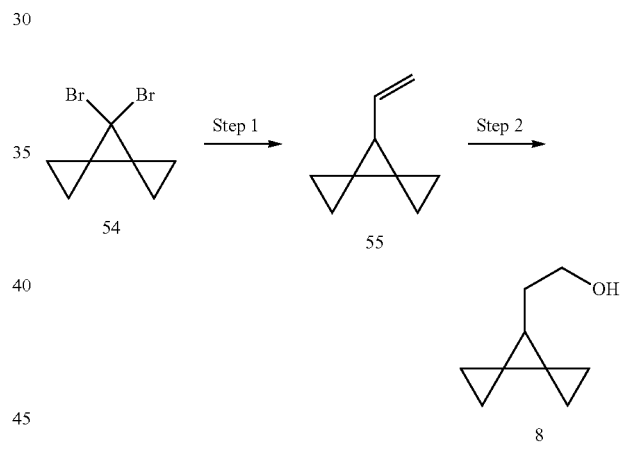

Compound 55 was prepared by reacting compound 54 with vinylmagnesium bromide and copper(I) iodide in the presence of THF at −40° C. to −10° C. for 4 h. Compound 55 was then reacted with borane-THF, hydrogen peroxide, and sodium hydroxide at 0° C. to provide compound 8.

Example 43: Alternative Synthesis of 2-(dispiro [2.0.2⁴.1³]heptan-7-yl)ethan-1-ol (8)

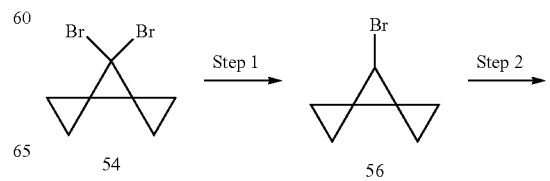

-continued

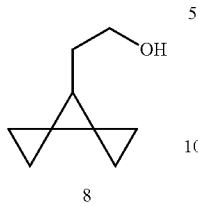

8

Compound 56 can be prepared by first reacting compound 54 with tert-butylmagnesium chloride and iron(III) acetylacetonate at −10° C. Compound 56 can then be treated in a first step with magnesium metal and iodine in the presence of THF at 50° C., and in a second step with ethylene oxide and Li$_2$CuCl in the presence of THF at −20° C., to provide compound 8.

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms defined in this disclosure is intended to be controlling.

The foregoing discussion discloses and describes exemplary embodiments of this disclosure. One skilled in the art will readily recognize, from such discussion and from the accompanying claims, that various changes, modifications, and variations can be made therein without departing from the spirit and scope of this disclosure as defined in the following claims.

The invention claimed is:

1. A method of preparing Compound I:

Compound I

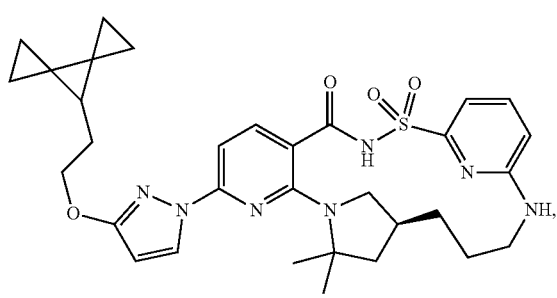

or a pharmaceutically acceptable salt thereof, comprising converting a compound of Formula (I):

(I)

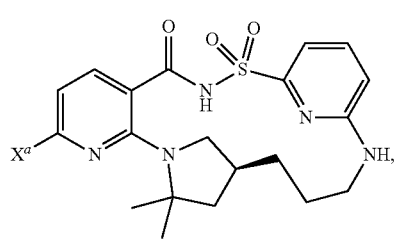

or a salt thereof, into Compound I, or a pharmaceutically acceptable salt thereof,
wherein:
   $X^a$ is selected from F, Cl, Br, I, and —OSO$_2$R;
      R is selected from —C$_{1-10}$alkyl, —C$_{1-10}$haloalkyl, and aryl optionally substituted with —C$_{1-10}$alkyl, —C$_{1-10}$haloalkyl, halo, or nitro; and
   $X^c$ is selected from F, Cl, Br, and I.

2. The method of claim 1, wherein the conversion of the compound of Formula (I), or a salt thereof, into Compound I, or a pharmaceutically acceptable salt thereof, comprises the steps of:
   1) combining the compound of Formula (I), or a salt thereof, with at least one first base to produce a compound of Formula (II):

(II)

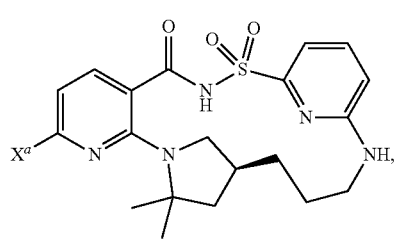

or a salt thereof; and
   2) combining the compound of Formula (II), or a salt thereof, with compound 1:

1

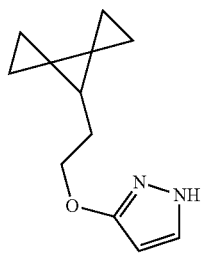

or a salt thereof,
and at least one second base to produce Compound I, or a pharmaceutically acceptable salt thereof,
wherein in the compound of Formula (II), or a salt thereof:
   $X^a$ is selected from F, Cl, Br, I, and —OSO$_2$R; and
      R is selected from —C$_{1-10}$alkyl, —C$_{1-10}$haloalkyl, and aryl optionally substituted with —C$_{1-10}$alkyl, —C$_{1-10}$haloalkyl, halo, or nitro.

3. The method of claim 1, wherein the conversion of the compound of Formula (I), or a salt thereof, into Compound I, or a pharmaceutically acceptable salt thereof, comprises combining the compound of Formula (I), or a salt thereof, with compound 1:

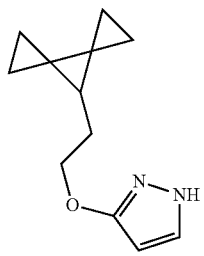

or a salt thereof, and at least one third base to produce Compound I, or a pharmaceutically acceptable salt thereof,
wherein in the compound of Formula (I), or a salt thereof:
$X^a$ is selected from F, Cl, Br, I, and —OSO$_2$R;
R is selected from —C$_{1-10}$alkyl, —C$_{1-10}$haloalkyl, and aryl optionally substituted with —C$_{1-10}$alkyl, —C$_{1-10}$haloalkyl, halo, or nitro; and
$X^c$ is selected from F, Cl, Br, and I.

4. The method of claim 1, wherein the compound of Formula (I):

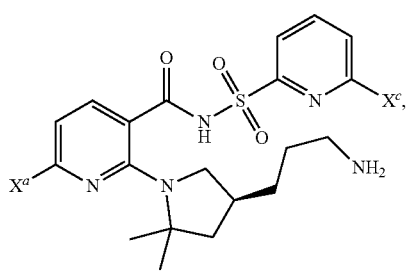

or a salt thereof, is prepared by converting a compound of Formula (III):

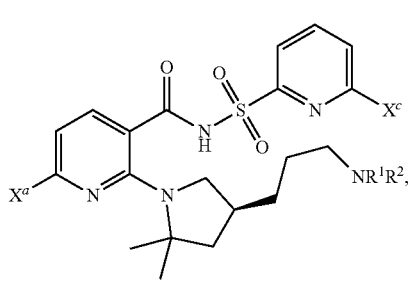

or a salt thereof, into the compound of Formula (I), or a salt thereof,
wherein in the compound of Formula (III), or a salt thereof:
$X^a$ is selected from F, Cl, Br, I, and —OSO$_2$R;
R is selected from —C$_{1-10}$alkyl, —C$_{1-10}$haloalkyl, and aryl optionally substituted with —C$_{1-10}$alkyl, —C$_{1-10}$haloalkyl, halo, or nitro;
$X^c$ is selected from F, Cl, Br, and I; and wherein:
$R^1$ is hydrogen and $R^2$ is a monovalent nitrogen protecting group;
$R^1$ and $R^2$ are independently selected from monovalent nitrogen protecting groups; or
$R^1$ and $R^2$, together with the atoms to which they are attached, form a nitrogen protecting group.

5. The method of claim 4, wherein the compound of Formula (III):

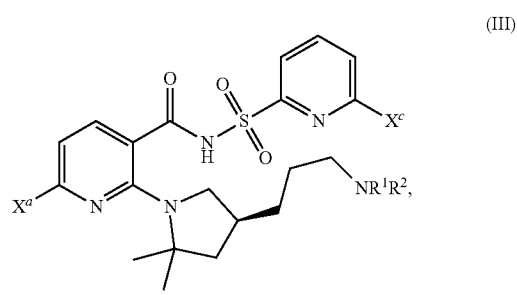

or a salt thereof, is prepared by combining a compound of Formula (IV):

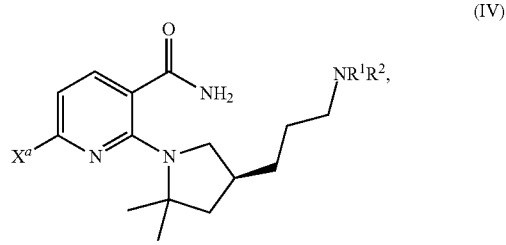

or a salt thereof, with a compound of Formula (V):

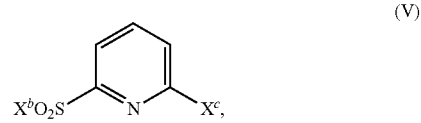

or a salt thereof, to produce the compound of Formula (III), or a salt thereof,
wherein:
$X^a$ is selected from F, Cl, Br, I, and —OSO$_2$R;
R is selected from —C$_{1-10}$alkyl, —C$_{1-10}$haloalkyl, and aryl optionally substituted with —C$_{1-10}$alkyl, —C$_{1-10}$haloalkyl, halo, or nitro
$X^b$ is selected from Cl, F, —OC$_6$F$_5$,

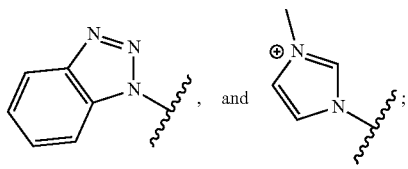

$X^c$ is selected from F, Cl, Br, and I; and wherein:
- R¹ is hydrogen and R² is a monovalent nitrogen protecting group;
- R¹ and R² are independently selected from monovalent nitrogen protecting groups; or
- R¹ and R², together with the atoms to which they are attached, form a nitrogen protecting group.

6. The method of claim 5, wherein the compound of Formula (IV):

(IV)

[Structure of Formula (IV): pyridine with C(=O)NH₂, X$^a$, and N-pyrrolidine (gem-dimethyl) bearing propyl-NR¹R² chain]

or a salt thereof, is prepared by converting a compound of Formula (VI):

(VI)

[Structure of Formula (VI): pyridine with C(=O)NH₂, X$^a$, and N-pyrrolidine (gem-dimethyl) bearing propyl-OH chain]

or a salt thereof, into the compound of Formula (IV), or a salt thereof, wherein in the compound of Formula (VI), or a salt thereof:
- X$^a$ is selected from F, Cl, Br, I, and —OSO₂R; and
- R is selected from —C$_{1-10}$alkyl, —C$_{1-10}$haloalkyl, and aryl optionally substituted with —C$_{1-10}$alkyl, —C$_{1-10}$haloalkyl, halo, or nitro.

7. The method of claim 6, wherein the compound of Formula (VI):

(VI)

[Structure of Formula (VI) repeated]

or a salt thereof, is prepared by combining compound 2:

2

[Structure of compound 2: 5,5-dimethylpyrrolidine with propyl-OH substituent]

or a salt thereof, with a compound of Formula (VII):

(VII)

[Structure of Formula (VII): pyridine with C(=O)NH₂, X$^a$, and X$^d$]

or a salt thereof, to produce the compound of Formula (VI), or a salt thereof, wherein in the compound of Formula (VII), or a salt thereof:
- X$^a$ is selected from F, Cl, Br, I, and —OSO₂R;
  - R is selected from —C$_{1-10}$alkyl, —C$_{1-10}$haloalkyl, and aryl optionally substituted with —C$_{1-10}$alkyl, —C$_{1-10}$haloalkyl, halo, or nitro; and
- X$^d$ is selected from F, Cl, Br, and I.

8. The method of claim 7, wherein compound 2:

2

[Structure of compound 2 repeated]

or a salt thereof, is prepared by converting compound 3:

3

[Structure of compound 3: 5,5-dimethyl-2-oxopyrrolidine (lactam) with propyl-OH substituent]

or a salt thereof, into compound 2, or a salt thereof.

9. The method of claim 8, wherein compound 3:

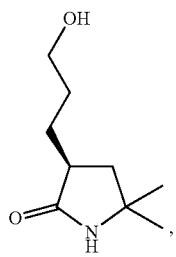

or a salt thereof, is prepared by converting compound 4:

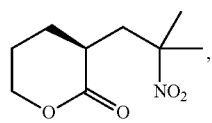

or a salt thereof, into compound 3, or a salt thereof.

10. The method of claim 9, wherein compound 4:

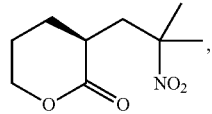

or a salt thereof, is prepared by chiral resolution of compound (±)-4:

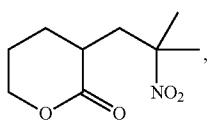

or a salt thereof.

11. A method of preparing Compound I:

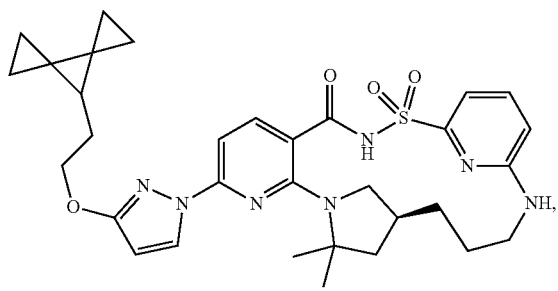

or a pharmaceutically acceptable salt thereof, comprising converting a compound of Formula (VIII):

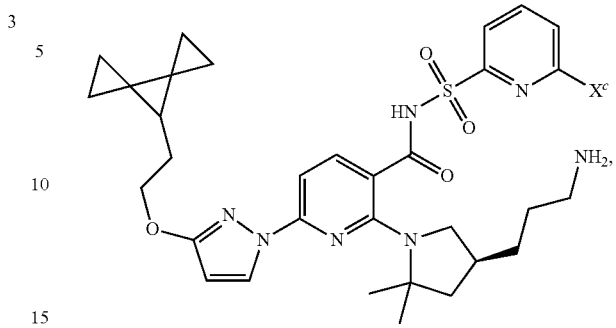

or a salt thereof, into Compound I, or a pharmaceutically acceptable salt thereof, wherein in the compound of Formula (VIII), or a salt thereof, $X^c$ is selected from F, Cl, Br, and I.

12. The method of claim 11, wherein the compound of Formula (VIII):

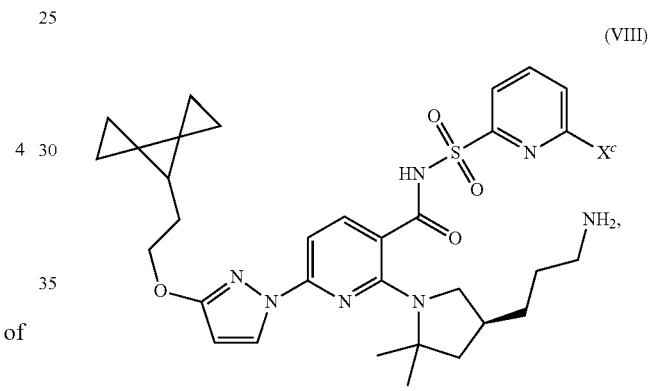

or a salt thereof, is prepared by converting a compound of Formula (IX):

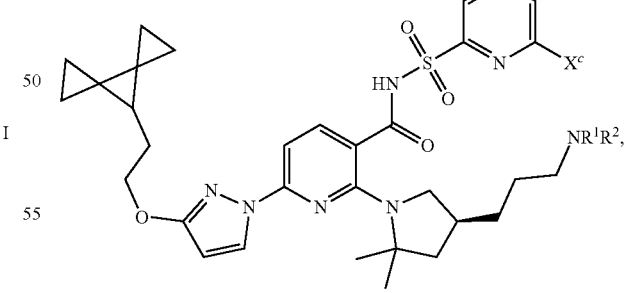

or a salt thereof, into the compound of Formula (VIII), or a salt thereof, wherein in the compound of Formula (IX), or a salt thereof:

$X^c$ is selected from F, Cl, Br, and I; and wherein:

$R^1$ is hydrogen and $R^2$ is a monovalent nitrogen protecting group;

R[1] and R[2] are independently selected from monovalent nitrogen protecting groups; or R[1] and R[2], together with the atoms to which they are attached, form a nitrogen protecting group.

13. The method of claim 12, wherein the compound of Formula (IX):

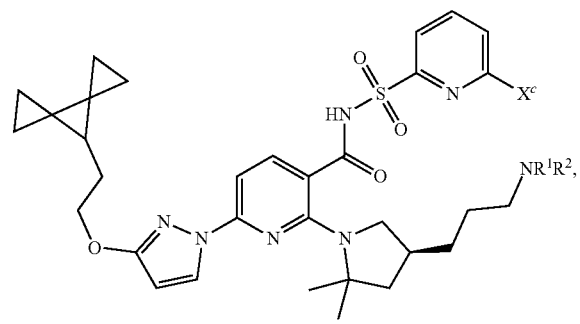

(IX)

or a salt thereof, is prepared by combining a compound of Formula (X):

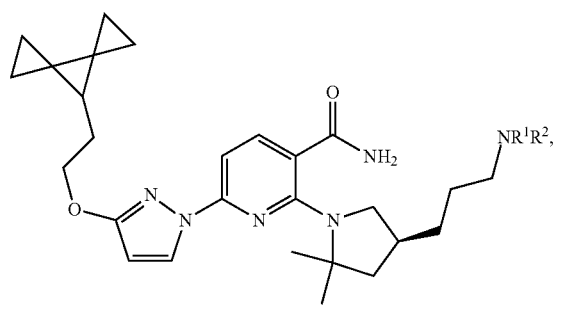

(X)

or a salt thereof, with a compound of Formula (V):

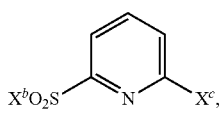

(V)

or a salt thereof, to produce the compound of Formula (IX), or a salt thereof, wherein in the compound of Formula (X), or a salt thereof:

R[1] is hydrogen and R[2] is a monovalent nitrogen protecting group;

R[1] and R[2] are independently selected from monovalent nitrogen protecting groups; or R[1] and R[2], together with the atoms to which they are attached, form a nitrogen protecting group; and wherein in the compound of Formula (V), or a salt thereof:

$X^b$ is selected from Cl, F, —OC$_6$F$_5$,

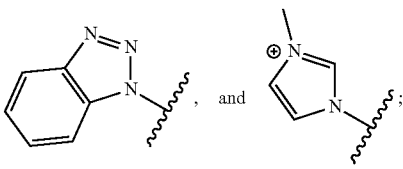

and $X^c$ is selected from F, Cl, Br, and I.

14. The method of claim 13, wherein the compound of Formula (X):

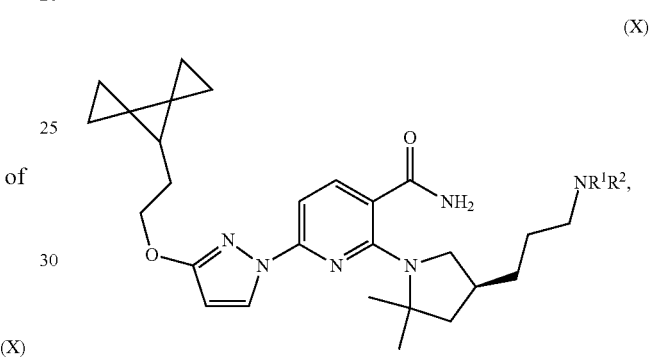

(X)

or a salt thereof, is prepared by combining a compound of Formula (IV):

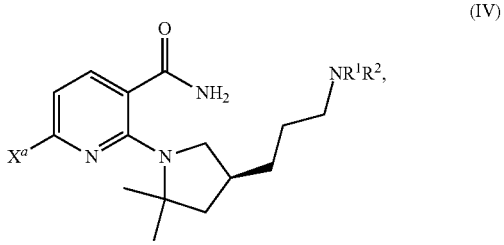

(IV)

or a salt thereof, with compound 1:

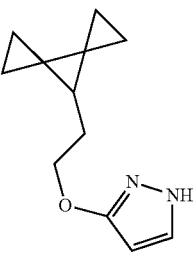

1 or a salt thereof, to produce the compound of Formula (X), or a salt thereof, wherein in the compound of Formula (IV), or a salt thereof:

$X^a$ is selected from F, Cl, Br, I, and —OSO$_2$R;

R is selected from —C$_{1-10}$alkyl, —C$_{1-10}$haloalkyl, and aryl optionally substituted with —C$_{1-10}$alkyl, —C$_{1-10}$haloalkyl, halo, or nitro; and wherein:

$R^1$ is hydrogen and $R^2$ is a monovalent nitrogen protecting group;

$R^1$ and $R^2$ are independently selected from monovalent nitrogen protecting groups; or $R^1$ and $R^2$, together with the atoms to which they are attached, form a nitrogen protecting group.

15. The method of claim 14, wherein the compound of Formula (IV):

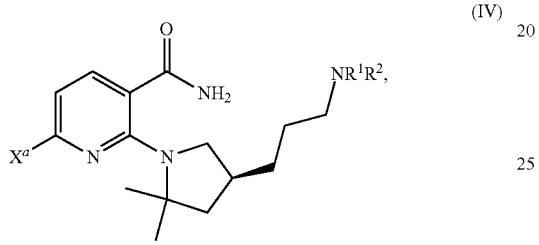

(IV)

or a salt thereof, is prepared by combining a compound of Formula (XI):

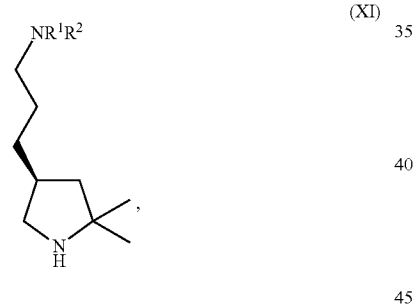

(XI)

or a salt thereof, with a compound of Formula (VII):

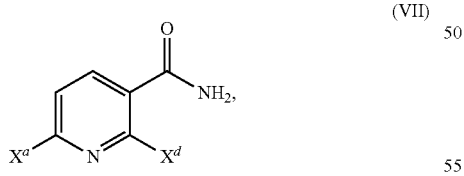

(VII)

or a salt thereof, to produce the compound of Formula (IV), or a salt thereof, wherein in the compound of Formula (XI), or a salt thereof:

$R^1$ is hydrogen and $R^2$ is a monovalent nitrogen protecting group;

$R^1$ and $R^2$ are independently selected from monovalent nitrogen protecting groups; or $R^1$ and $R^2$, together with the atoms to which they are attached, form a nitrogen protecting group; and wherein in the compound of Formula (VII), or a salt thereof:

$X^a$ is selected from F, Cl, Br, I, and —OSO$_2$R;

R is selected from —C$_{1-10}$alkyl, —C$_{1-10}$haloalkyl, and aryl optionally substituted with —C$_{1-10}$alkyl, —C$_{1-10}$haloalkyl, halo, or nitro; and $X^d$ is selected from F, Cl, Br, and I.

16. The method of claim 15, wherein the compound of Formula (XI):

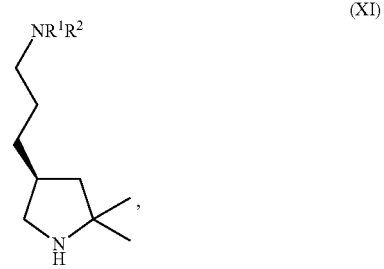

(XI)

or a salt thereof, is prepared by converting a compound of Formula (XII):

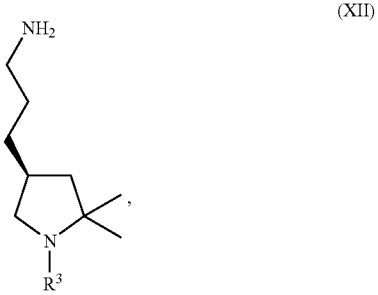

(XII)

or a salt thereof, into the compound of Formula (XI), or a salt thereof, wherein in the compound of Formula (XII), or a salt thereof, $R^3$ is a monovalent nitrogen protecting group.

17. The method of claim 16, wherein the compound of Formula (XII):

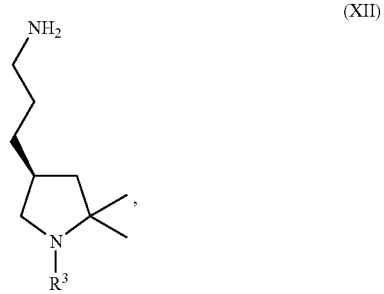

(XII)

or a salt thereof, is prepared by converting the compound of Formula (XV):

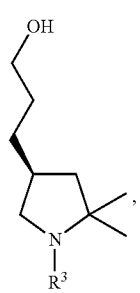

(XV)

or a salt thereof, into the compound of Formula (XII), or a salt thereof, wherein in the compound of Formula (XV), or a salt thereof, $R^3$ is a monovalent nitrogen protecting group.

18. The method of claim 17, wherein the conversion of the compound of Formula (XV), or a salt thereof, into the compound of Formula (XII), or a salt thereof, comprises the steps of:

1) Converting the compound of Formula (XV):

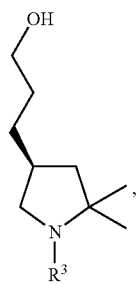

(XV)

or a salt thereof, into the compound of Formula (XIV):

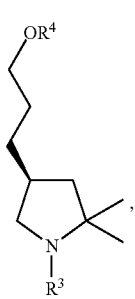

(XIV)

or a salt thereof;

2) Converting the compound of Formula (XIV), or a salt thereof, into the compound of Formula (XIII):

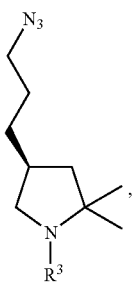

(XIII)

or a salt thereof; and

3) Converting the compound of Formula (XIII), or a salt thereof, into the compound of Formula (XII), or a salt thereof, wherein in the compounds of Formulae (XIII)-(XV), or a salt thereof, $R^3$ is a monovalent nitrogen protecting group; and wherein in the compound of Formula (XIV), or a salt thereof:

$R^4$ is —SO$_2$R; and

R is selected from —C$_{1-10}$alkyl, —C$_{1-10}$haloalkyl, and aryl optionally substituted with —C$_{1-10}$alkyl, —C$_{1-10}$haloalkyl, halo, or nitro.

19. The method of claim 18, wherein the compound of Formula (XV):

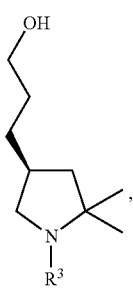

(XV)

or a salt thereof, is prepared by converting compound 2:

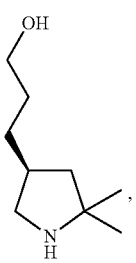

2 or a salt thereof, into the compound of Formula (XV), or a salt thereof.

20. The method of claim 19, wherein compound 2:

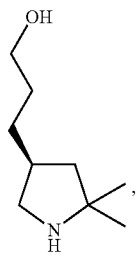

or a salt thereof, is prepared by converting compound 3:

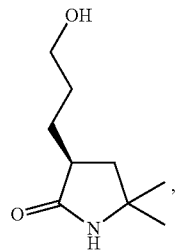

or a salt thereof, into compound 2, or a salt thereof.

21. The method of claim 20, wherein compound 3:

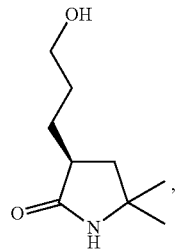

or a salt thereof, is prepared by chiral resolution of compound (±)-3:

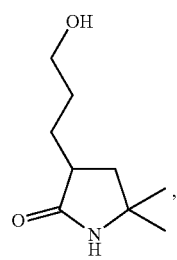

or a salt thereof.

22. The method of claim 21, wherein compound (±)-3:

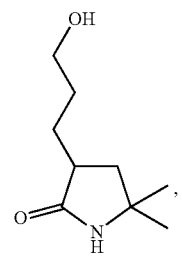

or a salt thereof, is prepared by converting compound (±)-4:

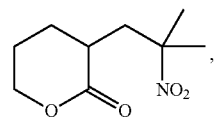

or a salt thereof, into compound (±)-3, or a salt thereof.

23. The method of claim 22, wherein compound (±)-4:

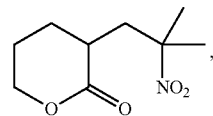

or a salt thereof, is prepared by combining compound 5:

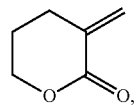

or a salt thereof, with 2-nitropropane to produce compound (±)-4, or a salt thereof.

24. The method of claim 2, wherein compound 1:

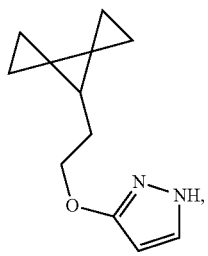

or a salt thereof, is prepared by converting compound 6:

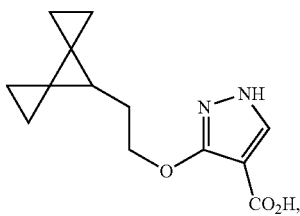
6 or a salt thereof, into compound 1, or a salt thereof.

25. The method of claim 24, wherein compound 6:

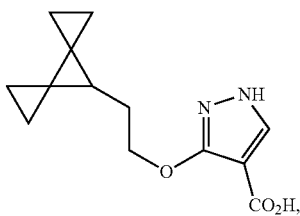
6 or a salt thereof, is prepared by converting compound 7:

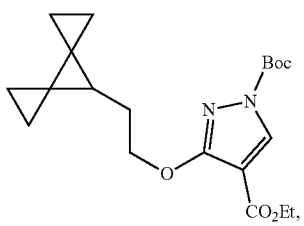
7 or a salt thereof, into compound 6, or a salt thereof.

26. The method of claim 25, wherein compound 7:

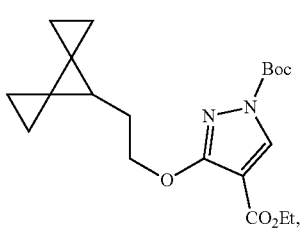
7 or a salt thereof, is prepared by combining compound 8:

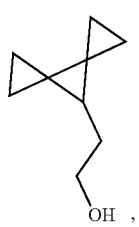
8 or a salt thereof, with compound 9:

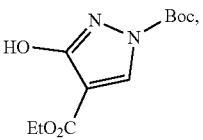
9 or a salt thereof, to produce compound 7, or a salt thereof.

27. The method of claim 26, wherein compound 8:

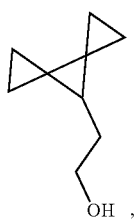
8 or a salt thereof, is prepared by converting compound 10:

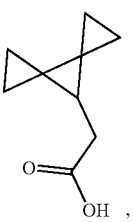
10 or a salt thereof, into compound 8, or a salt thereof.

28. The method of claim 27, wherein compound 10:

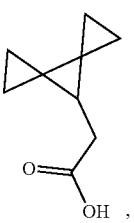
10 or a salt thereof, is prepared by converting compound 11:

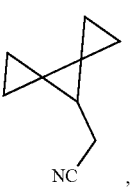
11 or a salt thereof, into compound 10, or a salt thereof.

29. The method of claim 28, wherein compound 11:

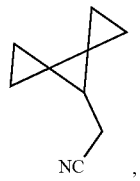

11 or a salt thereof, is prepared by converting compound 12:

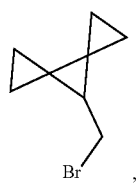

12 or a salt thereof, into compound 11, or a salt thereof.

30. The method of claim 29, wherein compound 12:

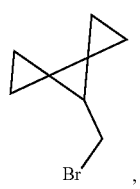

12 or a salt thereof, is prepared by converting compound 13:

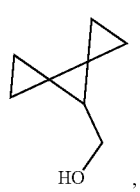

13 or a salt thereof, into compound 12, or a salt thereof.

31. The method of claim 30, wherein compound 13:

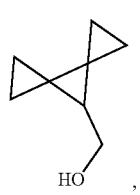

13 or a salt thereof, is prepared by converting compound 14:

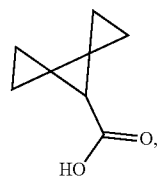

14 or a salt thereof, into compound 13, or a salt thereof.

32. The method of claim 31, wherein compound 14:

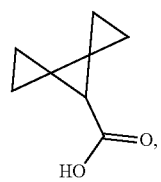

14 or a salt thereof, is prepared by converting compound 15:

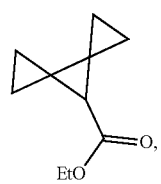

15 or a salt thereof, into compound 14, or a salt thereof.

33. The method of claim 32, wherein compound 15:

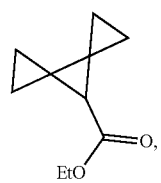

15 or a salt thereof, is prepared by converting compound 16:

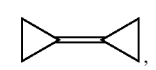

16 or a salt thereof, into compound 15, or a salt thereof.

34. The method of claim 33, wherein compound 16:

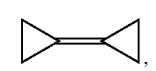

16 or a salt thereof, is prepared by converting compound 17:

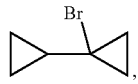   17 or a salt thereof, into compound 16, or a salt thereof.

35. The method of claim 34, wherein compound 17:

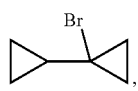   17 or a salt thereof, is prepared by converting compound 18:

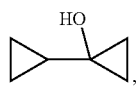   18 or a salt thereof, into compound 17, or a salt thereof.

36. The method of claim 35, wherein compound 18:

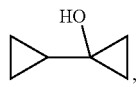   18 or a salt thereof, is prepared by converting compound 19:

   19 or a salt thereof, into compound 18, or a salt thereof.

37. A compound selected from:

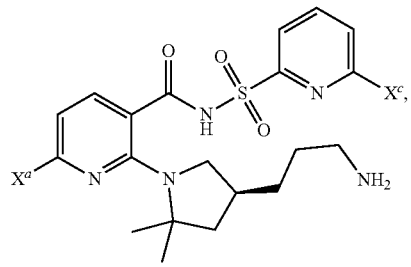   (I)

-continued

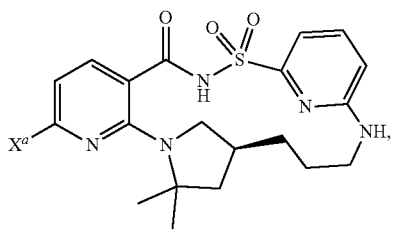   (II)

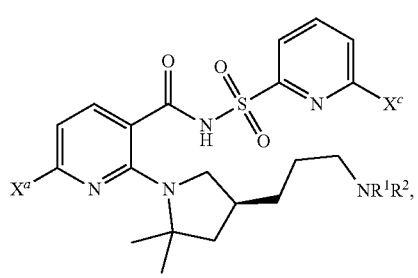   (III)

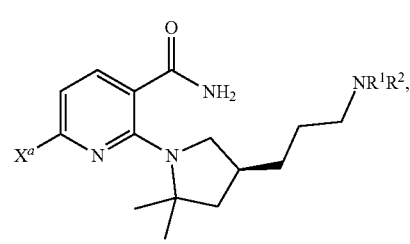   (IV)

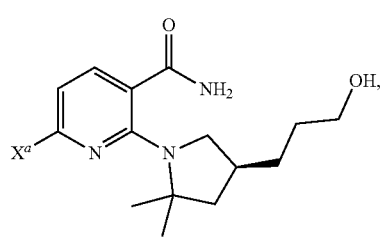   (VI)

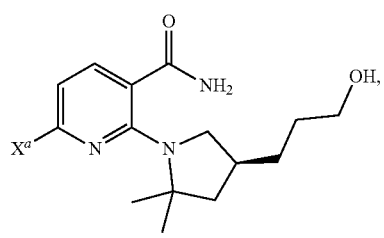   (VI)

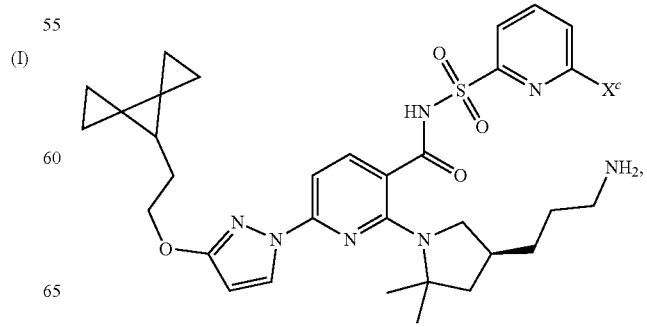   (VIII)

(IX)
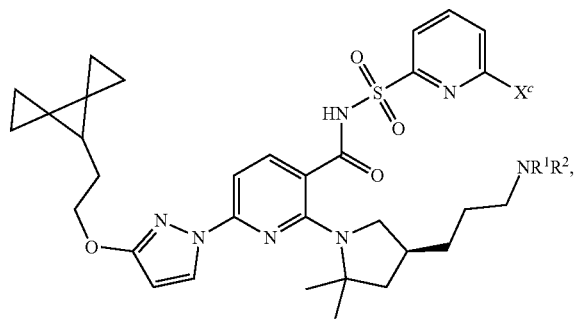

(X)
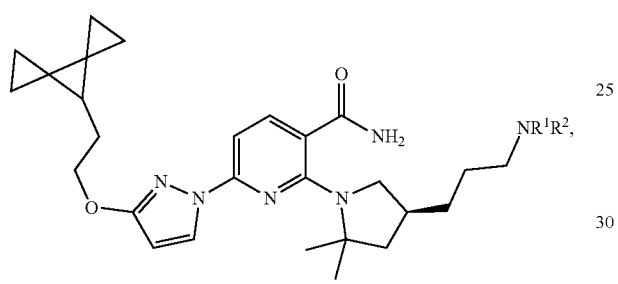

(XI)
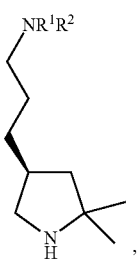

(XII)
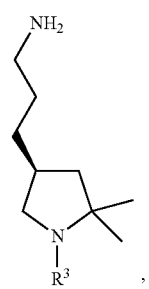

(XIII)
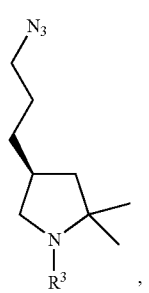

(XIV)

(XIVa)
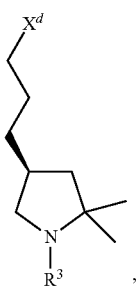

6
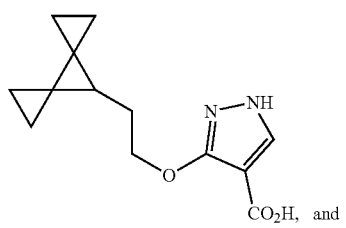

7
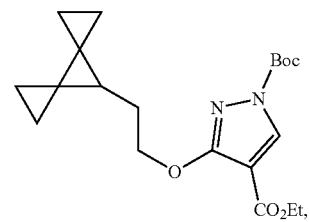

and salts thereof,
wherein:
Xa is selected from F, Cl, Br, I, and —OSO$_2$R;
R is selected from —C$_{1-10}$alkyl, —C$_{1-10}$haloalkyl, and aryl optionally substituted with —C$_{1-10}$alkyl, —C$_{1-10}$haloalkyl, halo, or nitro;
X$^b$ is selected from Cl, F, —OC$_6$F$_5$,

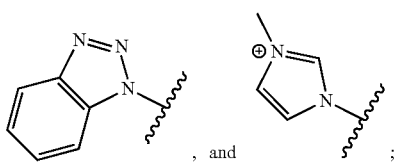
, and ;

X$^c$ is selected from F, Cl, Br, and I;
X$^d$ is selected from F, Cl, Br, and I;
R$^3$ is a monovalent nitrogen protecting group;
R$^4$ is —SO$_2$R; and
R is selected from —C$_{1-10}$alkyl, —C$_{1-10}$haloalkyl, and aryl optionally substituted with —C$_{1-10}$alkyl, —C$_{1-10}$haloalkyl, halo, or nitro; and wherein:
R[1] is hydrogen and R[2] is a monovalent nitrogen protecting group;
R[1] and R[2] are independently selected from monovalent nitrogen protecting groups; or
R[1] and R[2], together with the atoms to which they are attached, form a nitrogen protecting group; and
wherein the compound is not:
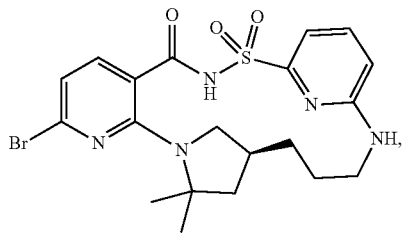
40
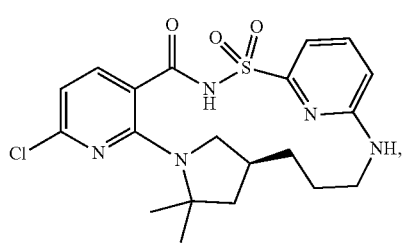
41
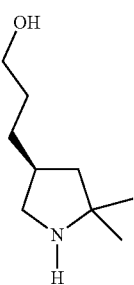
2
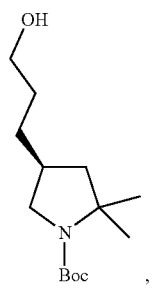
42
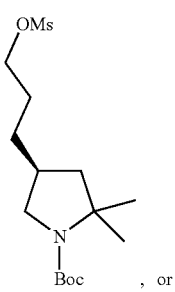
43
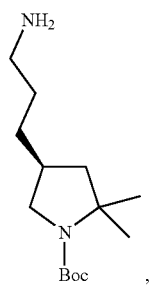
44
or a salt thereof.
* * * * *

UNITED STATES PATENT AND TRADEMARK OFFICE
CERTIFICATE OF CORRECTION

PATENT NO. : 11,584,761 B2
APPLICATION NO. : 16/992419
DATED : February 21, 2023
INVENTOR(S) : Paul Angell et al.

It is certified that error appears in the above-identified patent and that said Letters Patent is hereby corrected as shown below:

In the Claims

Claim 37, Column 224, Line 46, "Xa" should read as --$X^a$--.

Claim 37, Column 224, Line 50, "CI," should read as --Cl,--.

Signed and Sealed this
Eleventh Day of April, 2023

Katherine Kelly Vidal
*Director of the United States Patent and Trademark Office*